(12) United States Patent
Kato et al.

(10) Patent No.: US 9,871,203 B2
(45) Date of Patent: Jan. 16, 2018

(54) AROMATIC AMINE DERIVATIVE, ORGANIC ELECTROLUMINESCENT ELEMENT AND ELECTRONIC DEVICE

(71) Applicant: IDEMITSU KOSAN CO., LTD., Chiyoda-ku (JP)

(72) Inventors: Tomoki Kato, Sodegaura (JP); Takayasu Sado, Sodegaura (JP); Takahiro Fujiyama, Yao (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 707 days.

(21) Appl. No.: 14/377,784

(22) PCT Filed: Feb. 7, 2013

(86) PCT No.: PCT/JP2013/052951
§ 371 (c)(1),
(2) Date: Aug. 8, 2014

(87) PCT Pub. No.: WO2013/118846
PCT Pub. Date: Aug. 15, 2013

(65) Prior Publication Data
US 2015/0287921 A1 Oct. 8, 2015

(30) Foreign Application Priority Data

Feb. 10, 2012 (JP) .................. 2012-027829
Apr. 12, 2012 (JP) .................. 2012-091368

(51) Int. Cl.
*C07C 211/61* (2006.01)
*C07C 211/54* (2006.01)
(Continued)

(52) U.S. Cl.
CPC .......... *H01L 51/006* (2013.01); *C07C 211/61* (2013.01); *C07D 307/91* (2013.01);
(Continued)

(58) Field of Classification Search
CPC . C07C 211/61; C07C 211/54; H01L 51/5032; C09K 11/06; H05B 33/14
(Continued)

(56) References Cited

U.S. PATENT DOCUMENTS 8,980,442 B2 * 3/2015 Yabunouchi .......... C07C 211/61
257/40
2007/0278938 A1 12/2007 Yabunouchi et al.
(Continued)

FOREIGN PATENT DOCUMENTS

CN 101341115 A 1/2009
CN 102186819 A 9/2011
(Continued)

OTHER PUBLICATIONS

Combined Chinese Office Action and Search Report dated Jun. 11, 2015 in Patent Application No. 201380008683.9 (with English Translation of Categories of Cited Documents).
(Continued)

*Primary Examiner* — Venkataraman Balasubramanian
(74) *Attorney, Agent, or Firm* — Oblon, McClelland, Maier & Neustadt, L.L.P.

(57) ABSTRACT

An organic EL device that has a high efficiency and a long service life, an electronic apparatus containing the organic EL device, and a compound capable of providing the organic EL device. The compound is specifically represented by the following general formula (1):

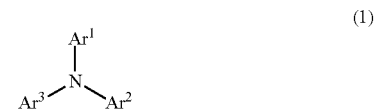

wherein in the general formula (1), $Ar^1$ represents an organic group A represented by the following general formula (A-1); $Ar^2$ represents the organic group A or an organic group B represented by the following general formula (B-1); and $Ar^3$ represents the organic group B or an organic group C represented by the following general formula (C-1), provided that in the case where both $Ar^1$ and $Ar^2$ are the organic groups A, the organic groups A may be the same as or different from each other,

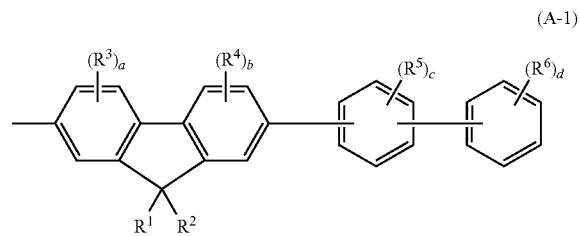

in the general formula (A-1), $R^1$ and $R^2$ each represent a hydrogen atom, an alkyl group or an aryl group, and $R^1$ and $R^2$ may be bonded to each other to form a hydrocarbon ring; $R^3$ to $R^6$ each represent an alkyl group, a cycloalkyl group or an aryl group; and a, b, c and d each independently represent an integer of from 0 to 2, provided that $R^3$ and $R^4$ may be bonded to each other to form a hydrocarbon ring; and in the case where a or b is 2, adjacent groups of $R^3$ or adjacent groups of $R^4$ may be bonded to each other to form a hydrocarbon ring,

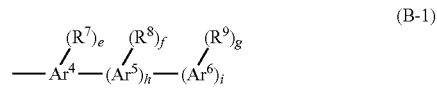

(Continued)

in the general formula (B-1), $Ar^4$ and $Ar^5$ each represent an arylene group; $Ar^6$ represents an aryl group; $R^7$ to $R^9$ each represent an alkyl group, a cycloalkyl group or an aryl group; e, f and g each represent an integer of from 0 to 2; and h and i each represent 0 or 1, provided that $R^7$ to $R^9$ may be bonded to each other to form a hydrocarbon ring; and in the case where e, f or g is 2, adjacent groups of $R^7$, adjacent groups of $R^8$ or adjacent groups of $R^9$ may be bonded to each other to form a hydrocarbon ring,

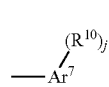

(C-1)

in the general formula (C-1), $Ar^7$ represents an aryl group; $R^{10}$ represents an alkyl group, a cycloalkyl group or an aryl group; and j represents an integer of from 0 to 2, provided that in the case where j is 2, adjacent groups of $R^{10}$ may be bonded to each other to form a hydrocarbon ring.

36 Claims, No Drawings

(51) Int. Cl.

| | | |
|---|---|---|
| *C09K 11/06* | (2006.01) | |
| *H01L 51/50* | (2006.01) | |
| *H05B 33/14* | (2006.01) | |
| *H01L 51/00* | (2006.01) | |
| *C07D 307/91* | (2006.01) | |
| *C07D 405/12* | (2006.01) | |
| *C07D 405/14* | (2006.01) | |
| *H01L 51/52* | (2006.01) | |

(52) U.S. Cl.
CPC ......... *C07D 405/12* (2013.01); *C07D 405/14* (2013.01); *C09K 11/06* (2013.01); *H01L 51/0052* (2013.01); *H01L 51/0059* (2013.01); *H01L 51/0061* (2013.01); *H01L 51/0067* (2013.01); *H01L 51/0072* (2013.01); *H01L 51/0073* (2013.01); *H01L 51/0085* (2013.01); *C07C 2603/18* (2017.05); *H01L 51/0058* (2013.01); *H01L 51/506* (2013.01); *H01L 51/5012* (2013.01); *H01L 51/5016* (2013.01); *H01L 51/5056* (2013.01); *H01L 51/5064* (2013.01); *H01L 51/5088* (2013.01); *H01L 51/5206* (2013.01); *H01L 51/5221* (2013.01)

(58) Field of Classification Search
USPC .................................... 564/308, 427; 257/40
See application file for complete search history.

(56) References Cited

U.S. PATENT DOCUMENTS

| | | |
|---|---|---|
| 2008/0200736 A1 | 8/2008 | Kosuge et al. |
| 2009/0066235 A1 | 3/2009 | Yabunouchi et al. |
| 2009/0131673 A1 | 5/2009 | Tanabe et al. |
| 2009/0160323 A1 | 6/2009 | Nomura et al. |
| 2009/0236974 A1 | 9/2009 | Tamaru et al. |
| 2009/0295281 A1 | 12/2009 | Shin et al. |
| 2010/0033081 A1 | 2/2010 | Yamada et al. |
| 2010/0102710 A1 | 4/2010 | Cho et al. |
| 2010/0181562 A1 | 7/2010 | Seo et al. |
| 2010/0244008 A1 | 9/2010 | Lee et al. |
| 2011/0006295 A1 | 1/2011 | Kathirgamanathan et al. |
| 2011/0071317 A1 | 3/2011 | Osaka et al. |
| 2011/0127495 A1 | 6/2011 | Hong et al. |
| 2011/0215308 A1 | 9/2011 | Im et al. |
| 2011/0297924 A1 | 12/2011 | Yabunouchi et al. |
| 2012/0012832 A1* | 1/2012 | Yabunouchi .......... C07C 211/61 257/40 |
| 2012/0037894 A1 | 2/2012 | Okabe |
| 2012/0074395 A1 | 3/2012 | Yabunouchi et al. |
| 2012/0077987 A1 | 3/2012 | Osaka et al. |
| 2012/0175600 A1 | 7/2012 | Yabunouchi et al. |
| 2012/0193612 A1 | 8/2012 | Chun et al. |
| 2012/0286653 A1 | 11/2012 | Abe et al. |
| 2012/0326137 A1 | 12/2012 | Song et al. |
| 2013/0105771 A1 | 5/2013 | Ryu et al. |
| 2013/0161593 A1 | 6/2013 | Seo et al. |
| 2014/0027747 A1 | 1/2014 | Mun et al. |
| 2014/0037472 A1 | 2/2014 | Hibi et al. |
| 2014/0042412 A1 | 2/2014 | Ryu et al. |
| 2014/0231774 A1 | 8/2014 | Huh et al. |
| 2014/0330025 A1 | 11/2014 | Baba et al. |
| 2014/0374722 A1 | 12/2014 | Kim et al. |
| 2015/0255728 A1 | 9/2015 | Nomura et al. |

FOREIGN PATENT DOCUMENTS

| | | |
|---|---|---|
| JP | 9-249876 A | 9/1997 |
| JP | 2003 519432 | 6/2003 |
| JP | 2004-171808 A | 6/2004 |
| JP | 2005 232097 | 9/2005 |
| JP | 2005-255986 A | 9/2005 |
| JP | 3792029 | 6/2006 |
| JP | 3801330 | 7/2006 |
| JP | 3813003 | 8/2006 |
| JP | 3835917 | 10/2006 |
| JP | 2007-110093 A | 4/2007 |
| JP | 2008 19238 | 1/2008 |
| JP | 2008 37755 | 2/2008 |
| JP | 2008 201716 | 9/2008 |
| JP | 2009 147276 | 7/2009 |
| JP | 2010-212675 A | 9/2010 |
| JP | 2011-051936 A | 3/2011 |
| JP | 2011-129275 A | 6/2011 |
| JP | 2012-074707 A | 4/2012 |
| JP | 2012-089581 A | 5/2012 |
| KR | 10-2010-0121238 A | 11/2010 |
| KR | 10-2011-0041727 A | 4/2011 |
| KR | 10-2011-0134581 A | 12/2011 |
| KR | 10-1108519 B1 | 1/2012 |
| KR | 10-1111406 61 | 4/2012 |
| KR | 10-1165698 B1 | 7/2012 |
| KR | 10-2013-0007461 A | 1/2013 |
| WO | 01 49806 | 7/2001 |
| WO | 2005 079118 | 8/2005 |
| WO | 2009 041635 | 4/2009 |
| WO | 2010 106806 | 9/2010 |
| WO | 2010 114017 | 10/2010 |
| WO | 2010 134350 | 11/2010 |
| WO | 2010 134352 | 11/2010 |
| WO | 2011 024451 | 3/2011 |
| WO | 2011 090149 | 7/2011 |
| WO | 2012 096382 | 7/2012 |
| WO | 2012 148127 | 11/2012 |
| WO | WO 2013/032303 A2 | 3/2013 |
| WO | WO 2013/032304 A2 | 3/2013 |

OTHER PUBLICATIONS

International Search Report dated Apr. 23, 2013 in PCT/JP13/052951 Filed Feb. 7, 2013.

* cited by examiner

AROMATIC AMINE DERIVATIVE, ORGANIC ELECTROLUMINESCENT ELEMENT AND ELECTRONIC DEVICE

TECHNICAL FIELD

The present invention relates to an aromatic amine derivative and an organic electroluminescence device (organic EL device) using the same. The present invention also relates to an electronic apparatus equipped with the organic EL device.

BACKGROUND ART

An organic EL device is a self-luminescence device utilizing the principle that a fluorescent substance emits light with recombination energy of holes injected from an anode and electrons injected from a cathode. Subsequent to the reports of a low voltage driven organic EL device with a stacked device by C. W. Tang, et al., Eastman Kodak Company (C. W. Tang and S. A. Vanslyke, Applied Physics Letters, vol. 51, p. 913 (1987), etc.), studies on organic EL devices using an organic material as a constitutional material have been made actively.

For example, Patent document 1 to Patent document 4 disclose a diamine compound having a fluorene skeleton between two nitrogen atoms, and disclose an organic EL device that uses the diamine compound as a material for a hole transporting layer "adjacent to a light emitting layer", thereby suppressing crystallization of the hole transporting material due to heat generation on light emission of the light emitting layer or the like, the organic EL device being improved in stability and durability as compared to a diamine compound having a biphenylene group between two nitrogen atoms and a monoamine compound having a fluorene skeleton.

Patent document 5 discloses production of an organic EL device having a low driving voltage and a long service life, by using a diamine compound having two nitrogen atoms bonded through a biphenylene group as a material for a first hole transporting layer and an aromatic amine derivative having a dibenzofuran structure and a carbazole structure as a material for a second hole transporting layer adjacent to a light emitting layer. Patent document 6 discloses a phosphorescent organic EL device that uses a diamine compound having two nitrogen atoms bonded through a biphenylene group in a first hole transporting layer and an amine compound having a particular heteroaryl structure in a second hole transporting layer, whereby the second hole transporting layer has electron blocking property, electroresistance, and hole injection and transporting property, thereby achieving a high efficiency and a long service life for the organic EL device. Patent document 7 discloses the use of a compound having a carbazole ring structure in a hole transporting layer "adjacent to a light emitting layer", thereby providing an organic EL device having a high light emission efficiency and a low driving voltage.

In summary, an organic EL device, particularly a phosphorescent device, has been improved in device capability by using a hole transporting layer having a two-layer structure including a first hole transporting layer and a second hole transporting layer, and using a material having a higher capability in the second hole transporting layer "adjacent to a light emitting layer".

The capability demanded for the second hole transporting layer includes that (i) the layer has a large triplet energy (preferably 2.6 eV or more) for preventing the excitation energy of the phosphorescent layer from being diffused, (ii) the layer has electroresistance since the layer is adjacent to the light emitting layer, (iii) the layer is an organic layer that has a small affinity (preferably 2.4 eV or less) for preventing electrons from being leaked from the light emitting layer, and (iv) the layer is an organic layer that has a large ionization potential (preferably 5.5 eV or more) for facilitating hole injection to the light emitting layer. As a material that satisfies these characteristics, a molecular skeleton having high electroresistance having a triphenylamine skeleton bonded to a heteroaryl ring, such as carbazole and dibenzofuran, is preferably used.

The first hole transporting layer is generally demanded to have excellent hole injection property to the second hole transporting layer.

For enhancing the hole injection property, it has been studied to add a compound having a p-type semiconductor property (which may be referred herein to as an acceptor material) as a hole injection layer (see Patent document 8 and Patent document 9).

CITATION LIST

Patent document 1: Japanese Patent No. 3,813,003
Patent document 2: Japanese Patent No. 3,801,330
Patent document 3: Japanese Patent No. 3,792,029
Patent document 4: Japanese Patent No. 3,835,917
Patent document 5: WO 2010/114017
Patent document 6: WO 2009/041635
Patent document 7: WO 2011/024451
Patent document 8: WO 01/49806 (JP-T-2003-519432)
Patent document 9: WO 2011/090149

SUMMARY OF INVENTION

Technical Problem

Under the progress of the research and development of an organic EL device described above, in a commercial device, light emitted in the organic EL device is necessarily taken out to the outside of the device with high efficiency for each color of emitted light. Thus, it is necessary to control the light path length of the entire device by controlling the thickness of the hole transporting layer, which has large carrier transporting property than the other organic layers. Accordingly, such a hole transporting material is being currently demanded that has a large mobility to such an extent that the driving voltage is not increased when the thickness of the hole transporting layer is increased, and it is also demanded that a hole transporting material exhibiting a large carrier generation amount through mutual action with the acceptor material is developed and applied to the first hole transporting layer.

The present invention has been made for solving the problems, and an object thereof is to provide an organic EL device that has a high efficiency and a long service life, an electronic apparatus containing the organic EL device, and a compound capable of providing the organic EL device.

Solution to Problem

As a result of earnest investigations made by the present inventors for developing the compound having the preferred properties and the organic EL device using the same, it has been found that the problems are solved by using a compound represented by the general formula (1). Furthermore, it has also been found that the use of a heteroaryl-substituted amine derivative in a hole transporting layer adjacent to a light emitting layer exhibits excellent results not only as a phosphorescent organic EL device but also as a fluorescent organic EL device. The present invention has been completed based on the knowledge.

The present invention provides, as one embodiment, a compound represented by the following general formula (1):

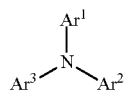
(1)

wherein in the general formula (1), $Ar^1$ represents an organic group A represented by the following general formula (A-1); $Ar^2$ represents the organic group A or an organic group B represented by the following general formula (B-1); and $Ar^3$ represents the organic group B or an organic group C represented by the following general formula (C-1), provided that in the case where both $Ar^1$ and $Ar^2$ are the organic groups A, the organic groups A may be the same as or different from each other,

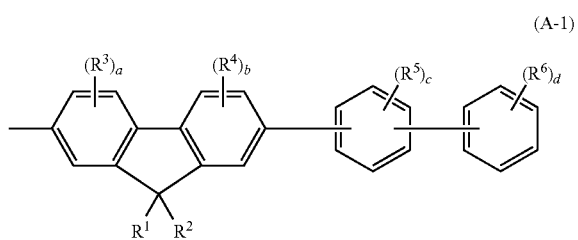
(A-1)

wherein in the general formula (A-1), $R^1$ and $R^2$ each independently represent a hydrogen atom, an alkyl group having from 1 to 10 carbon atoms or an aryl group having from 6 to 12 ring carbon atoms, provided that $R^1$ and $R^2$ may be bonded to each other to form a hydrocarbon ring;

$R^3$ to $R^6$ each independently represent an alkyl group having from 1 to 10 carbon atoms, a cycloalkyl group having from 3 to 10 ring carbon atoms or an aryl group having from 6 to 12 ring carbon atoms; and a, b, c and d each independently represent an integer of from 0 to 2, provided that $R^3$ and $R^4$ may be bonded to each other to form a hydrocarbon ring; and in the case where a or b is 2, adjacent groups of $R^3$ or adjacent groups of $R^4$ may be bonded to each other to form a hydrocarbon ring,

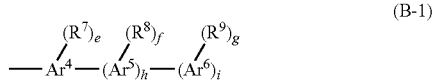
(B-1)

wherein in the general formula (B-1), $Ar^4$ and $Ar^5$ each independently represent an arylene group having from 6 to 14 ring carbon atoms; $Ar^6$ represents an aryl group having from 6 to 14 ring carbon atoms; $R^7$ to $R^9$ each independently represent an alkyl group having from 1 to 10 carbon atoms, a cycloalkyl group having from 3 to 10 ring carbon atoms or an aryl group having from 6 to 12 ring carbon atoms; e, f and g each independently represent an integer of from 0 to 2; and h and i each independently represent 0 or 1, provided that $R^7$ to $R^9$ may be bonded to each other to form a hydrocarbon ring; and in the case where e, f or g is 2, adjacent groups of $R^7$, adjacent groups of $R^8$ or adjacent groups of $R^9$ may be bonded to each other to form a hydrocarbon ring,

(C-1)

wherein in the general formula (C-1), $Ar^7$ represents a substituted or unsubstituted aryl group having from 6 to 14 ring carbon atoms; $R^{10}$ represents an alkyl group having from 1 to 10 carbon atoms, a cycloalkyl group having from 3 to 10 ring carbon atoms or an aryl group having from 6 to 12 ring carbon atoms; and j represents an integer of from 0 to 2, provided that in the case where j is 2, adjacent groups of $R^{10}$ may be bonded to each other to form a hydrocarbon ring.

The present invention also provides, as another embodiment, an organic EL device containing a cathode and an anode, and intervening therebetween an organic thin film layer containing one layer or plural layers containing at least a light emitting layer, at least one layer of the organic thin film layer containing the compound represented by the general formula (1) solely or as a component of a mixture.

The present invention also provides, as still another embodiment, an electronic apparatus containing the organic EL device.

Advantageous Effects of Invention

The compound of the present invention is a hole transporting material that has such a mobility that the driving voltage is not increased when the thickness of the hole transporting layer of the organic EL device is increased, and may provide such an organic EL device that the light path length of the organic EL device may be controlled, and the device has a high efficiency and a long service life.

In the case where the compound is used as a hole transporting material of an organic EL device having an anode coupled to an acceptor layer, in particular, the hole injection amount from the acceptor layer to the hole transporting layer is increased due to the excellent affinity to the acceptor material, and thereby the aforementioned advantage may be further enhanced.

DESCRIPTION OF EMBODIMENTS

In the present specification, the preferred ranges may be arbitrarily selected, and a combination of the preferred ranges may be more preferred.

The compound of the present invention is represented by the following general formula (1):

(1)

In the general formula (1), $Ar^1$ represents an organic group A represented by the following general formula (A-1); $Ar^2$ represents the organic group A or an organic group B represented by the following general formula (B-1); and $Ar^3$ represents the organic group B or an organic group C represented by the following general formula (C-1).

In the case where both $Ar^1$ and $Ar^2$ are the organic groups A, the organic groups A may be the same as or different from each other.

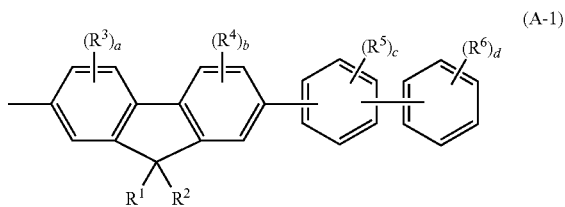

(A-1)

In the general formula (A-1), $R^1$ and $R^2$ each independently represent a hydrogen atom, an alkyl group having from 1 to 10 carbon atoms or an aryl group having from 6 to 12 ring carbon atoms.

Examples of the alkyl group include a methyl group, an ethyl group, various propyl group (the term "various" herein includes all linear and branched groups, which is hereinafter the same), various butyl groups, various octyl groups and various decyl groups. The number of carbon atoms of the alkyl group is preferably from 1 to 5.

Examples of the aryl group include a phenyl group, a biphenyl group, a terphenyl group, a naphthyl group and an anthryl group. The number of ring carbon atoms of the aryl group is preferably from 6 to 20, more preferably from 6 to 12, and further preferably from 6 to 10. The aryl group is preferably a phenyl group.

$R^1$ and $R^2$ each are preferably a hydrogen atom, a methyl group or a phenyl group, and both of them are more preferably a methyl group.

$R^1$ and $R^2$ may be bonded to each other to form a hydrocarbon ring, and examples of the organic group A in this case include the following group, but the groups are preferably not bonded to each other to form a hydrocarbon ring.

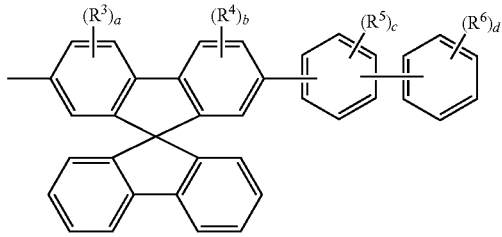

In the general formula (A-1), $R^3$ to $R^6$ each independently represent an alkyl group having from 1 to 10 carbon atoms, a cycloalkyl group having from 3 to 10 ring carbon atoms or an aryl group having from 6 to 12 ring carbon atoms.

Examples of the alkyl group and the aryl group include the same groups as in $R^1$ and $R^2$, and preferred examples thereof are also the same.

Examples of the cycloalkyl group include a cyclopropyl group, a cyclopentyl group, a cyclohexyl group and a cyclooctyl group. The number of ring carbon atoms of the cycloalkyl group is preferably from 5 to 8.

In the general formula (A-1), a, b, c and d each independently represent an integer of from 0 to 2, preferably 0 or 1, and more preferably 0.

$R^3$ and $R^4$ each preferably independently represent an alkyl group having from 1 to 10 carbon atoms, and more preferred examples of the groups are as described above. $R^5$ and $R^6$ each preferably independently represent an alkyl group having from 1 to 10 carbon atoms or an aryl group having from 6 to 12 ring carbon atoms, and more preferred examples of the groups are as described above.

$R^3$ and $R^4$ may be bonded to each other to form a hydrocarbon ring, and examples of the organic group A in this case include the following groups.

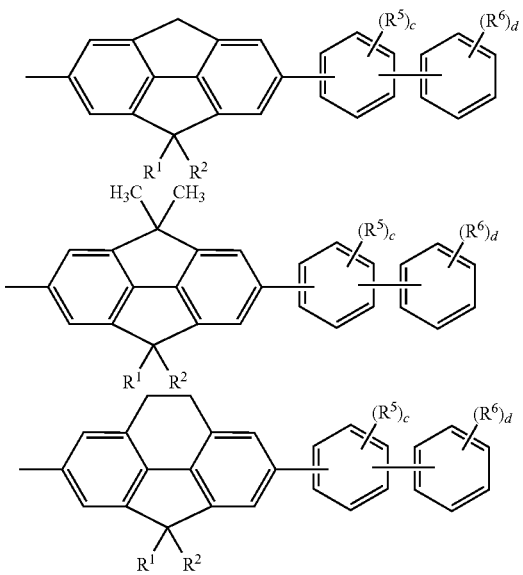

In the case where a or b is 2, adjacent groups of $R^3$ or adjacent groups of $R^4$ may be bonded to each other to form a hydrocarbon ring, and examples of the organic group A in this case include the following groups.

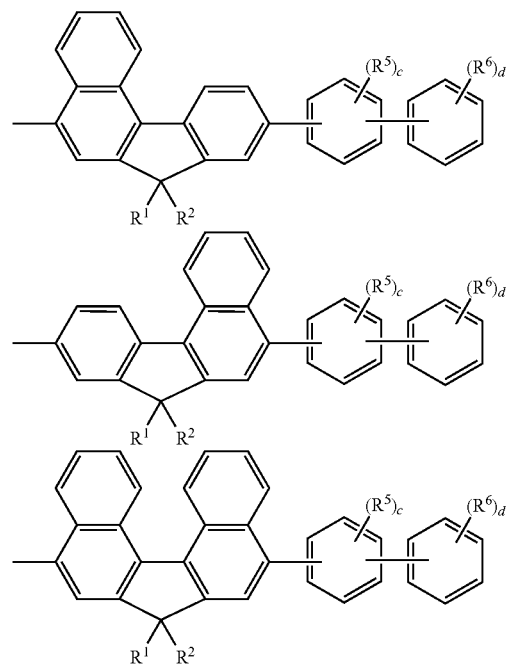

As described above, $Ar^2$ represents the organic group A or an organic group B represented by the following general formula (B-1):

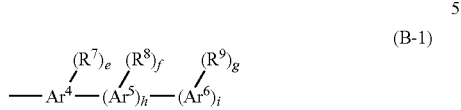
(B-1)

In the general formula (B-1), $Ar^4$ and $Ar^5$ each independently represent an arylene group having from 6 to 14 ring carbon atoms. Examples of the arylene group include a phenylene group, a naphthylene group, an anthrylene group and a phenanthrylene group. Among these, an arylene group having from 6 to 10 ring carbon atoms is preferred, and a phenylene group is more preferred.

$Ar^6$ represents an aryl group having from 6 to 14 ring carbon atoms. Examples of the aryl group include a phenyl group, a naphthyl group, an anthryl group and a phenanthryl group. Among these, an aryl group having from 6 to 10 ring carbon atoms is preferred, and a phenyl group is more preferred.

$R^7$ to $R^9$ each independently represent an alkyl group having from 1 to 10 carbon atoms, a cycloalkyl group having from 3 to 10 ring carbon atoms or an aryl group having from 6 to 12 ring carbon atoms. Examples of the alkyl group, the cycloalkyl group and the aryl group include the same groups as in $R^3$ and $R^4$, and preferred examples thereof are also the same. $R^7$ to $R^9$ each preferably represent an alkyl group having from 1 to 10 carbon atoms, more preferably an alkyl group having from 1 to 5 carbon atoms, and further preferably a methyl group.

e, f and g each independently represent an integer of from 0 to 2, and preferably 0 or 1. h and i each independently represent 0 or 1.

In the general formula (B-1), $R^7$ to $R^9$ may be bonded to each other to form a hydrocarbon ring, and examples of the organic group B in this case wherein $Ar^4$ to $Ar^6$ each represent a phenyl group include the following groups.

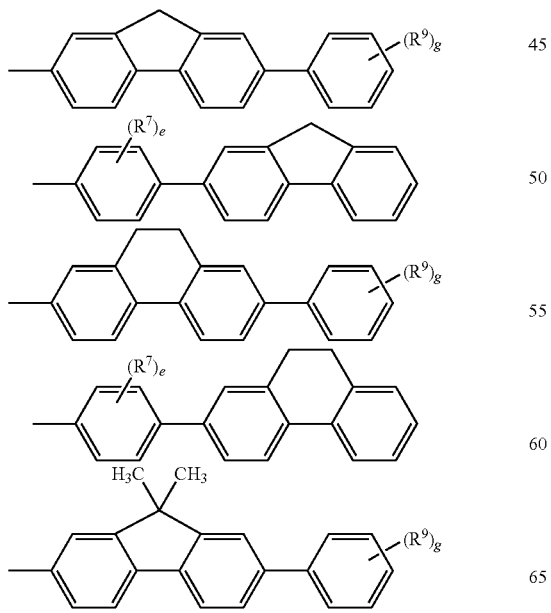

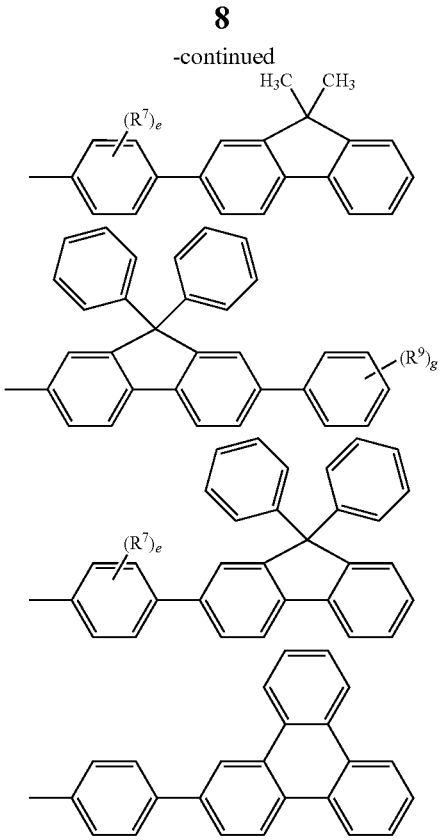

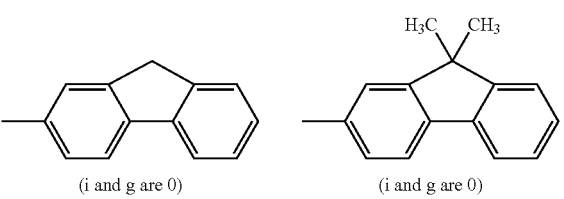

(i and g are 0)    (i and g are 0)

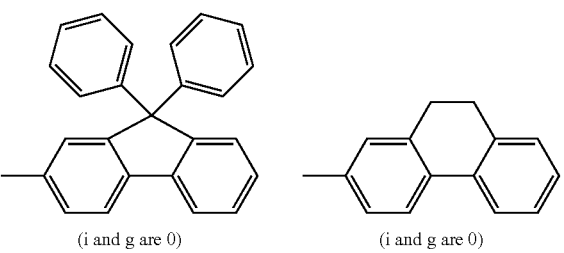

(i and g are 0)    (i and g are 0)

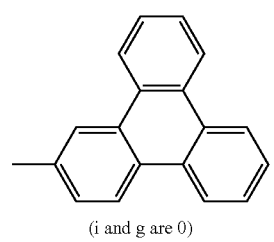

(i and g are 0)

Among the aforementioned examples of the organic group B having a hydrocarbon ring formed by bonding the groups, the following groups are preferred.

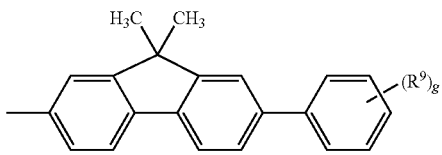

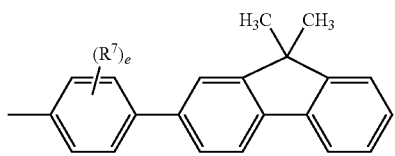

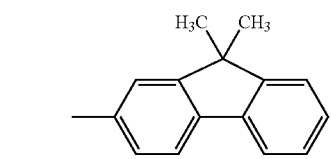

(i and g are 0)

In the general formula (B-1), in the case where e, f or g is 2, adjacent groups of $R^7$, adjacent groups of $R^8$ or adjacent groups of $R^9$ may be bonded to each other to form a hydrocarbon ring. Examples of the organic group B in this case wherein $Ar^4$ to $Ar^6$ each represent a phenyl group include the following groups.

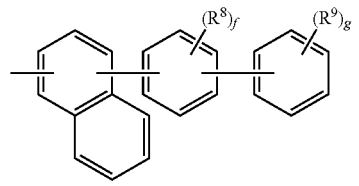

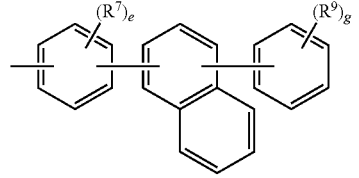

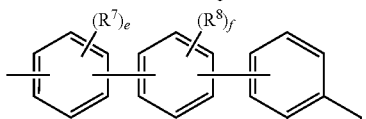

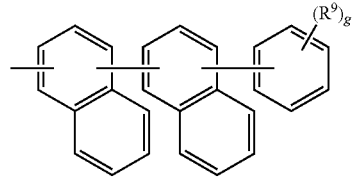

The organic group B is preferably a group represented by the following general formula (B-2):

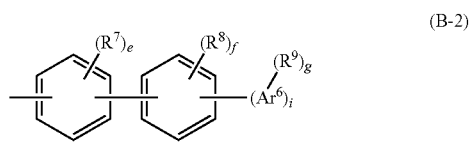

wherein $Ar^6$, $R^7$ to $R^9$, e, f and g are as defined above, and preferred examples thereof are the same.

The organic group B is preferably a group represented by any one of the following general formulae (B-3) to (B-5):

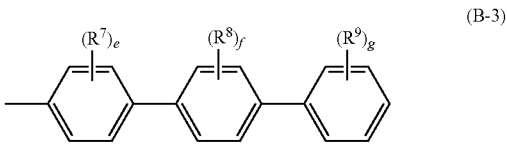

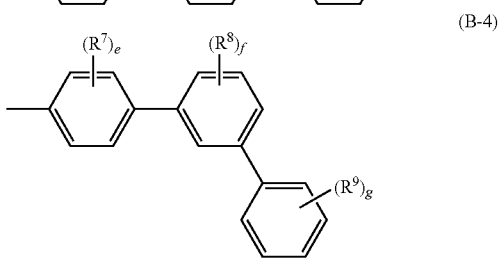

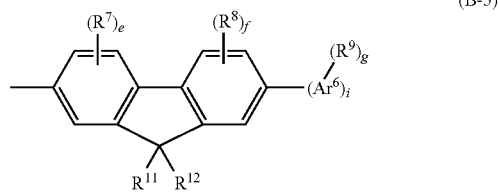

wherein $Ar^4$ to $Ar^6$, $R^7$ to $R^9$, e, f and g are as defined above, and preferred examples thereof are the same.

As described above, $Ar^3$ represents the organic group B or an organic group C represented by the following general formula (C-1):

In the general formula (C-1), $Ar^7$ represents an aryl group having from 6 to 14 ring carbon atoms. Examples of the aryl group include a phenyl group, a naphthyl group, an anthryl group and a phenanthryl group. Among these, a phenyl group and a naphthyl group are preferred.

$R^{10}$ represents an alkyl group having from 1 to 10 carbon atoms, a cycloalkyl group having from 3 to 10 ring carbon atoms or an aryl group having from 6 to 12 ring carbon atoms. Examples of the alkyl group, the cycloalkyl group and the aryl group include the same groups as in $R^3$ and $R^4$, and preferred examples thereof are also the same.

j represents an integer of from 0 to 2, and preferably 0 or 1.

In the case where j is 2, adjacent groups of $R^{10}$ may be bonded to each other to form a hydrocarbon ring.

The production method of the compound represented by the general formula (1) of the present invention is not particularly limited, and the compound may be produced with reference to the examples and any known method.

The compound of the present invention is useful as a material for an organic EL device, particularly a hole transporting material for an organic EL device, as described later. Furthermore, the compound is useful as a material for a hole transporting layer that is adjacent to (coupled to) an acceptor layer of an organic EL device.

Specific examples of the compound of the present invention are shown below, but the compound is not limited to these example compounds.

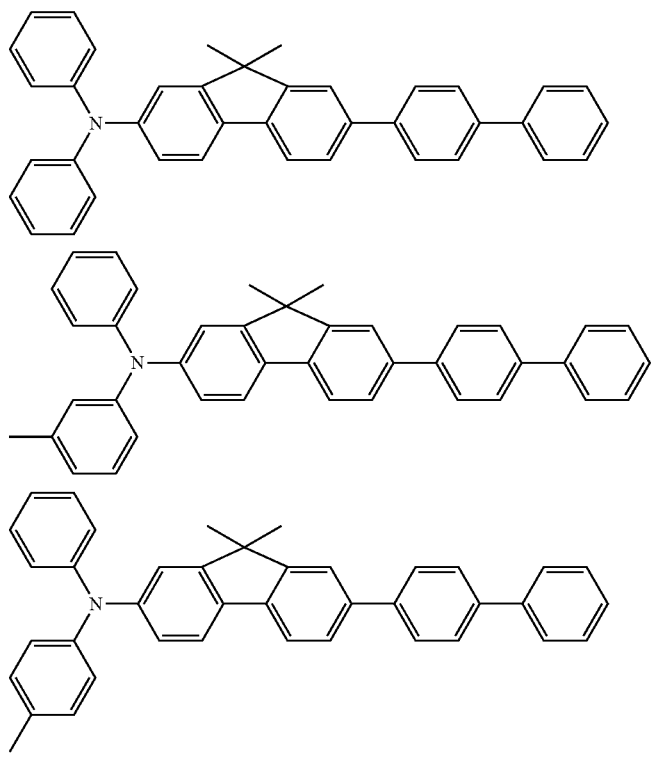

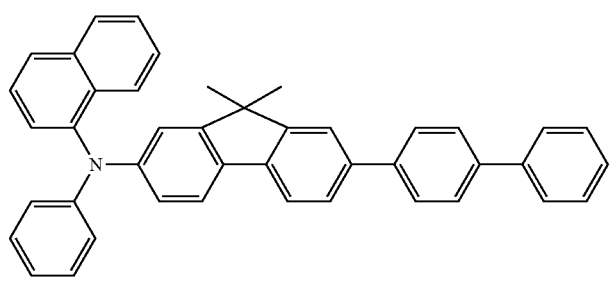

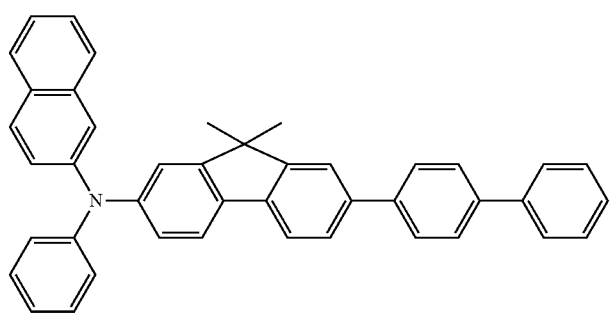

-continued
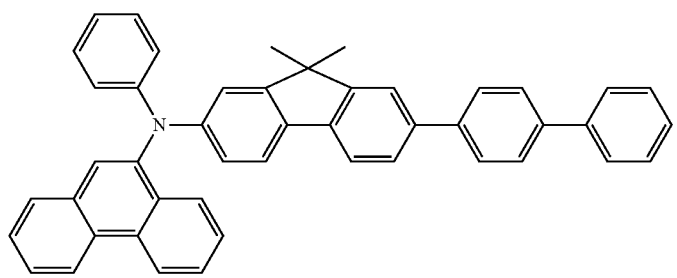
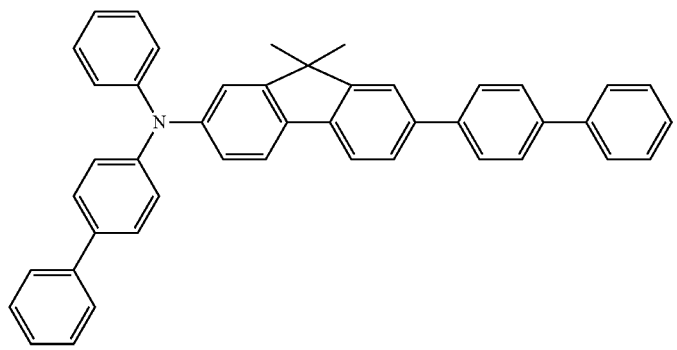
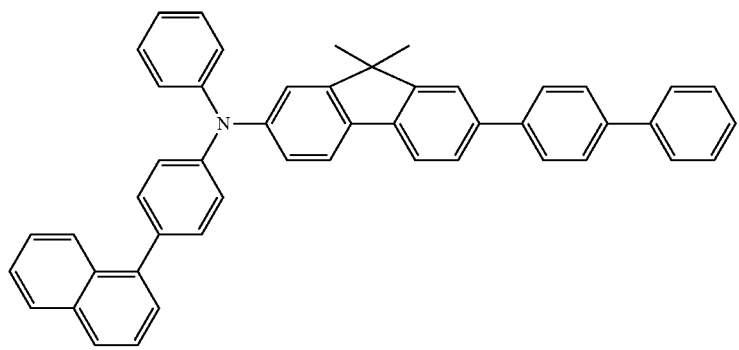
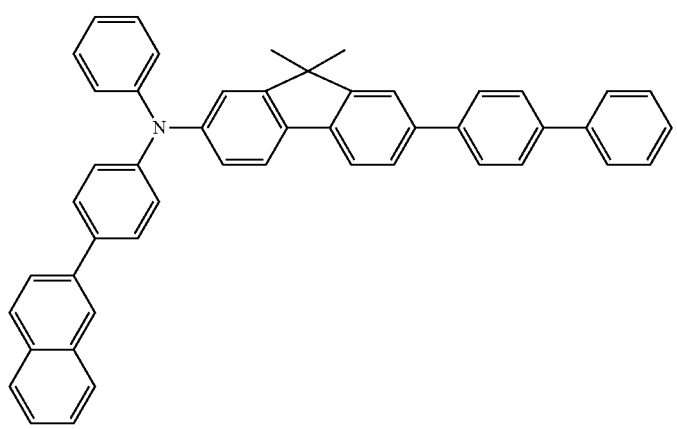

-continued
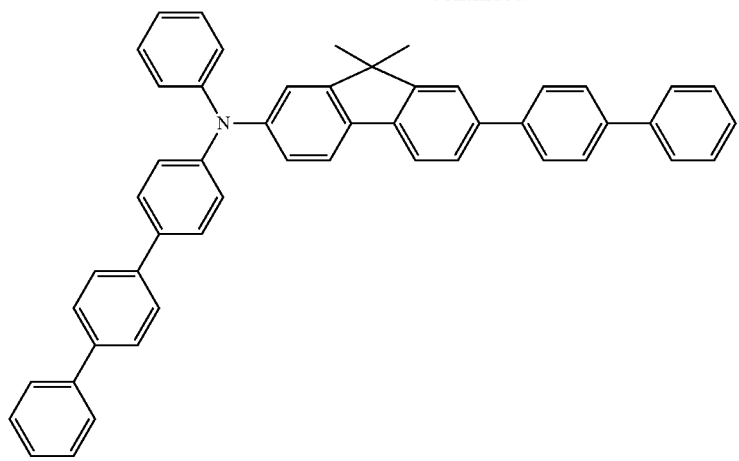
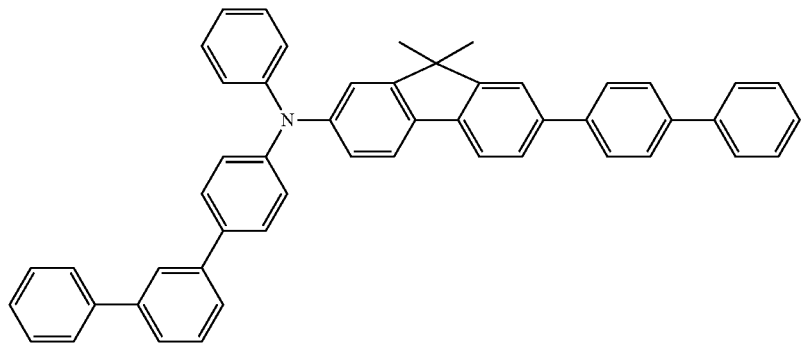
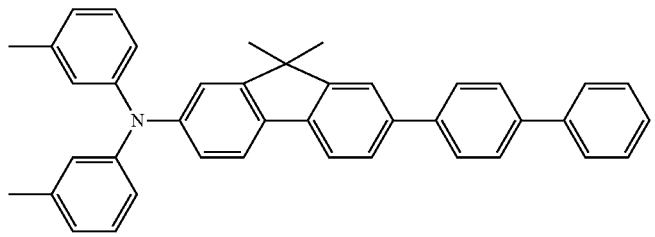
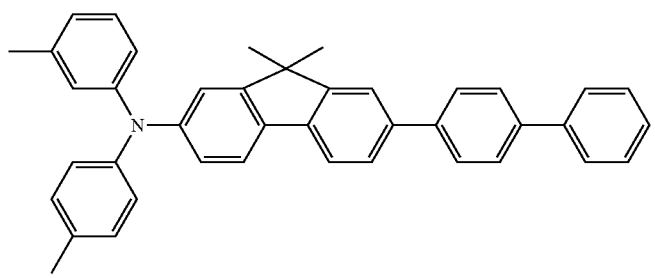
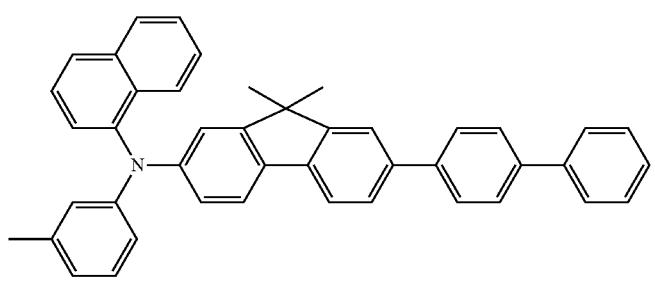

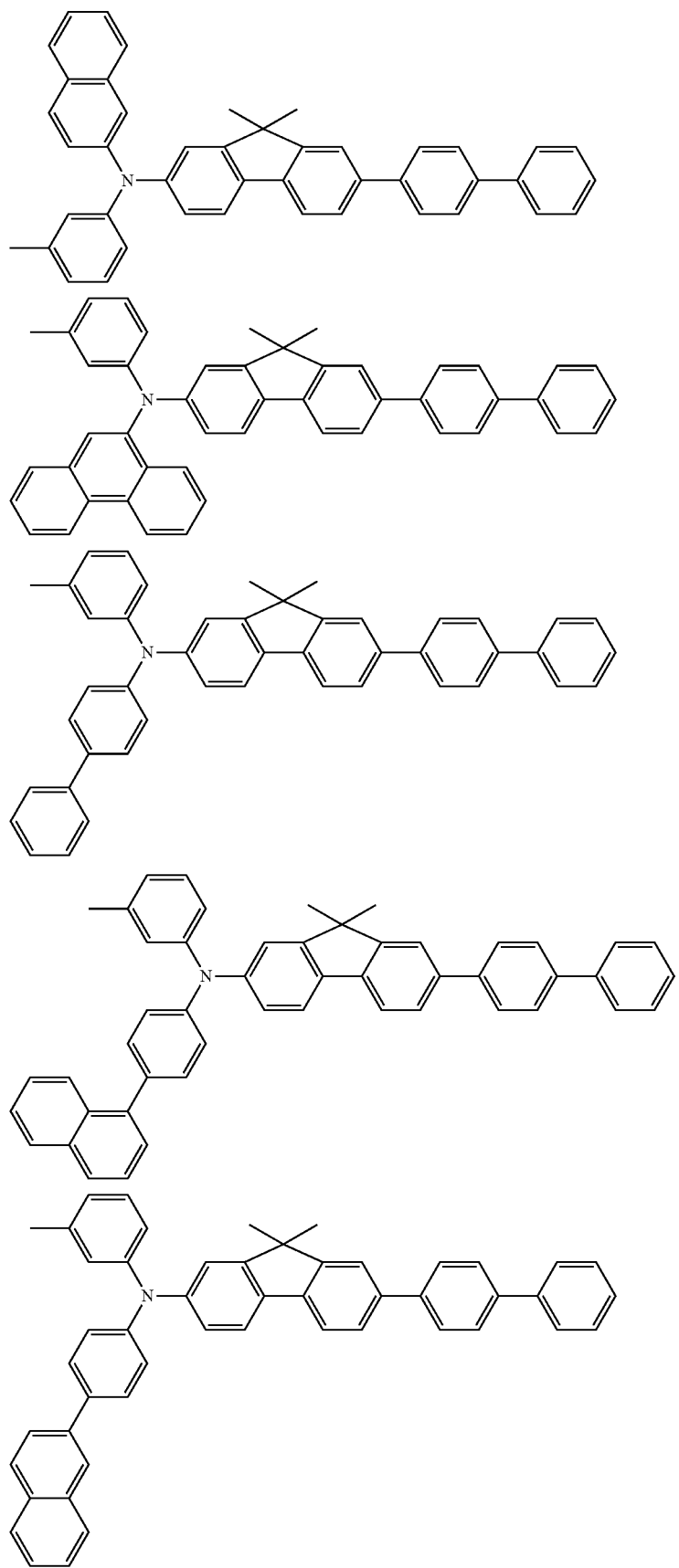

-continued
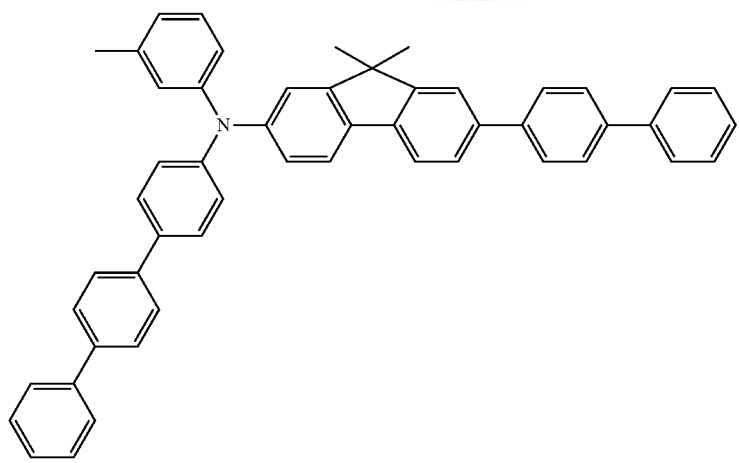
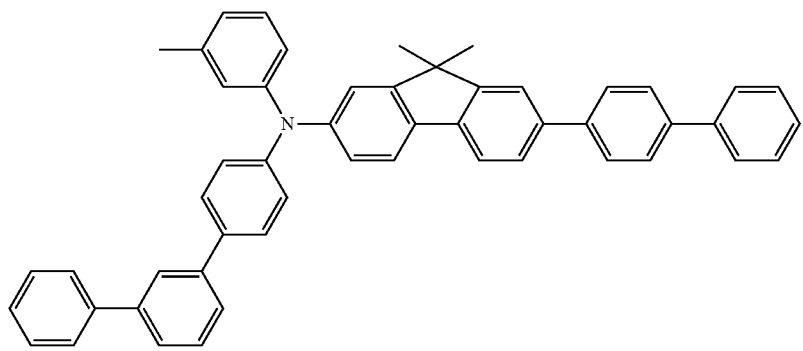
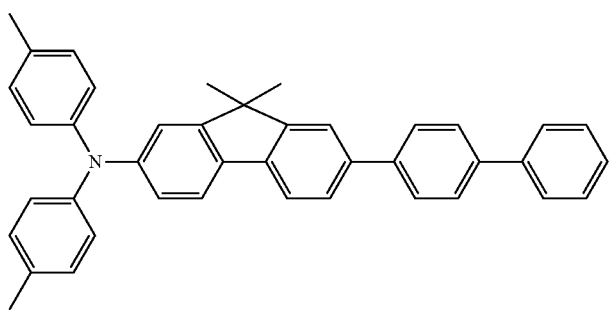
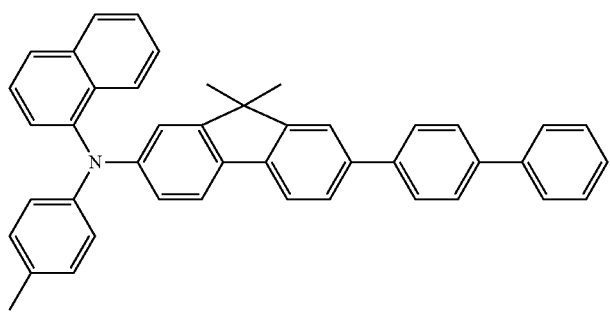

-continued
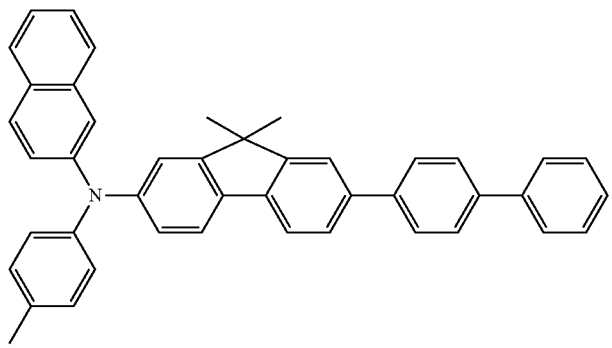
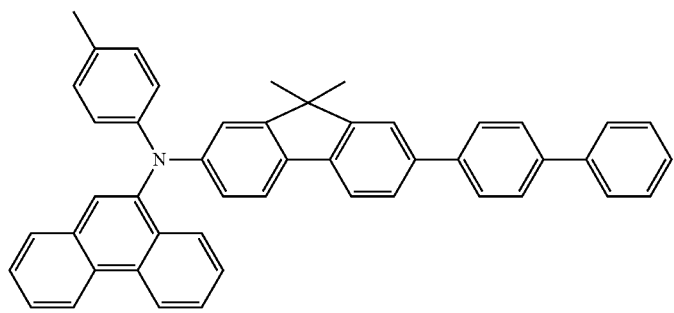
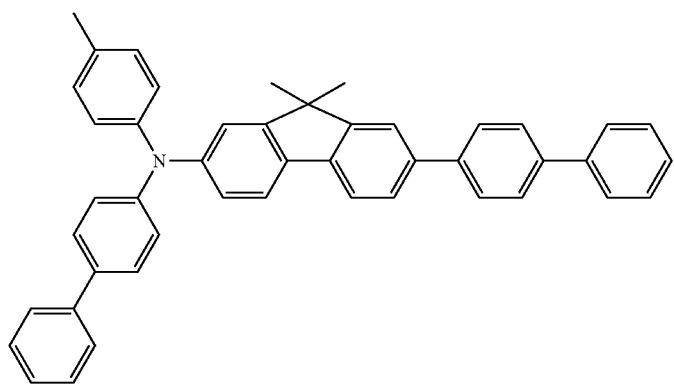
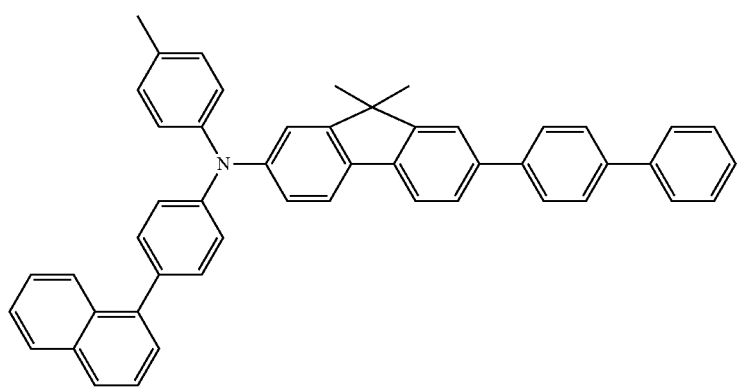

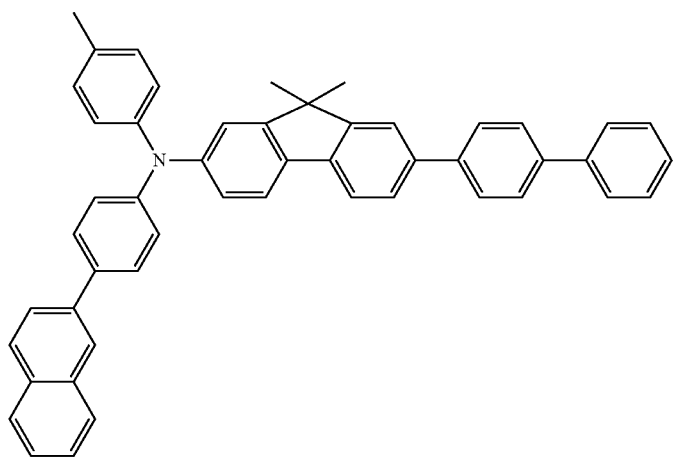

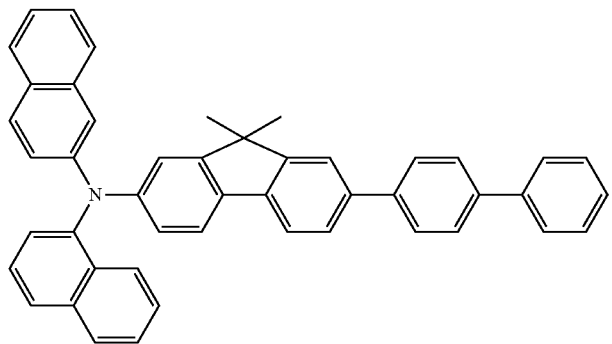
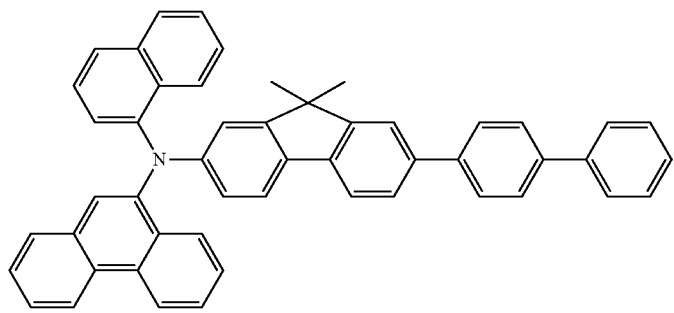
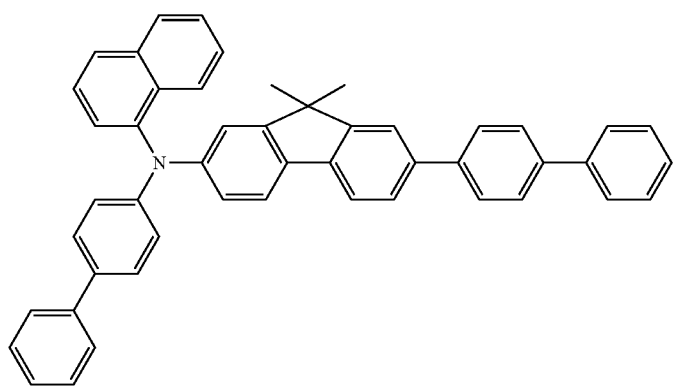
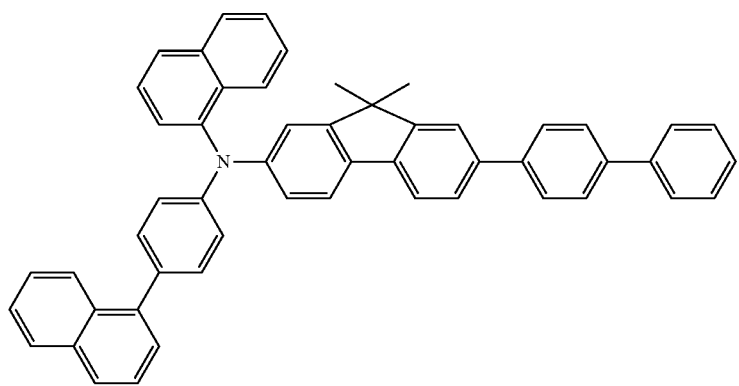

-continued
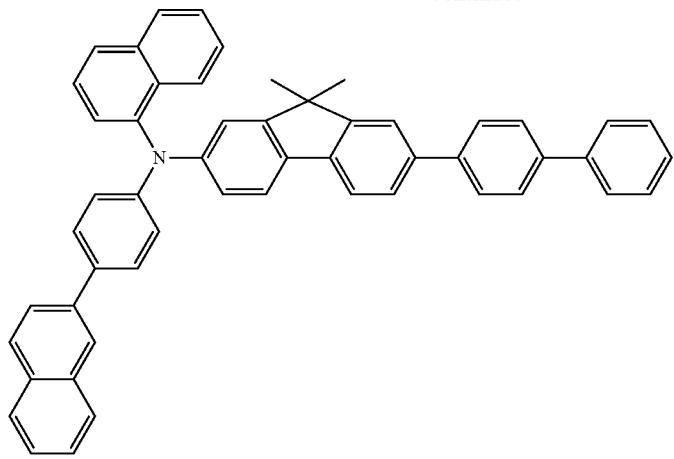
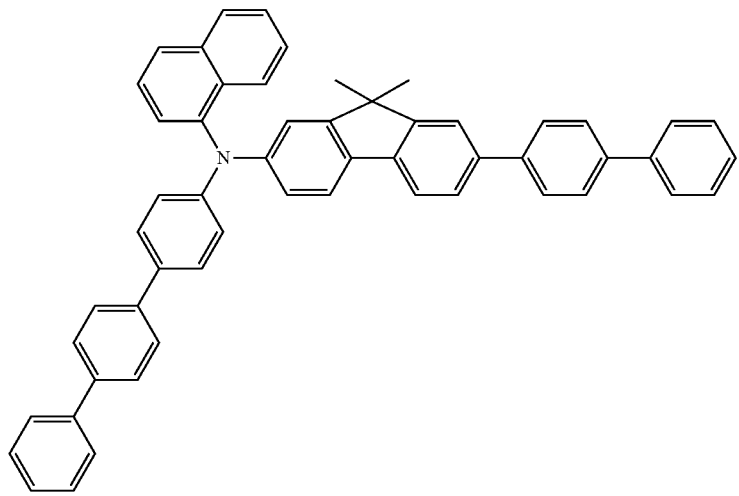
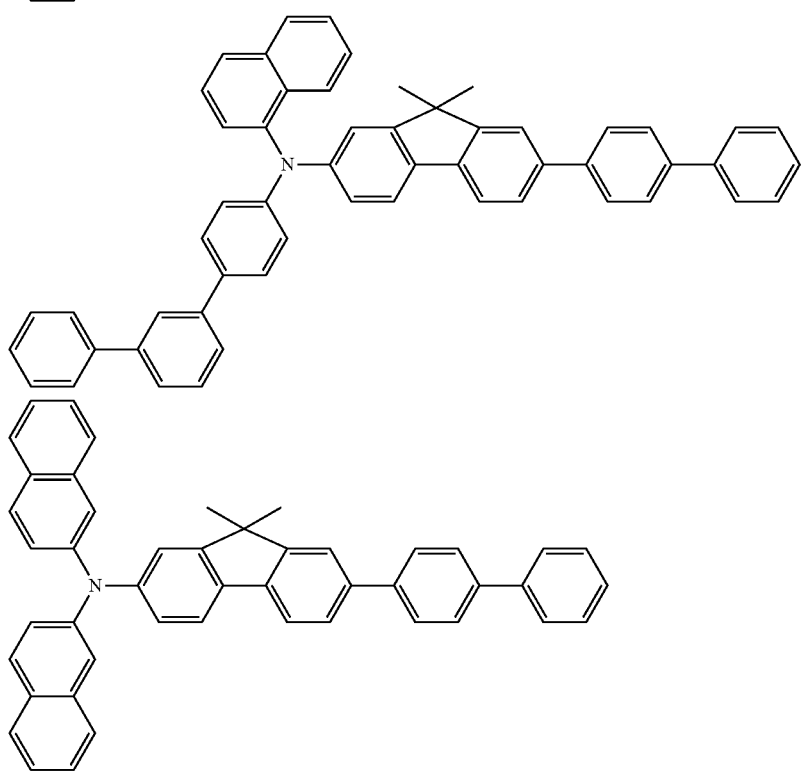

-continued
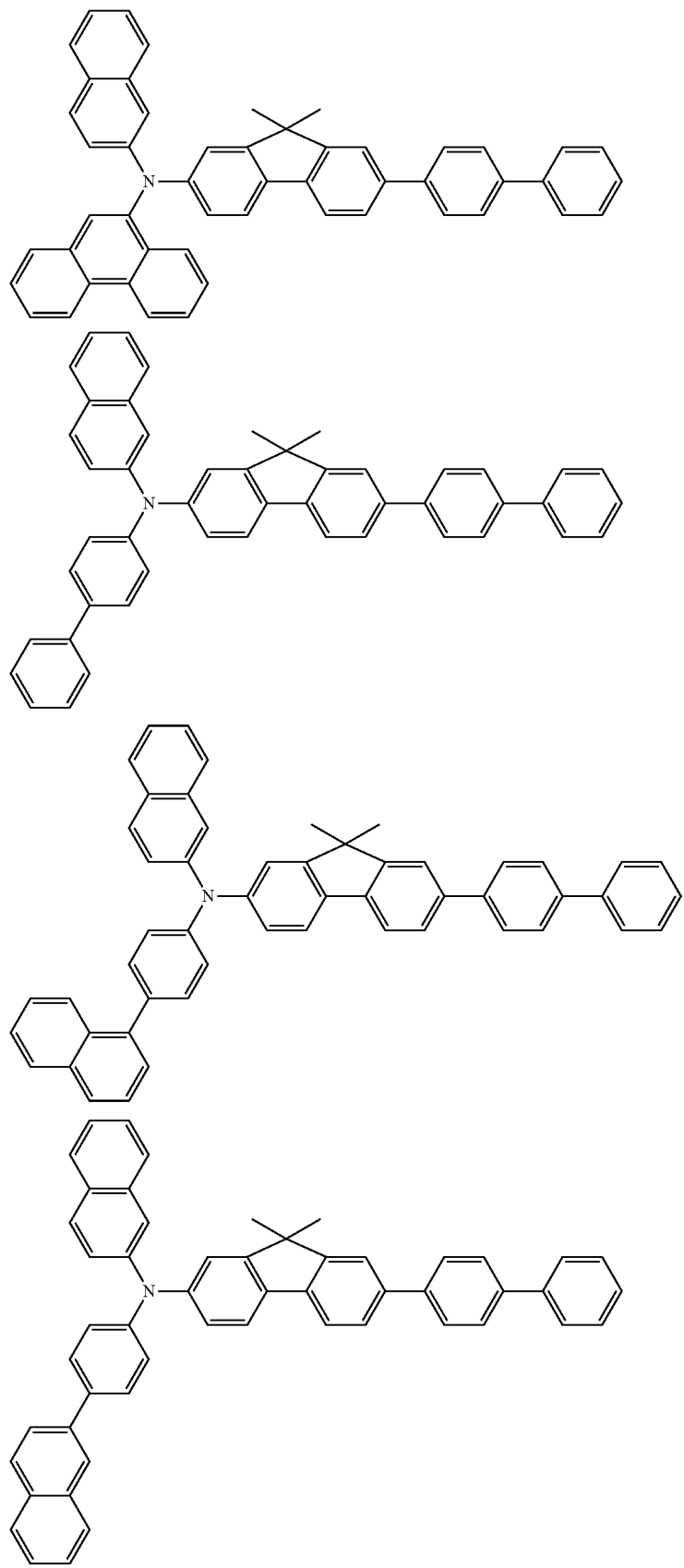

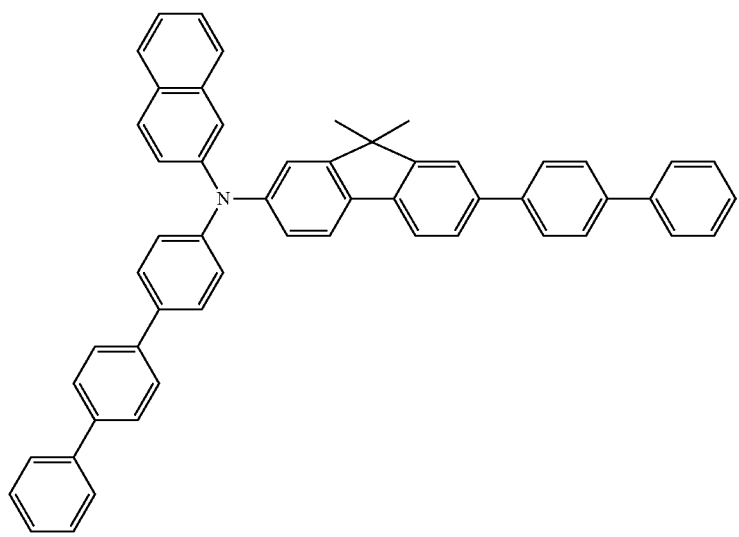
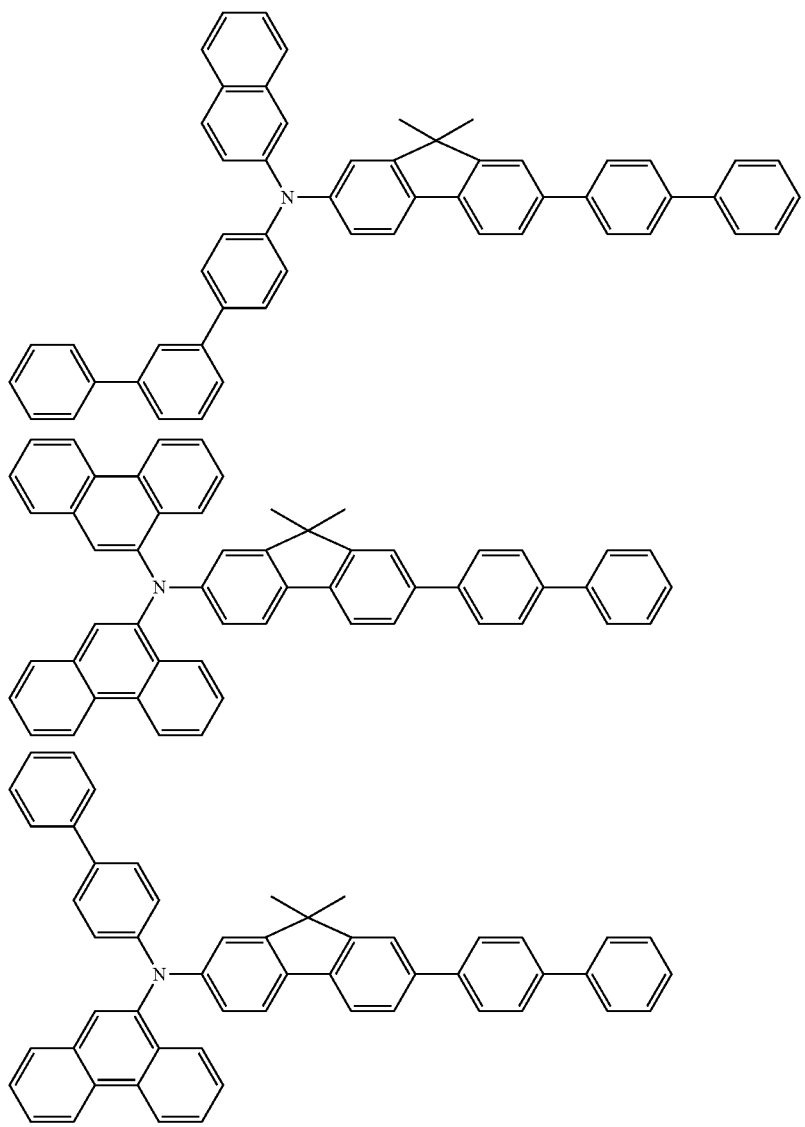

-continued
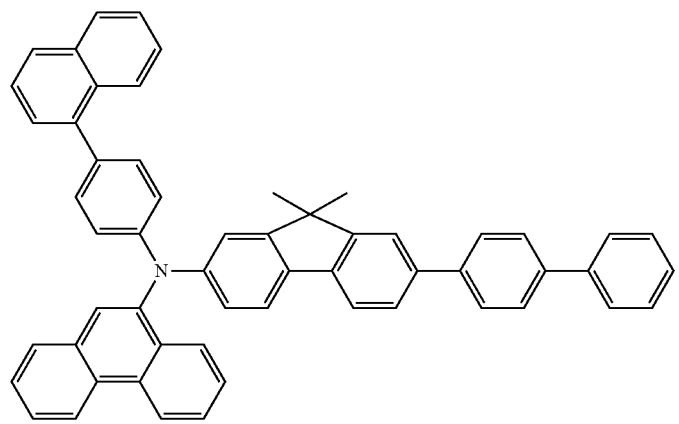
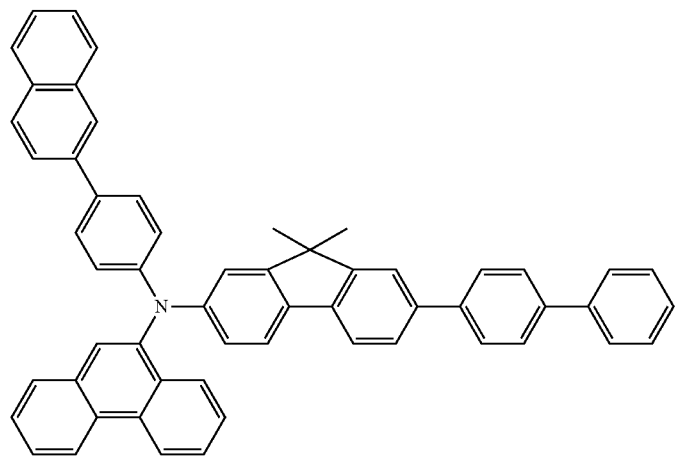
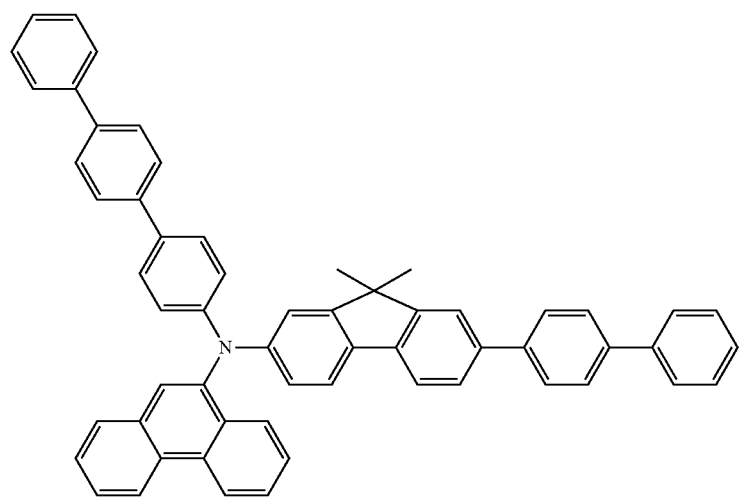

-continued
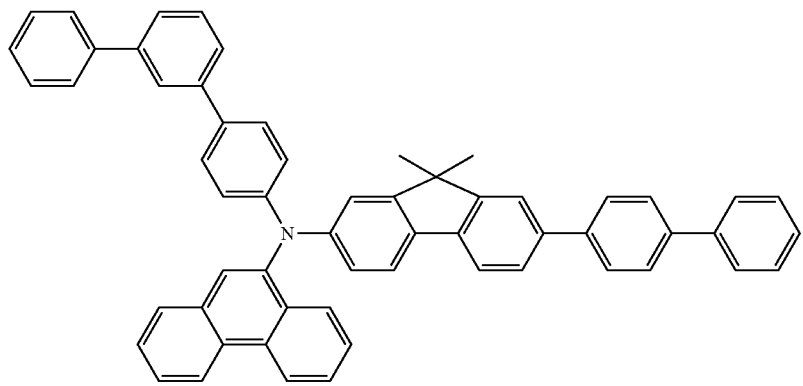
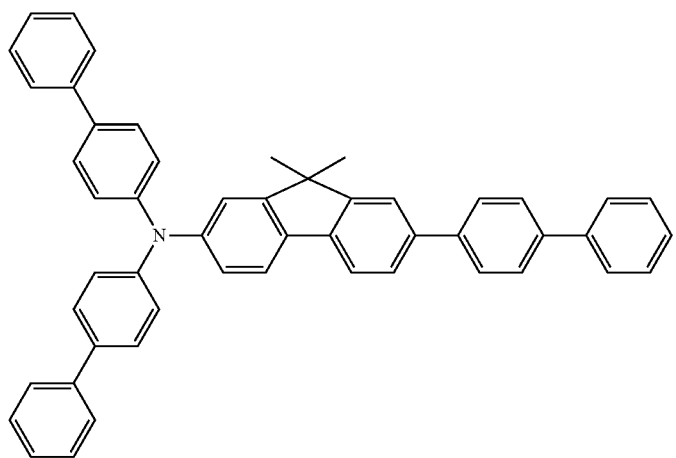
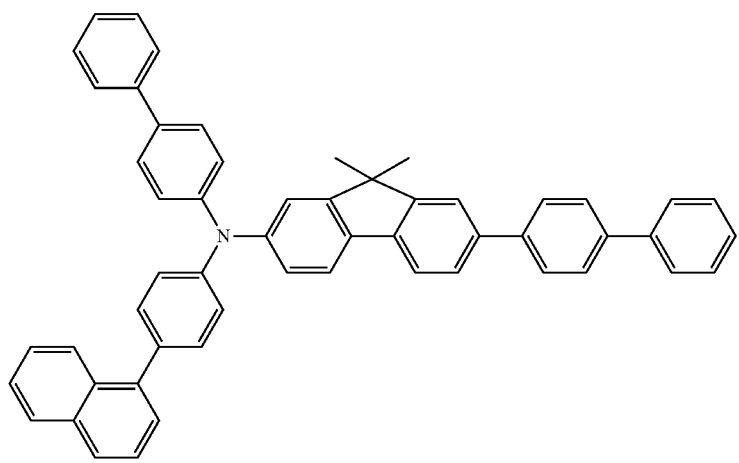

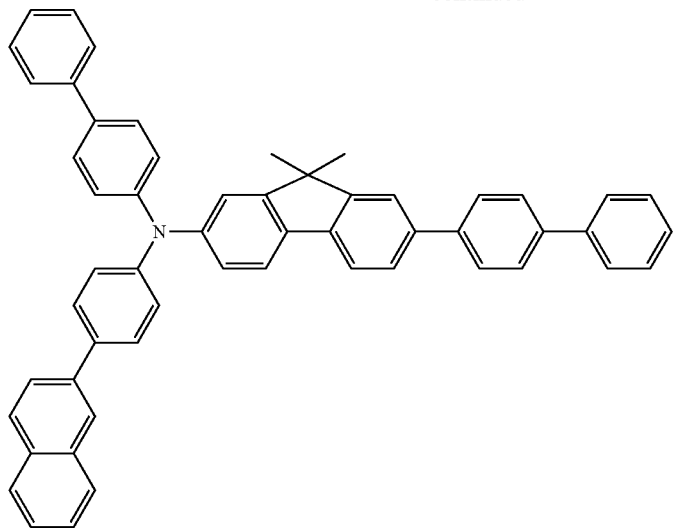
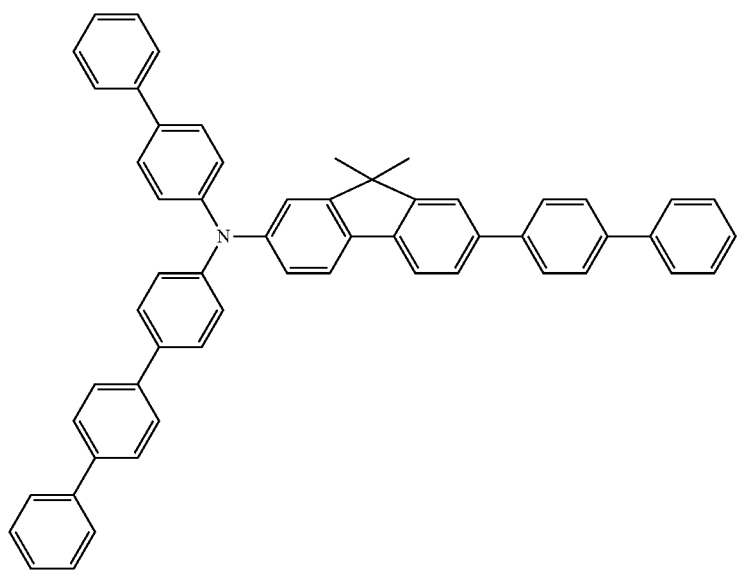
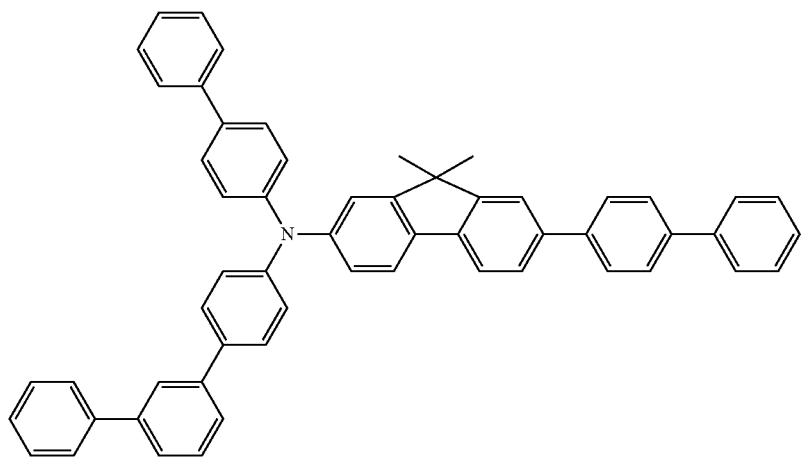

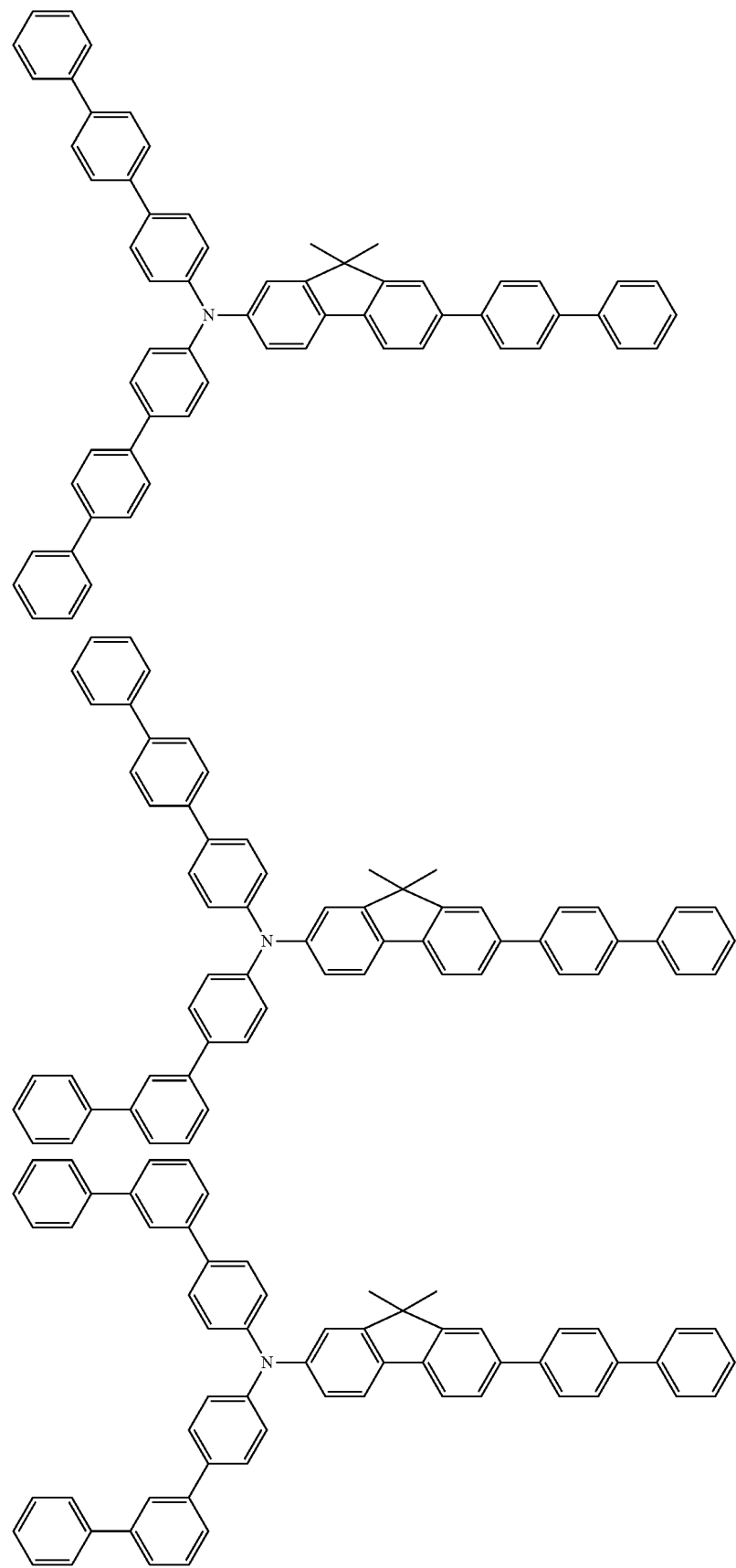

-continued
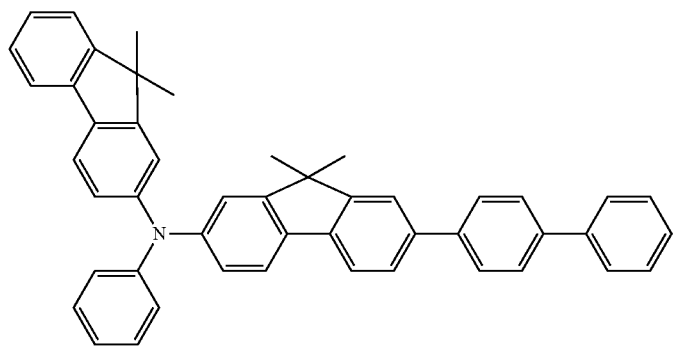
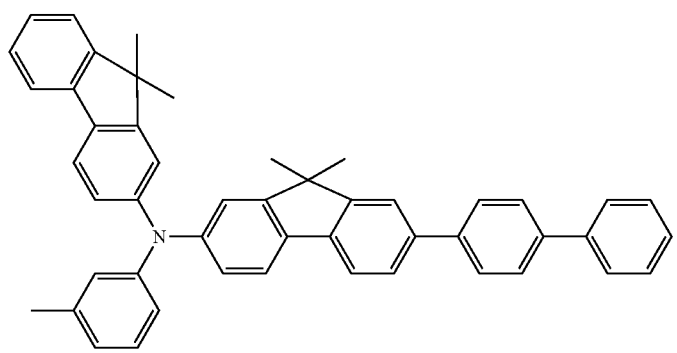
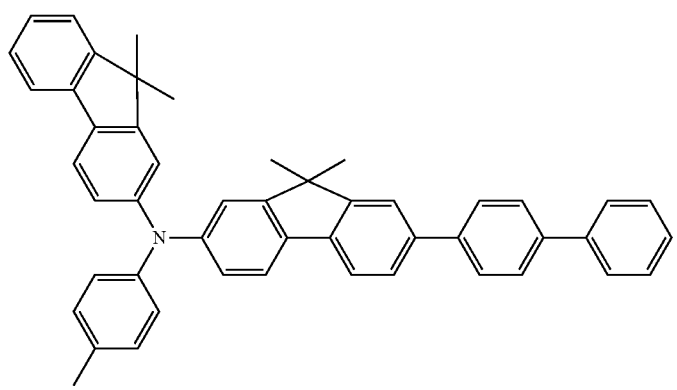
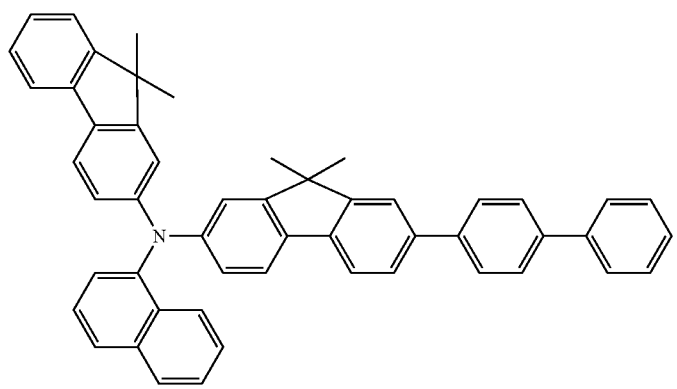

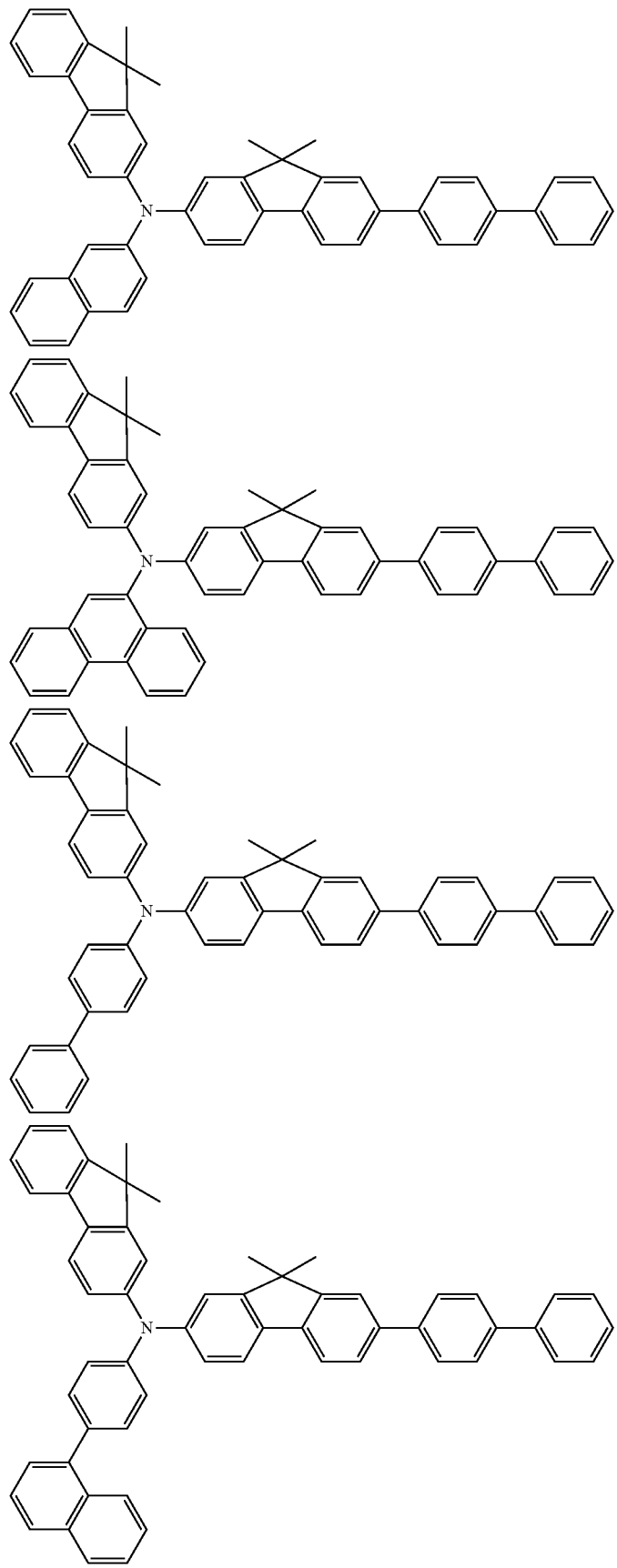

-continued
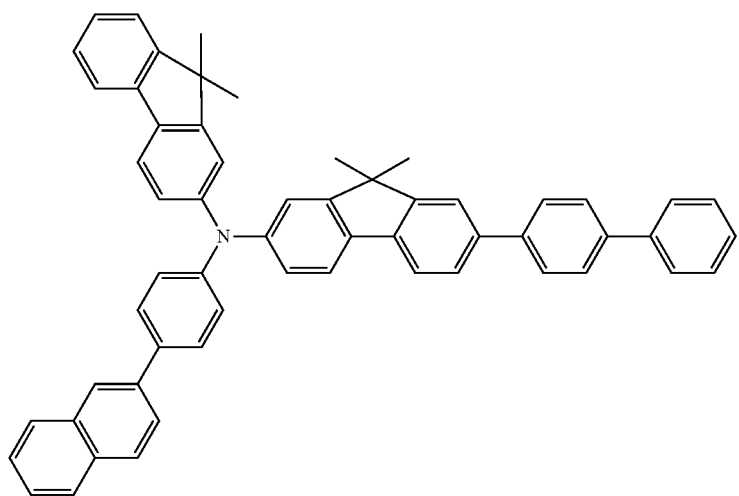
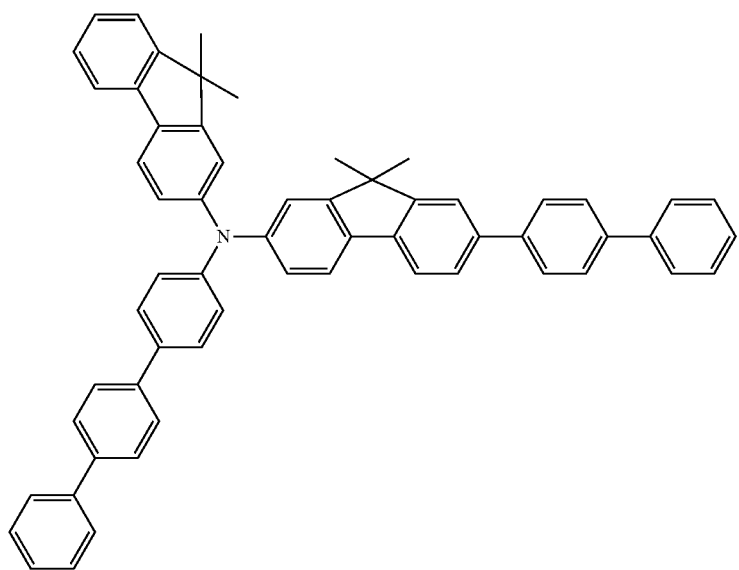
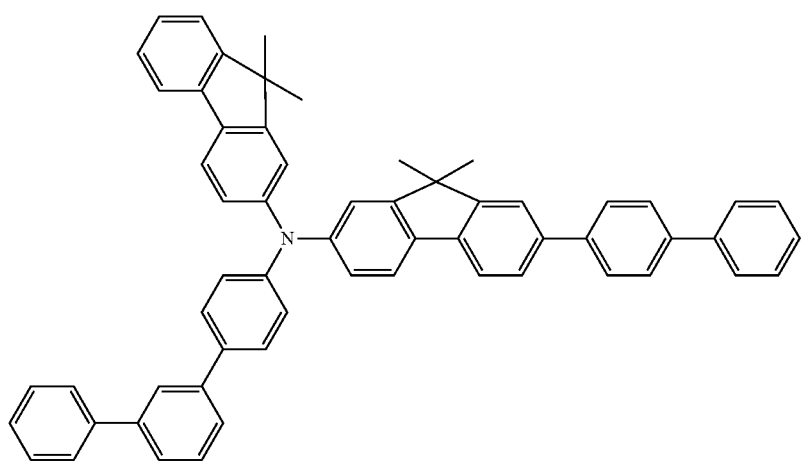

-continued
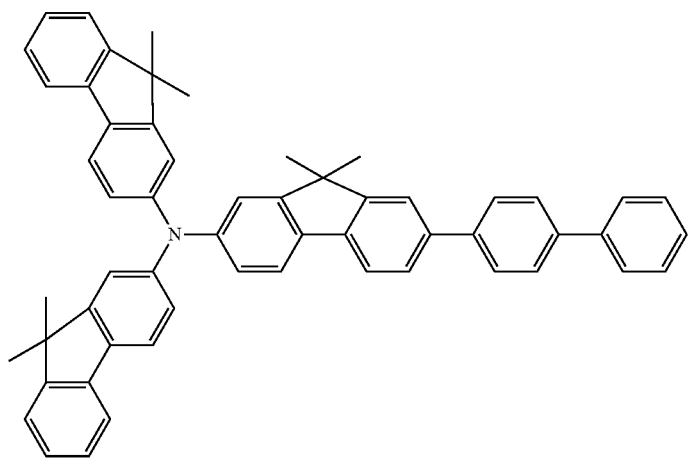 [SMILES: CC1(C)c2ccccc2-c2ccc(N(c3ccc4c(c3)C(C)(C)c3ccccc3-4)c3ccc4c(c3)C(C)(C)c3cc(-c5ccc(-c6ccccc6)cc5)ccc3-4)cc21]
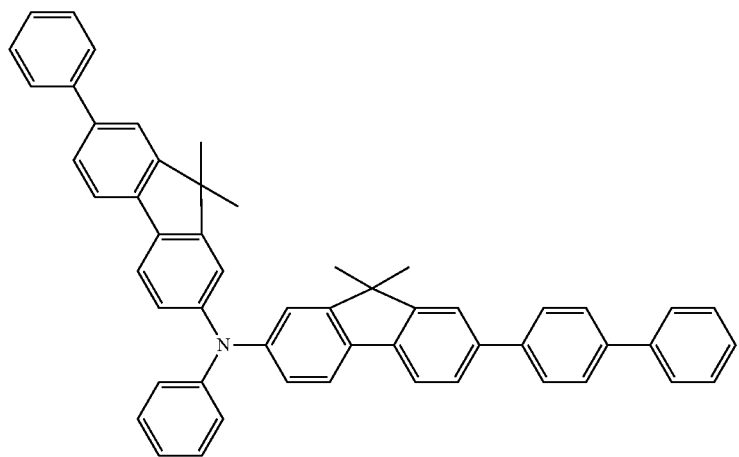
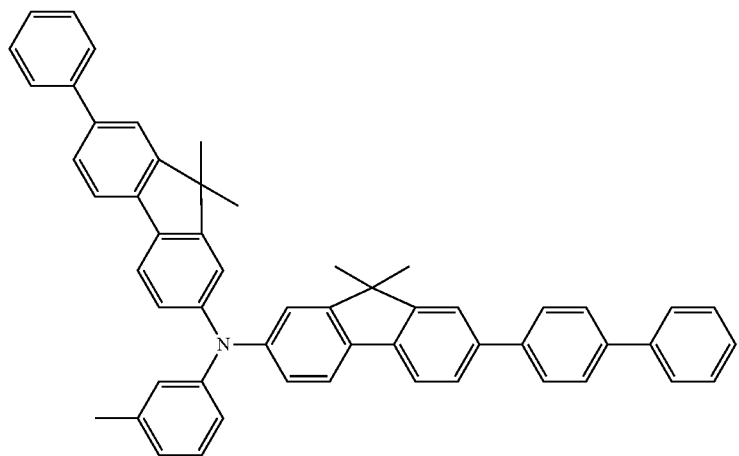

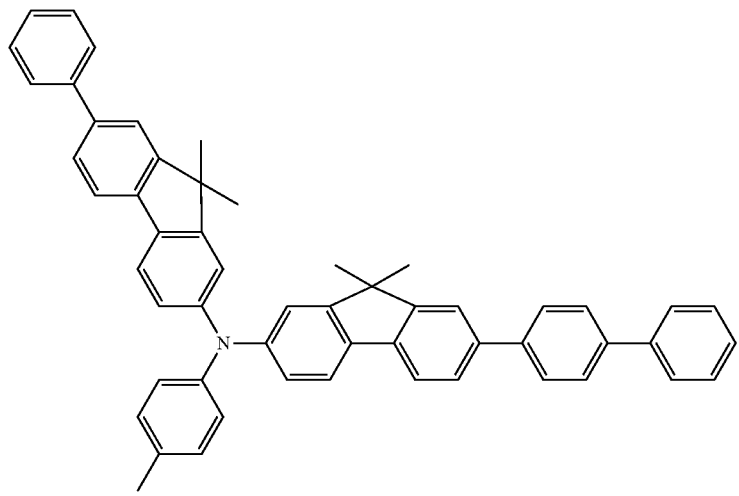
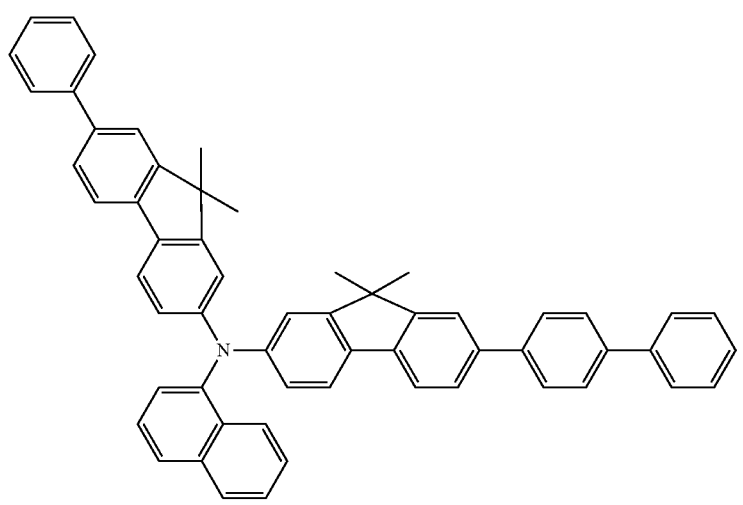
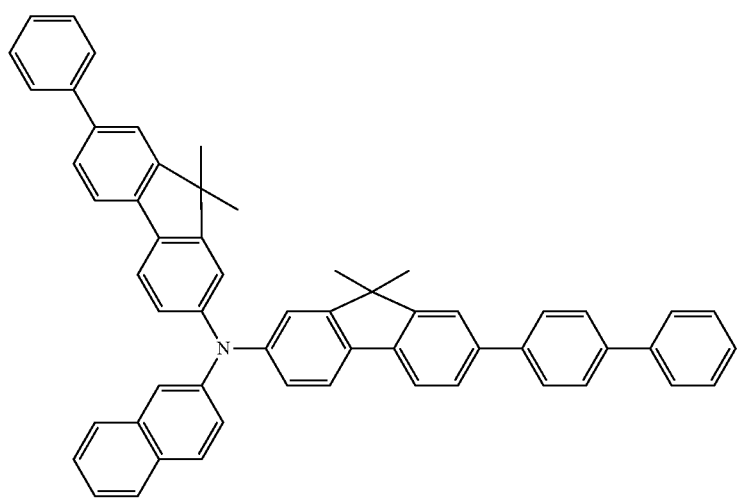

-continued
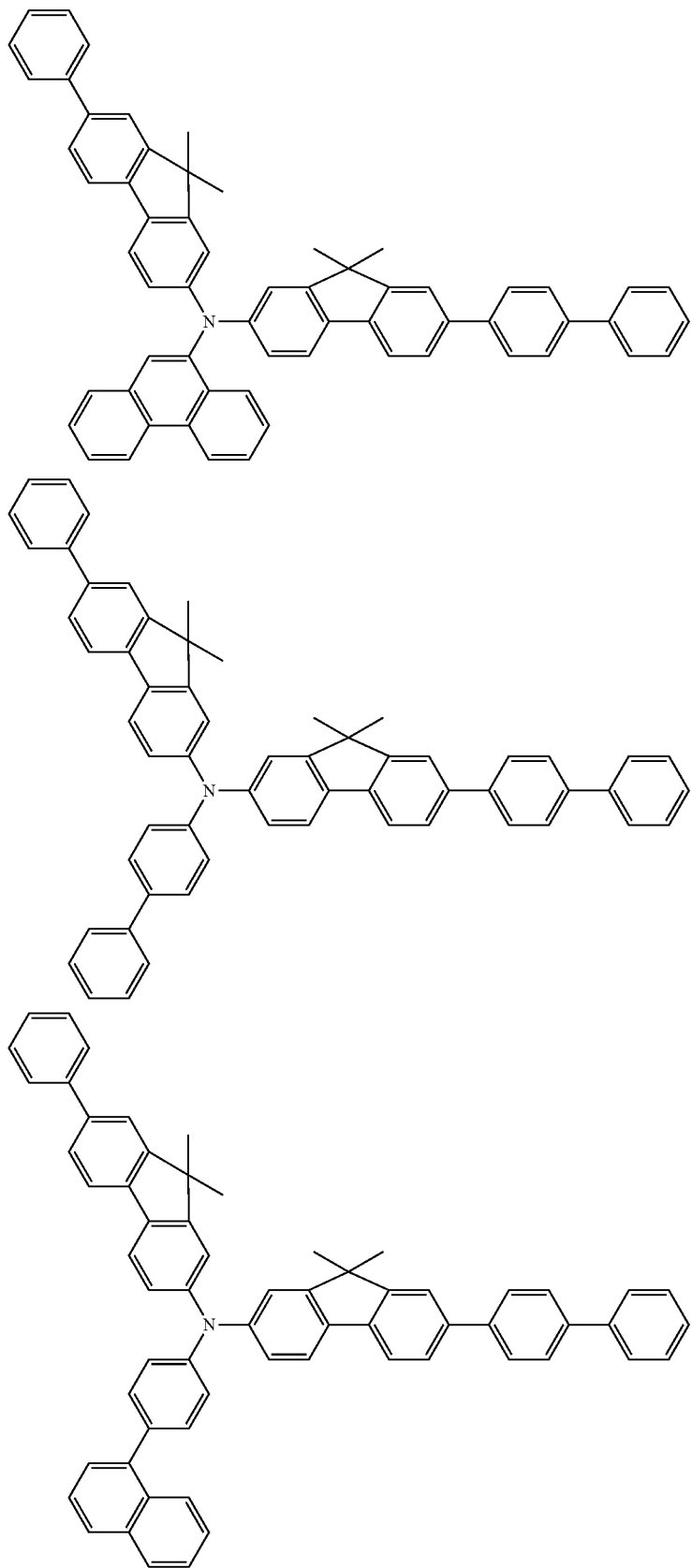

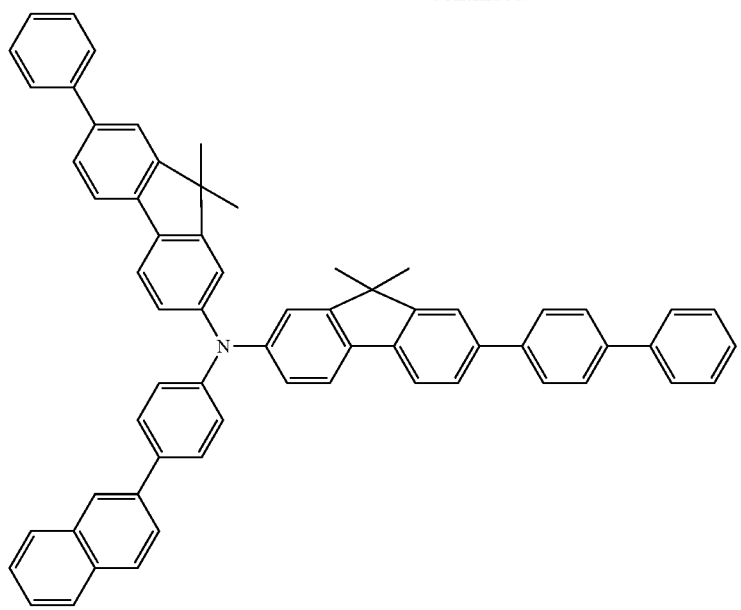
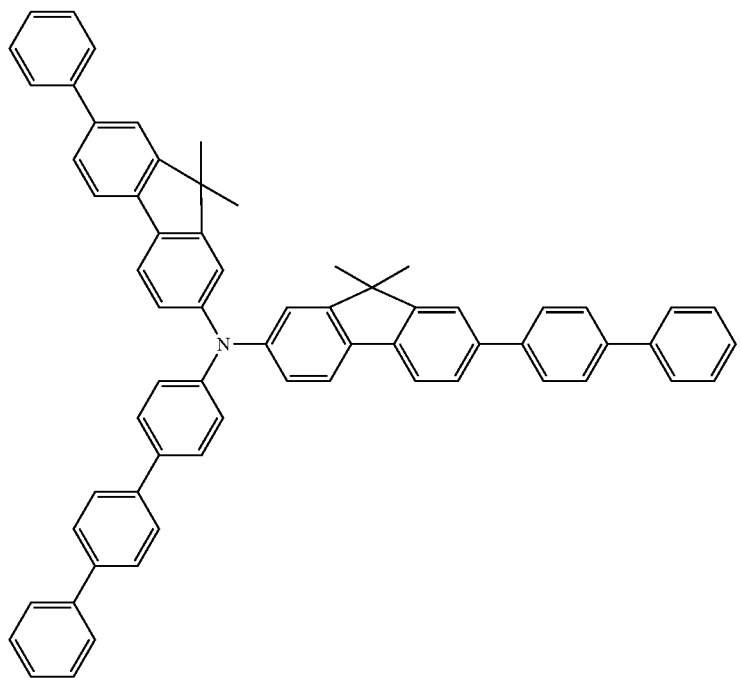

-continued
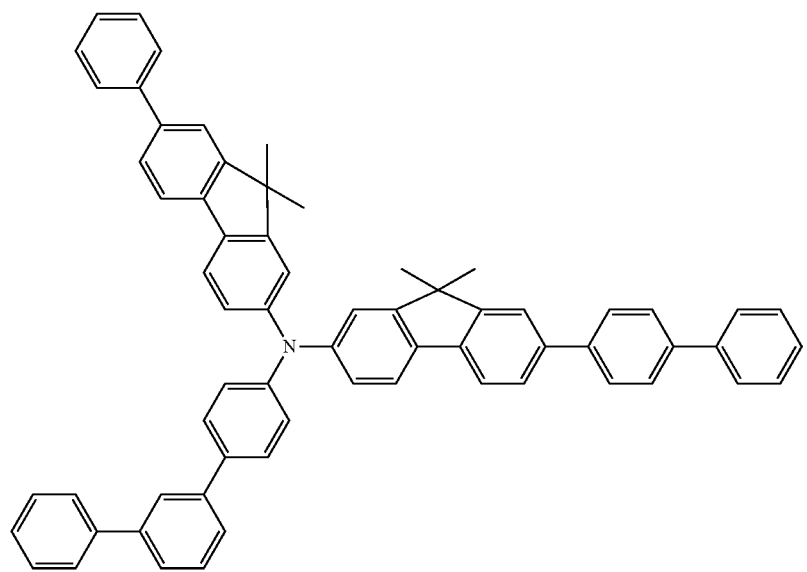
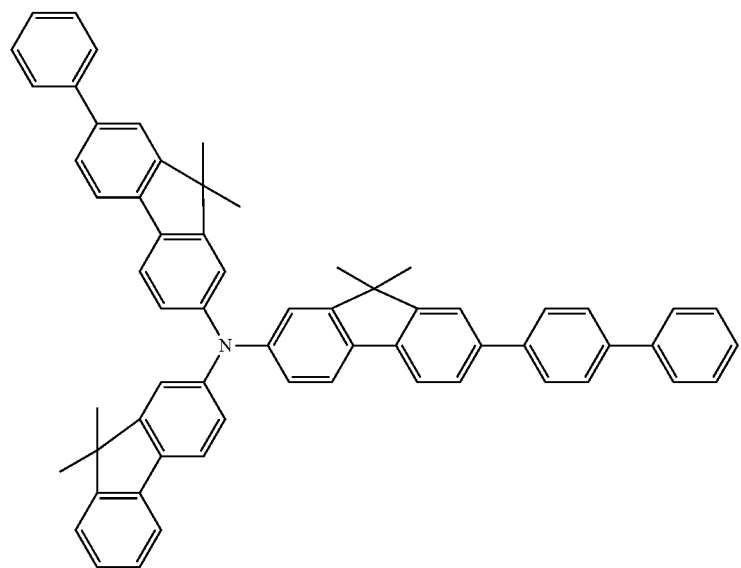

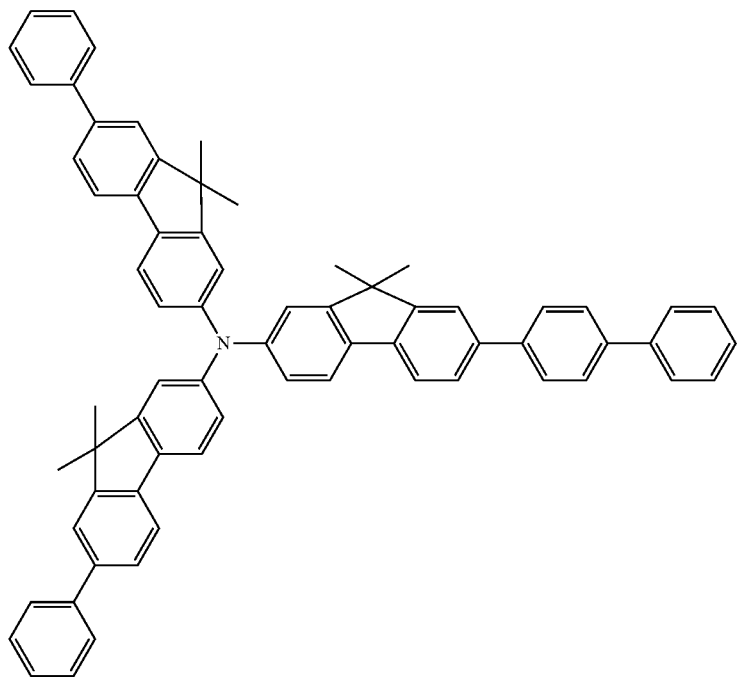
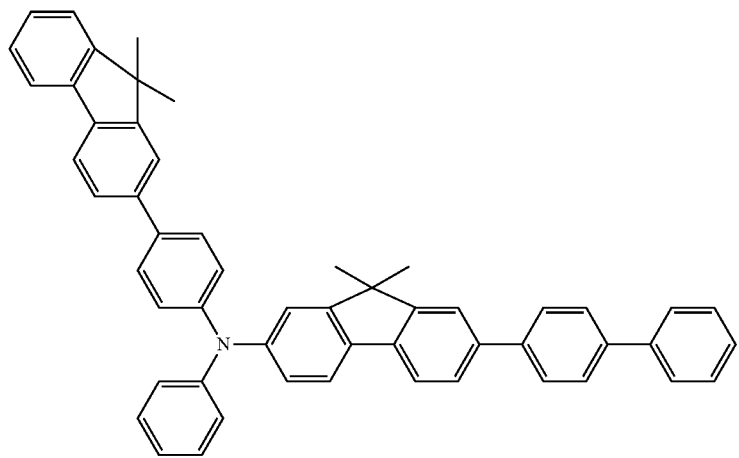
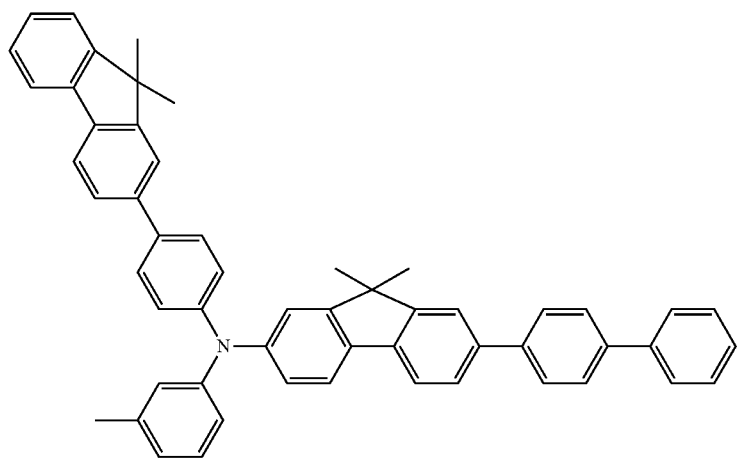

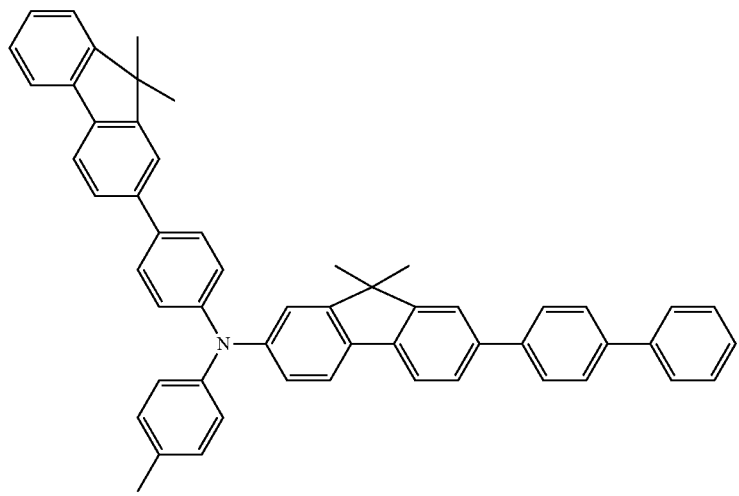
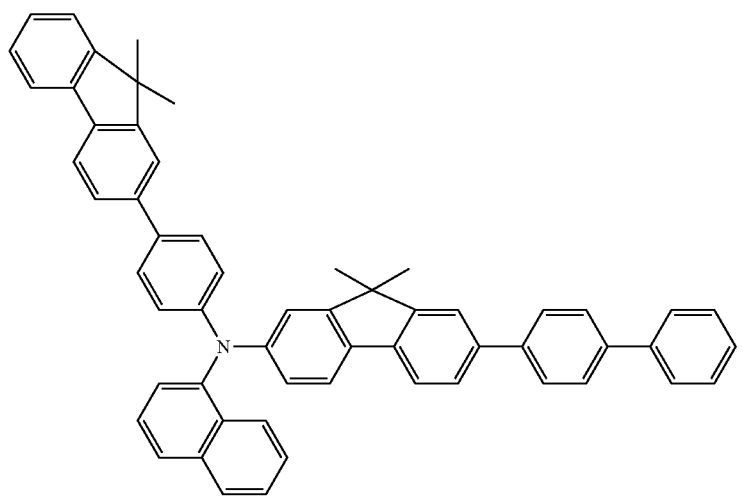
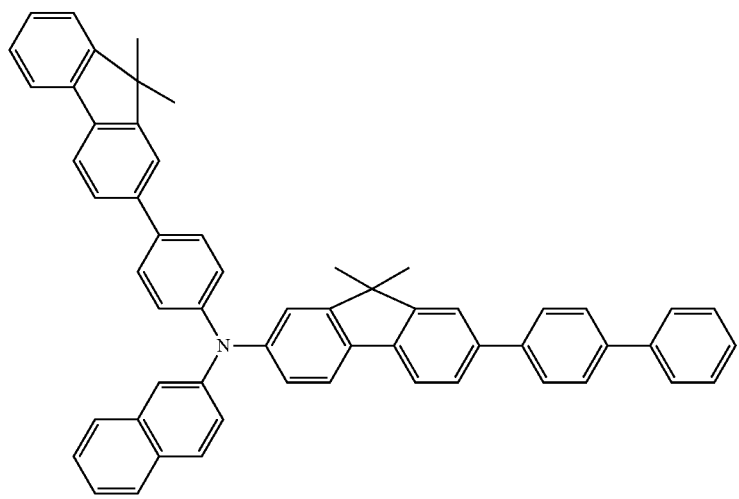

-continued
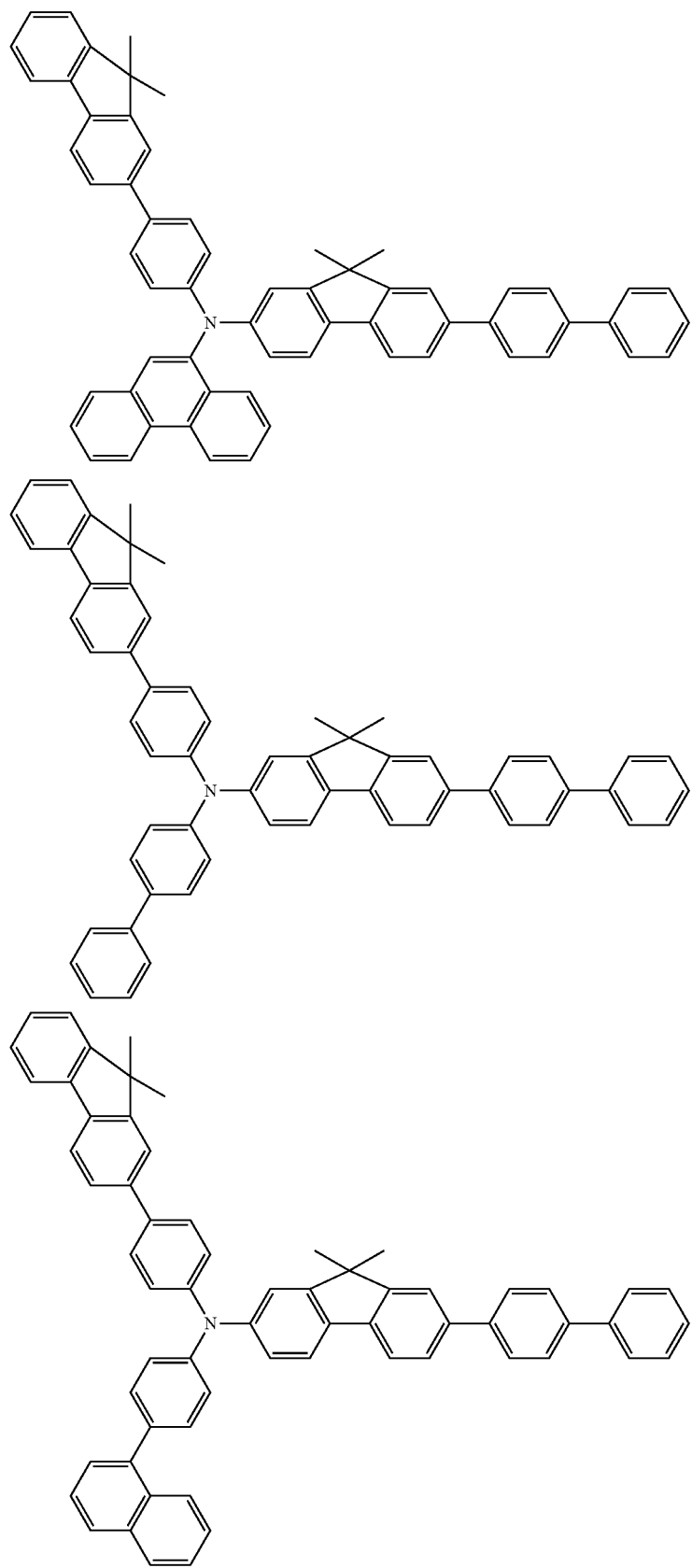

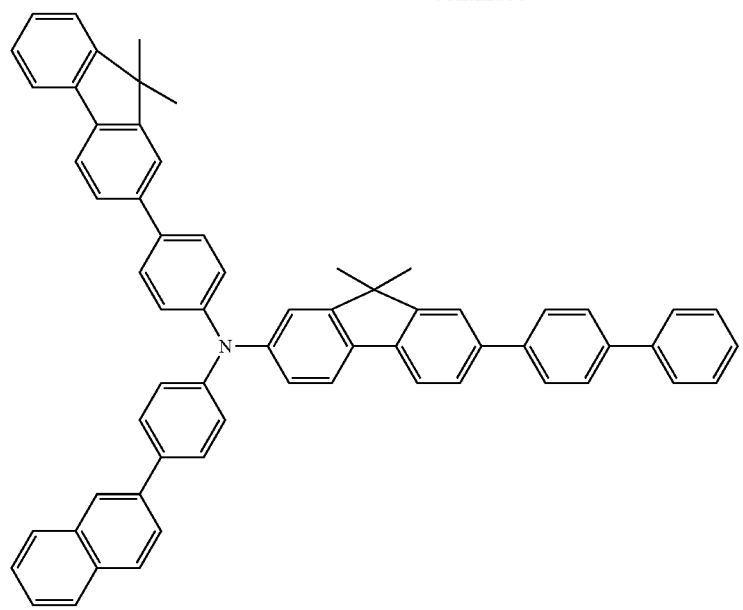
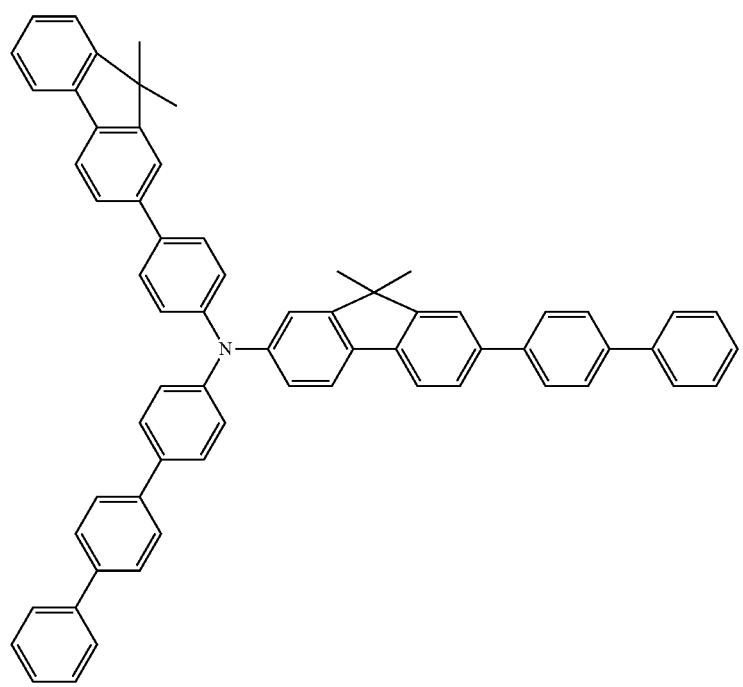

-continued
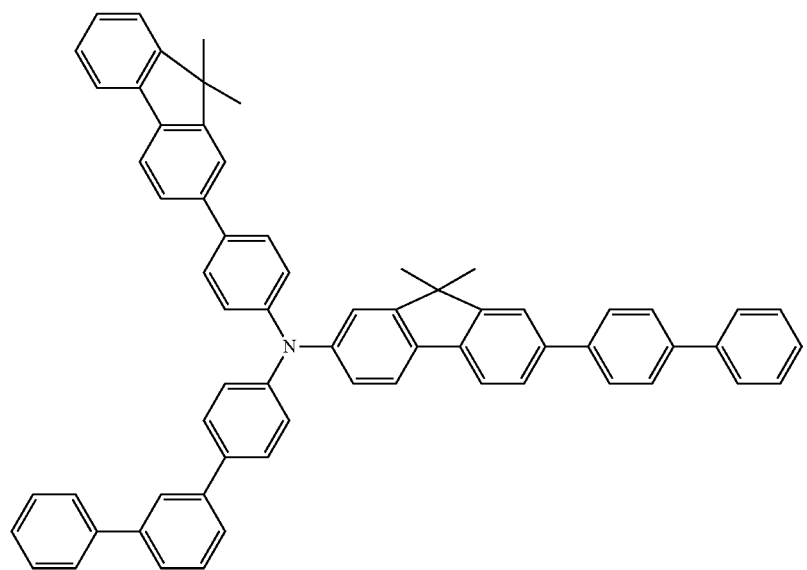
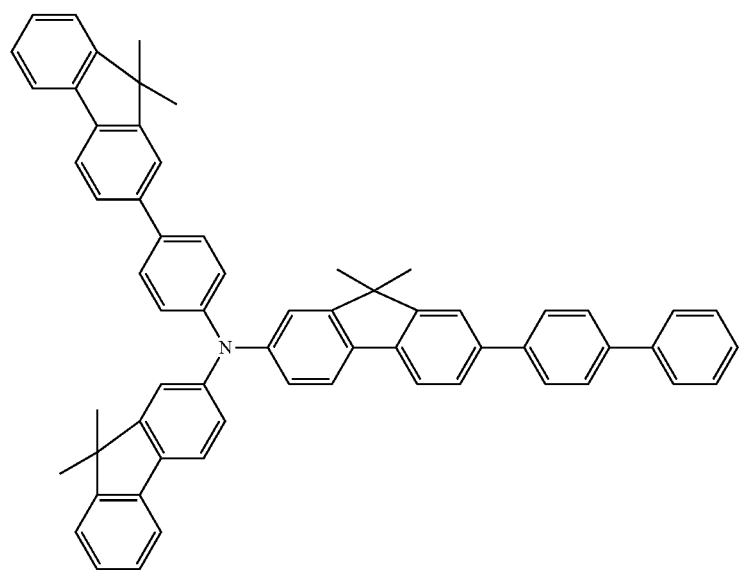

-continued
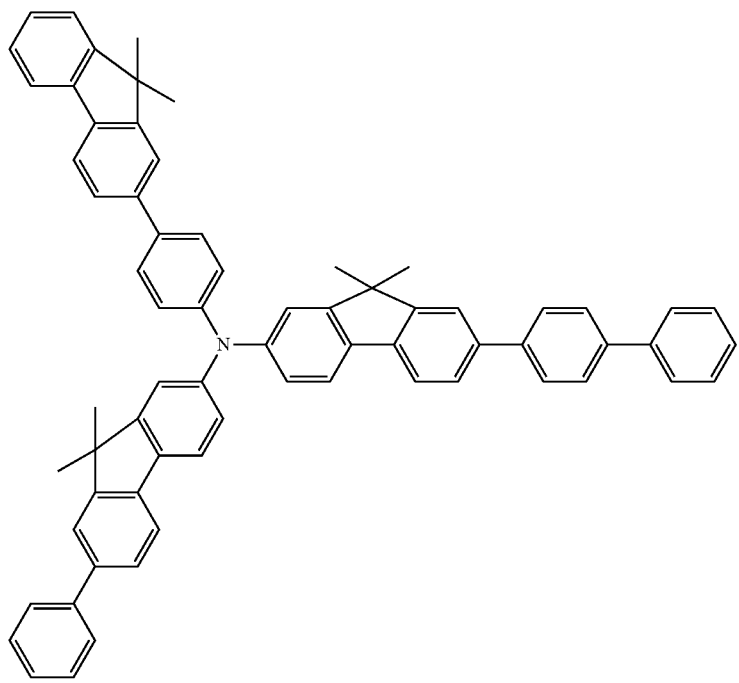
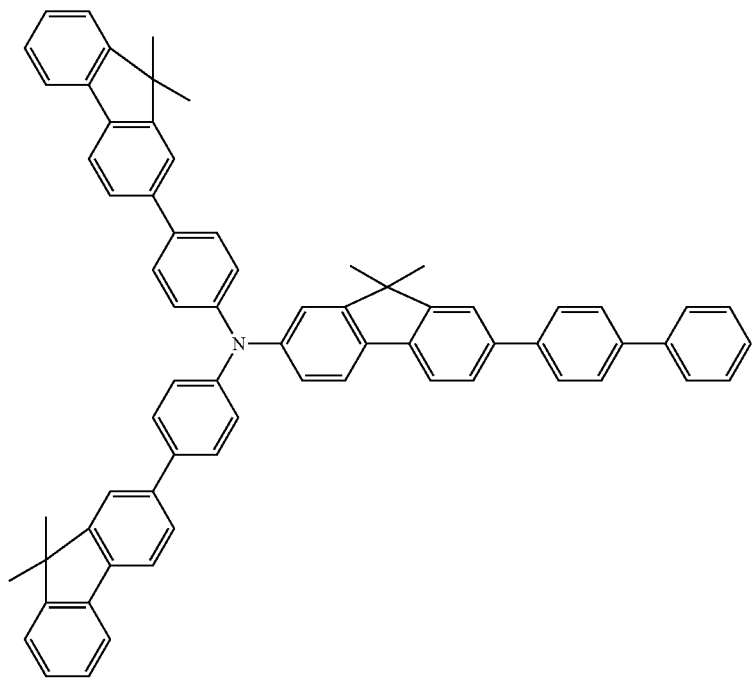

-continued
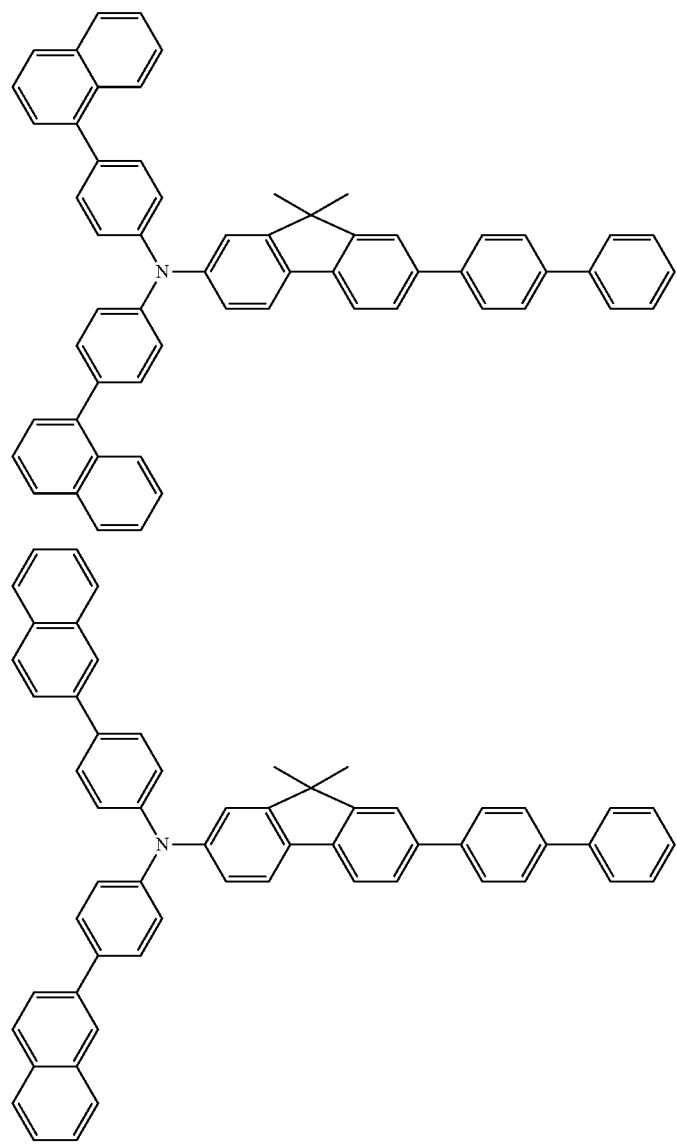
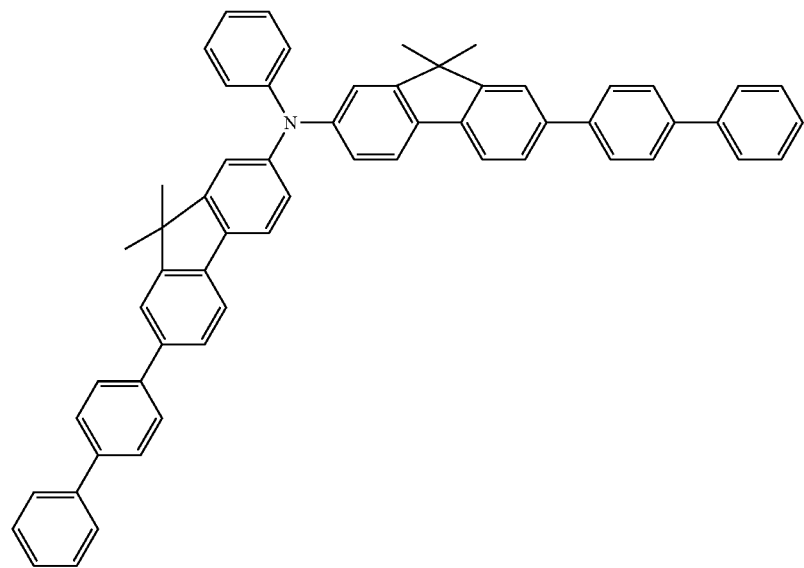

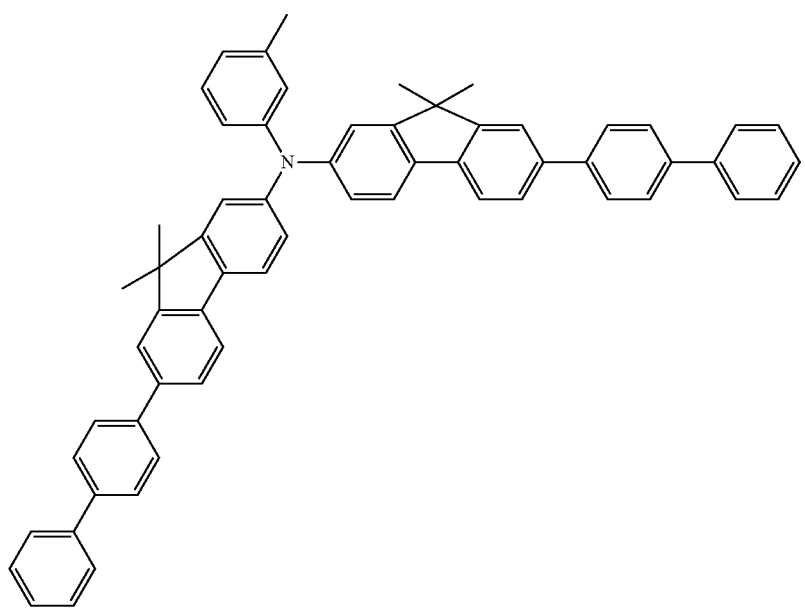
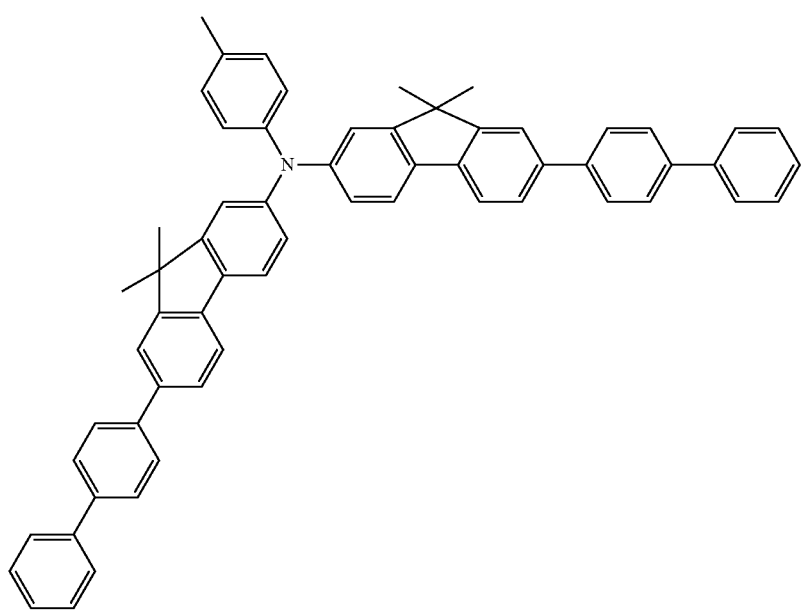

-continued
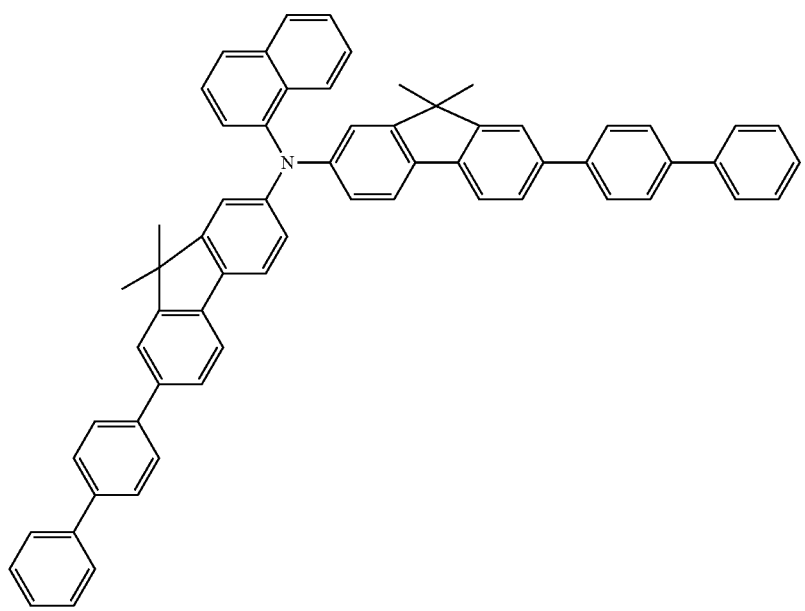
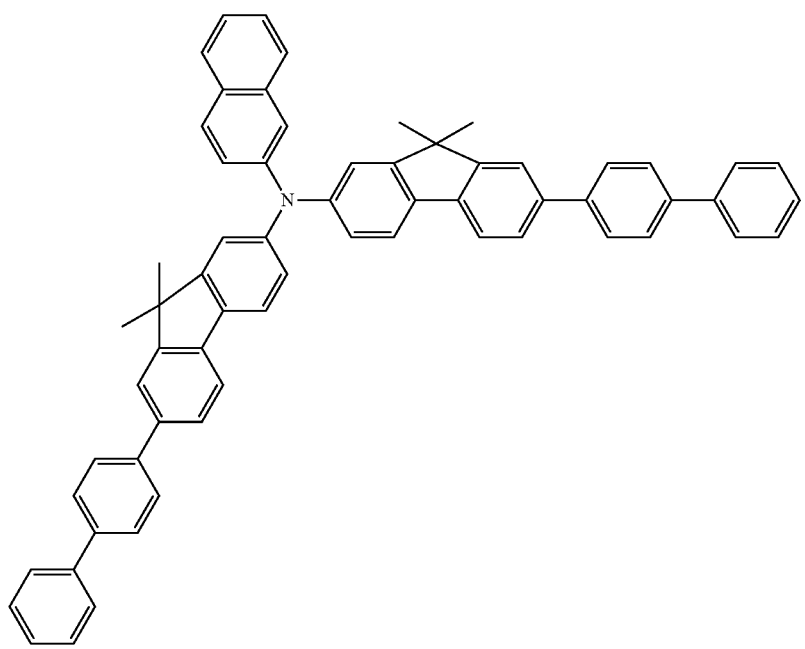

-continued
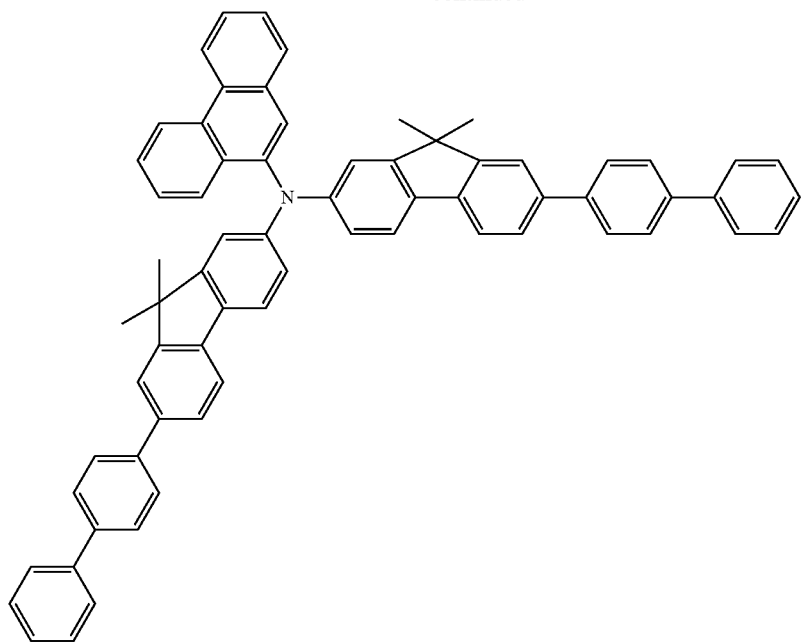
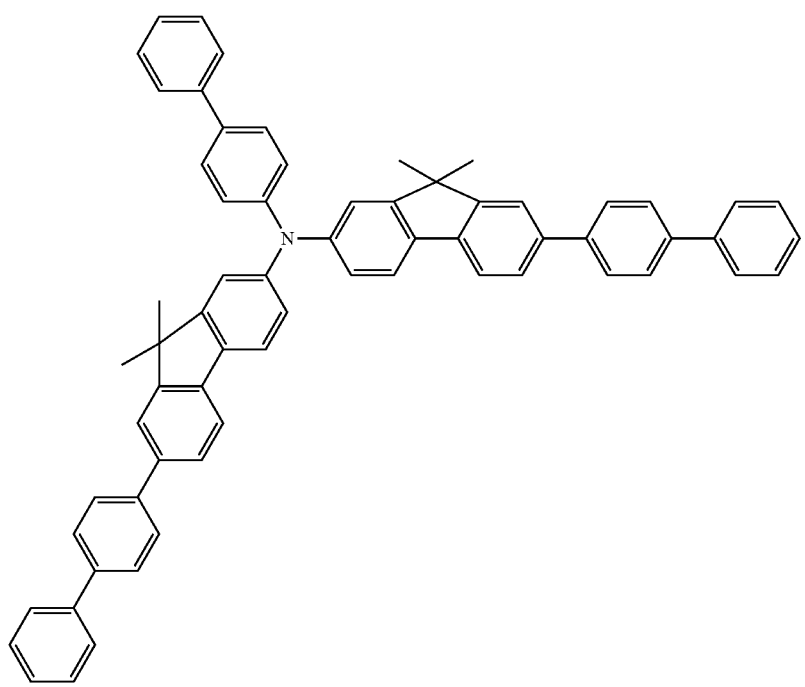

-continued
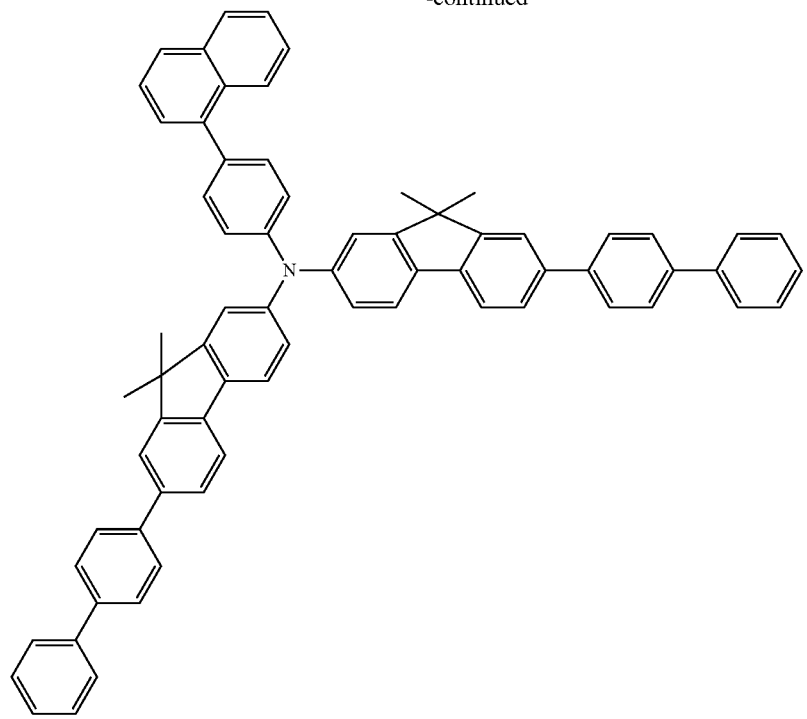
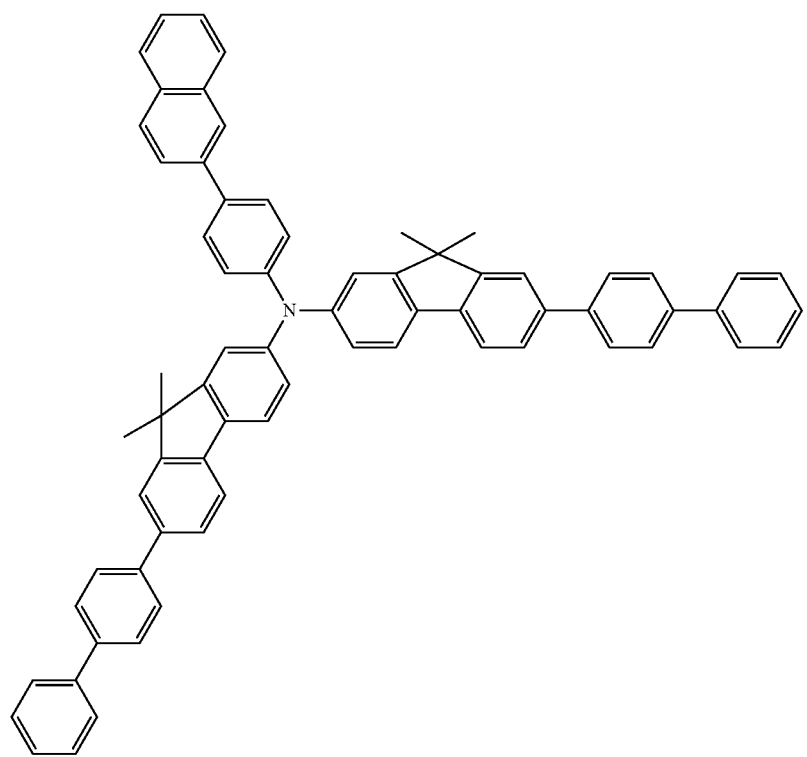

-continued
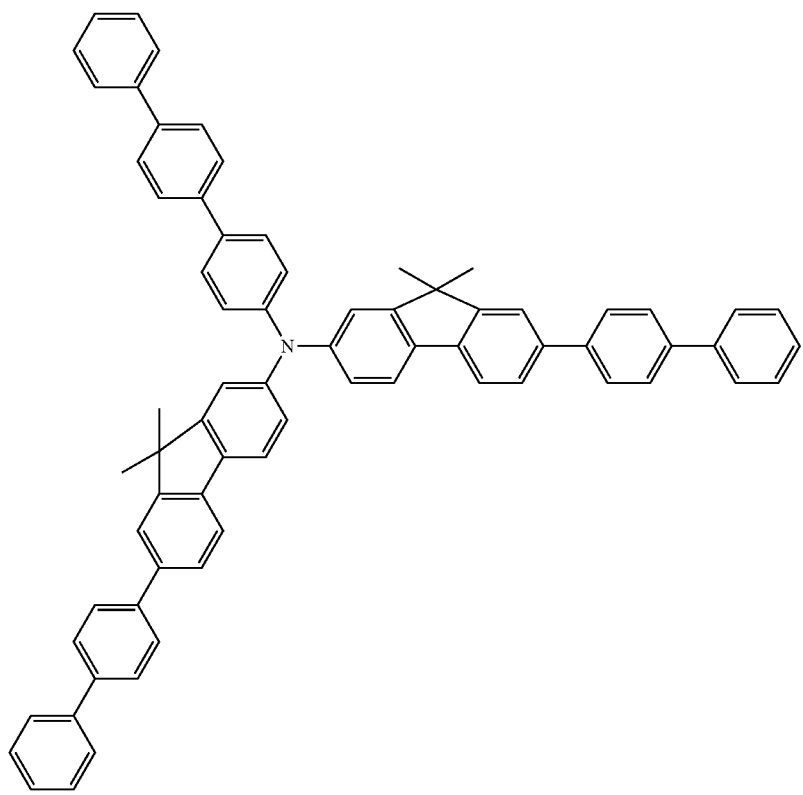
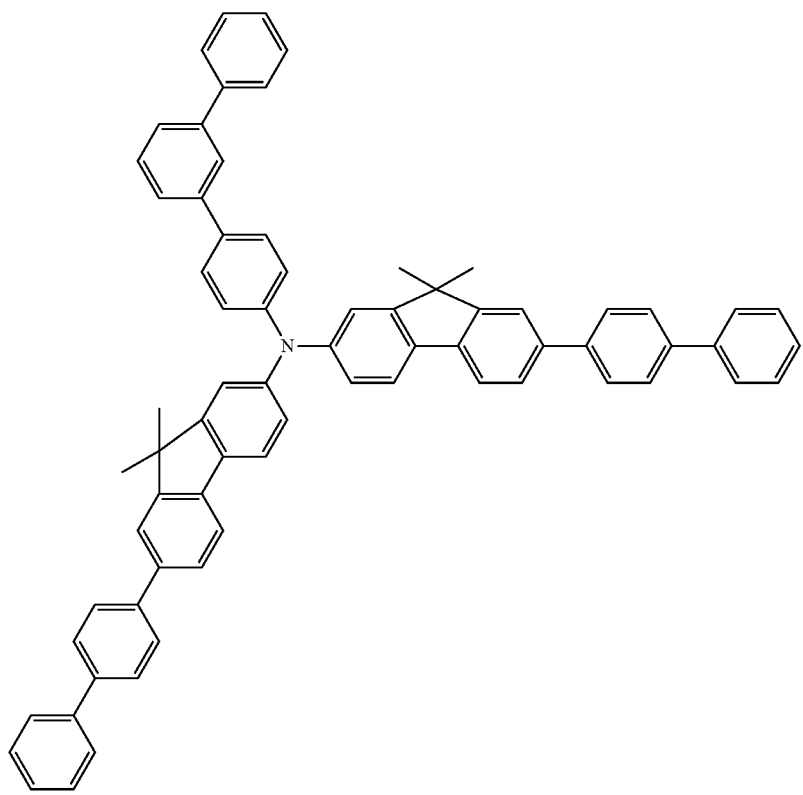

-continued
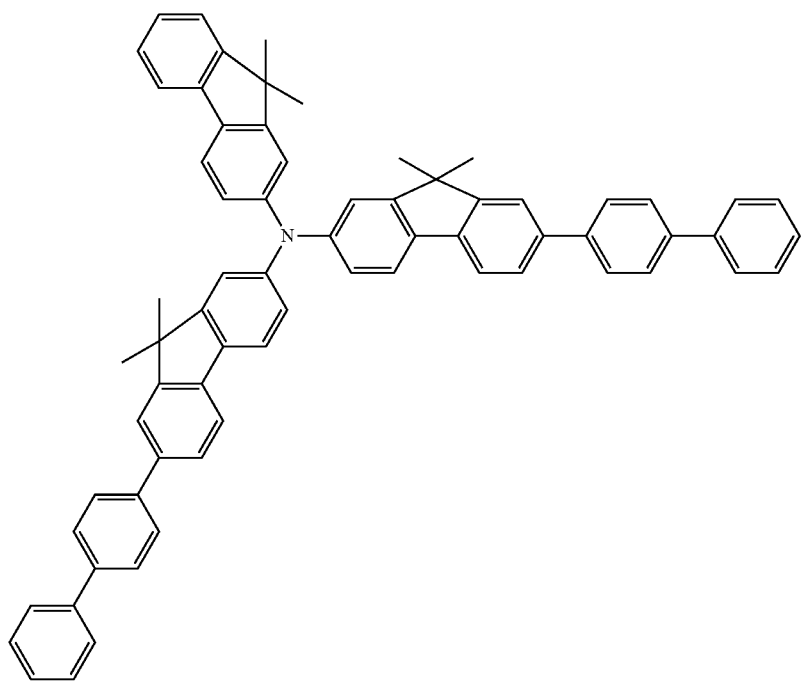
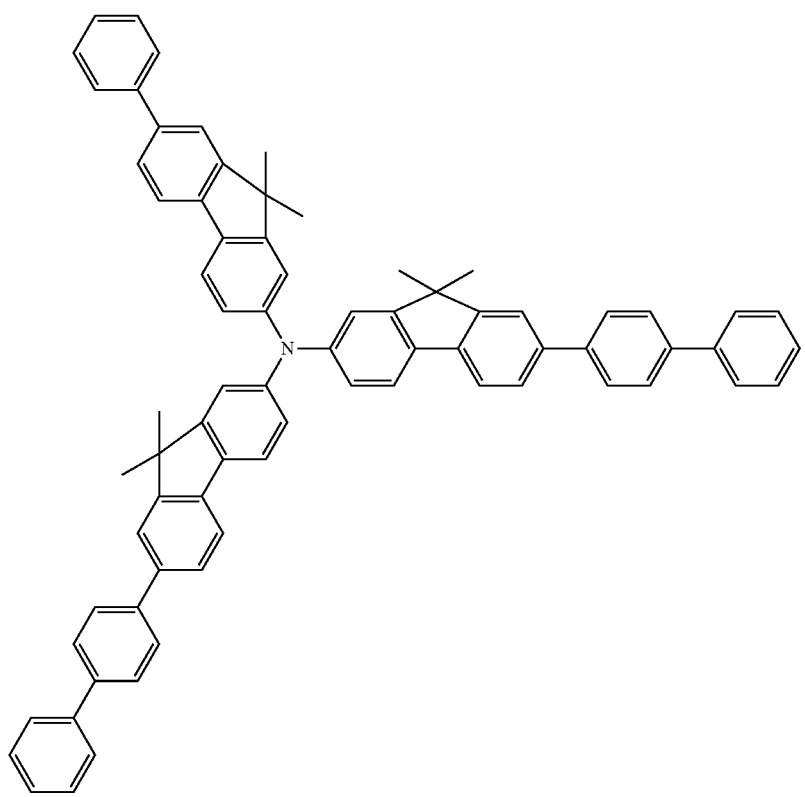

-continued
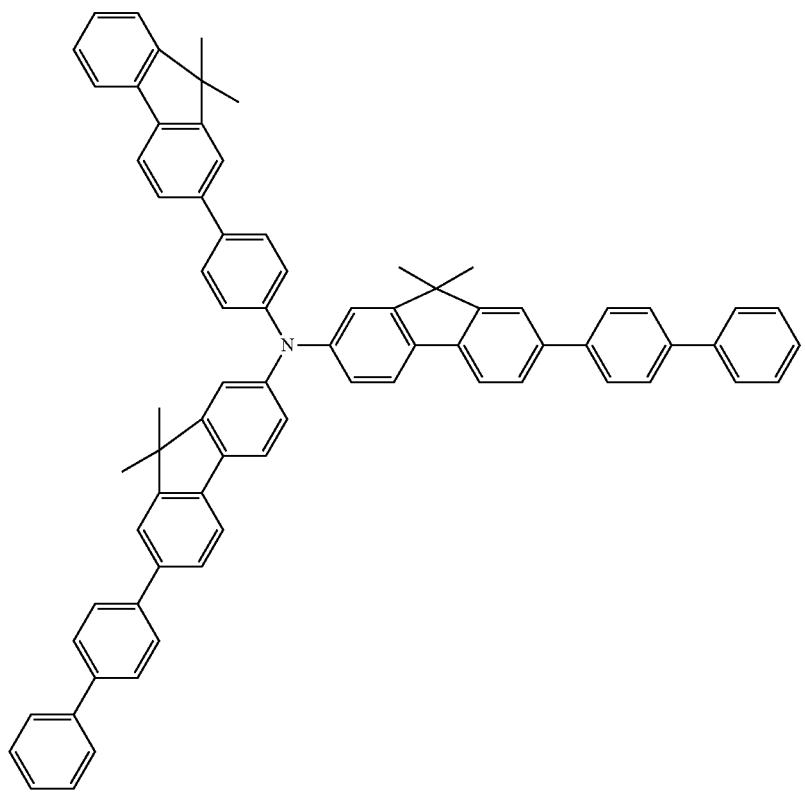
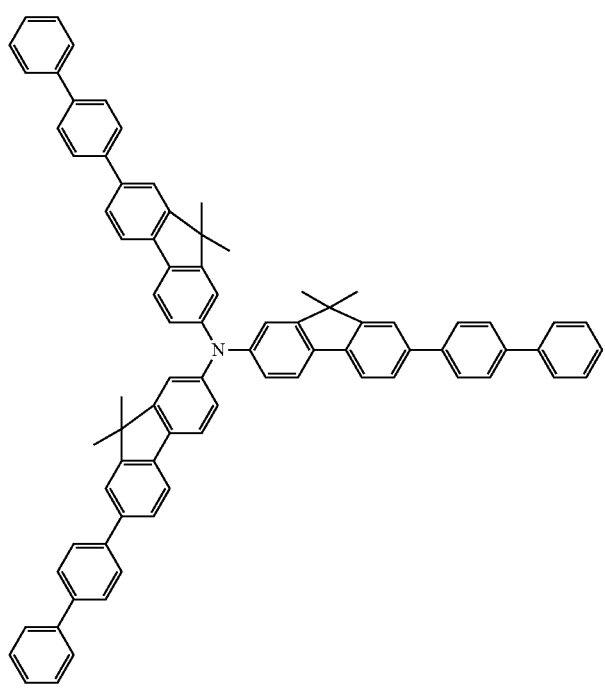

-continued
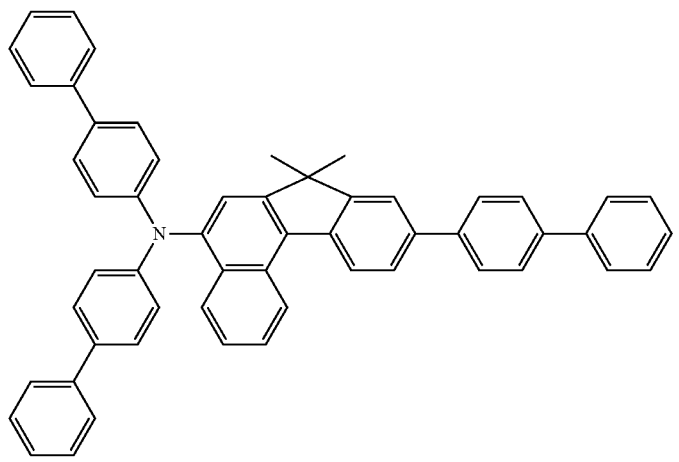
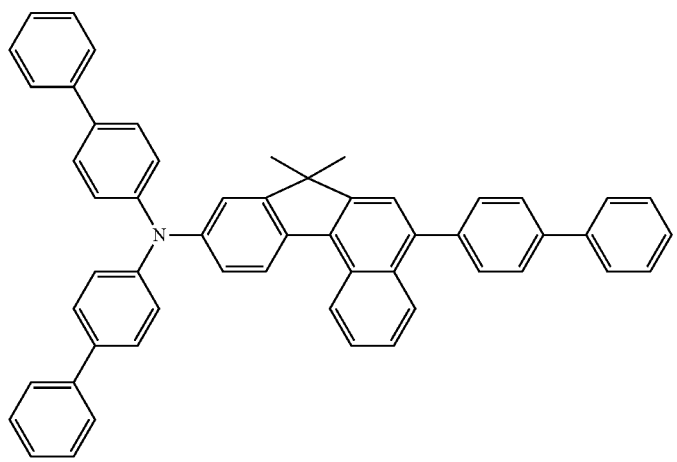
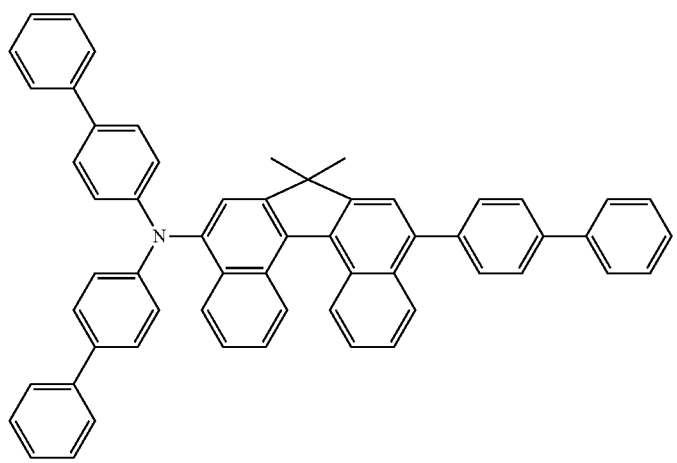

-continued
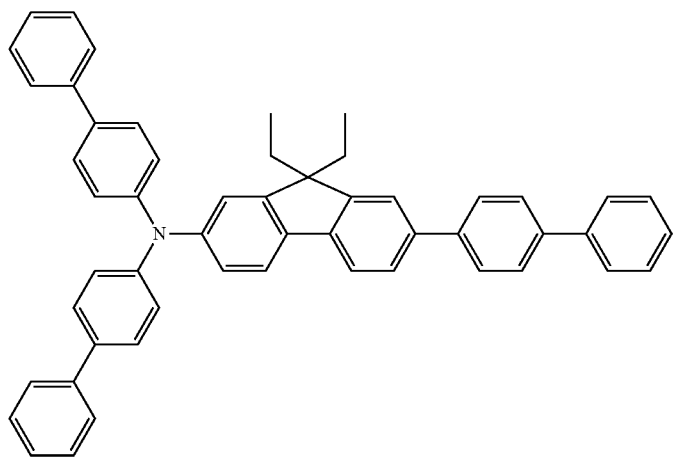
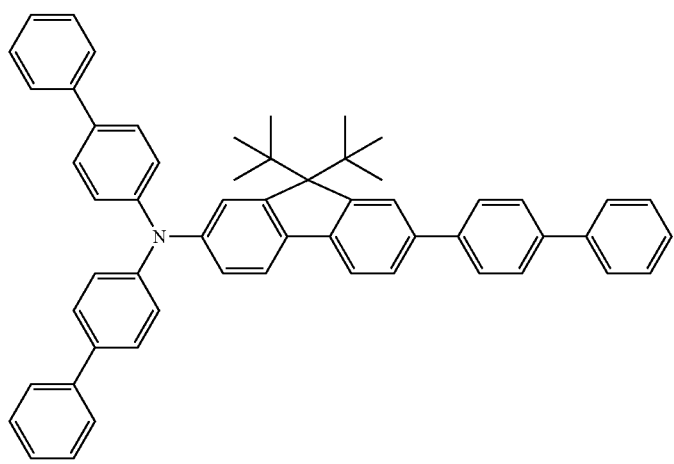
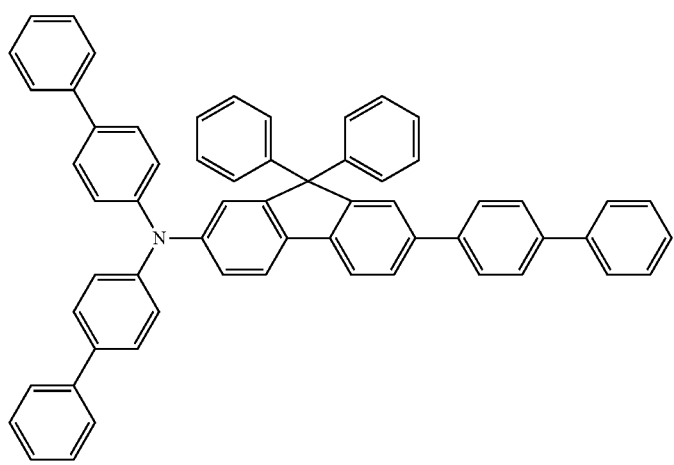

-continued
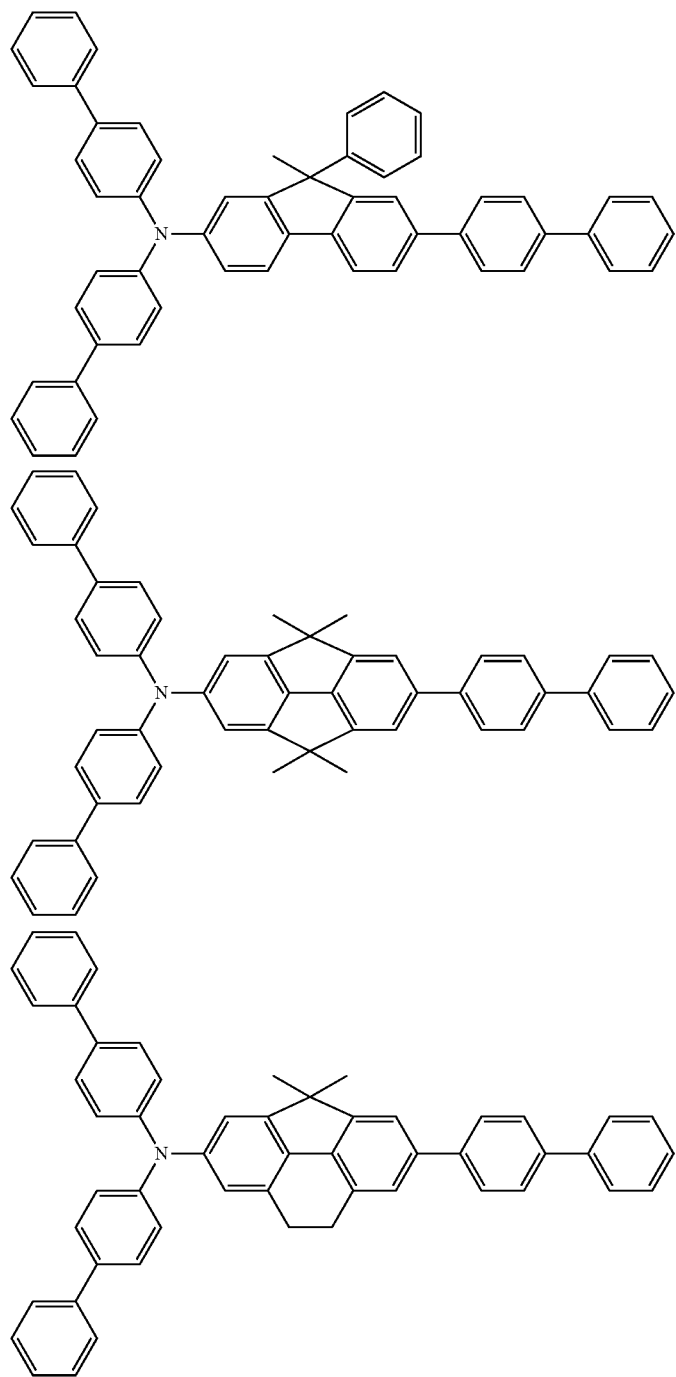
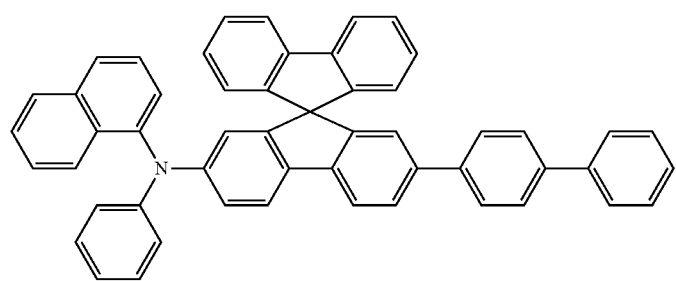

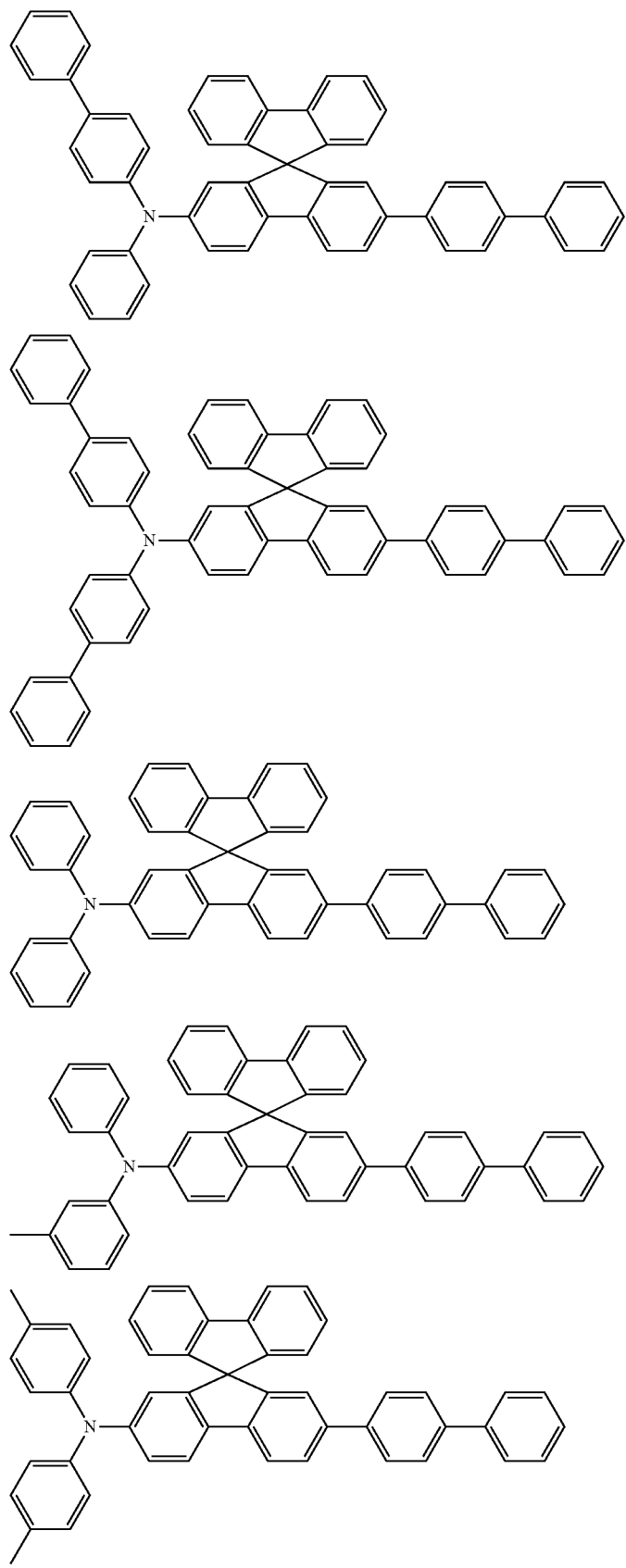

-continued
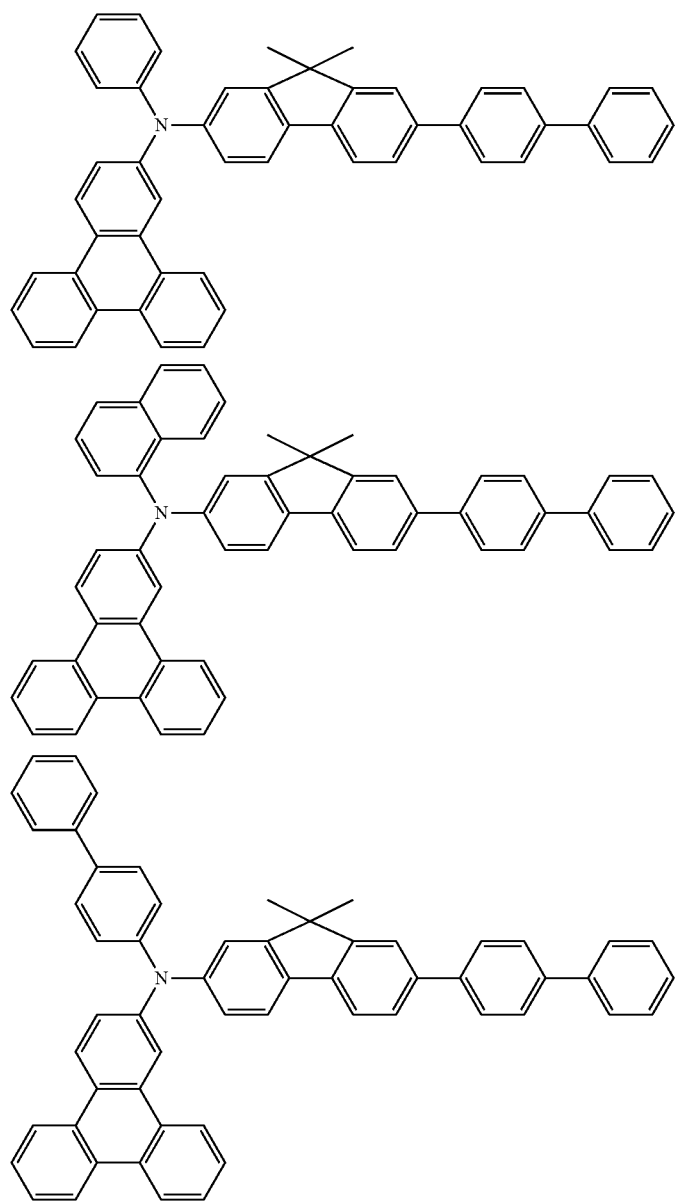
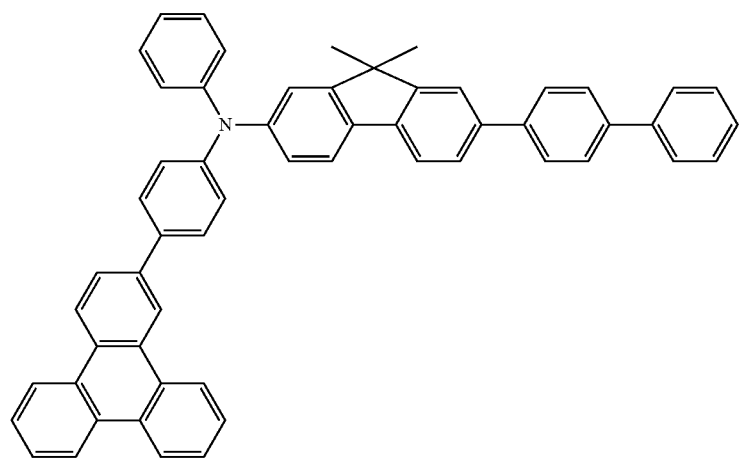

-continued
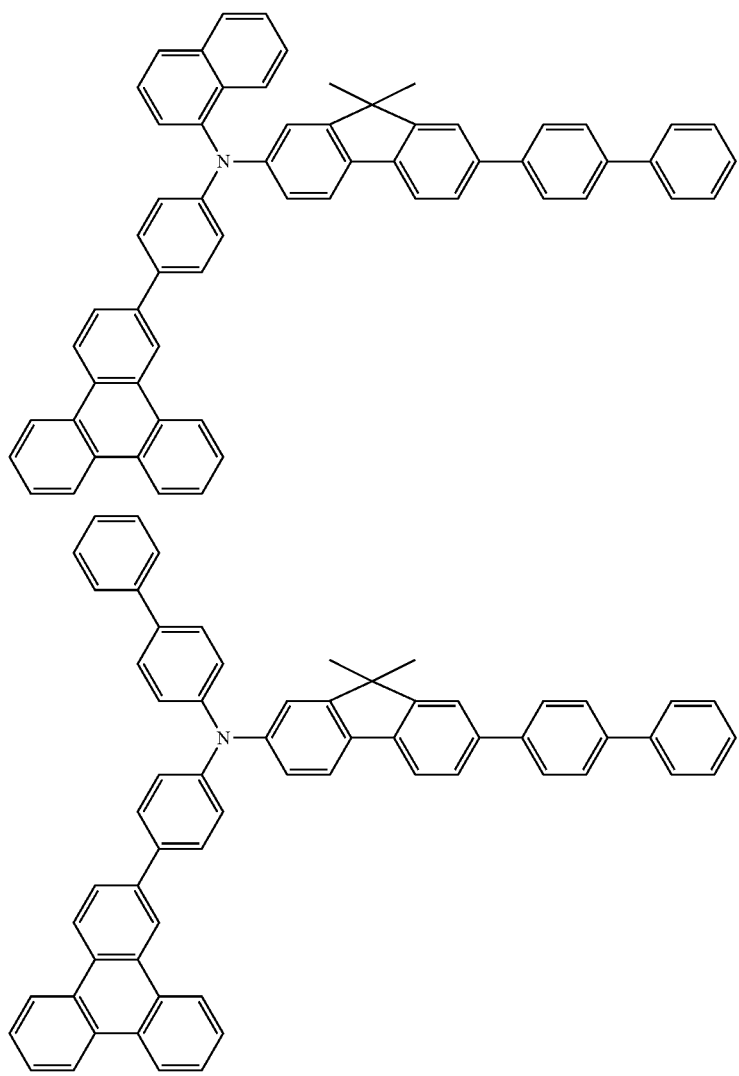
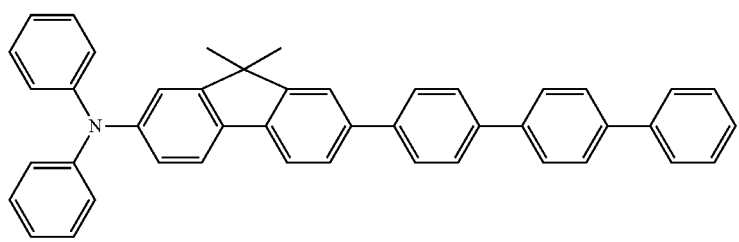
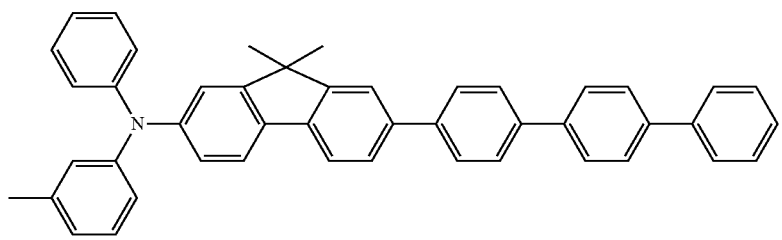

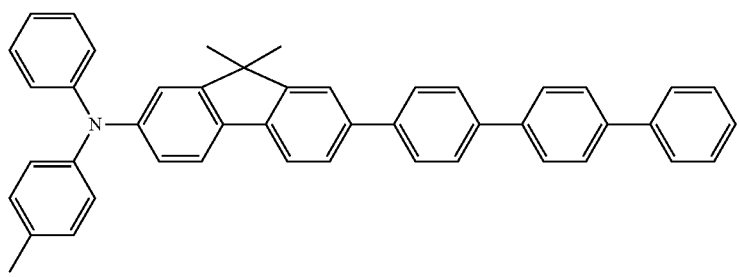
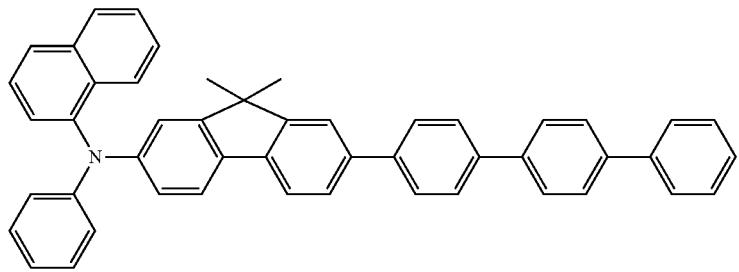
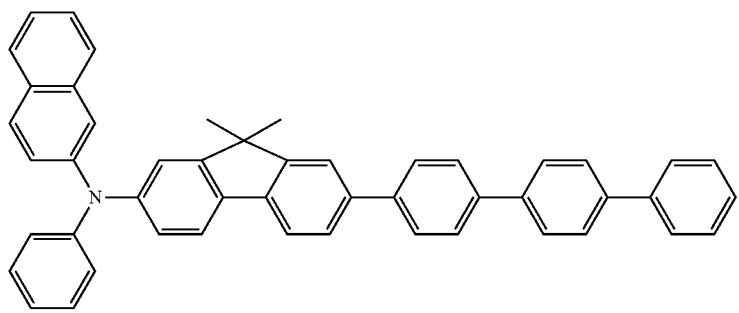
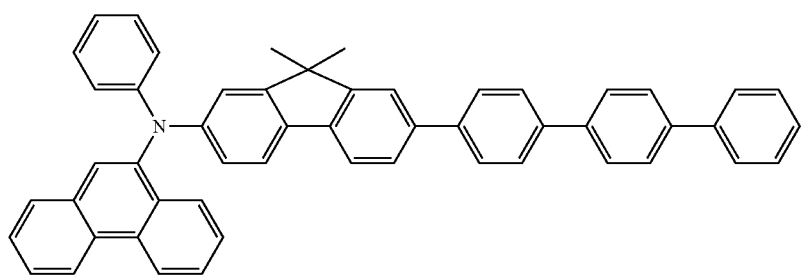
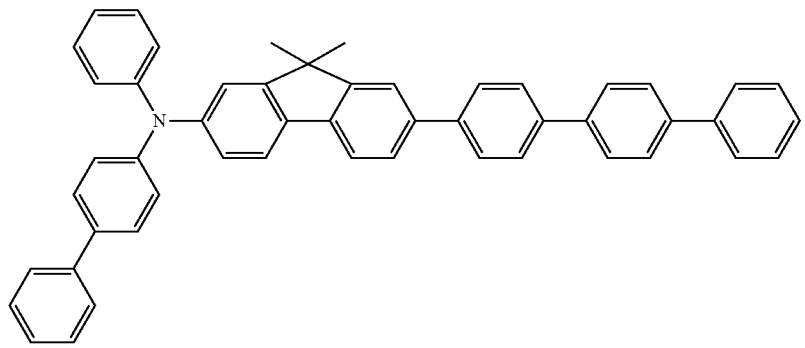

-continued
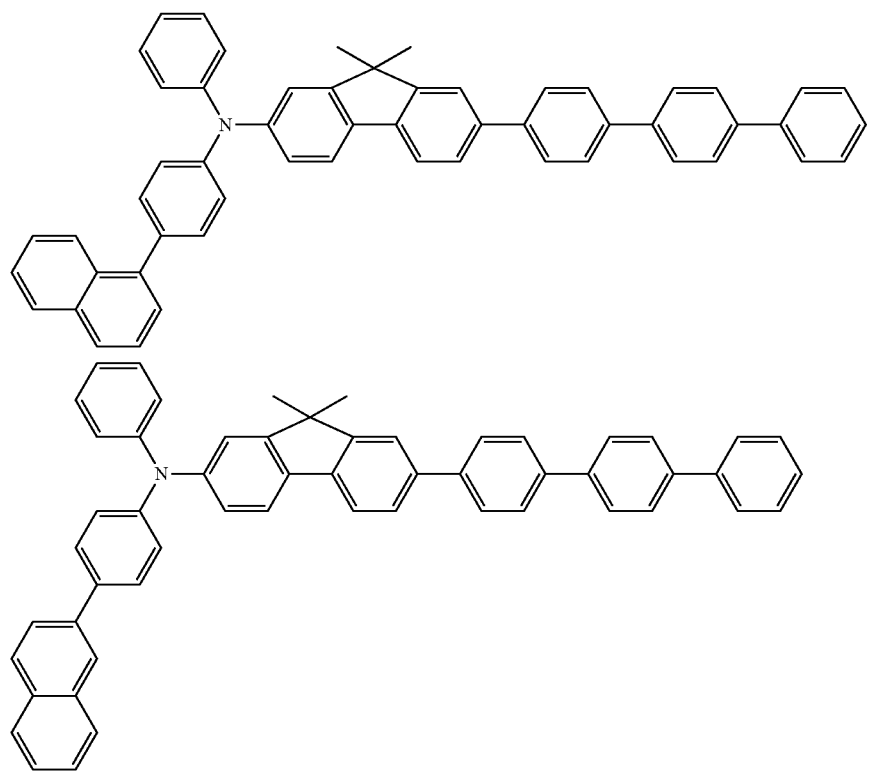
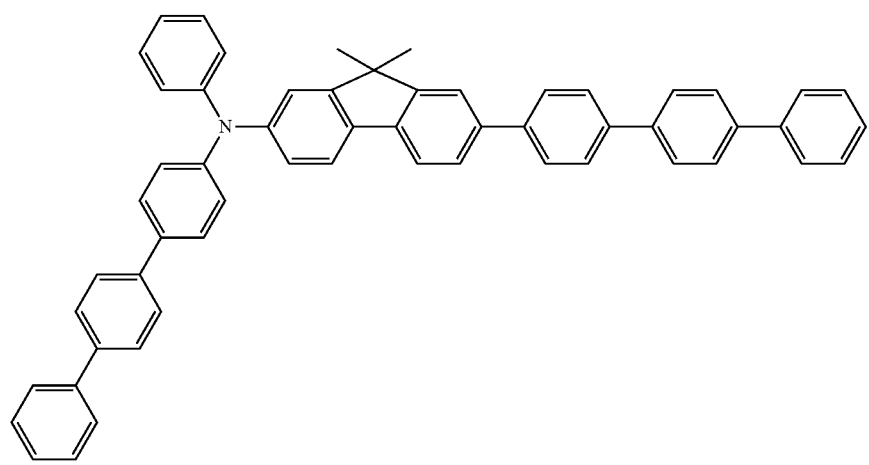
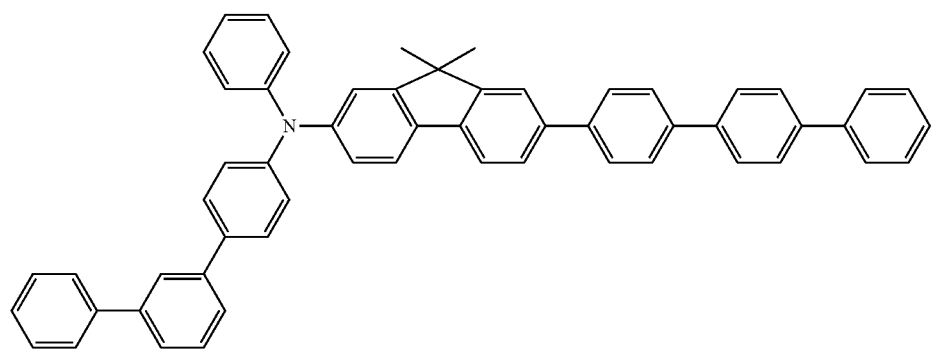

-continued
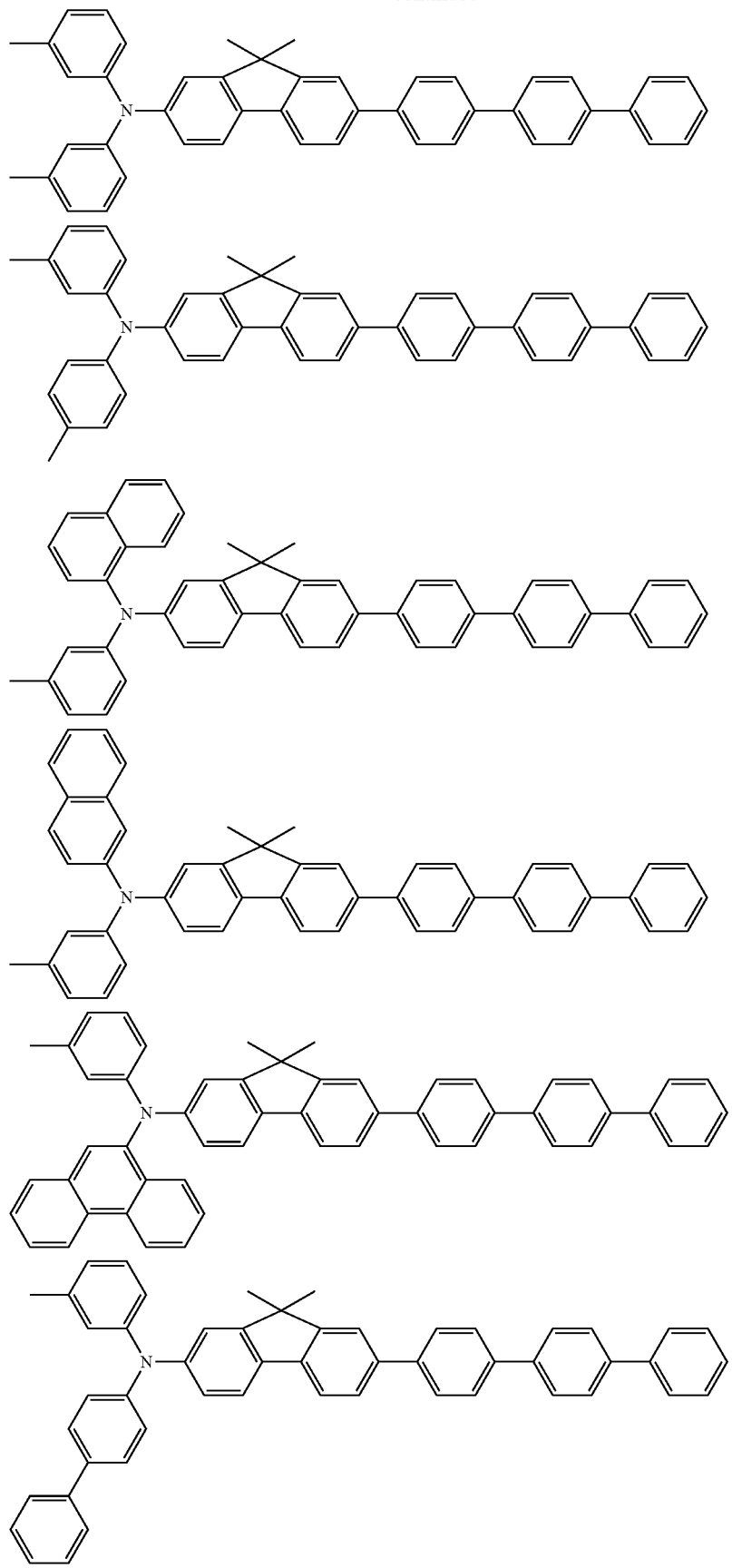

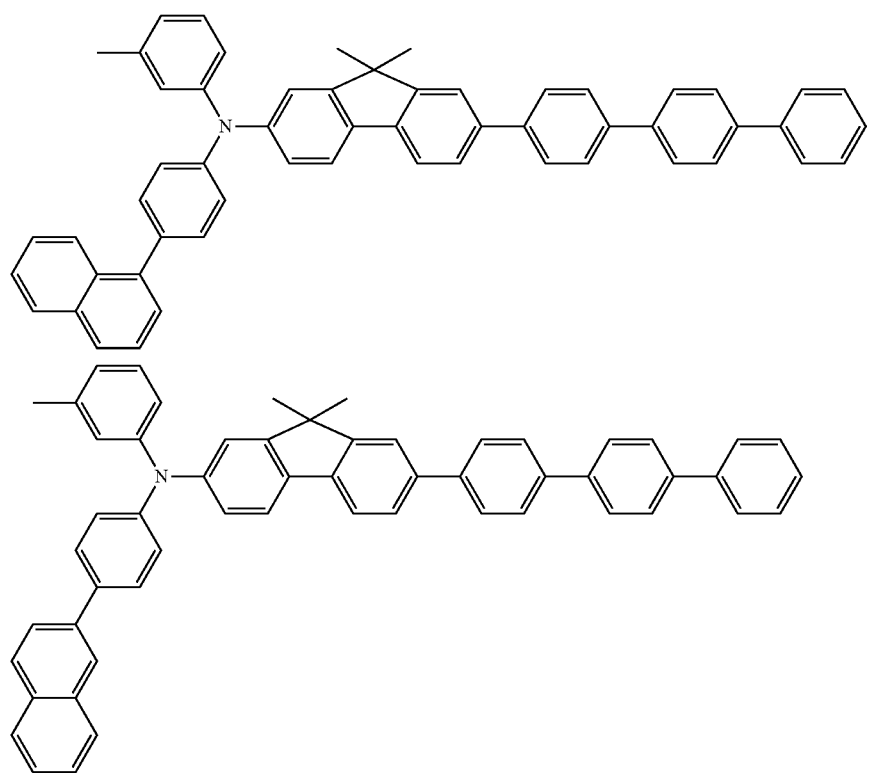
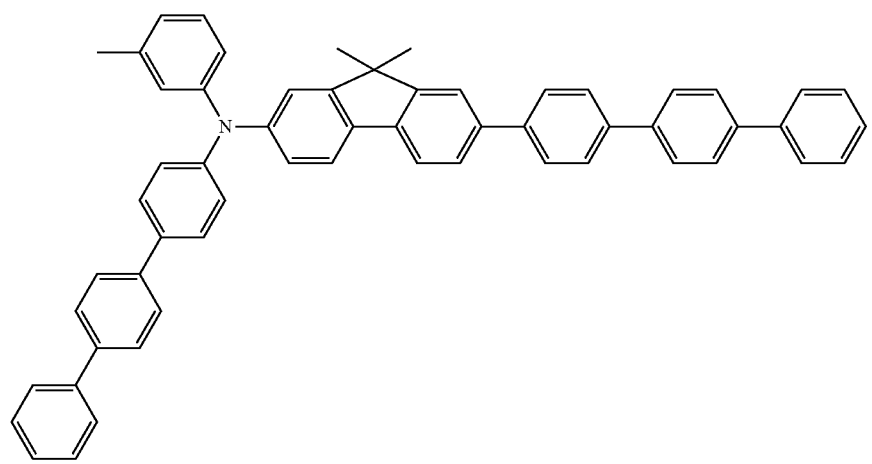
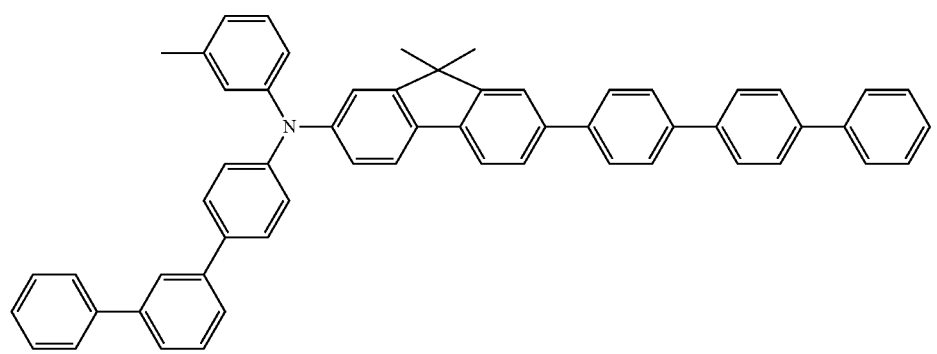

-continued
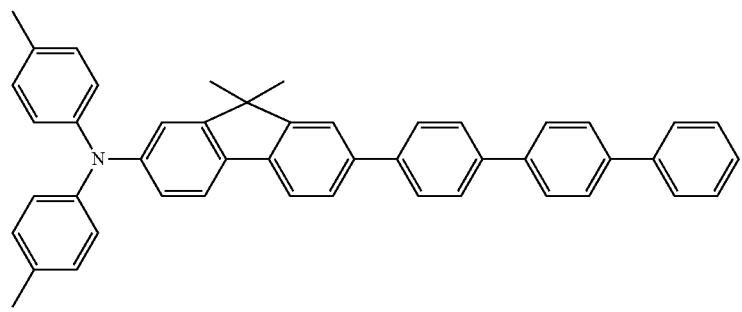
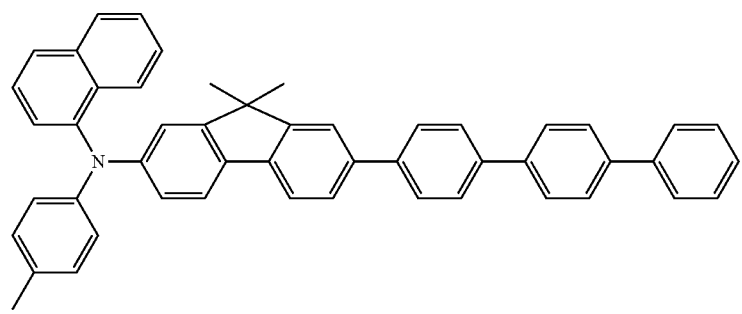
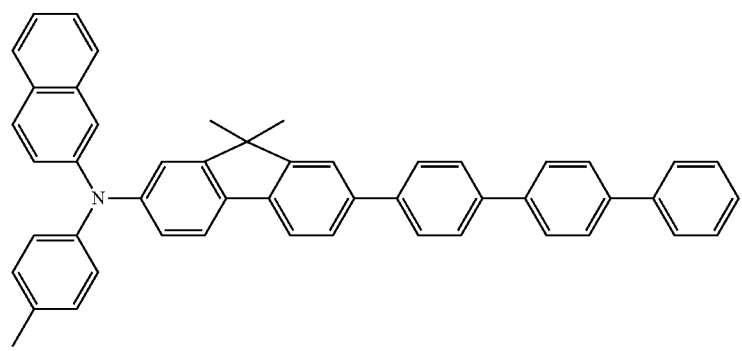
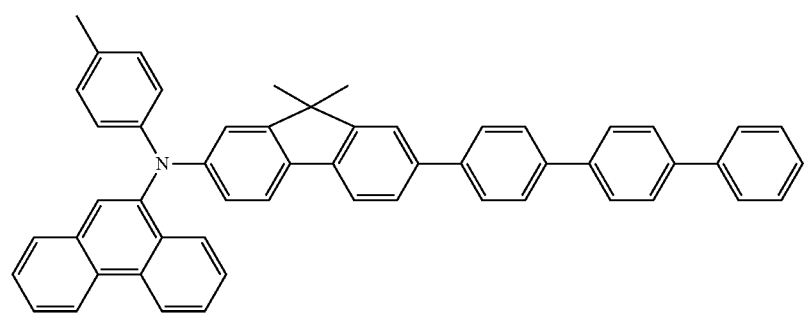
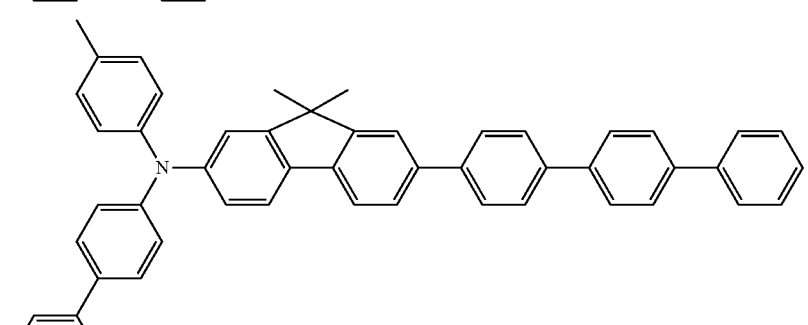

-continued
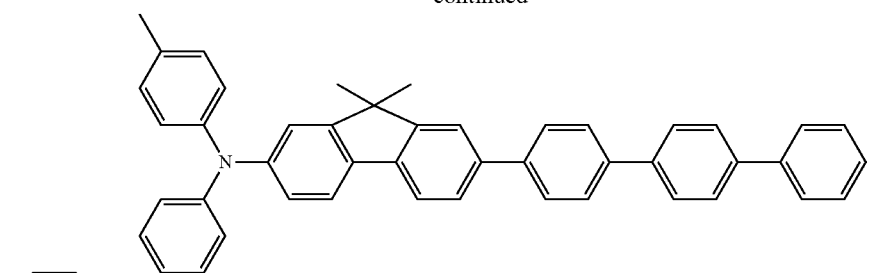
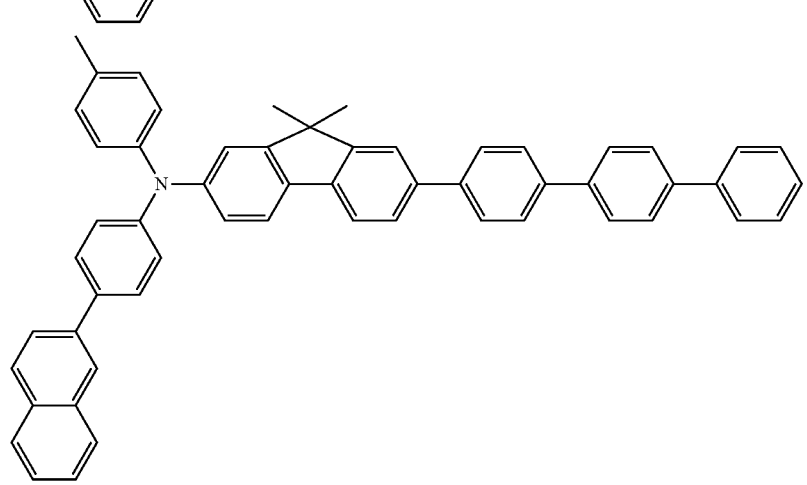
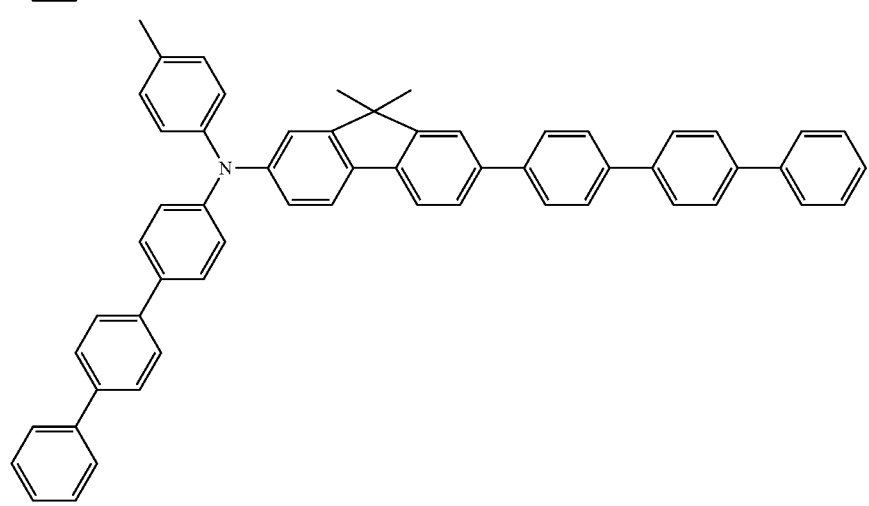
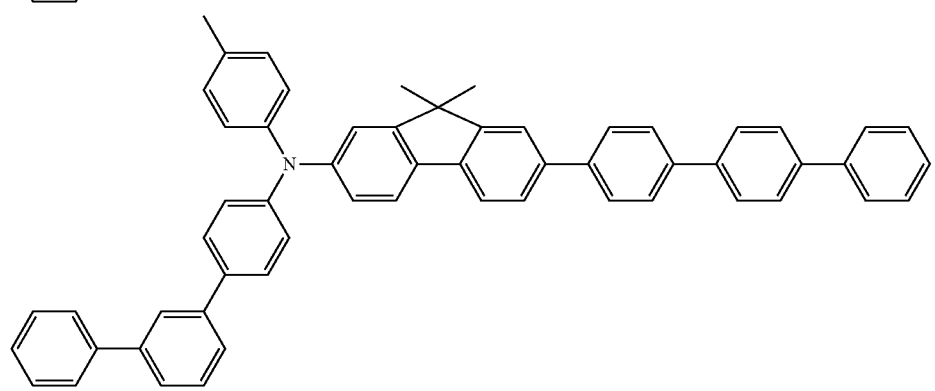

-continued
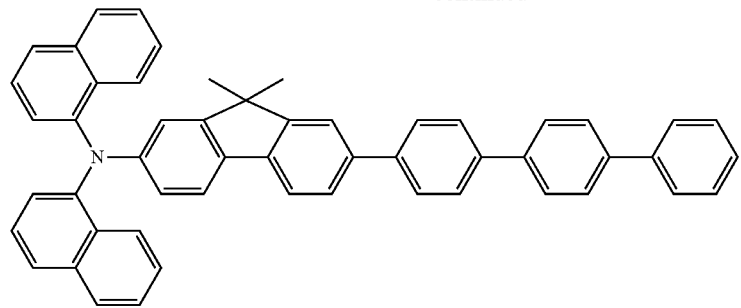
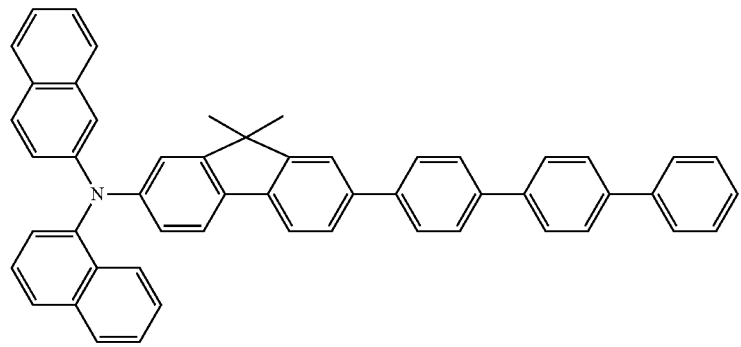
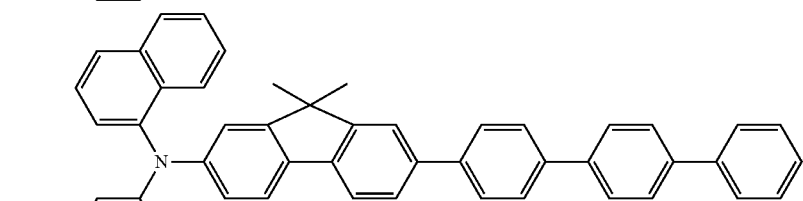
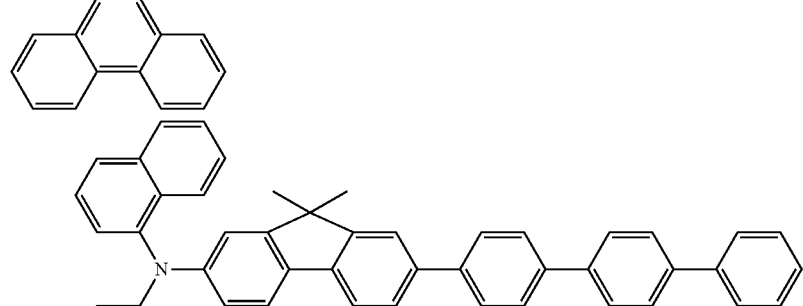
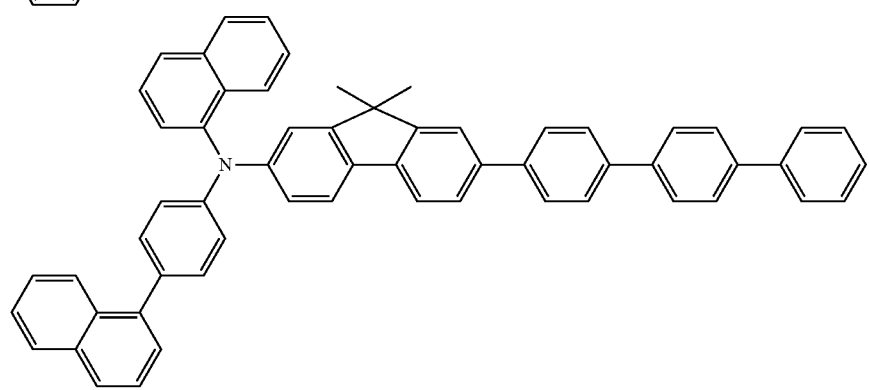

-continued
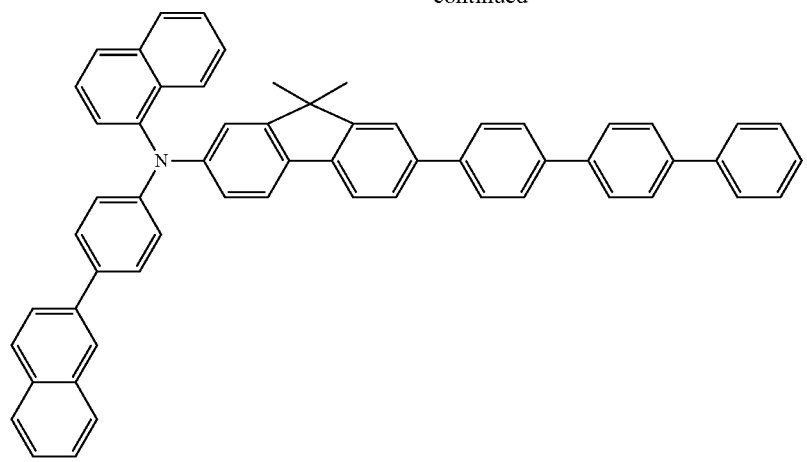
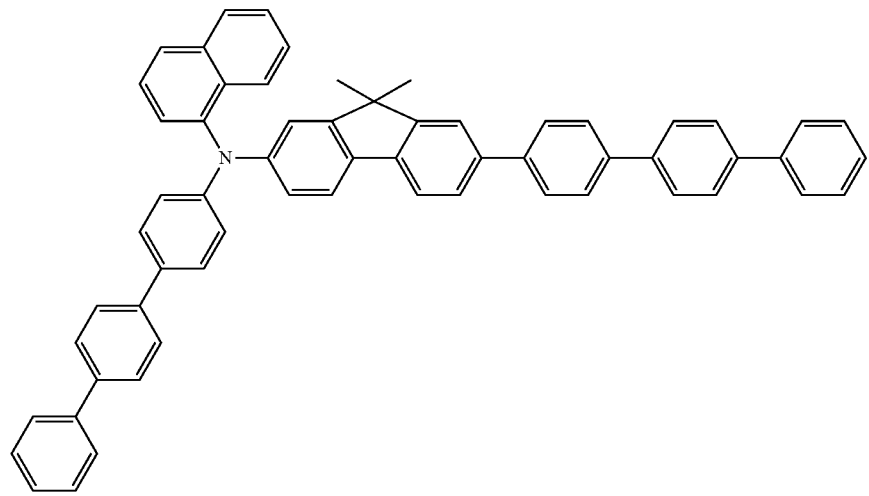
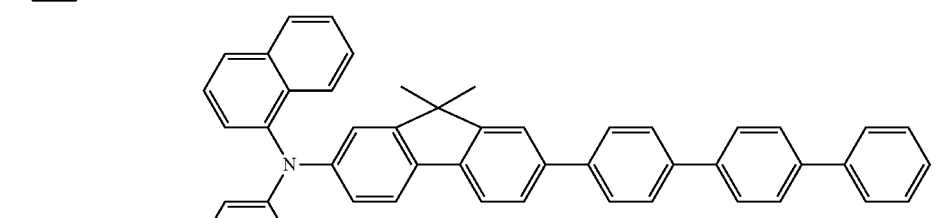
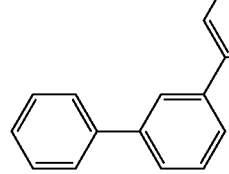
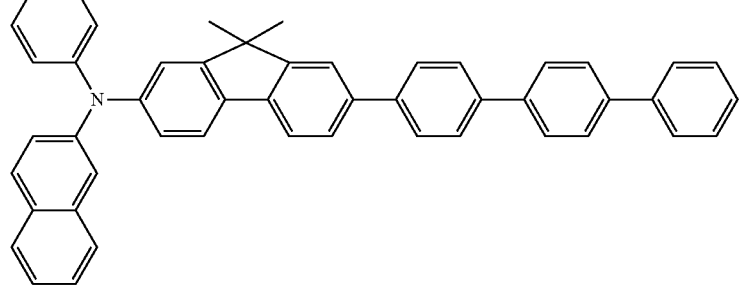

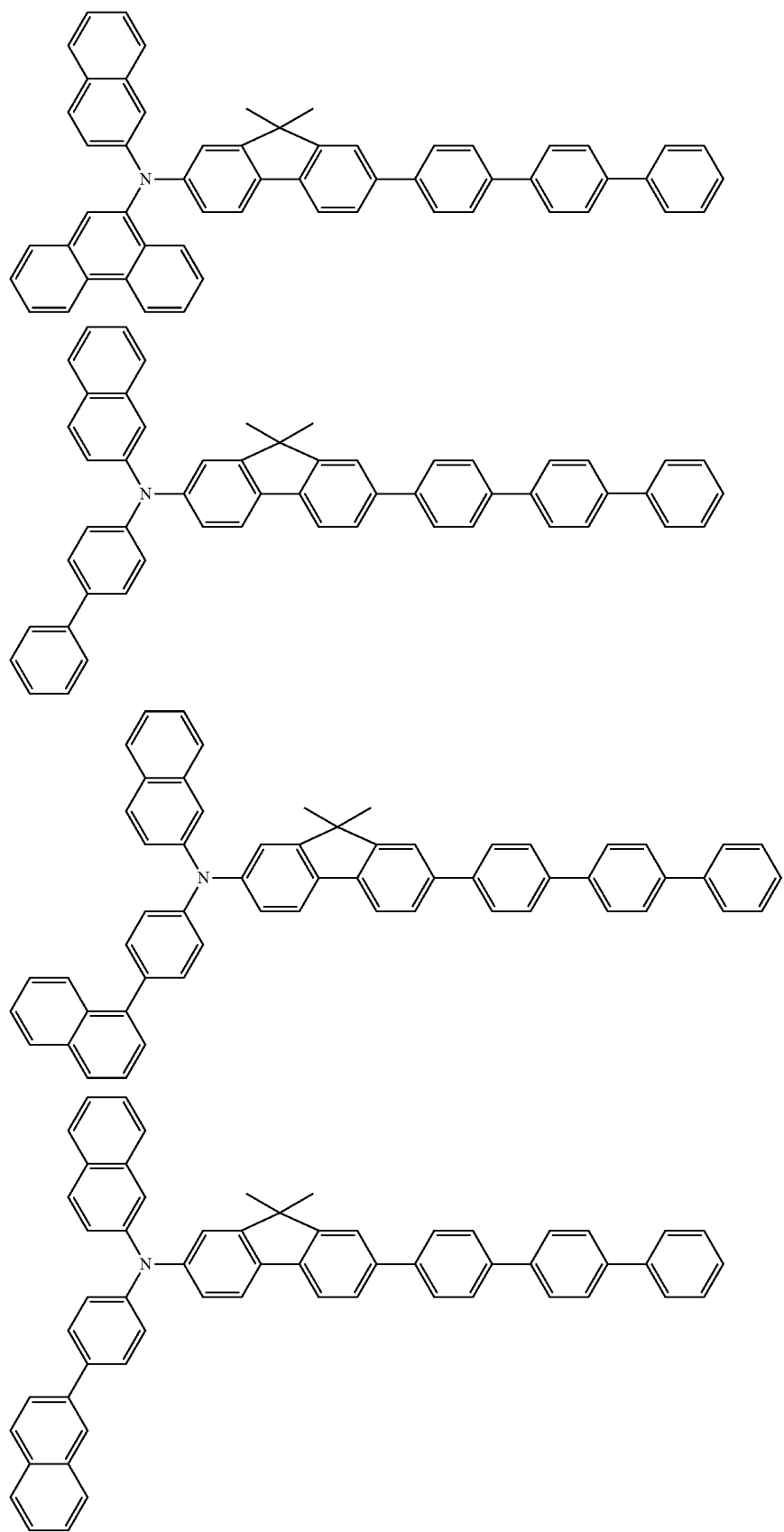

-continued
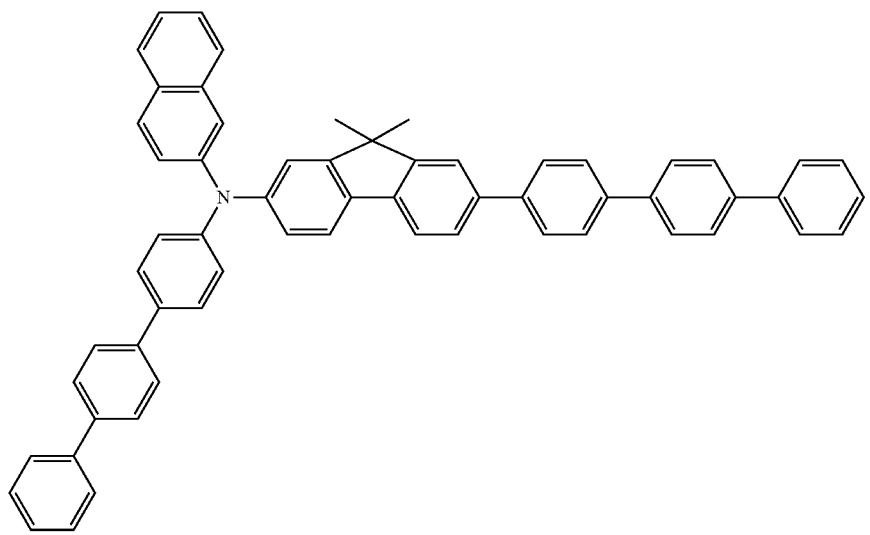
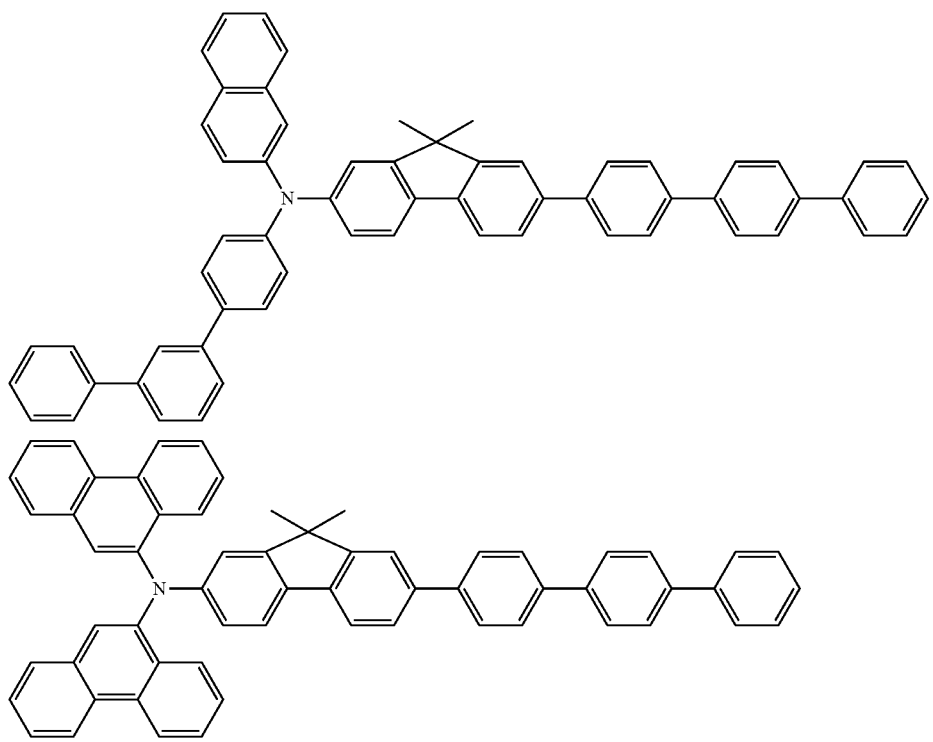
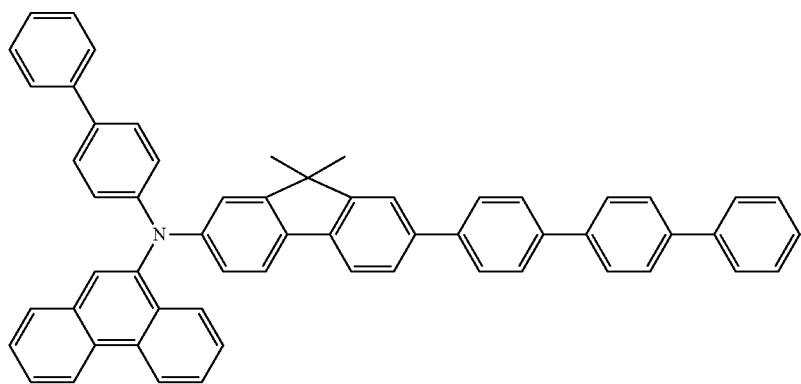

-continued
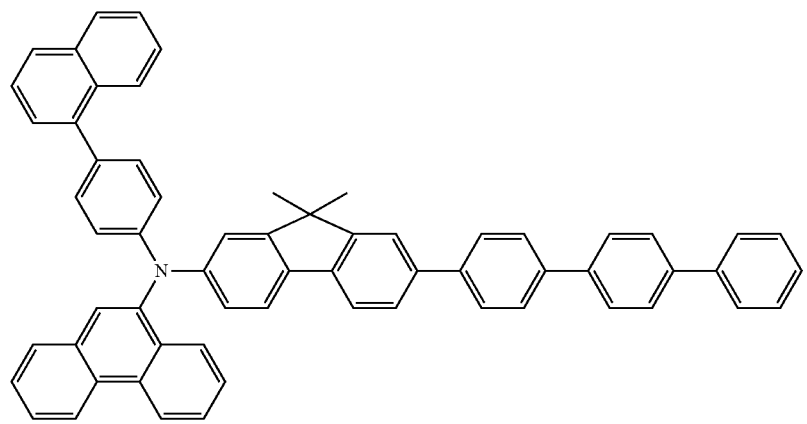
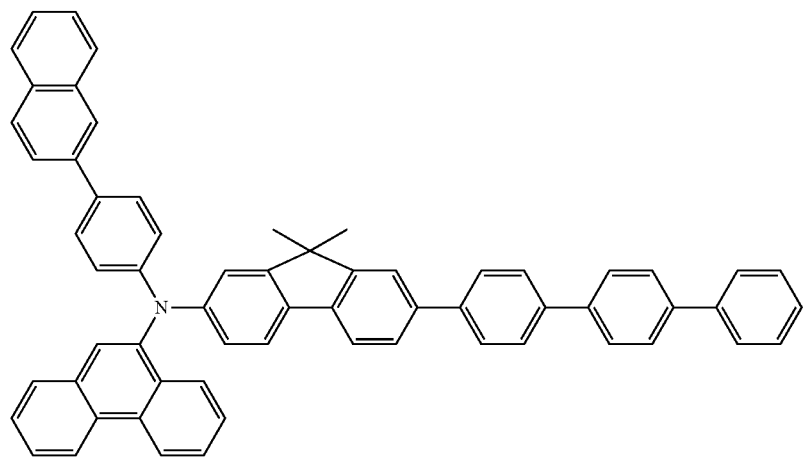
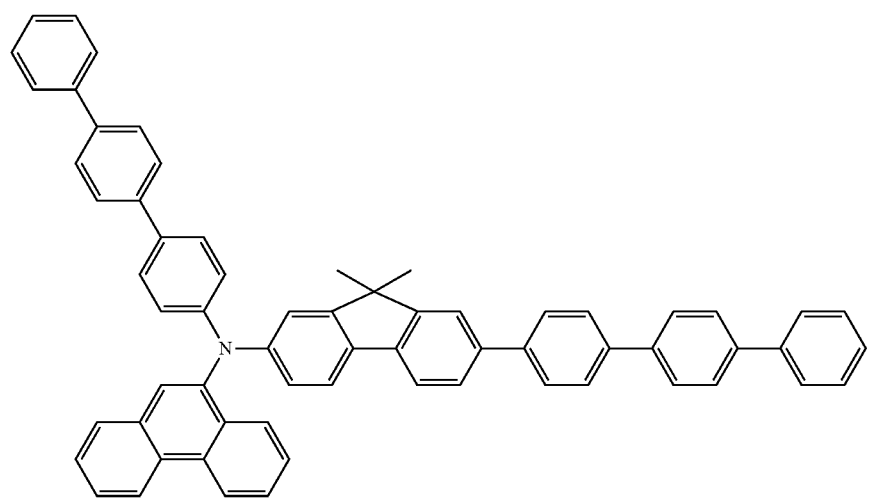

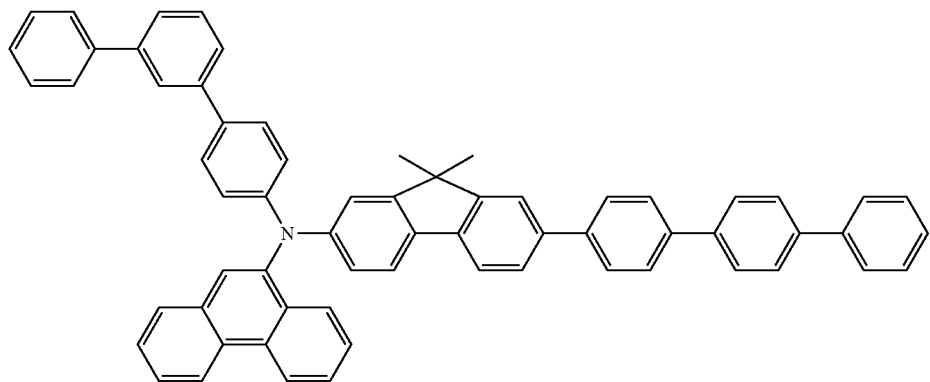
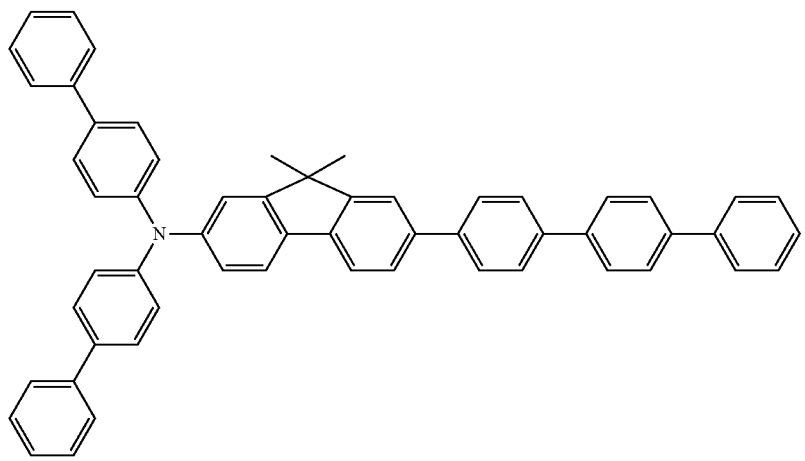
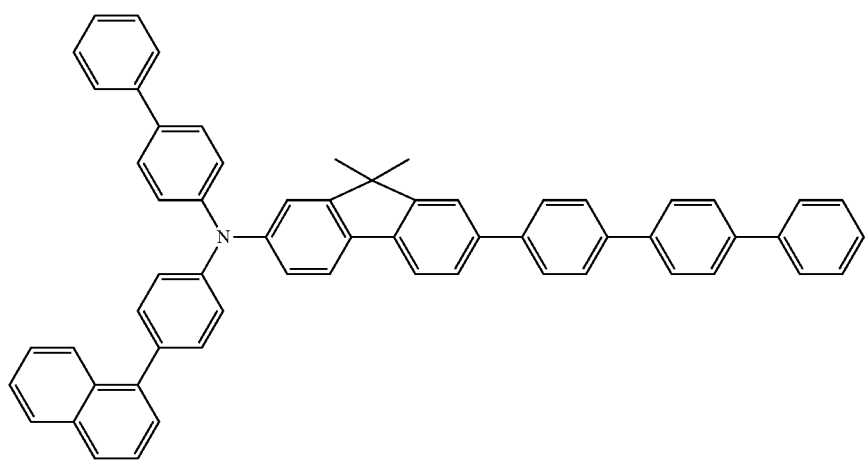

-continued
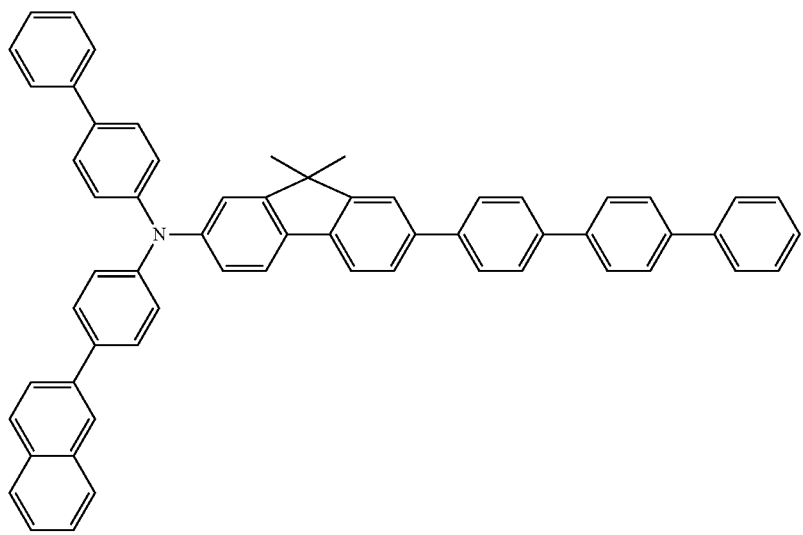
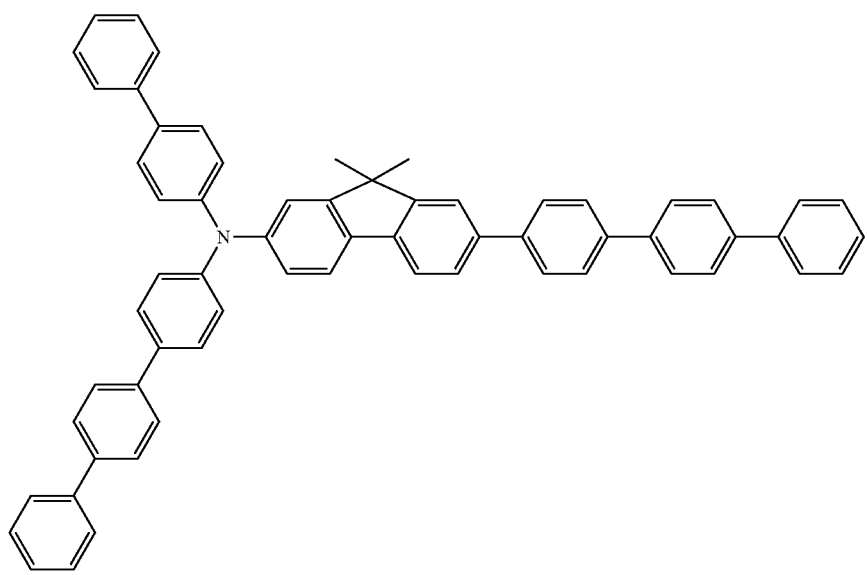
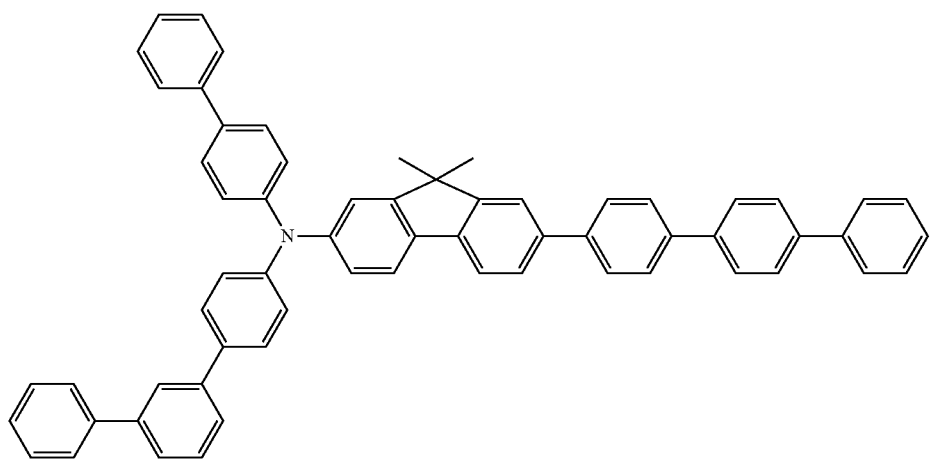

-continued
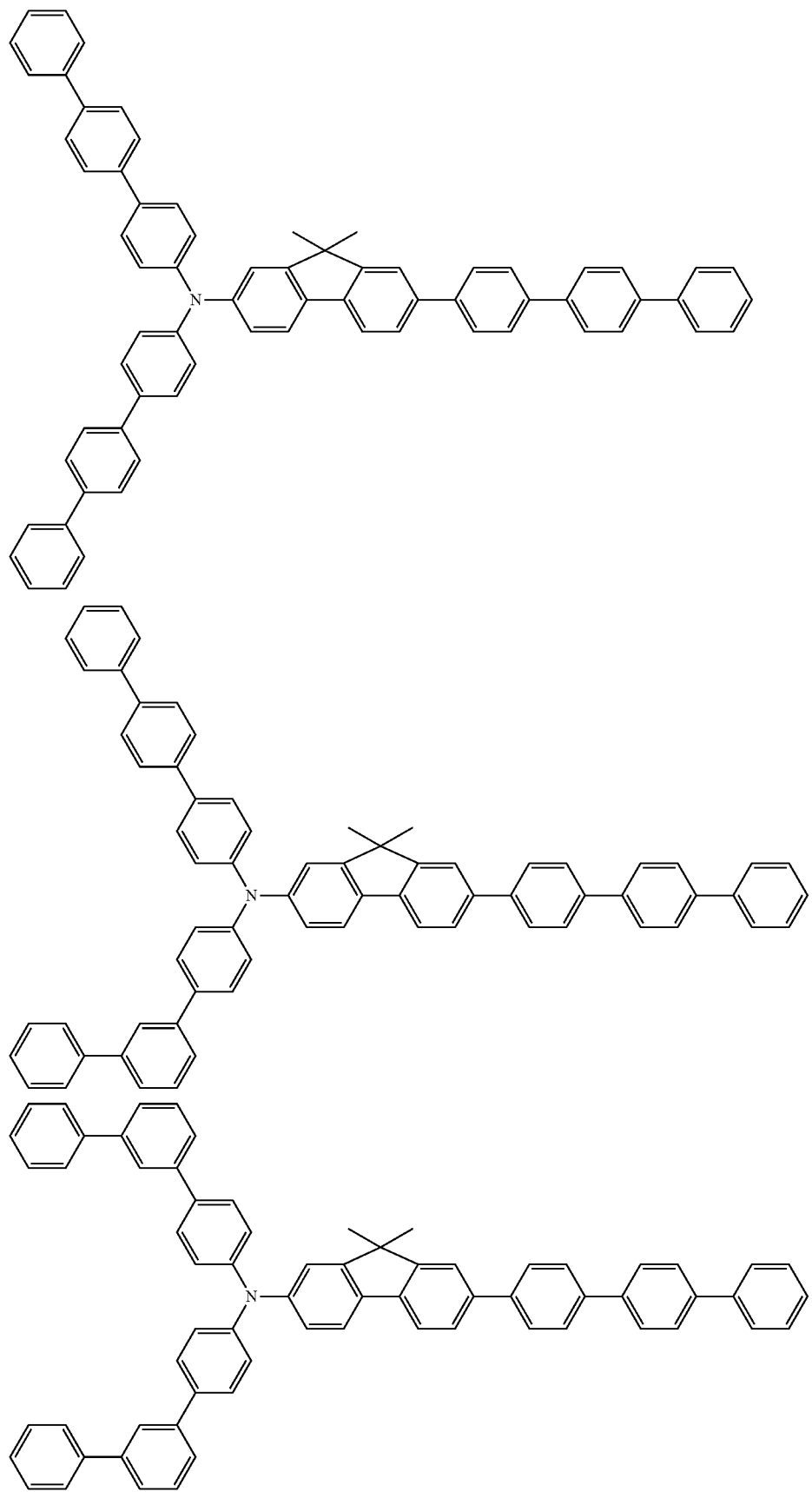

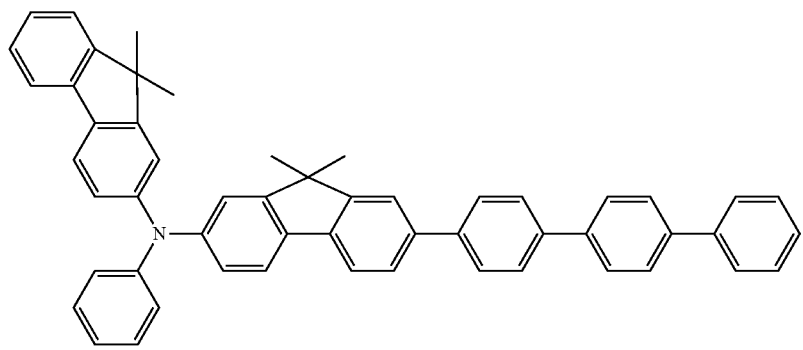
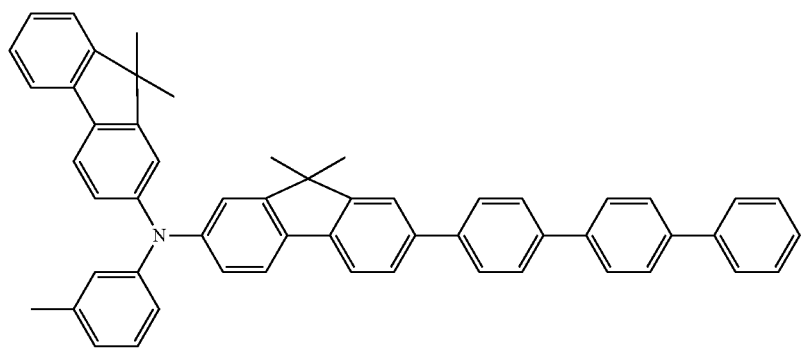
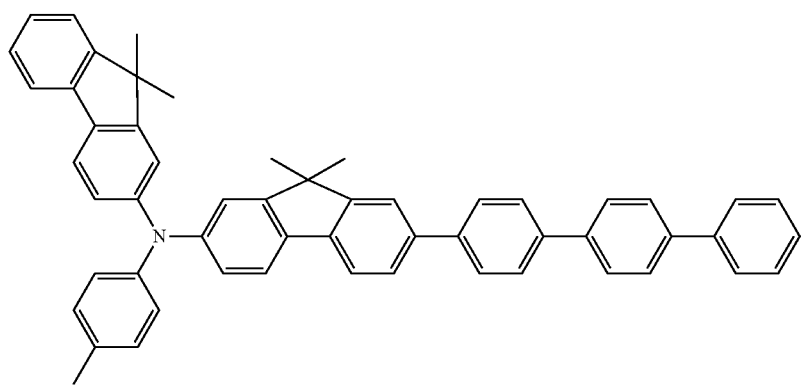
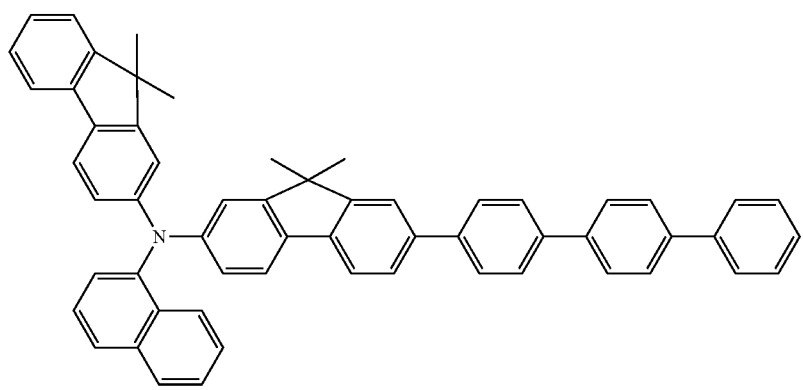

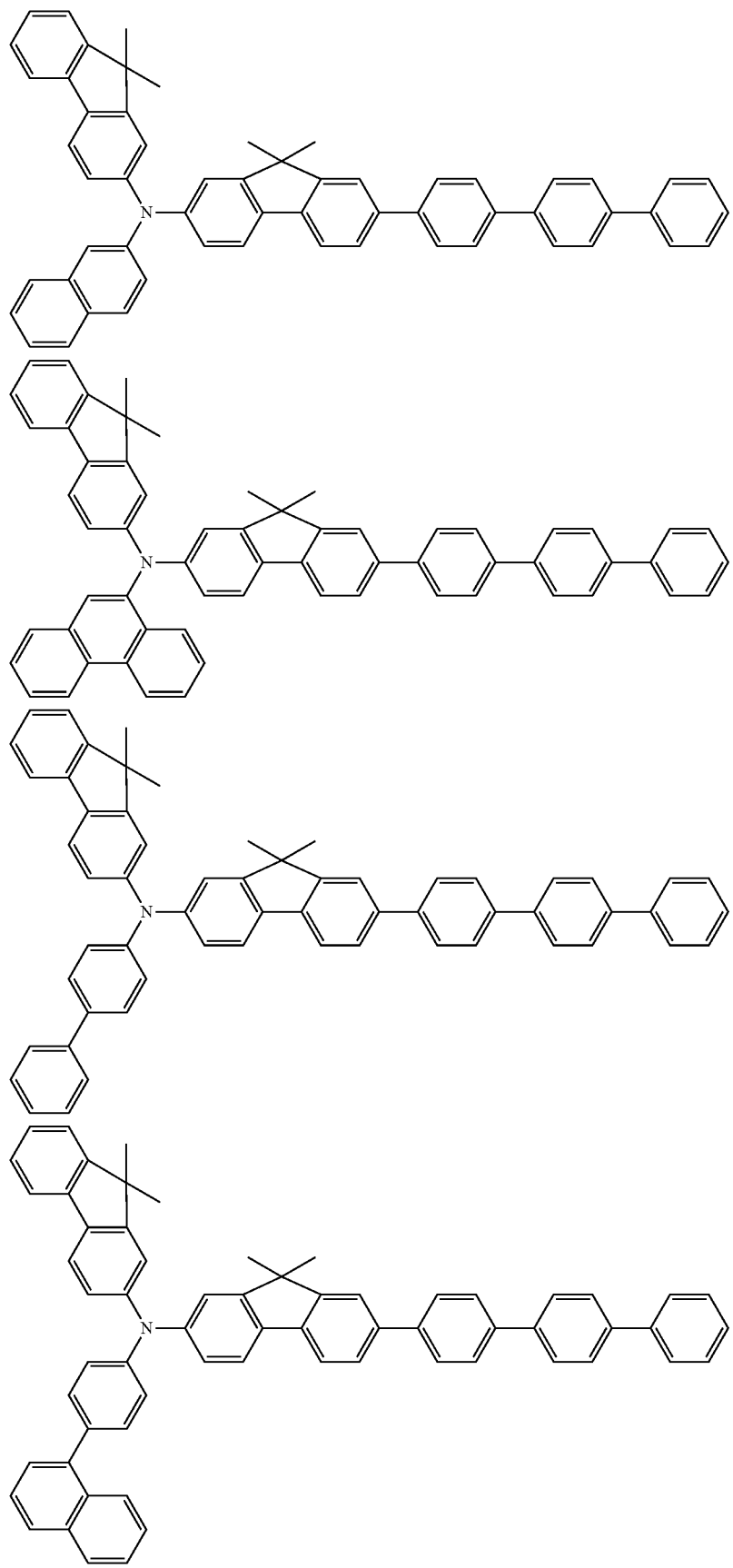

-continued
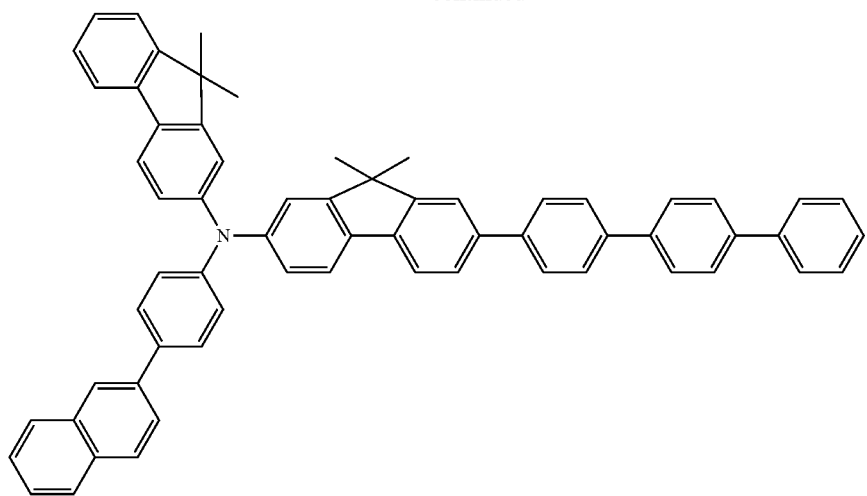
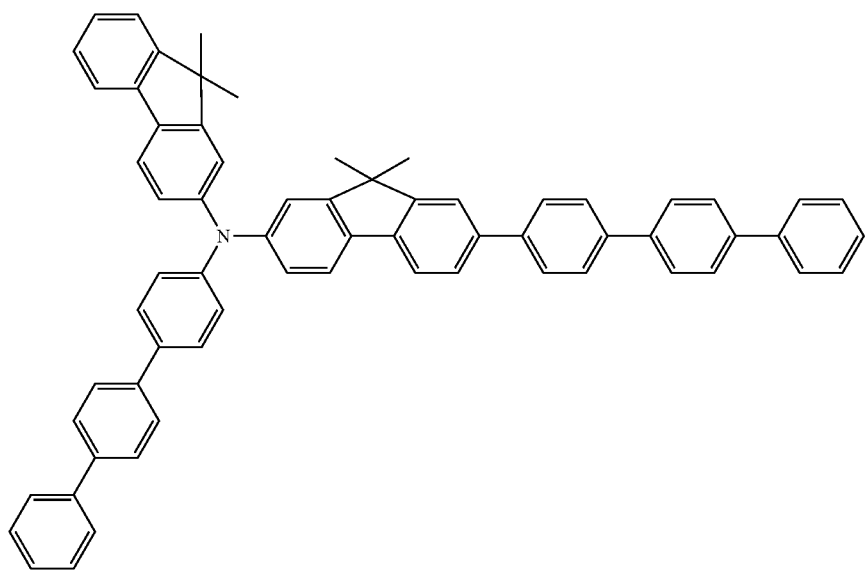
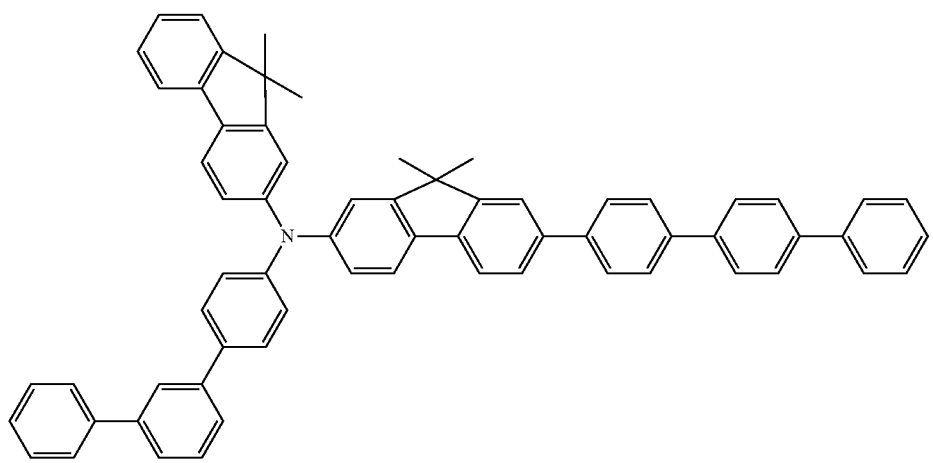

-continued
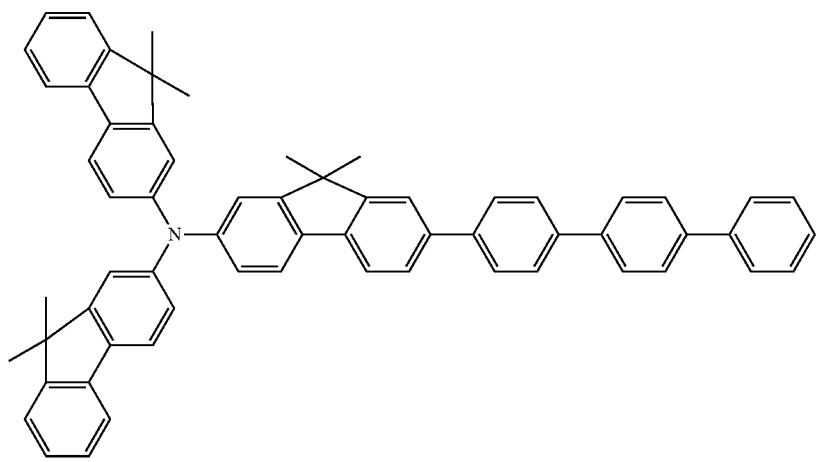 [SMILES: CC1(C)c2ccccc2-c2ccc(N(c3ccc4c(c3)C(C)(C)c3ccccc3-4)c3ccc4c(c3)C(C)(C)c3cc(-c5ccc(-c6ccc(-c7ccccc7)cc6)cc5)ccc3-4)cc21]
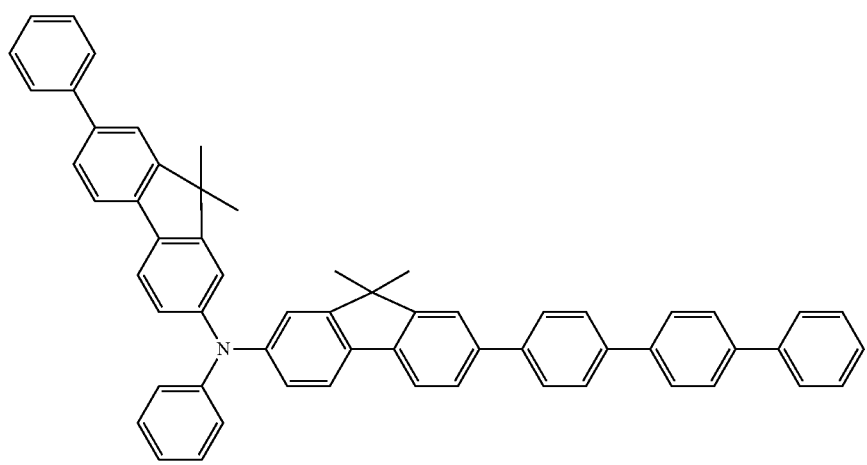
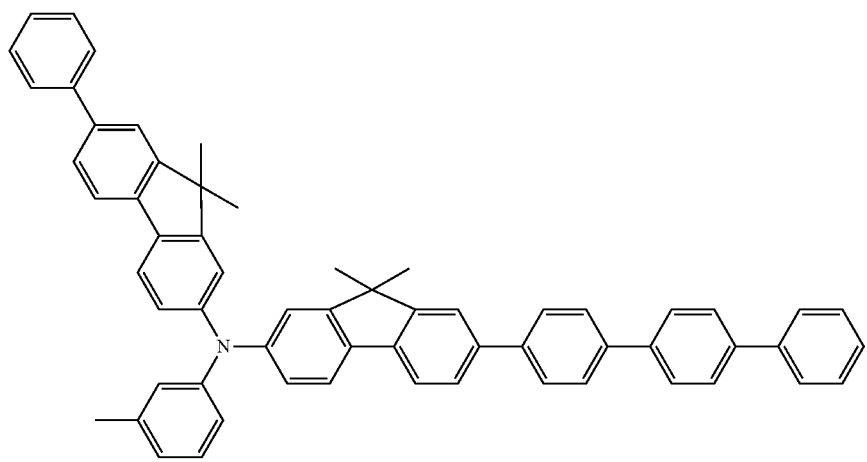

-continued
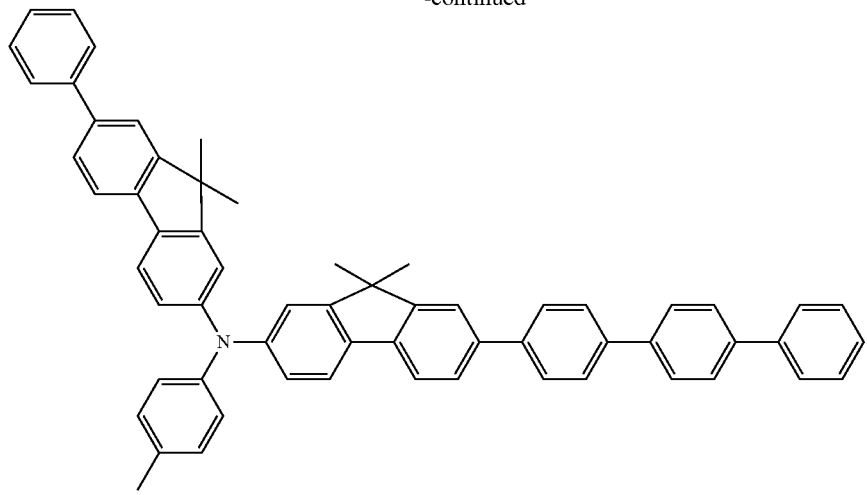
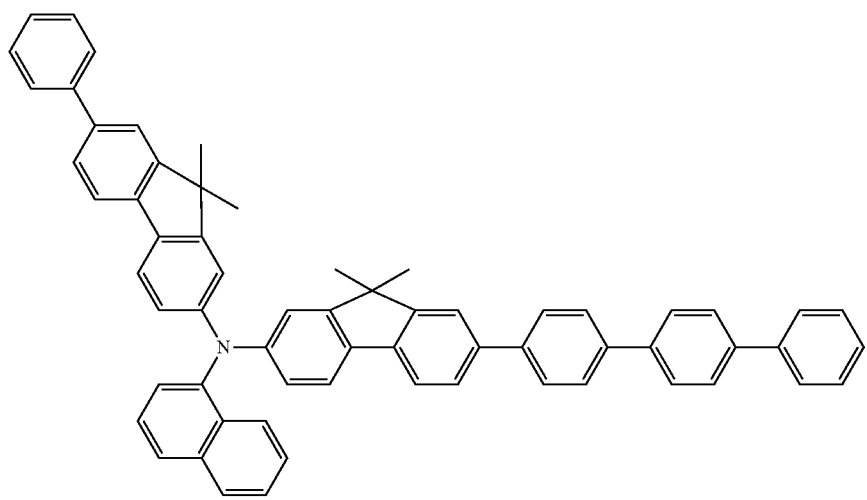
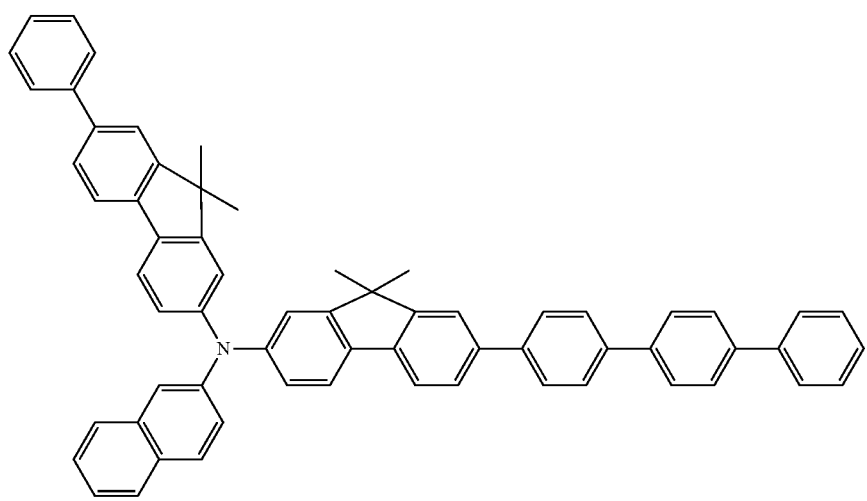

-continued
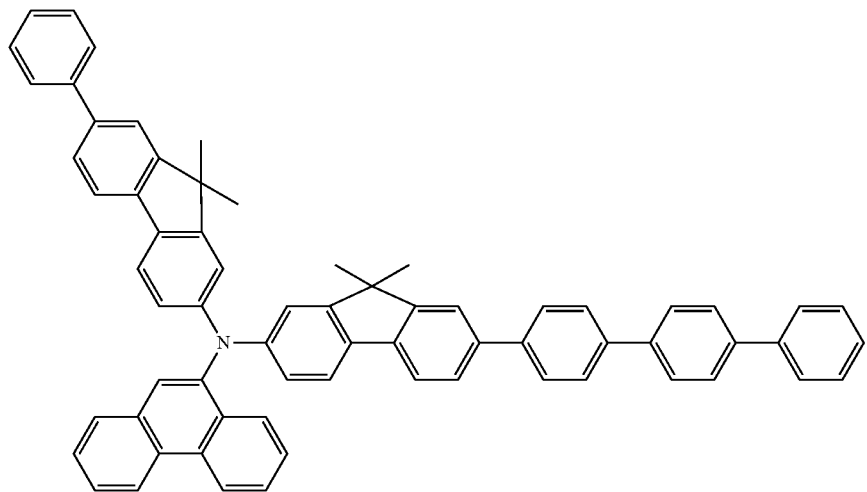
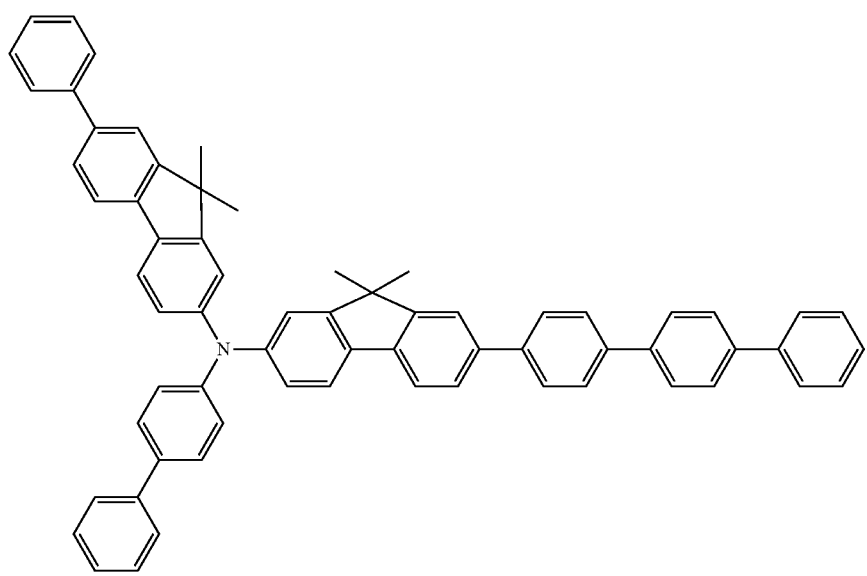
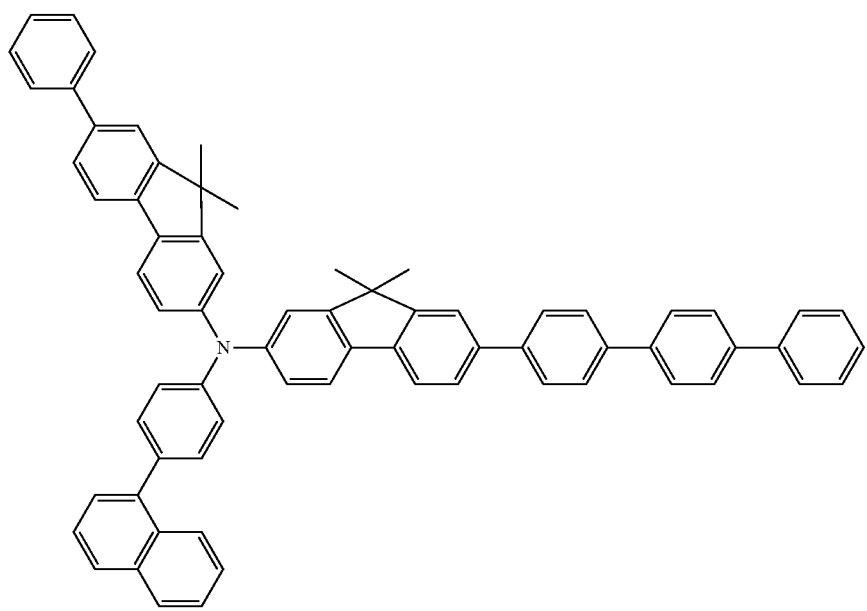

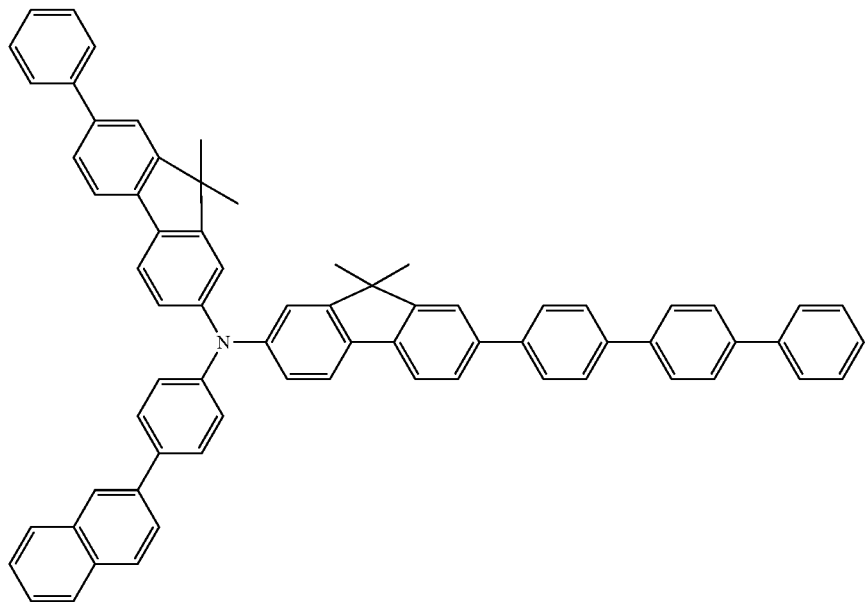
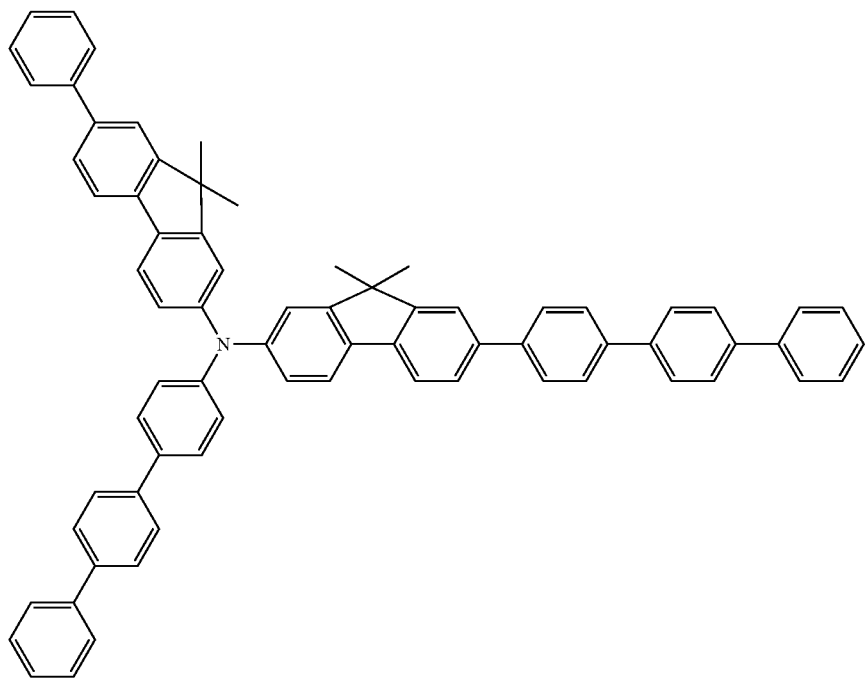

-continued
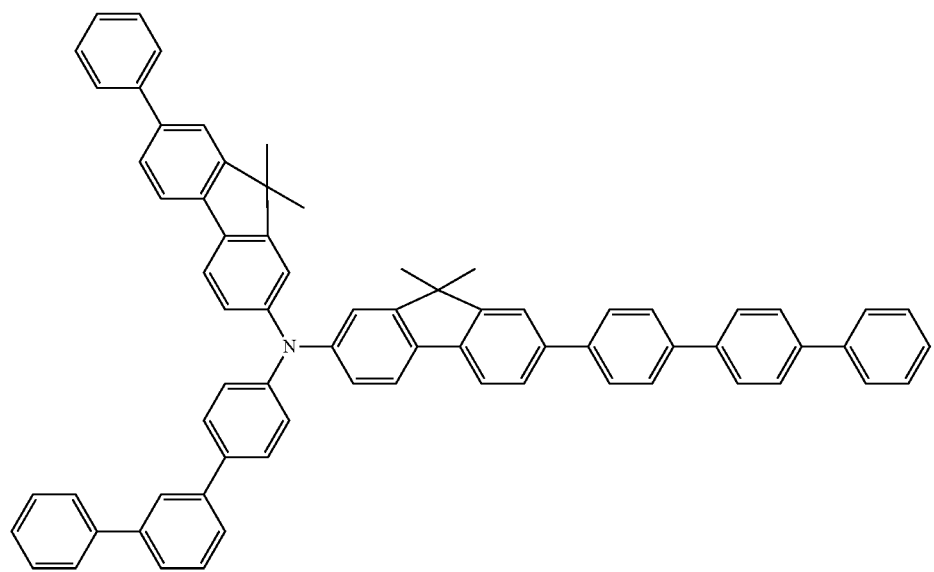
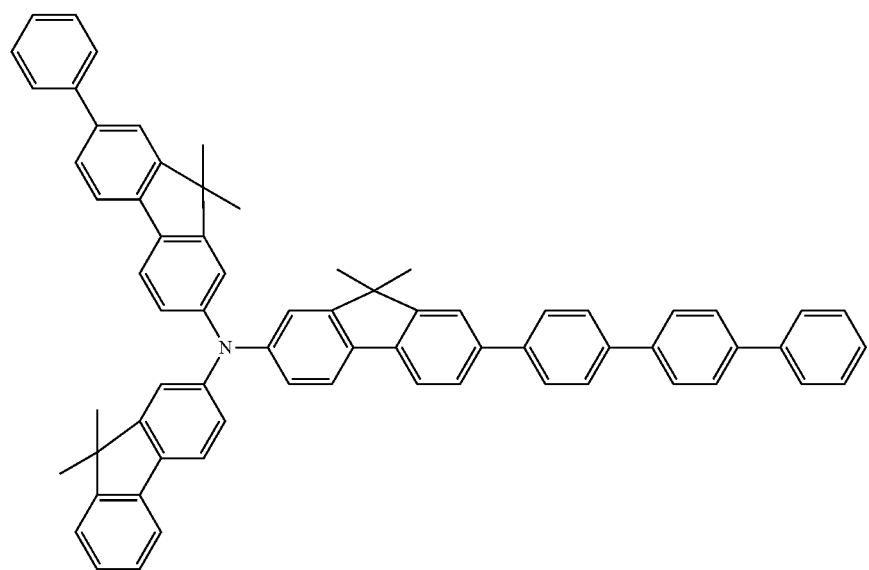

-continued
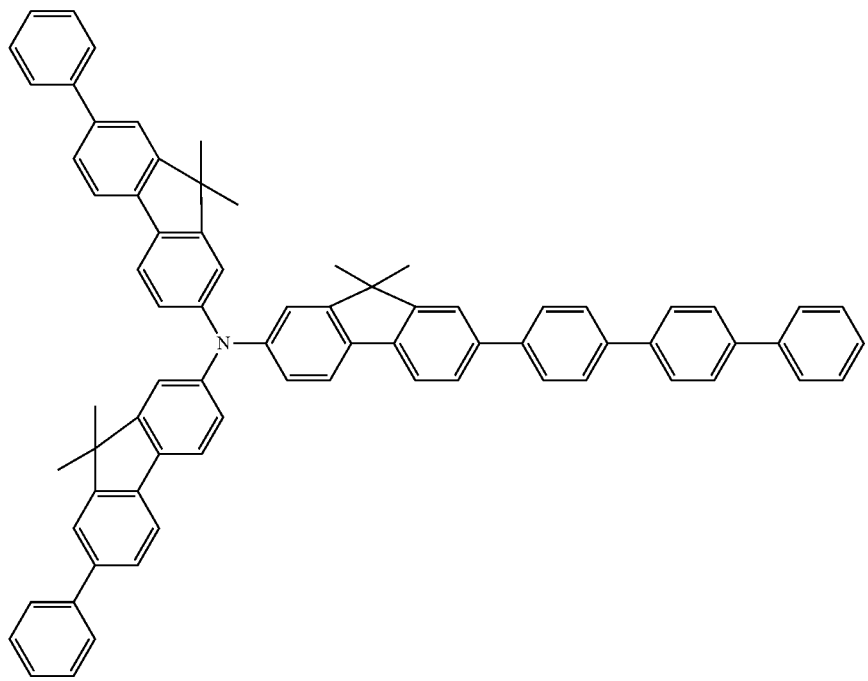
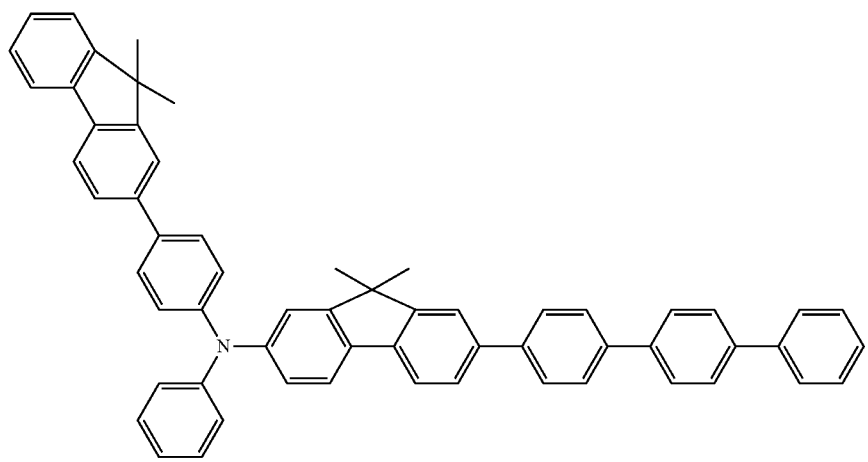
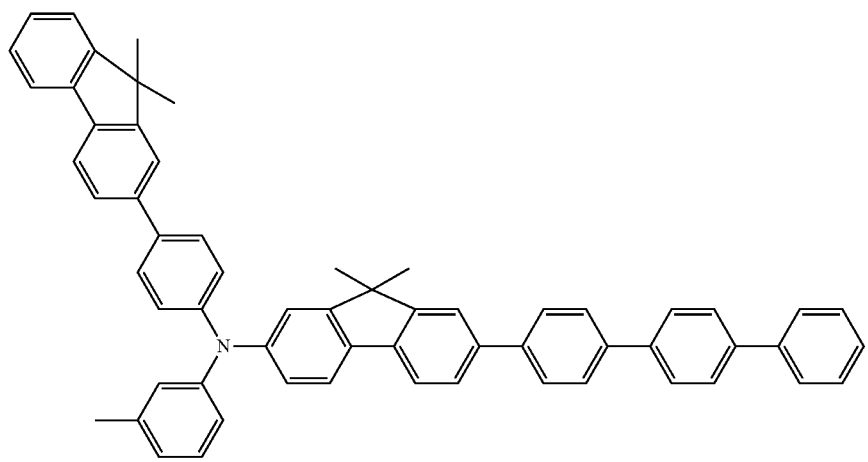

-continued
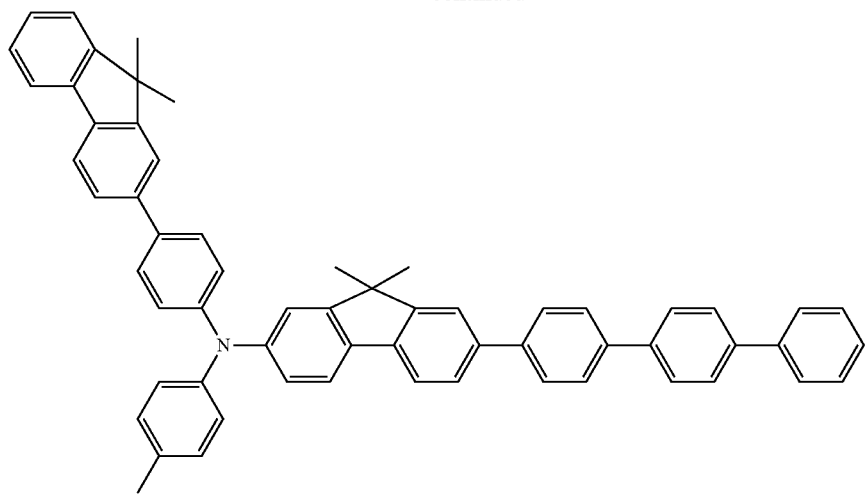
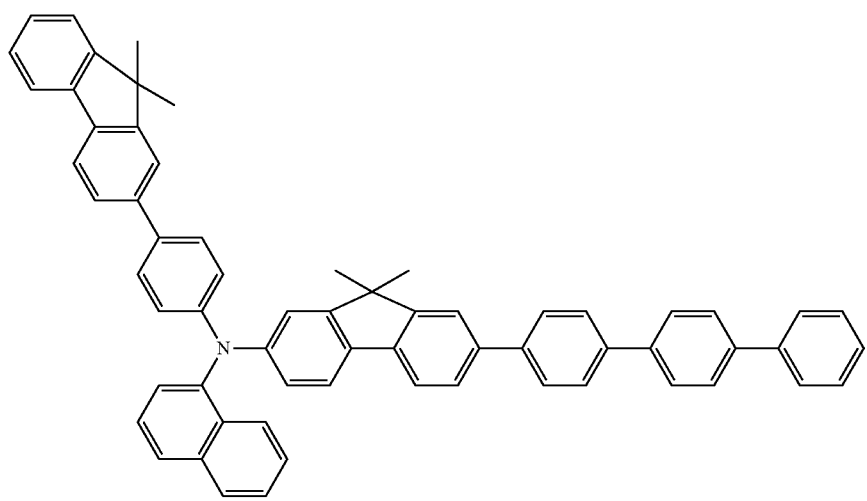
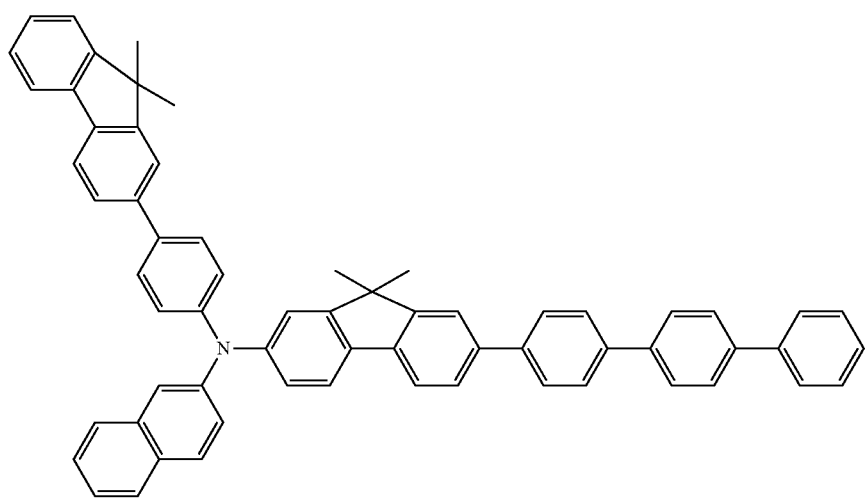

-continued
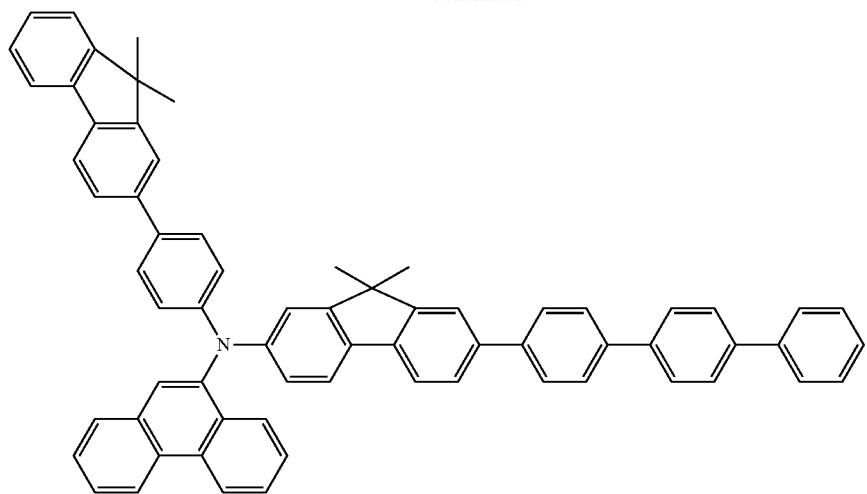
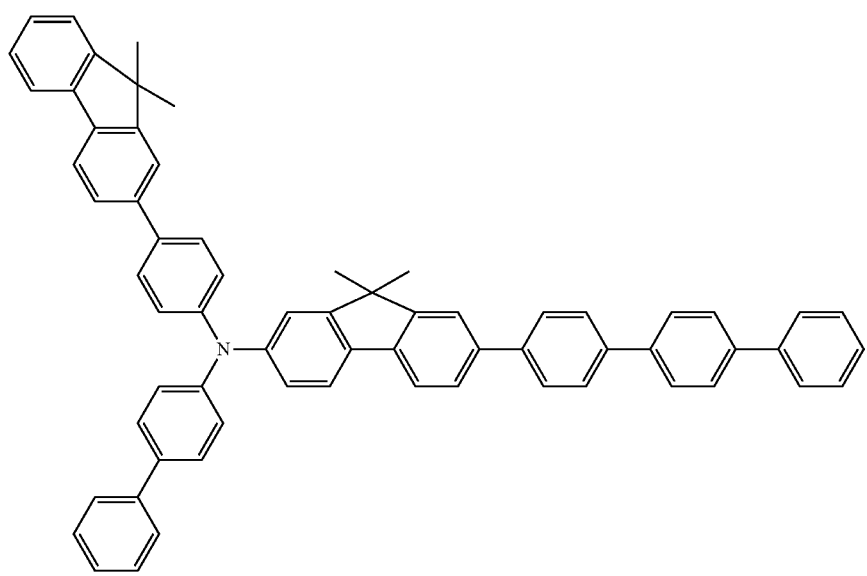
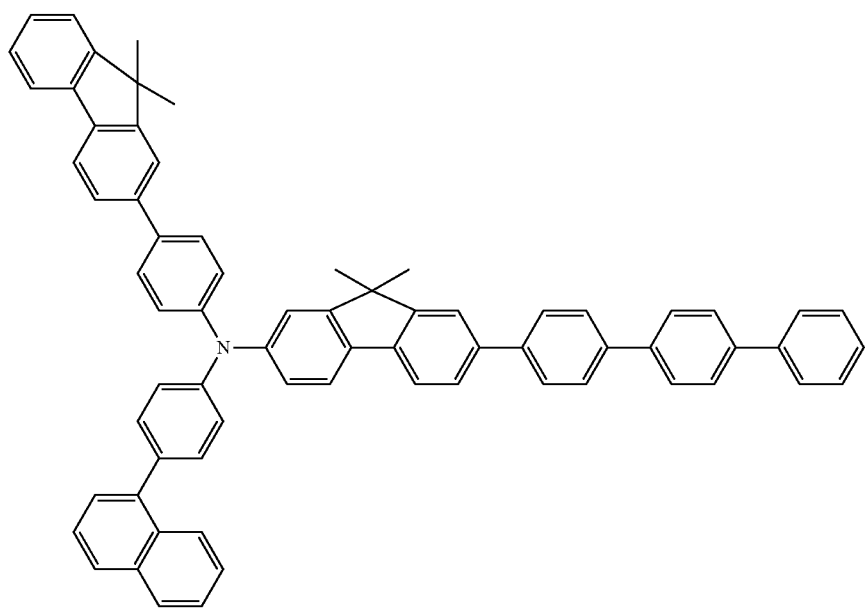

-continued
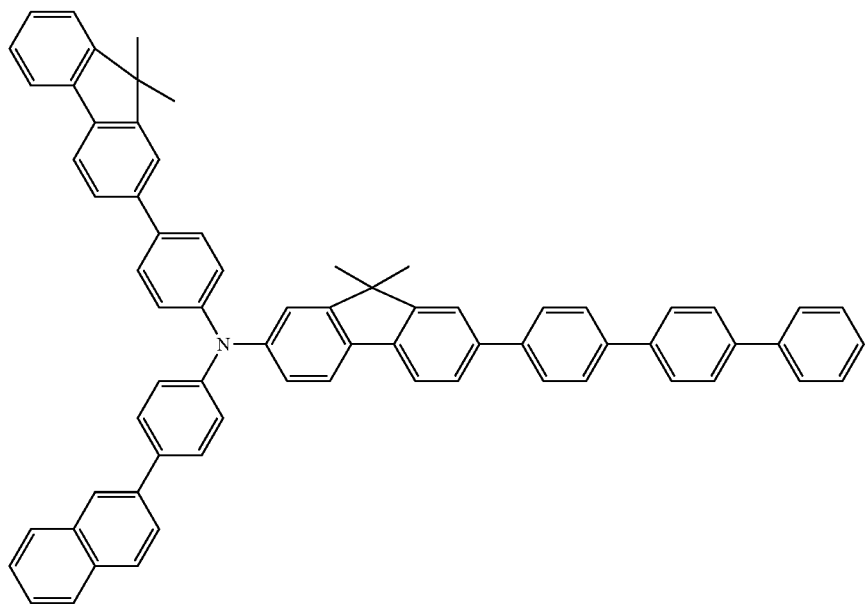
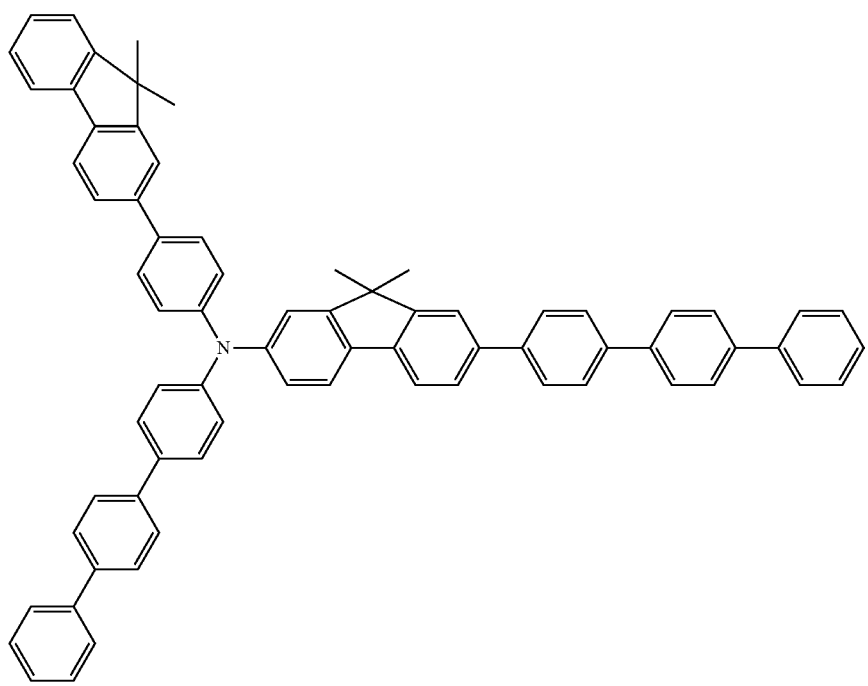

-continued
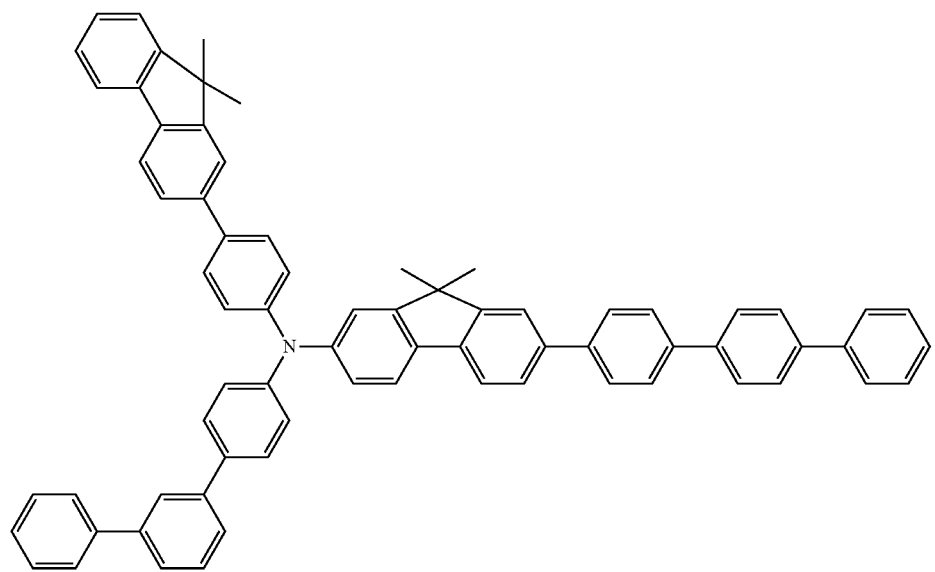
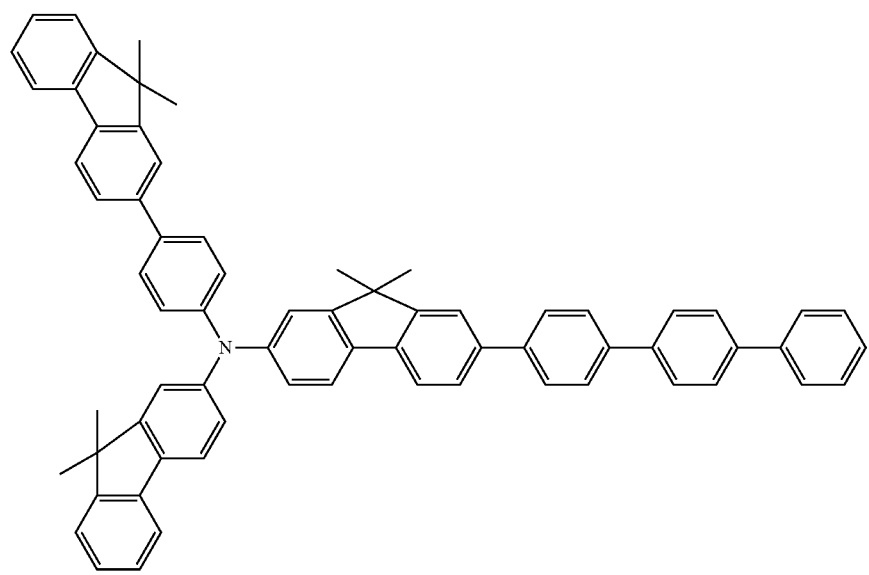

-continued

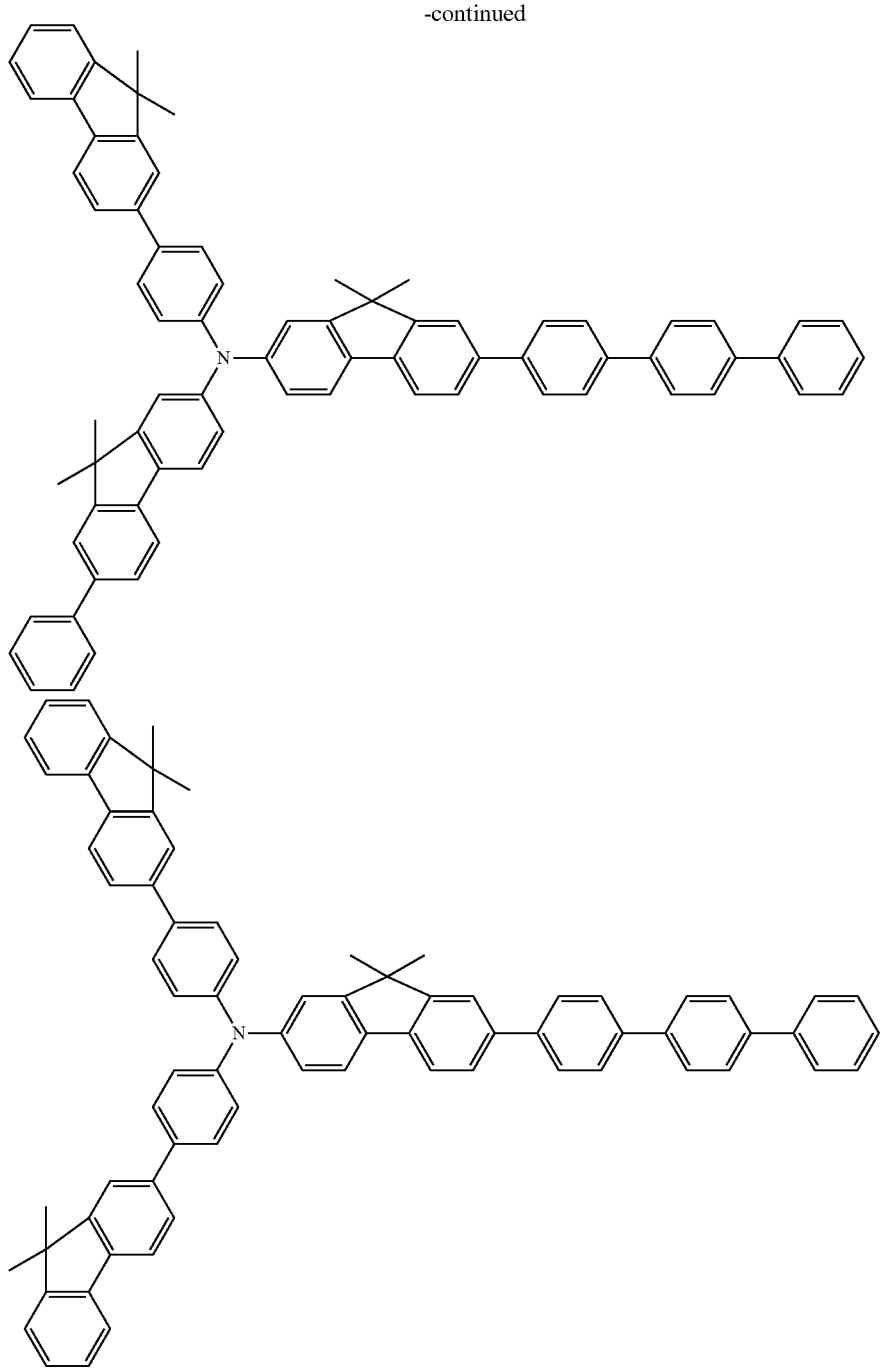

Organic Electroluminescent Device

Embodiments of the organic electroluminescent device (organic EL device) of the present invention will be described.

The organic EL device of the present invention contains a cathode and an anode facing to each other, and intervening therebetween an organic thin film layer, and has at least one organic thin film layer containing the compound represented by the general formula (1).

A preferred embodiment of the organic EL device of the present invention contains a cathode and an anode facing each other, and intervening therebetween at least two hole transporting layers and a light emitting layer sequentially, and at least one of the hole transporting layers containing the compound represented by the general formula (1) and being not adjacent to the light emitting layer.

For example, it is more preferred that the at least two hole transporting layers include a first hole transporting layer on the side of the anode and a second hole transporting layer on the side of the light emitting layer, and the first hole transporting layer contains the compound represented by the general formula (1).

In the present invention, the organic EL device may contain plural hole transporting layers, and the hole transporting layer that is not adjacent to the light emitting layer may contain the compound having a large mobility represented by the general formula (1) as a hole transporting material, whereby the driving voltage is not increased even when the thickness of the hole transporting layer thereof is increased, and the light path length of the organic EL device may be controlled, thereby achieving a high efficiency and a long service life of the device. Furthermore, it is considered that the compound represented by the general formula (1) has good affinity to the acceptor material excellent in hole injection property, and the carrier generation amount is increased to transport and inject a large amount of holes to the light emitting layer, which may lead the enhancement of the efficiency of the device. The organic EL device of the present invention is excellent as a phosphorescent organic EL device, and in addition, especially by using a heteroaryl-substituted amine derivative in the hole transporting layer adjacent to the light emitting layer, excellent advantages may be obtained not only as a phosphorescent organic EL device but also as a fluorescent organic EL device.

The organic EL device of the present invention may be a fluorescent or phosphorescent monochromic light emitting device or a fluorescent-phosphorescent hybrid white light emitting device, and may be a simple light emitting device having a single light emitting unit or a tandem light emitting device having plural light emitting units. The term "light emitting unit" herein means a minimum unit that contains at least one organic layer, at least one layer of which is a light emitting layer, and is capable of emitting light through recombination of injected holes and electrons.

The device structure of the organic EL device of the present invention will be described.

(1) Structure of Organic EL Device

Representative examples of the device structure of the organic EL device of the present invention include the following.

(1) anode/acceptor material-containing layer (acceptor layer)/first hole transporting layer/second hole transporting layer/light emitting layer/cathode (2) anode/acceptor material-containing layer (acceptor layer)/first hole transporting layer/second hole transporting layer/light emitting layer/electron injection layer/cathode (3) anode/acceptor material-containing layer (acceptor layer)/first hole transporting layer/second hole transporting layer/light emitting layer/electron transporting layer/electron injection layer/cathode (4) anode/first hole transporting layer/second hole transporting layer/light emitting layer/electron injection layer/cathode (5) anode/first hole transporting layer/second hole transporting layer/light emitting layer/electron transporting layer/electron injection layer/cathode Third, fourth and more hole transporting layers may be provided between the second hole transporting layer and the light emitting layer. An electron barrier layer or an exciton barrier layer may be provided between the light emitting layer and the hole transporting layer, and the hole transporting layer adjacent to the light emitting layer may be an electron barrier layer or an exciton barrier layer.

The hole transporting layer adjacent to the acceptor layer, for example, the first hole transporting layer adjacent to the acceptor layer in the devices structures (1) to (3), may be referred to as an acceptor layer-proximate hole transporting layer.

The organic EL device of the present invention preferably has an acceptor layer containing acceptor material between the anode and the at least two hole transporting layers (particularly the hole transporting layer that is proximate to the anode).

The hole transporting layer containing the compound represented by the general formula (1) may contain the acceptor material.

Preferred examples of the acceptor material include compounds having a skeleton with high planarity, such as compounds represented by the following general formulae (A), (B) and (C), since good coupling property may be obtained to the hole transporting layer containing the compound represented by the general formula (1), thereby further enhancing the device capability.

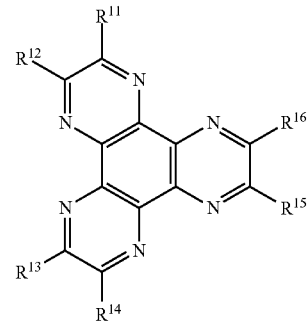

(A)

wherein in the formula (A), $R^{11}$ to $R^{16}$ each independently represent a cyano group, —$CONH_2$, a carboxyl group or —$COOR^{17}$ (wherein $R^{17}$ represents an alkyl group having from 1 to 20 carbon atoms), or represent a group represented by —CO—O—CO— by bonding $R^{11}$ and $R^{12}$, $R^{13}$ and $R^{14}$, or $R^{15}$ and $R^{16}$.

Examples of the alkyl group represented by $R^{17}$ include a methyl group, an ethyl group, a n-propyl group, an isopropyl group, a n-butyl group, an isobutyl group, a tert-butyl group, a cyclopentyl group and a cyclohexyl group.

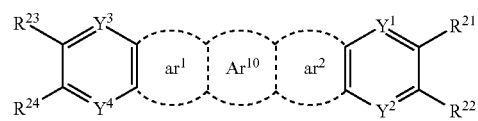

(B)

wherein in the general formula (B), $R^{21}$ to $R^{24}$ may be the same as or different from each other and each represent a hydrogen atom, a substituted or unsubstituted alkyl group having from 1 to 20 carbon atoms, a substituted or unsubstituted aryl group having from 6 to 50 ring carbon atoms, a substituted or unsubstituted heterocyclic group having from 5 to 50 ring atoms, a halogen atom, a substituted or unsubstituted fluoroalkyl group having from 1 to 20 carbon atoms, a substituted or unsubstituted alkoxy group having from 1 to 20 carbon atoms, a substituted or unsubstituted aryloxy group having from 6 to 50 ring carbon atoms, or a cyano group. The adjacent groups among $R^{21}$ to $R^{24}$ may be bonded to each other to form a ring.

$Y^1$ to $Y^4$ may be the same as or different from each other and each represent —N=, —CH= or $C(R^{25})$=, wherein $R^{25}$ represents a substituted or unsubstituted alkyl group having from 1 to 20 carbon atoms, a substituted or unsubstituted aryl group having from 6 to 50 ring carbon atoms, a substituted or unsubstituted heterocyclic group having from 5 to 50 ring atoms, a halogen atom, a substituted or unsubstituted alkoxy group having from 1 to 20 carbon atoms, a substituted or unsubstituted aryloxy group having from 6 to 50 ring carbon atoms, or a cyano group.

Ar$^{10}$ represents a condensed ring having from 6 to 24 ring carbon atoms or a heterocyclic ring having from 6 to 24 ring atoms. ar$^1$ and ar$^2$ each independently represent a ring represented by the following general formula (i) or (ii):

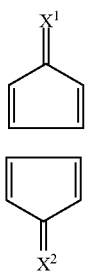

wherein X$^1$ and X$^2$ may be the same as or different from each other and each represent any one of the following divalent groups (a) to (g).

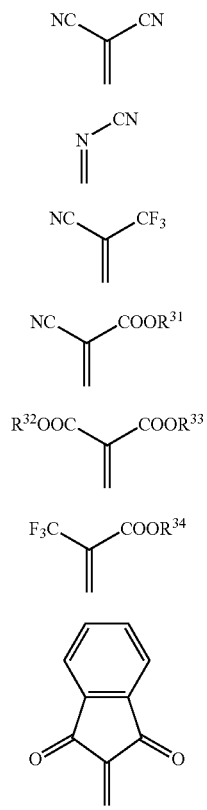

wherein R$^{31}$ to R$^{34}$ may be the same as or different from each other and each represent a hydrogen atom, a substituted or unsubstituted alkyl group having from 1 to 20 carbon atoms, a substituted or unsubstituted aryl group having from 6 to 50 ring carbon atoms or a substituted or unsubstituted heterocyclic group having from 5 to 50 ring atoms. R$^{32}$ and R$^{33}$ may be bonded to each other to form a ring.

Examples of the groups represented by R$^{21}$ to R$^{24}$ and R$^{31}$ to R$^{34}$ are as follows.

Examples of the alkyl group include a methyl group, an ethyl group, a n-propyl group, an isopropyl group, a n-butyl group, an isobutyl group, a tert-butyl group, a cyclopentyl group and a cyclohexyl group.

Examples of the aryl group include a phenyl group, a biphenyl group and a naphthyl group.

Examples of the heterocyclic group include residual groups of pyridine, pyrazine, furan, imidazole, benzimidazole and thiophene.

Examples of the halogen atom include a fluorine atom, a chlorine atom, a bromine atom and an iodine atom.

Examples of the alkoxy group include a methoxy group and an ethoxy group.

Examples of the aryloxy group include a phenyloxy group.

These groups may have a substituent. Examples of the substituted aryl group include an aryl group substituted by a halogen atom, such as a monofluorophenyl group and a trifluoromethylphenyl group; and an aryl group substituted by an alkyl group having from 1 to 10 (preferably from 1 to 5) carbon atoms, such as a tolyl group and a 4-t-butylphenyl group. Examples of the substituted alkyl group include an alkyl group substituted by a halogen atom, such as a trifluoromethyl group, a pentafluoroethyl group, a perfluorocyclohexyl group and a perfluoroadamantyl group. Examples of the substituted aryloxy group include an aryloxy group substituted by a halogen atom or substituted by a halogen atom-containing alkyl group (having from 1 to 5 carbon atoms), such as a 4-trifluoromethylphenyloxy group and a pentafluorophenyloxy group; and an aryloxy group substituted by an alkyl group having from 1 to 10 (preferably from 1 to 5) carbon atoms, such as a 4-t-butylphenoxy group.

The adjacent groups among R$^{21}$ to R$^{24}$ may be bonded to each other to form a ring. Examples of the ring include a benzene ring, a naphthalene ring, a pyrazine ring, a pyridine ring and a furan ring.

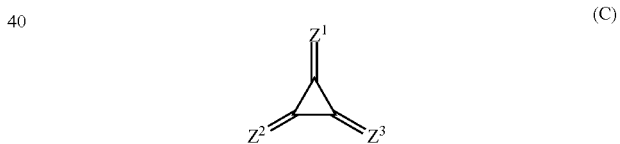

wherein in the formula (C), Z$^1$ to Z$^3$ each independently represent a divalent group represented by the following general formula (h):

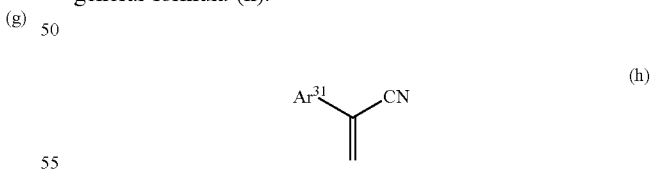

wherein in the formula (h), Ar$^{31}$ represents a substituted or unsubstituted aryl group having from 6 to 50 ring carbon atoms or a substituted or unsubstituted heteroaryl group having from 5 to 50 ring atoms.

Examples of the aryl group include a phenyl group and a naphthyl group.

Examples of the heteroaryl group include pyridine, pyrazine, pyrimidine, quinoline and isoquinoline.

Examples of the substituent thereon include an electron attracting group, such as a cyano group, a fluoro group, a trifluoromethyl group, a chloro group and a bromo group.

(2) Light Transmissive Substrate

The organic EL device of the present invention may be provided on a light transmissive substrate. The light transmissive substrate herein is a substrate for supporting the organic EL device, and is preferably a smooth substrate that has a light transmittance of 50% or more for light in the visible region of from 400 to 700 nm.

Specific examples thereof include a glass plate and a polymer plate. Examples of the glass plate include soda-lime glass, barium-strontium-containing glass, lead glass, aluminosilicate glass, borosilicate glass, barium-borosilicate glass and quartz. Examples of the polymer plate include polycarbonate, an acrylic resin, polyethylene terephthalate, polyether sulfide and polysulfone.

(3) Anode

The anode of the organic EL device of the present invention has a function of injecting holes to the hole transporting layer or the light emitting layer, and it is effective to have a work function of 4.5 eV or more. Specific examples of the material for the anode used in the present invention include indium tin oxide (ITO), tin oxide (NESA), indium zinc oxide (IZO), gold, silver, platinum and copper.

The anode may be produced by forming the electrode material into a thin film by such a method as a vapor deposition method and a sputtering method.

In the case where the light emitted from the light emitting layer is taken out through the anode, the anode preferably has a transmittance to the emitted light of 10% or more. The sheet resistance of the anode is preferably several hundred Ω per square or less. The thickness of the anode is generally selected from the range of from 10 nm to 1 μm, and preferably from the range of from 10 to 200 nm.

(4) Hole Transporting Layer

The organic EL device according to the preferred embodiment of the present invention has two or more hole transporting layers.

The hole transporting layer that is not adjacent to the light emitting layer may often be used in the form of a thick layer for optical adjustment of the organic EL layer, and may be demanded to have a large hole mobility for achieving a low driving voltage. Furthermore, the layer may often be laminated with the acceptor layer for generating the carrier efficiently, and may be demanded to exhibit high mutual action with the acceptor layer.

The compound represented by the general formula (1) of the present invention has a fluorene structure and thus has high planarity of the molecule, which provides a large hole mobility, as compared to a biphenyl structure. Furthermore, the compound is generally excellent in mutual action with an acceptor material having high planarity and thus provides a large carrier generation amount, and therefore, a larger amount of holes may be injected to the light emitting layer. Accordingly, the compound represented by the general formula (1) of the present invention satisfies the characteristics that are demanded for the hole transporting layer that is not adjacent to the light emitting layer (which corresponds to the first hole transporting layer in the case where there are two hole transporting layers), and thus is preferably used as the material for the hole transporting layer that is not adjacent to the light emitting layer.

The characteristics that are demanded for the hole transporting layer that is adjacent to the light emitting layer (which corresponds to the second hole transporting layer in the case where there are two hole transporting layers) include a large triplet energy (preferably 2.6 eV or more) for preventing the excitation energy of the light emitting layer from being diffused, electroresistance since the layer is adjacent to the light emitting layer, an organic layer that has a small affinity (preferably 2.4 eV or less) for preventing electrons from being leaked from the light emitting layer, and an organic layer that has a large ionization potential (preferably 5.5 eV or more) for facilitating hole injection to the light emitting layer. As a material that satisfies the characteristics, a heteroaryl-substituted amine derivative is preferred for providing not only an excellent phosphorescent organic EL device but also an excellent fluorescent organic EL device, and more preferred examples of the compound include compounds represented by the following general formulae (4) to (8).

Example of Material for Hole Transporting Layer Adjacent to Light Emitting Layer (Second Hole Transporting Material), General Formula (4)

wherein in the formula (4), at least one of $Ar^{11}$ to $Ar^{13}$ represents a group represented by the following general formula (4-2) or (4-4); the group that is not represented by the general formula (4-2) is a group represented by the following general formula (4-3) or (4-4) or a substituted or unsubstituted aryl group having from 6 to 40 ring carbon atoms; and the group that is not represented by the general formula (4-4) is a group represented by the following general formula (4-2) or (4-3) or a substituted or unsubstituted aryl group having from 6 to 40 ring carbon atoms.

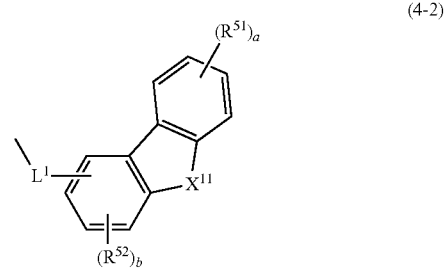

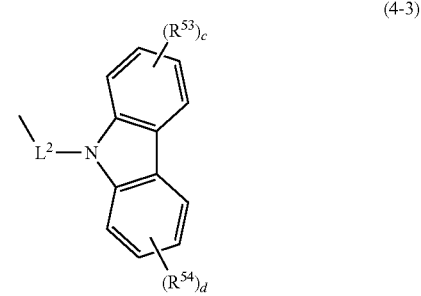

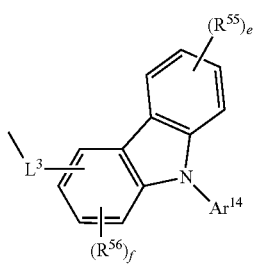

(4-4)

wherein $X^{11}$ represents an oxygen atom or a sulfur atom.

$L^1$ to $L^3$ each independently represent a single bond or a substituted or unsubstituted arylene group having from 6 to ring carbon atoms, and the substituent that may be substituted on $L^1$ to $L^3$ is a linear or branched alkyl group having from 1 to 10 carbon atoms, a cycloalkyl group having from 3 to 10 ring carbon atoms, a trialkylsilyl group having from 3 to 10 carbon atoms, a triarylsilyl group having from 18 to 30 ring carbon atoms, an alkylarylsilyl group having from 8 to 15 carbon atoms (wherein the alkyl group has from 1 to 5 carbon atoms, and the aryl group has from 6 to 14 ring carbon atoms), an aryl group having from 6 to 50 ring carbon atoms, a halogen atom or a cyano group.

$Ar^{14}$ represents a substituted or unsubstituted aryl group having from 6 to 50 ring carbon atoms, and the substituent that may be substituted on $Ar^{14}$ is a linear or branched alkyl group having from 1 to 10 carbon atoms, a cycloalkyl group having from 3 to 10 ring carbon atoms, a trialkylsilyl group having from 3 to 10 carbon atoms, a triarylsilyl group having from 18 to 30 ring carbon atoms, an alkylarylsilyl group having from 8 to 15 carbon atoms (wherein the alkyl group has from 1 to 5 carbon atoms, and the aryl group has from 6 to 14 ring carbon atoms), an aryl group having from 6 to 50 ring carbon atoms, a halogen atom or a cyano group.

$R^{51}$ to $R^{56}$ each independently represent a substituted or unsubstituted and linear or branched alkyl group having from 1 to 10 carbon atoms, a substituted or unsubstituted cycloalkyl group having from 3 to 10 ring carbon atoms, a substituted or unsubstituted trialkylsilyl group having from 3 to 10 carbon atoms, a substituted or unsubstituted triarylsilyl group having from 18 to 30 ring carbon atoms, a substituted or unsubstituted alkylarylsilyl group having from 8 to 15 carbon atoms (wherein the alkyl group has from 1 to 5 carbon atoms, and the aryl group has from 6 to 14 ring carbon atoms), a substituted or unsubstituted aryl group having from 6 to 50 ring carbon atoms, a halogen atom or a cyano group. The adjacent groups of $R^{51}$ to $R^{56}$ may be bonded to each other to form a ring.

b and f each independently represent an integer of from 0 to 3; and a, c, d and e each independently represent an integer of from 0 to 4.

Examples of the arylene group represented by $L^1$ to $L^3$ include a phenylene group, a naphthylene group, a biphenylene group, an anthrylene group, an acenaphthylenyl group, an anthranylene group, a phenanthrenylene group, a phenalenyl group, a quinolylene group, an isoquinolylene group, an s-indacenylene group, an as-indacenylene group and a chrysenylene group. Among these, an arylene group having from 6 to 30 ring carbon atoms is preferred, an arylene group having from 6 to 20 ring carbon atoms is more preferred, an arylene group having from 6 to 12 ring carbon atoms is further preferred, and a phenylene group is particularly preferred.

The balance of the groups will be described below, and the same description may be applied to the same group.

The alkyl group is preferably an alkyl group having from 1 to 5 carbon atoms, and more preferably an alkyl group having from 1 to 3 carbon atoms. Examples of the alkyl group include a methyl group, an ethyl group, a n-propyl group, an isopropyl group, a n-butyl group, an isobutyl group, a t-butyl group and a n-hexyl group.

Examples of the alkyl group in the trialkylsilyl group are the same as above, and preferred examples thereof are also the same. Examples of the aryl group in the triarylsilyl group include a phenyl group, a naphthyl group and a biphenyl group.

Examples of alkylarylsilyl group include a dialkylmonoarylsily group. The alkyl group may have from 1 to 5 carbon atoms, and preferably from 1 to 3 carbon atoms. The aryl group may have from 6 to 14 ring carbon atoms, and preferably from 6 to 10 ring carbon atoms.

Examples of the aryl group having from 6 to 50 ring carbon atoms include a phenyl group, a naphthyl group, a biphenyl group, an anthryl group, a phenanthryl group and a terphenylyl group. Among these, an aryl group having from 6 to 30 ring carbon atoms is preferred, an aryl group having from 6 to 20 ring carbon atoms is more preferred, and an aryl group having from 6 to 12 ring carbon atoms is further preferred.

Examples of the halogen atom include a fluorine atom, a chlorine atom and an iodine atom.

a to f are each preferably 0 or 1, and more preferably 0.

Preferred examples of the general formula (4-2) include the following general formulae (4-2') and (4-2'') (wherein the definitions of the groups are the same as above).

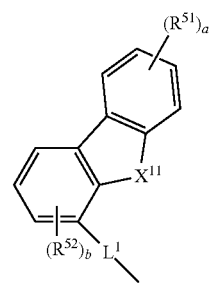

(4-2')

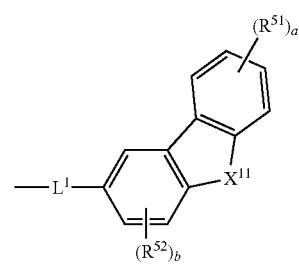

(4-2'')

Preferred examples of the general formula (4-4) include the following general formula (4-4') (wherein the definitions of the groups are the same as above).

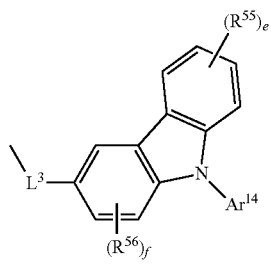

(4-4')

In the formula (4), it is preferred that at least one of $Ar^{11}$ to $Ar^{13}$ represents a group represented by the general formula (4-2). $X^{11}$ in the general formula (4-2) is preferably an oxygen atom.

It is preferred that two of $Ar^{11}$ to $Ar^{13}$ each are a group represented by the general formula (4-2), it is preferred that one of them is a group represented by the general formula (4-2) and another one of them is a group represented by the general formula (4-3), and it is preferred that three of them are each a group represented by the general formula (4-2).

In the case where $L^1$ in the general formula (4-2) represents an arylene group, or in the case where $L^3$ in the general formula (4-4) represents an arylene group, increase of the electron density of the compound represented by the general formula (4) is suppressed, the Ip is increased, and the hole injection to the light emitting layer is facilitated, whereby the driving voltage of the device tends to be lowered advantageously. When a dibenzofuran structure or a carbazole structure is bonded to the nitrogen atom through an arylene group, the amine is difficult to be oxidized, and the compound is often stabilized, which may prolong the service life of the device. In the case where $L^3$ in the general formula (4-4) represents an arylene group, the compound may be stabilized and thus may be easily synthesized. The arylene group is particularly preferably a phenylene group.

In the general formula (4), in the case where all $Ar^{11}$ to $Ar^{13}$ are not a group represented by any one of the general formulae (4-2) to (4-4), $Ar^{11}$ to $Ar^{13}$ each represent an aryl group having from 6 to 40 ring carbon atoms. The aryl group is preferably represented by the following general formulae (4-5) to (4-7):

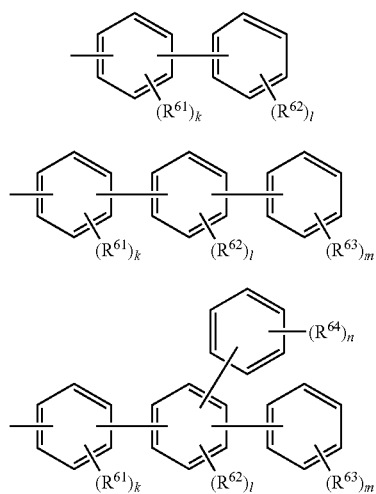

wherein $R^{61}$ to $R^{64}$ each independently represent a linear or branched alkyl group having from 1 to 10 carbon atoms, a cycloalkyl group having from 3 to 10 ring carbon atoms, a trialkylsilyl group having from 3 to 10 carbon atoms, a triarylsilyl group having from 18 to 30 ring carbon atoms, an alkylarylsilyl group having from 8 to 15 carbon atoms (wherein the aryl moiety has from 6 to 14 ring carbon atoms), an aryl group having from 6 to 50 ring carbon atoms, a halogen atom or a cyano group. The adjacent groups of $R^{61}$ to $R^{64}$ may be bonded to each other to form a ring.

k, l, m and n each independently represent an integer of from 0 to 4.

Furthermore, the general formulae (4-5) to (4-7) are preferably the following general formulae (4-5') to (4-7') (wherein the definitions of the groups are the same as above).

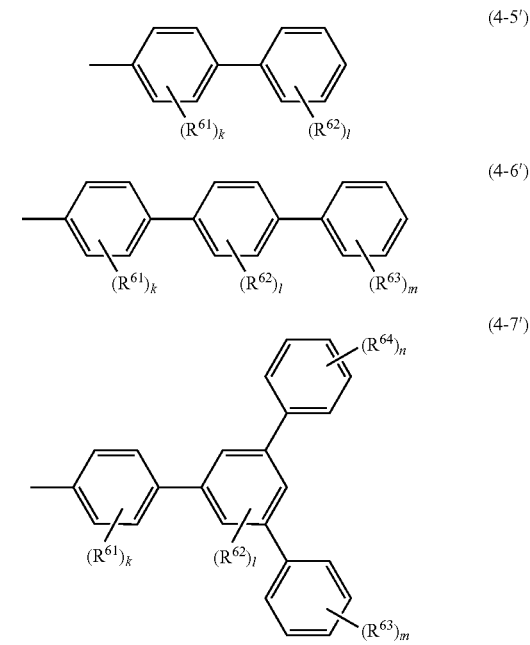

The general formula (4-5') includes the following groups.

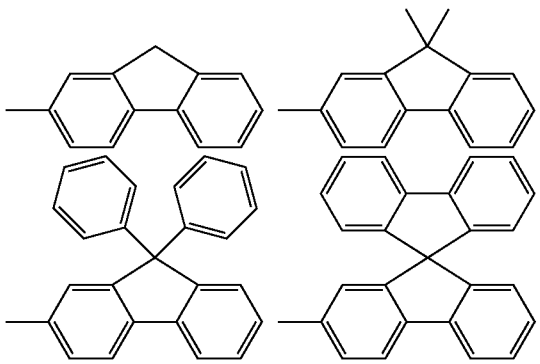

Specific examples of the compound represented by the general formula (4) are shown below, but the compound is not limited to these example compounds.

163 164
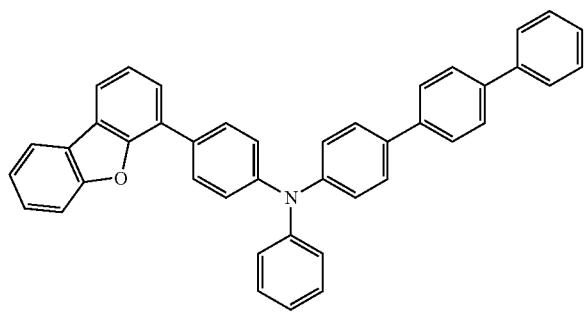
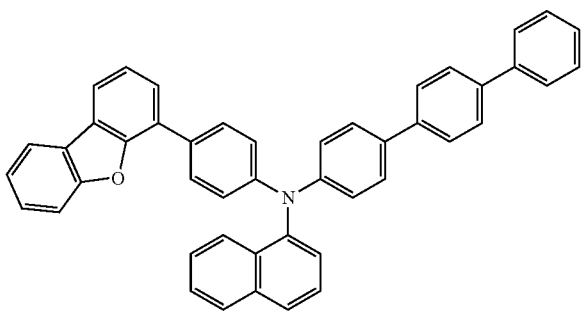
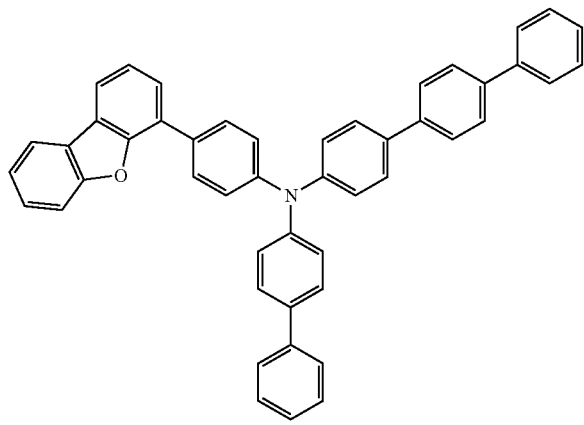
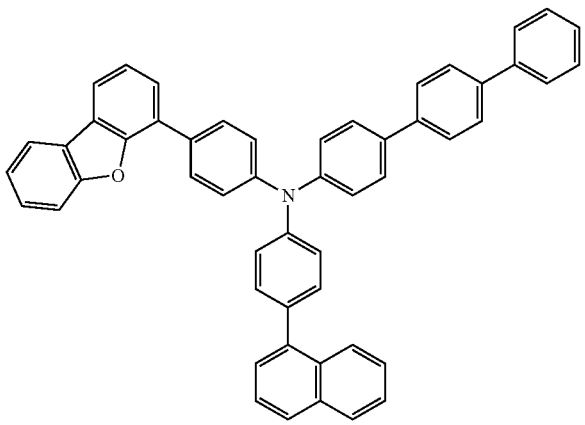
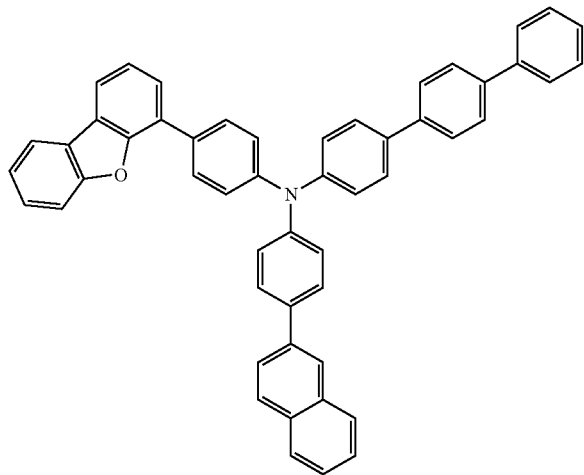
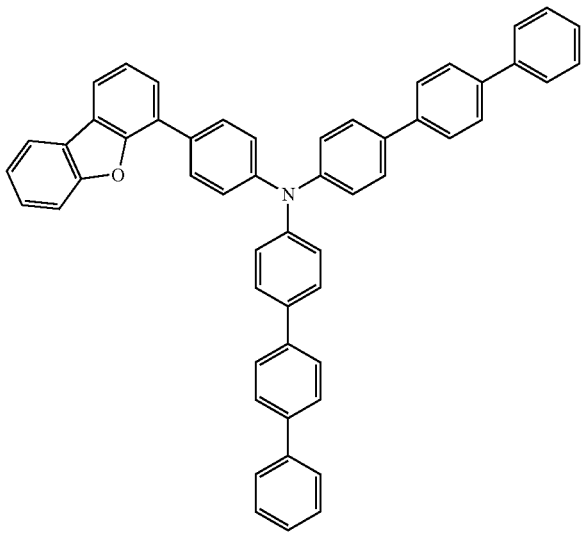
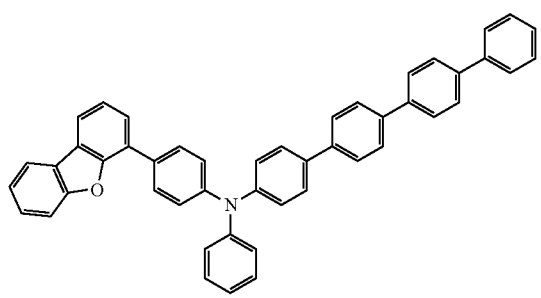
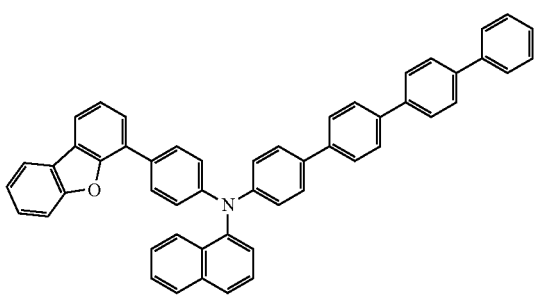

165 166
-continued
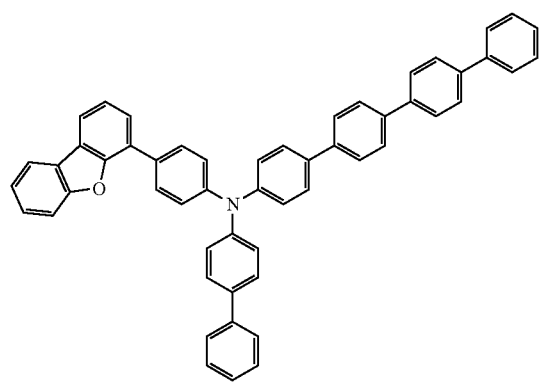
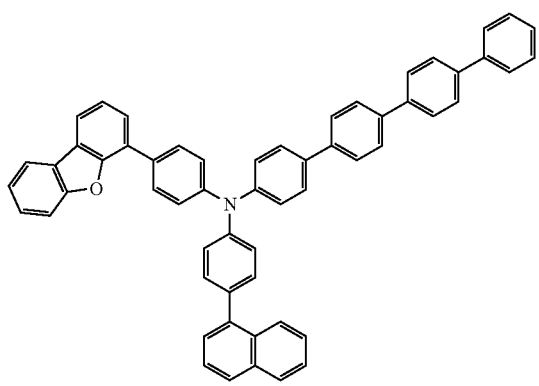
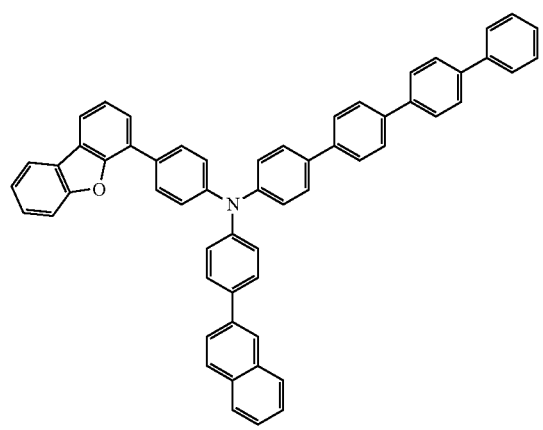
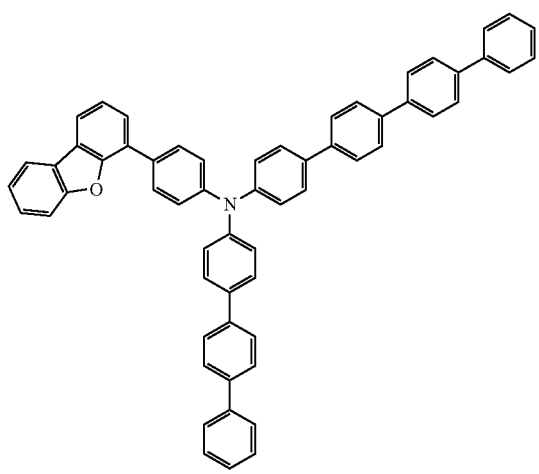
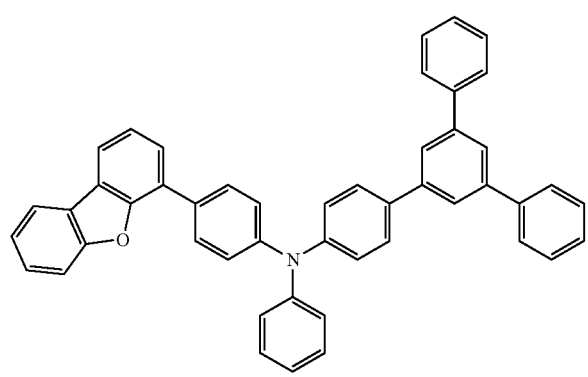
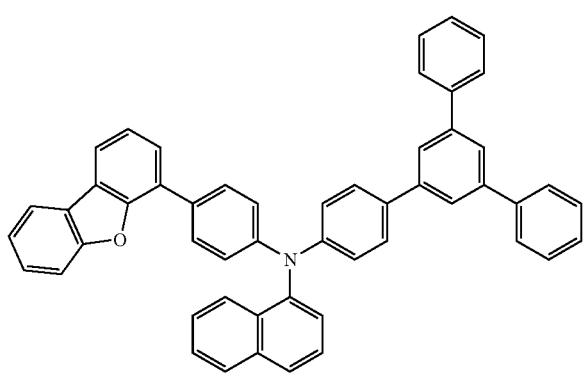
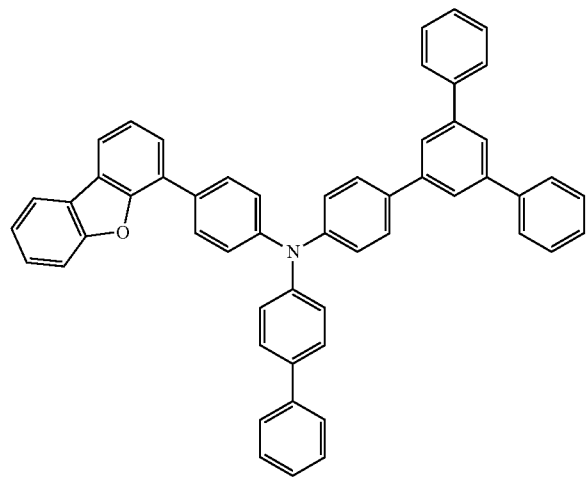
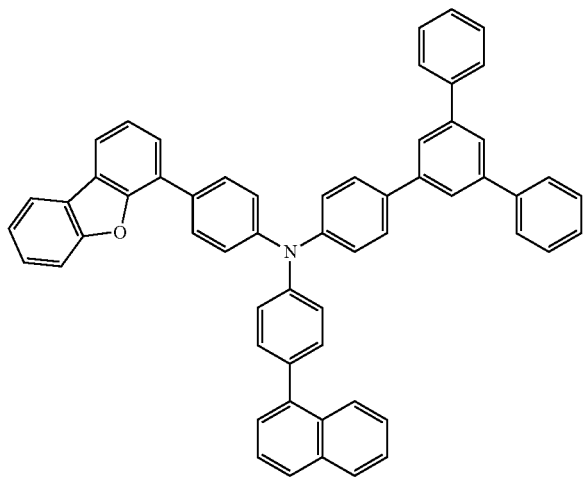

-continued
167
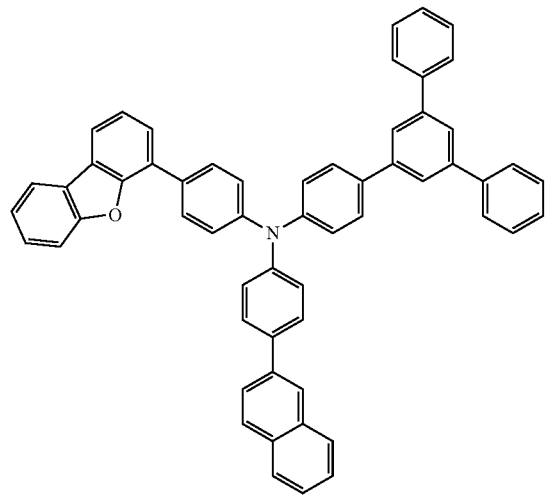
168
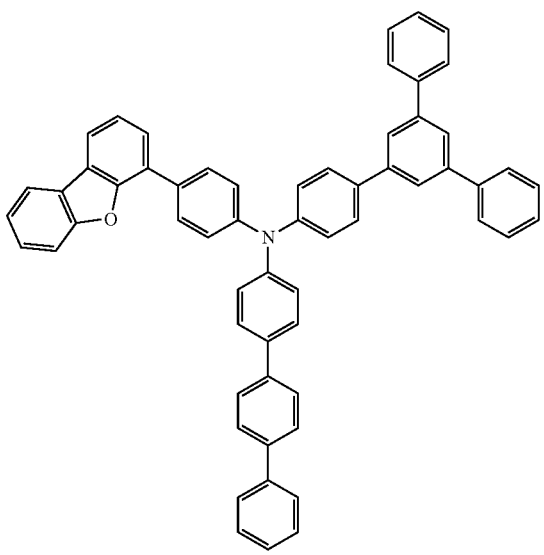
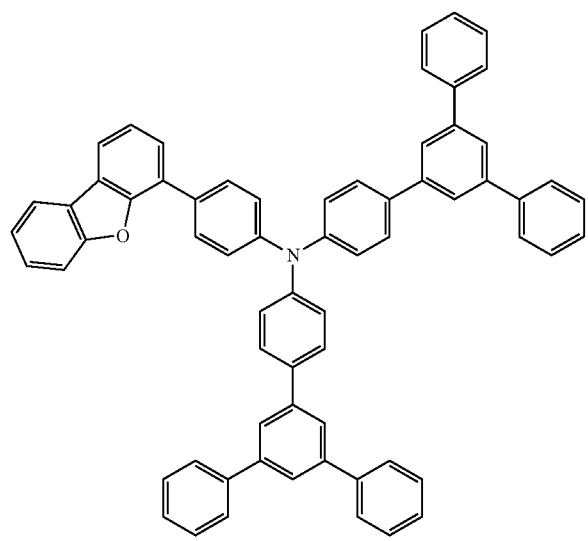
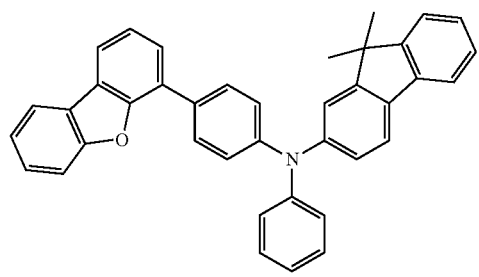
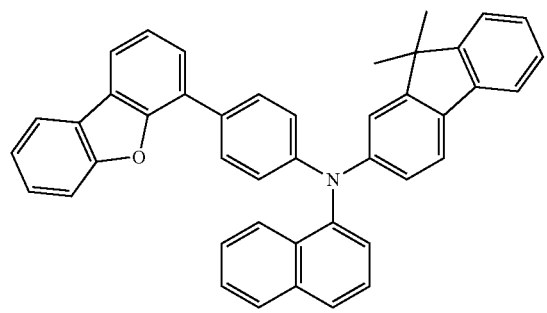
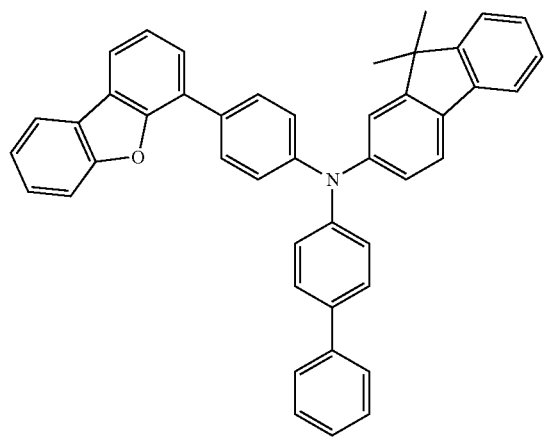

-continued
169
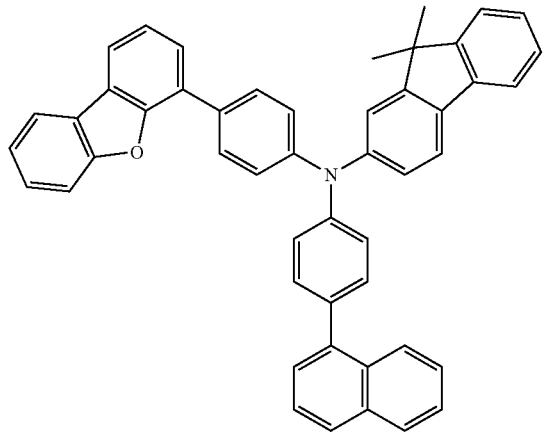
170
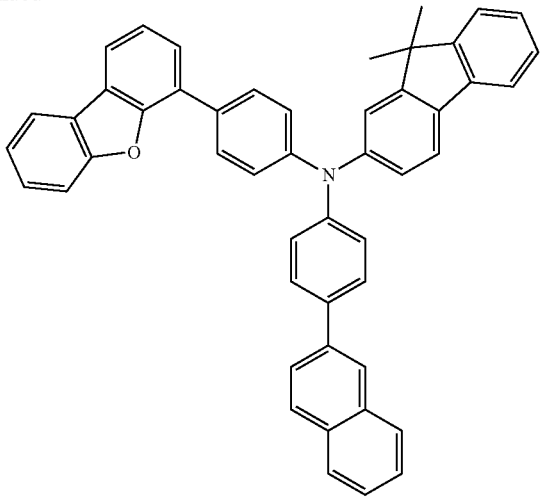
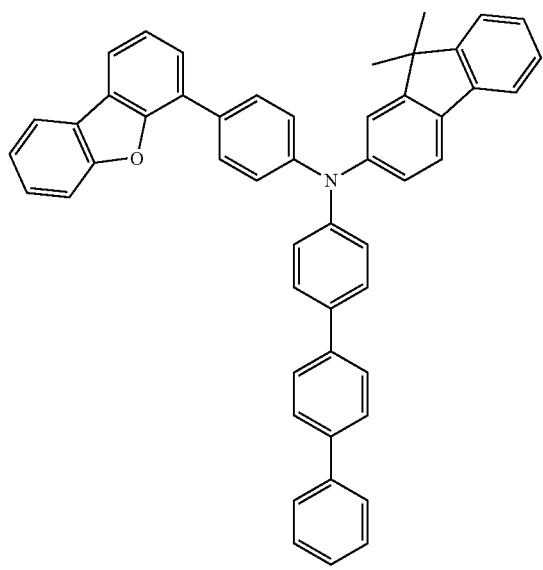
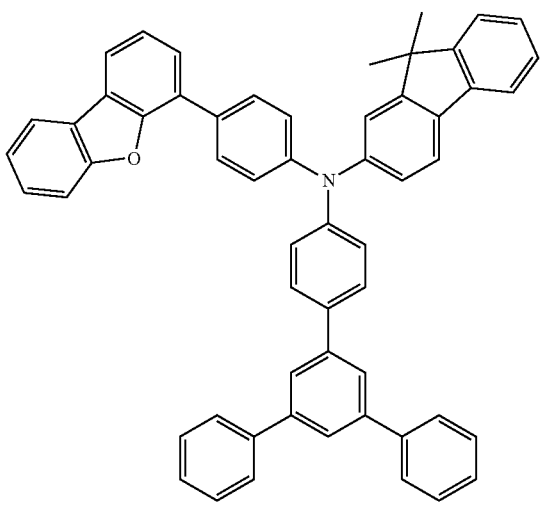
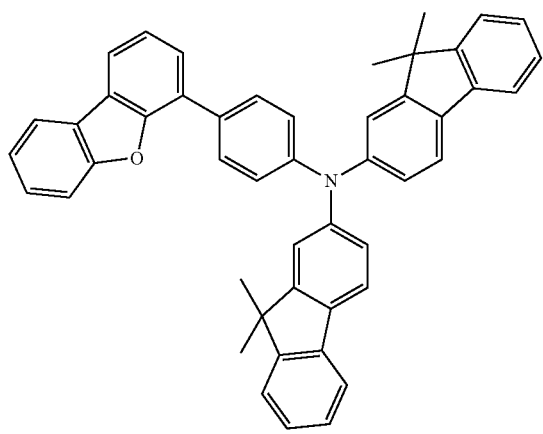
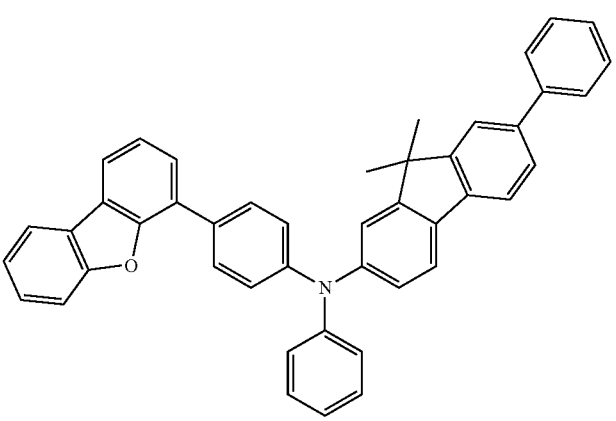

-continued
171
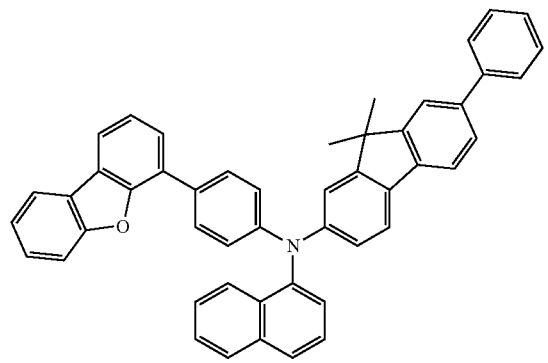
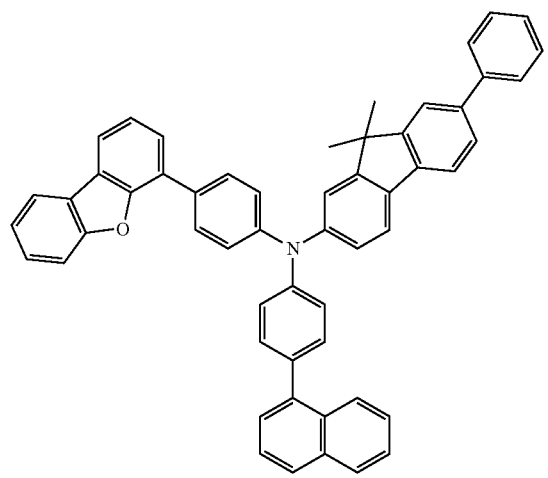
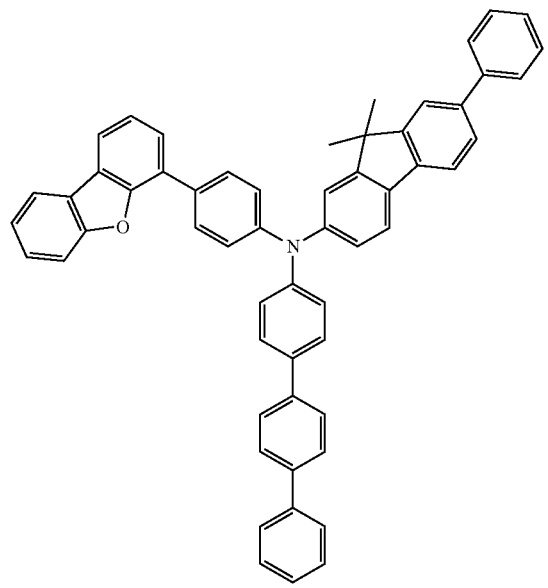
172
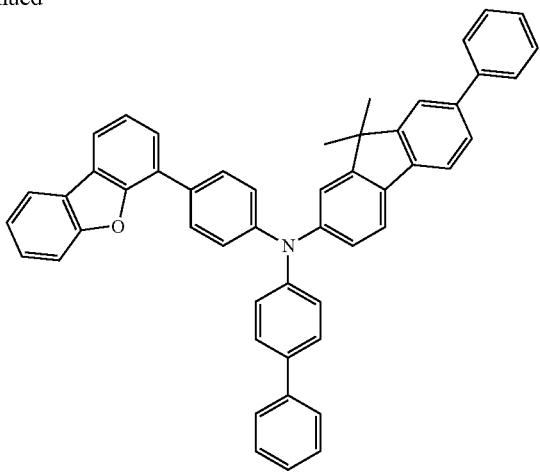
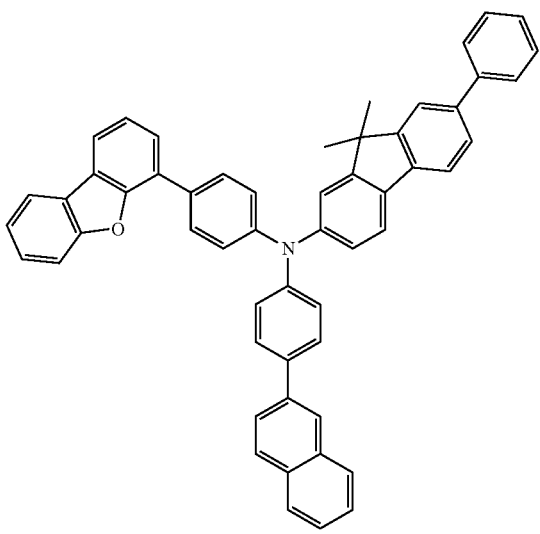
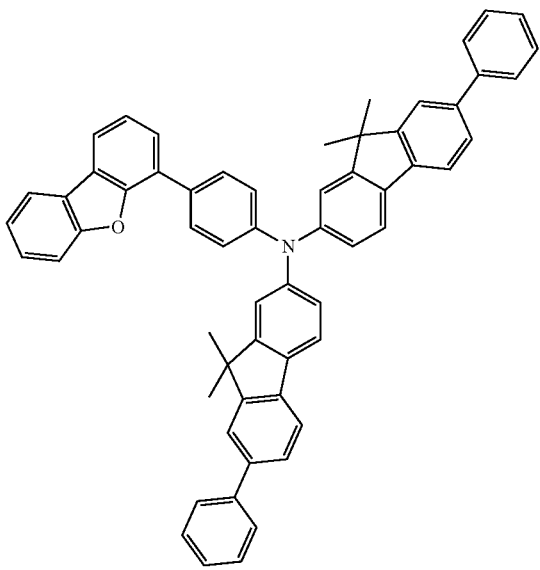

-continued
| 173 | 174 |
|---|---|
| 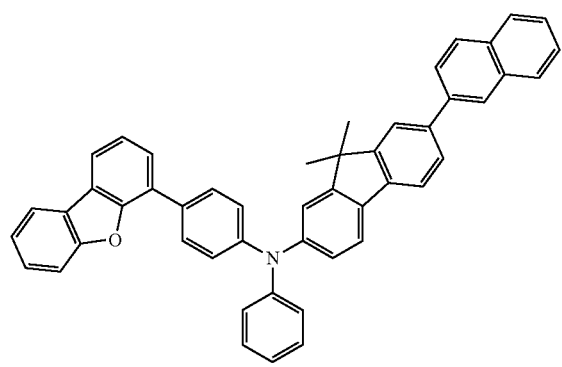 | 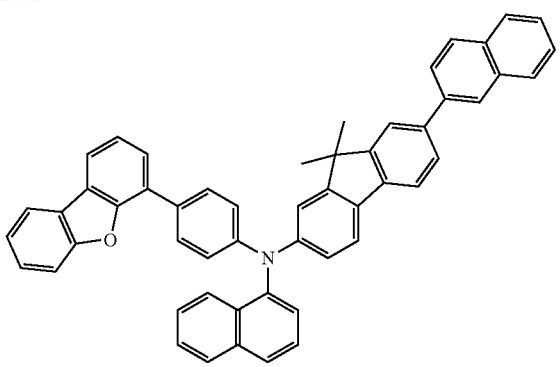 |
| 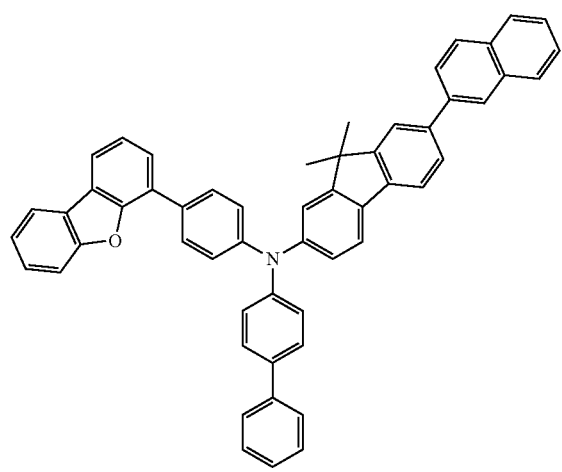 | 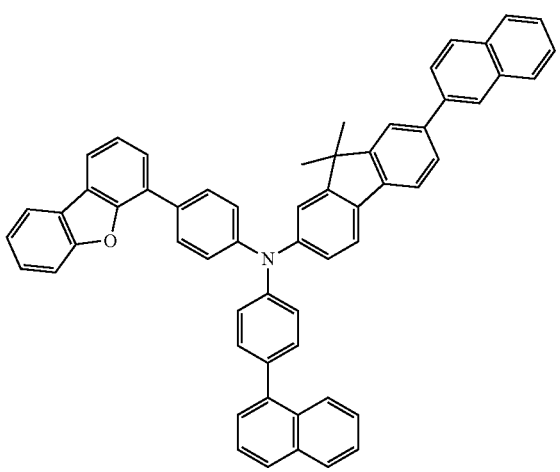 |
| 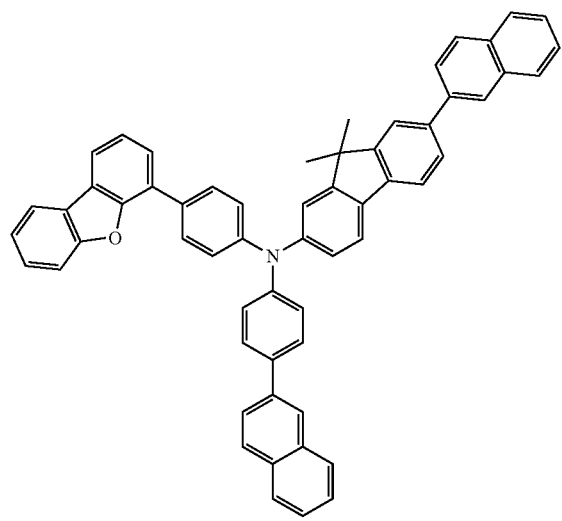 | 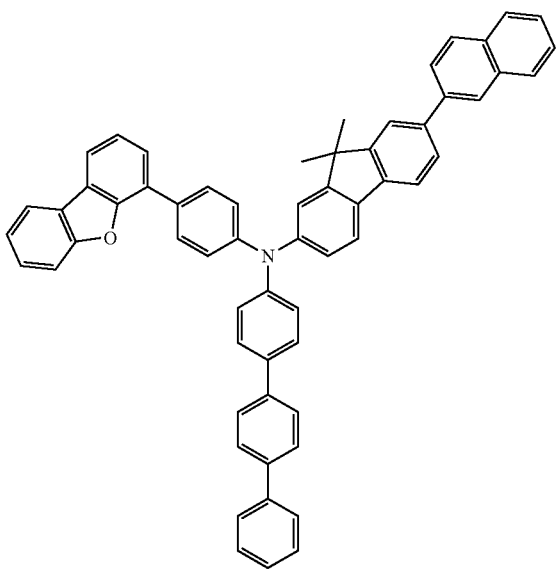 |

-continued
175
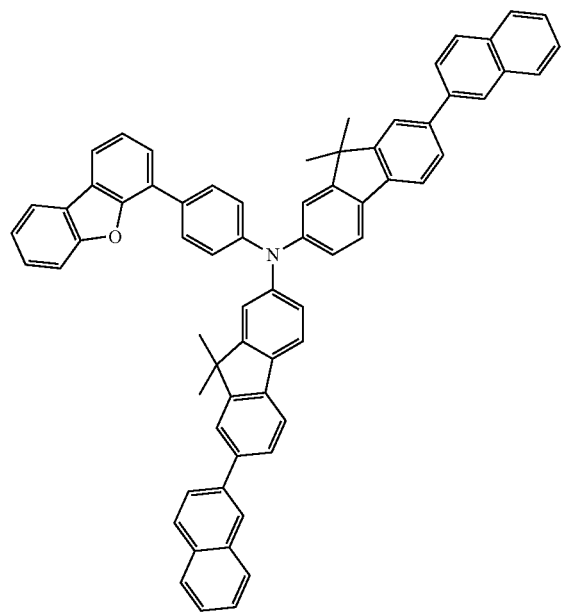
176
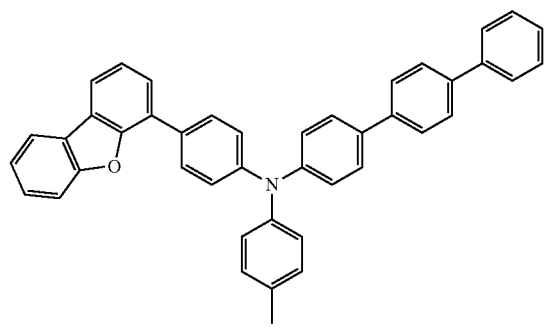
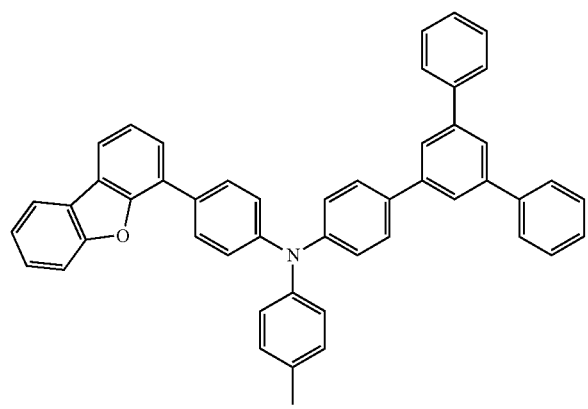
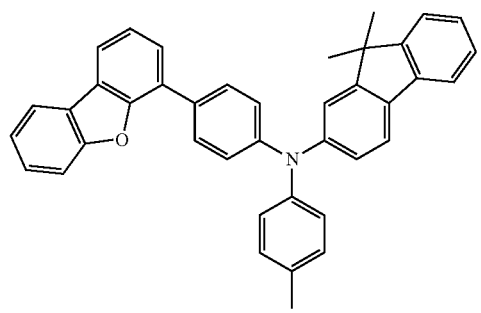
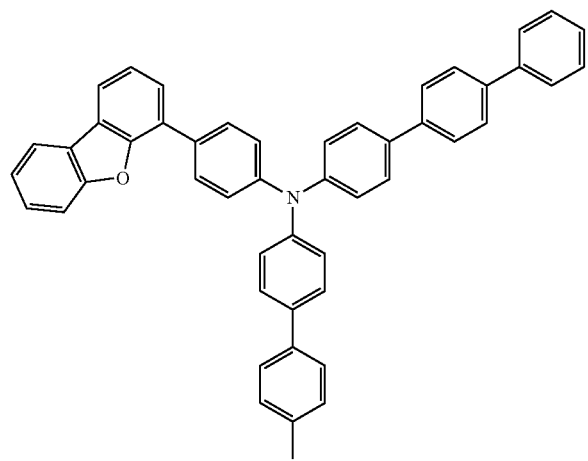
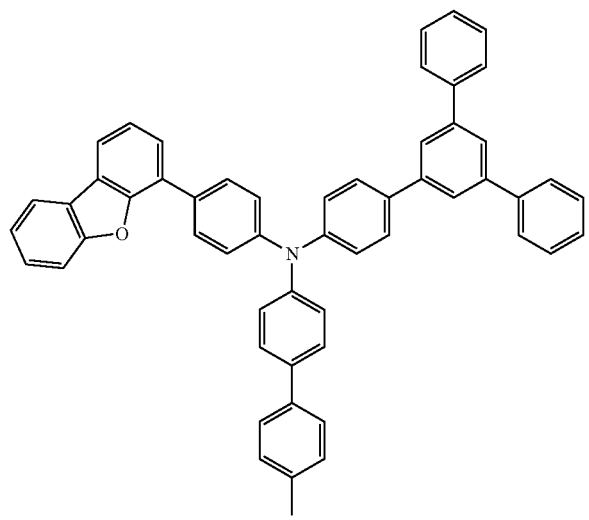

177 178
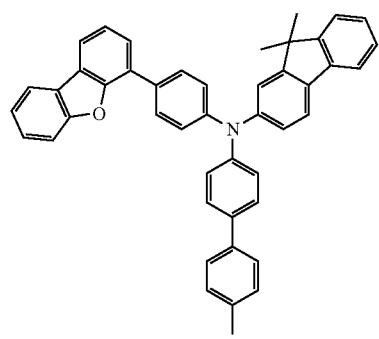
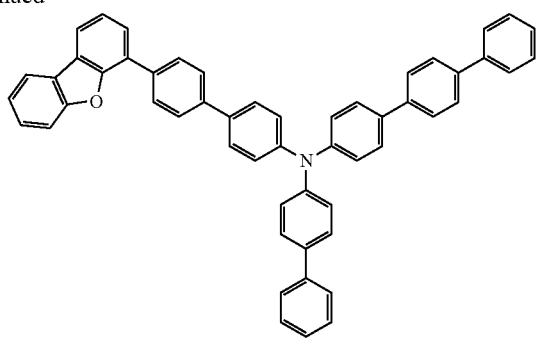
-continued
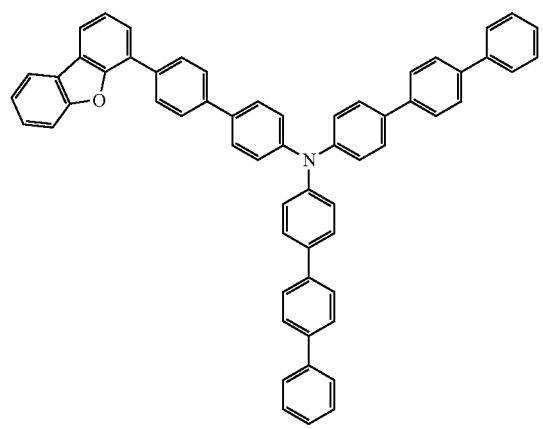
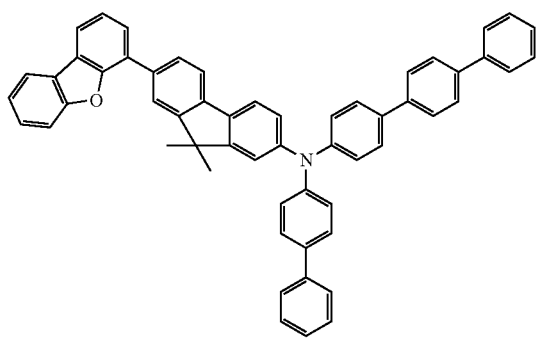
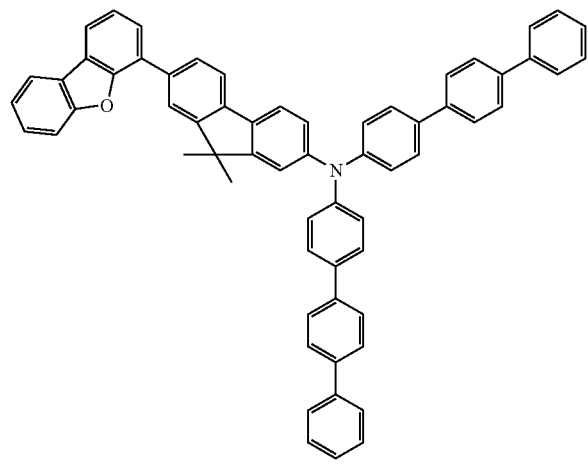
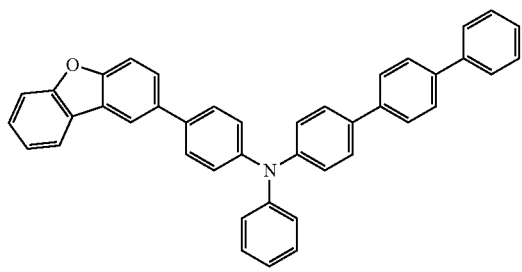
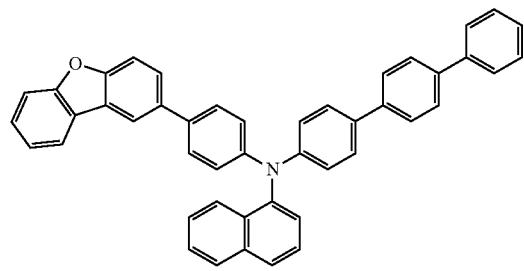
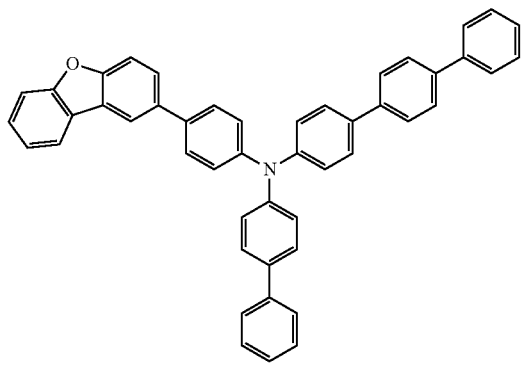

-continued
| 179 | 180 |
|---|---|
| 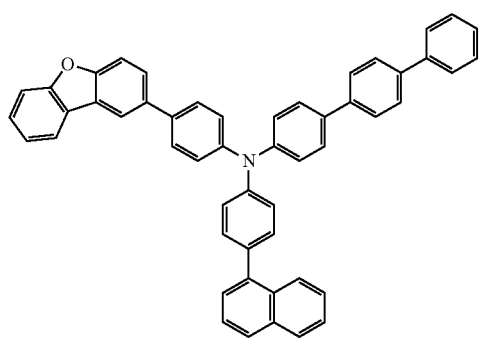 | 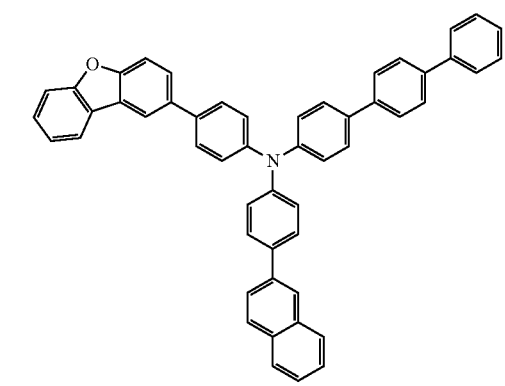 |
| 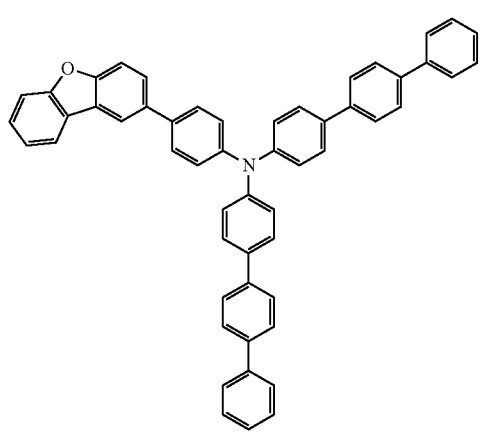 | 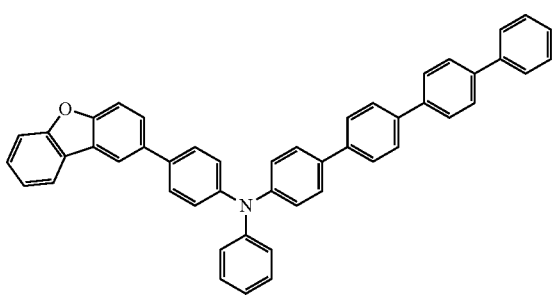 |
| 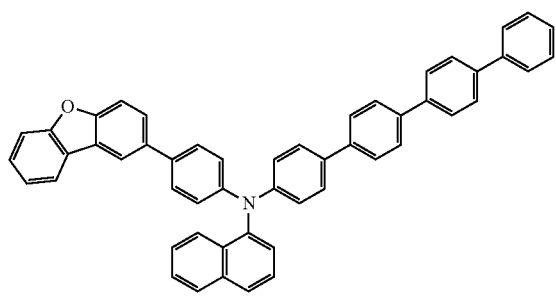 | 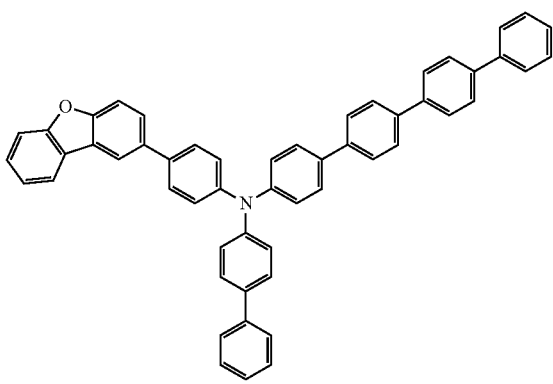 |
| 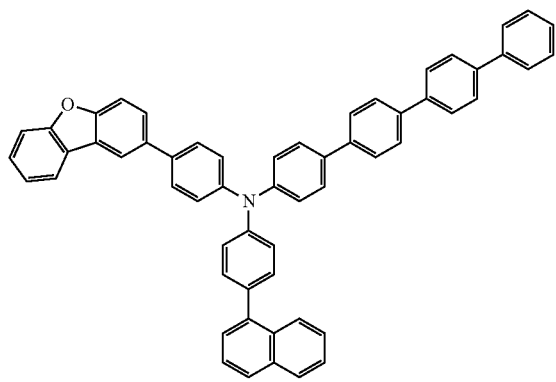 | 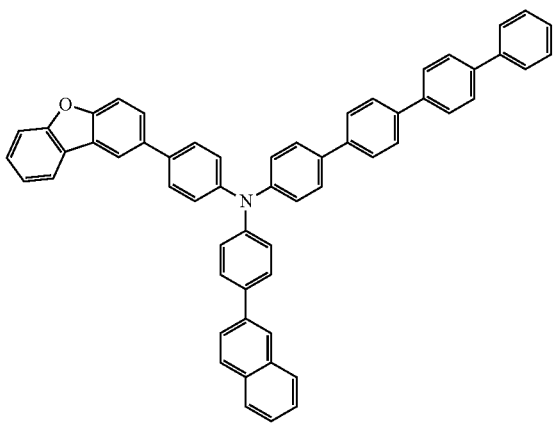 |

-continued
| 181 | 182 |
|---|---|
| 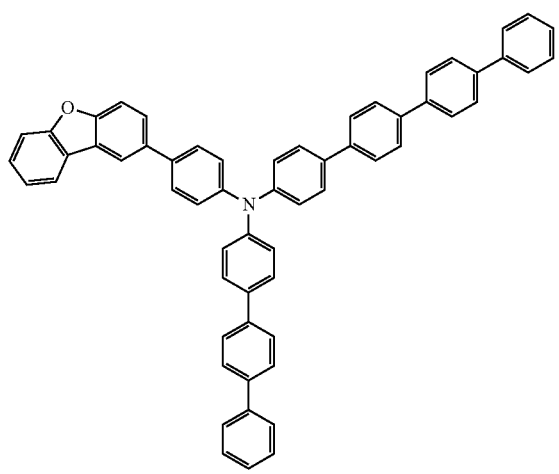 | 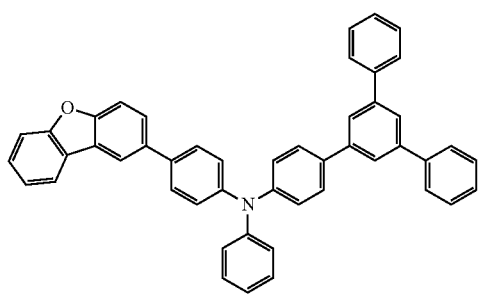 |
| 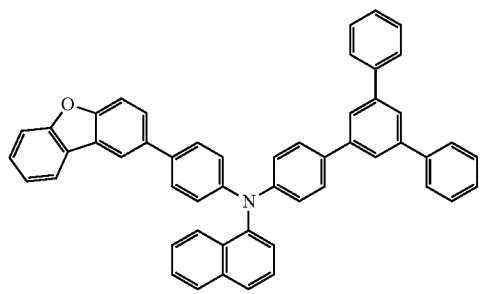 | 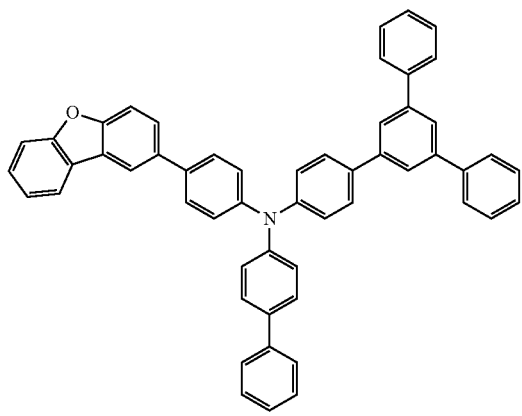 |
| 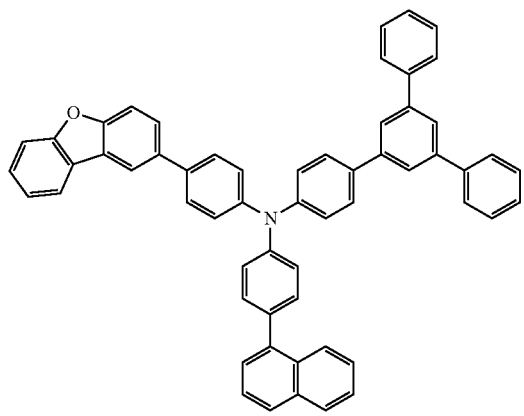 | 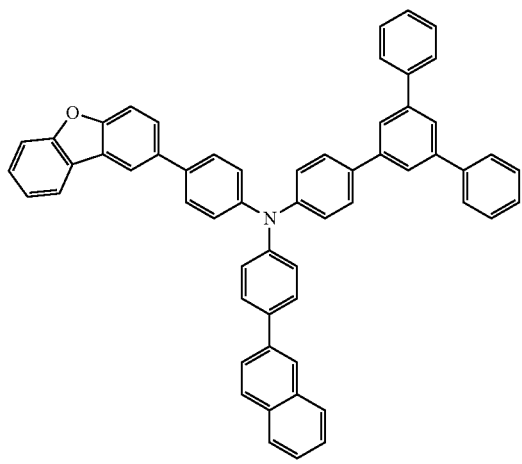 |

-continued
| 183 | 184 |
|---|---|
| 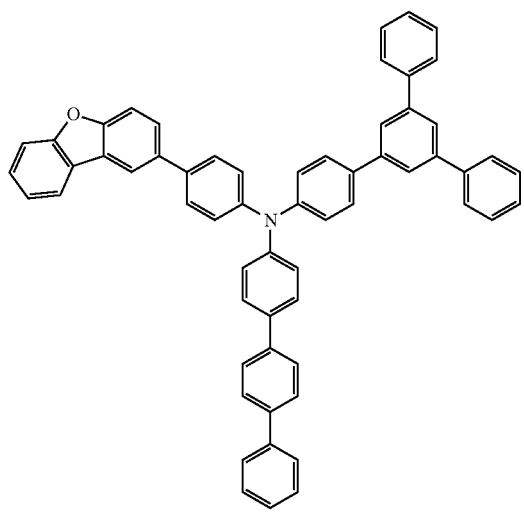 | 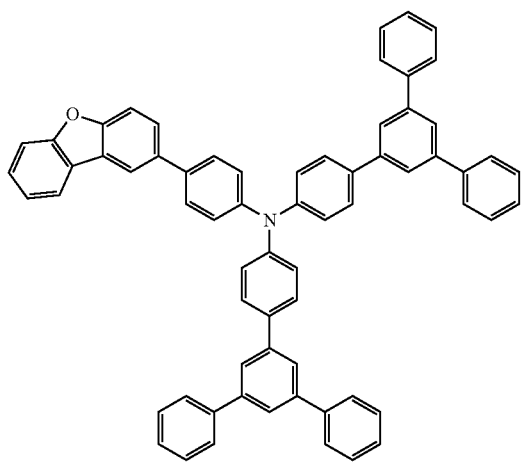 |
| 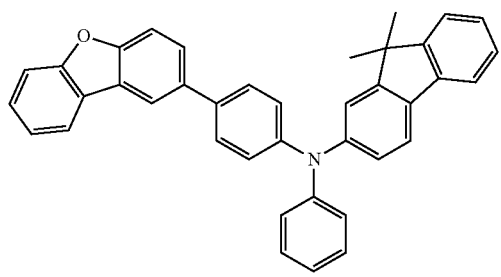 | 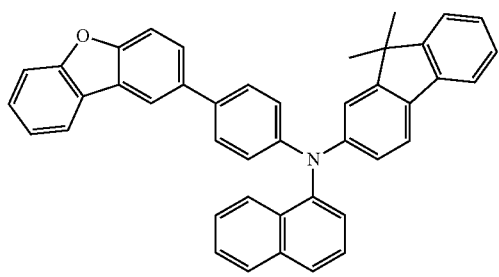 |
| 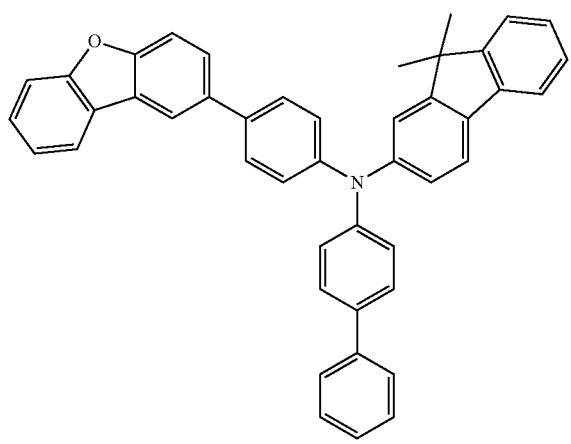 | 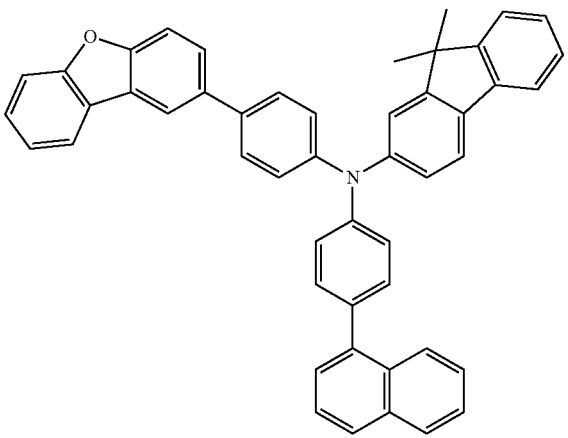 |

-continued
| 185 | 186 |
|---|---|
| 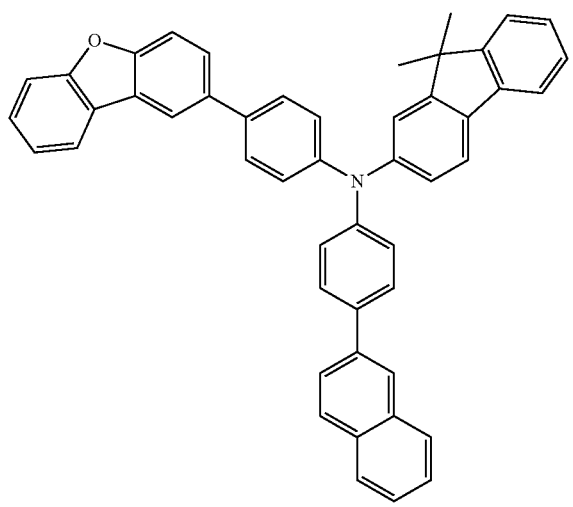 | 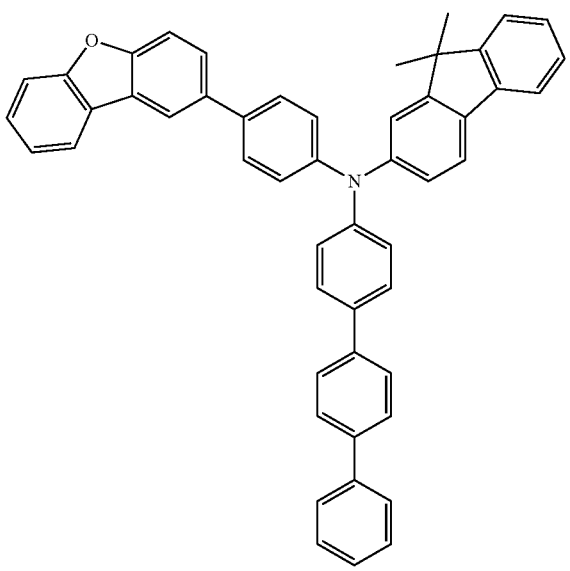 |
| 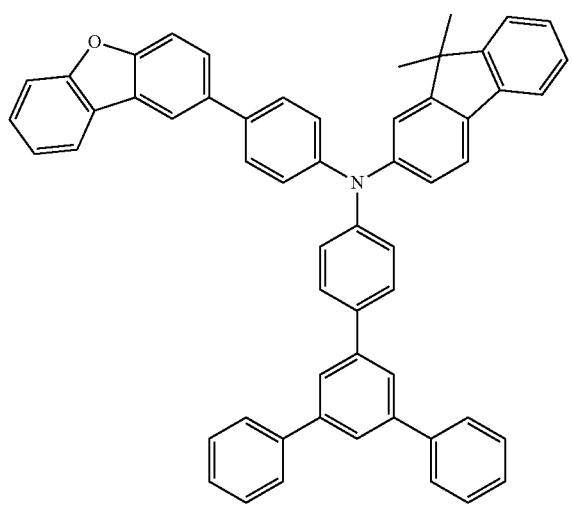 | 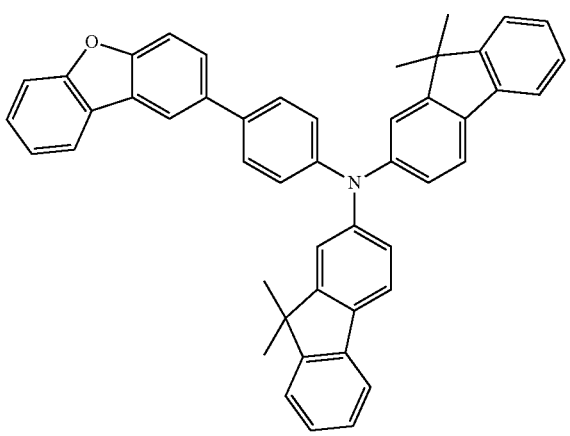 |
| 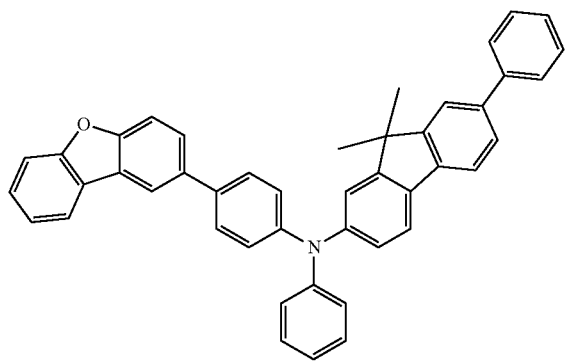 | 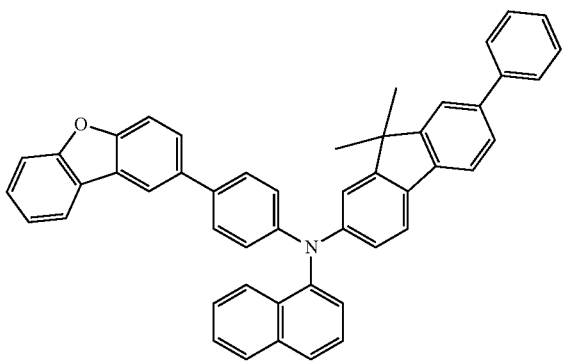 |

-continued
187
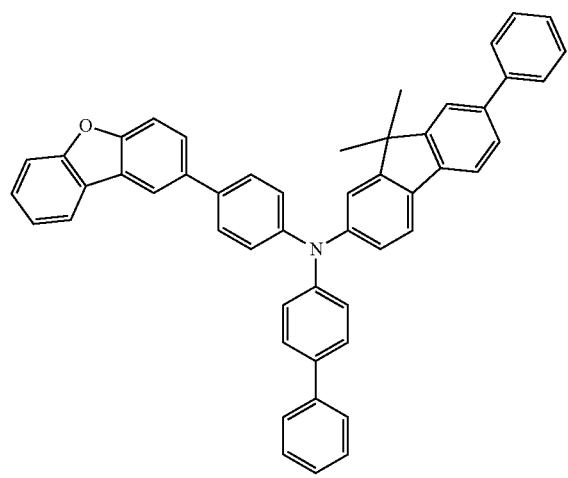
188
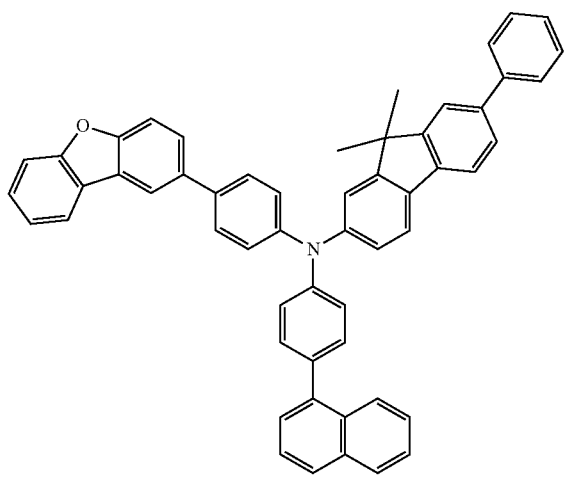
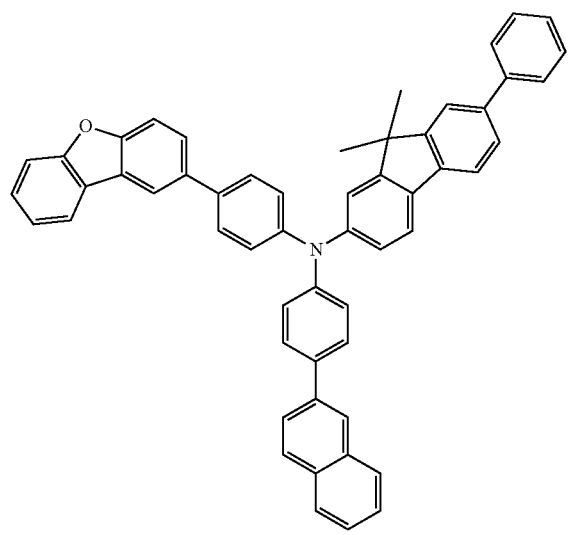
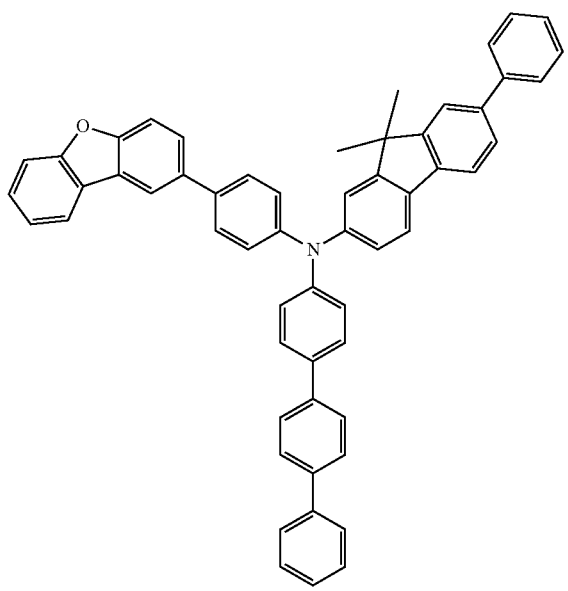
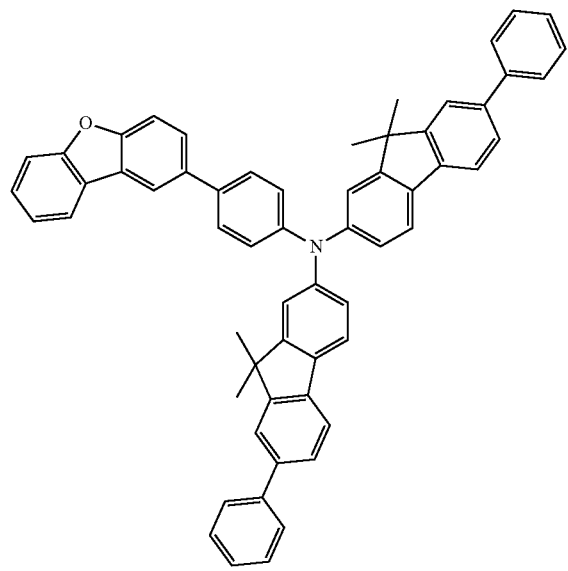
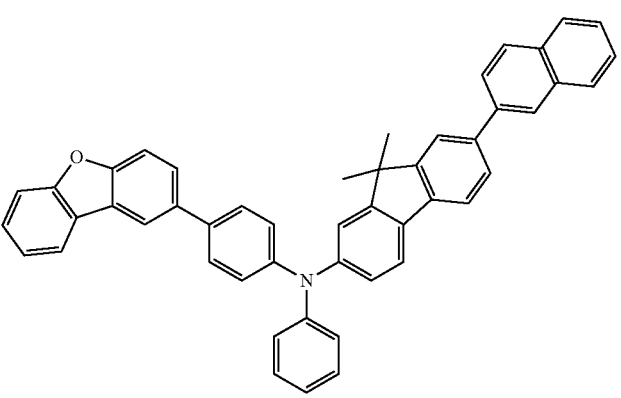

-continued
| 189 | 190 |
|---|---|
| 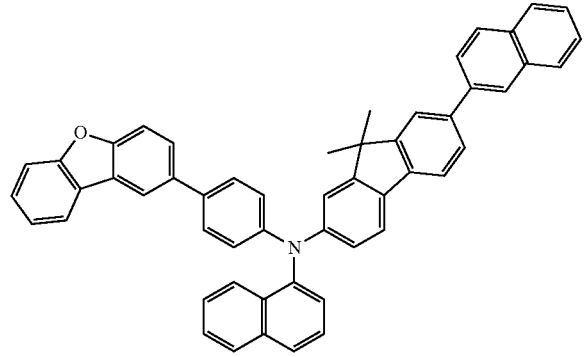 | 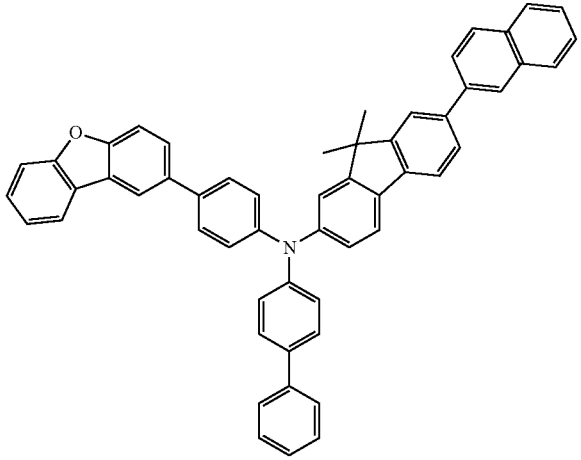 |
| 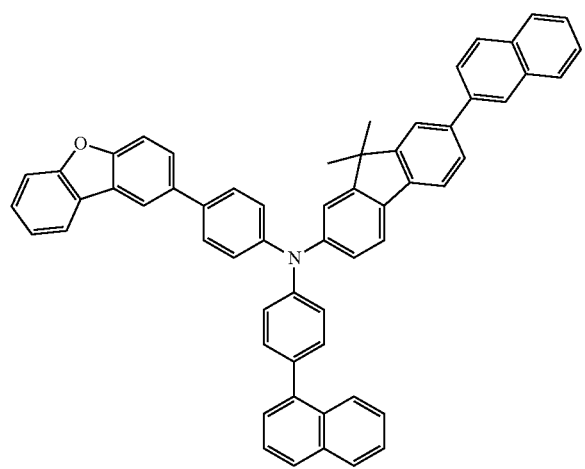 | 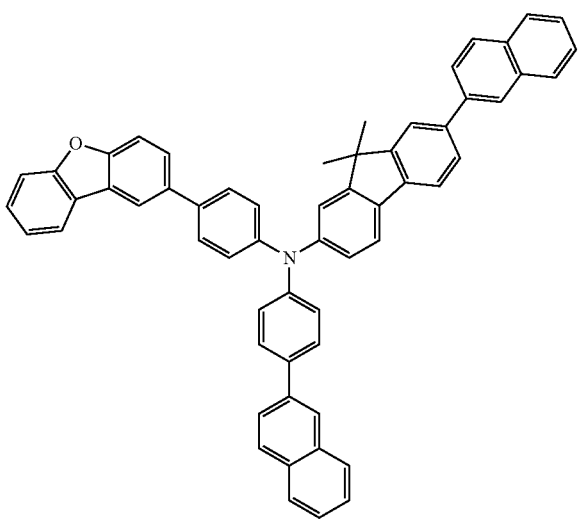 |
| 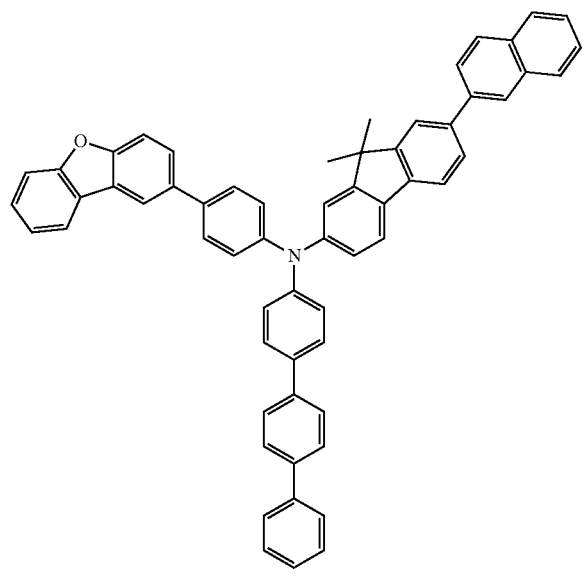 | 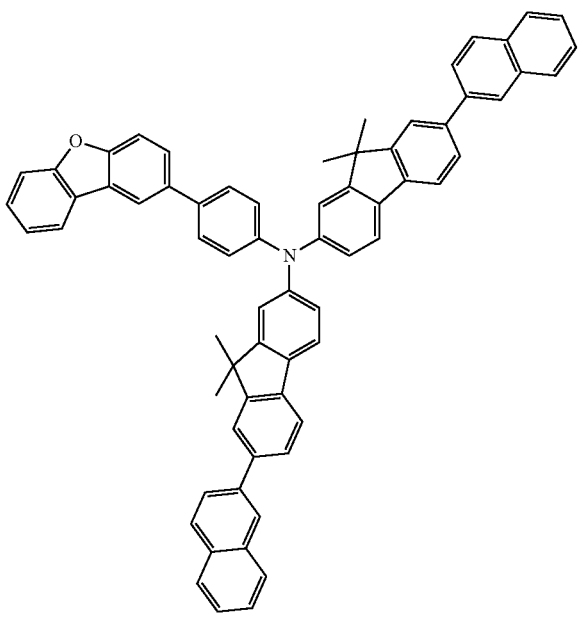 |

-continued
| 191 | 192 |
|---|---|
| 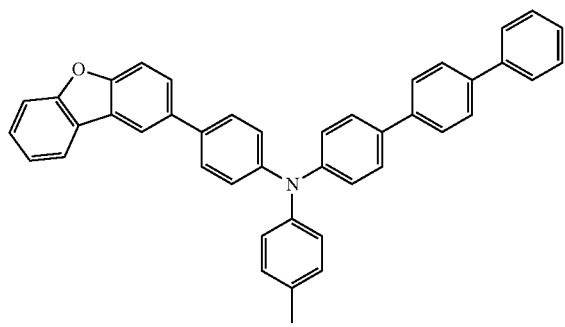 | 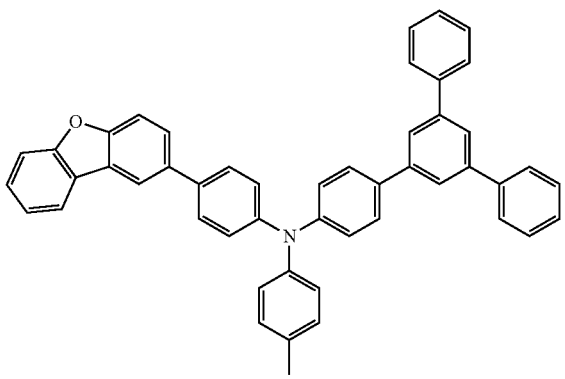 |
| 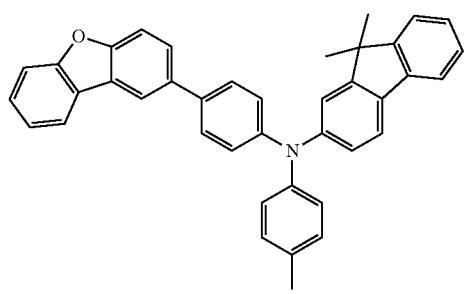 | 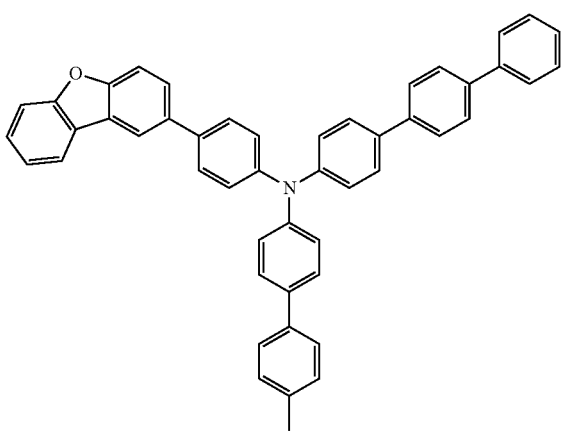 |
| 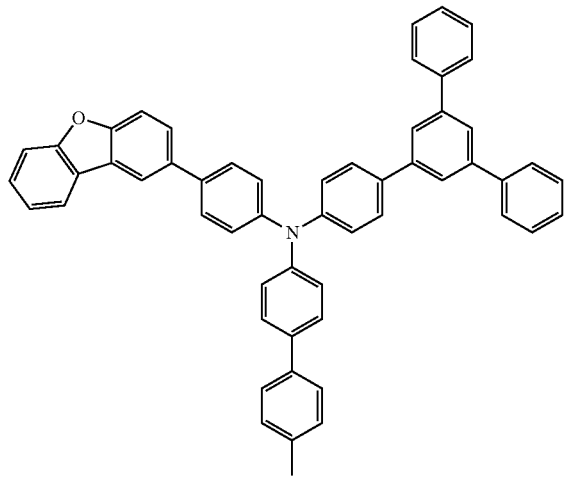 | 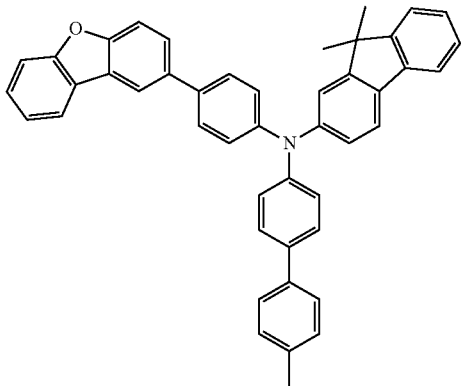 |
| 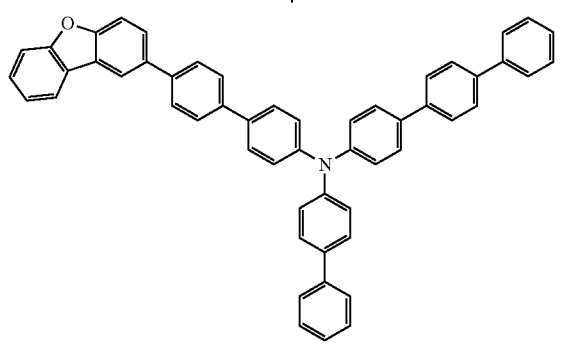 | 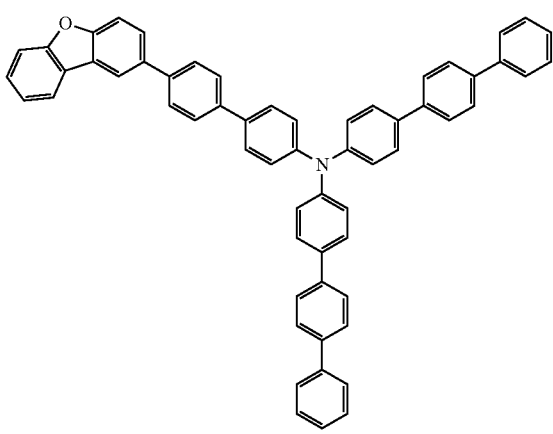 |

-continued
| 193 | 194 |
|---|---|
| 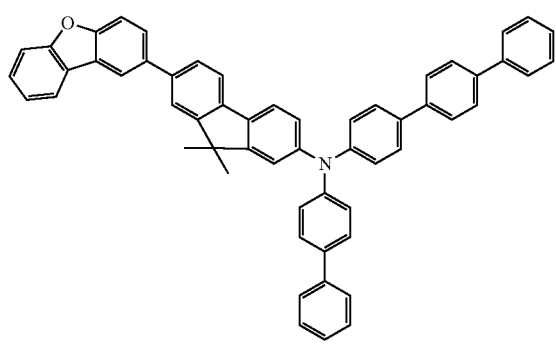 | 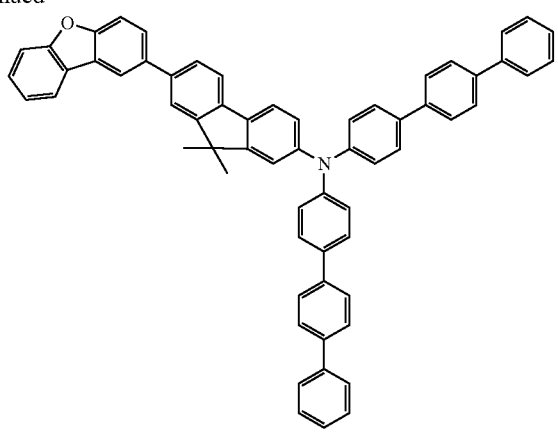 |
| 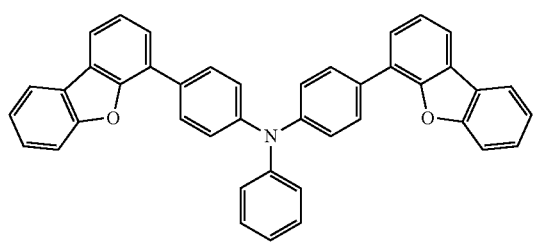 | 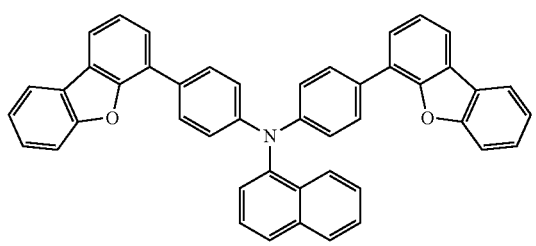 |
| 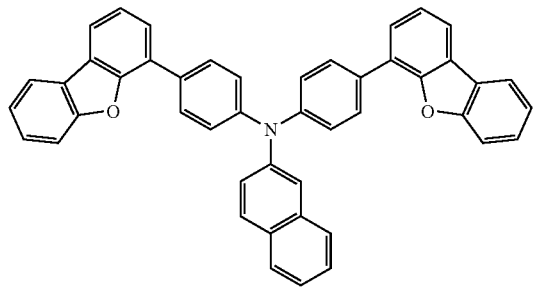 | 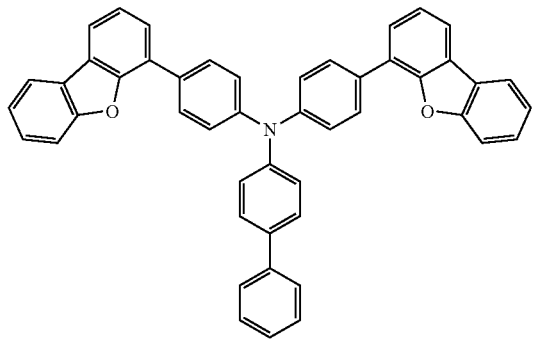 |
| 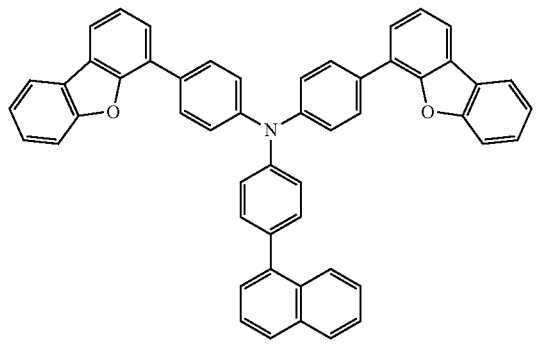 | 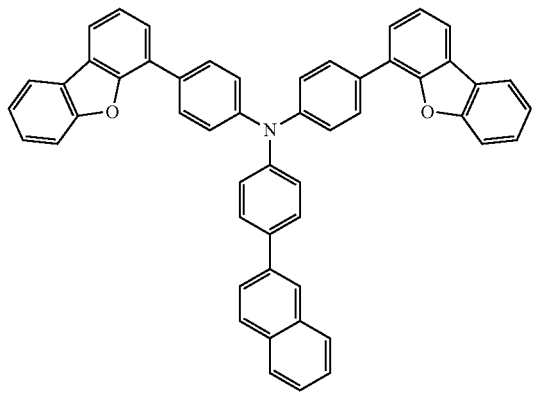 |

195
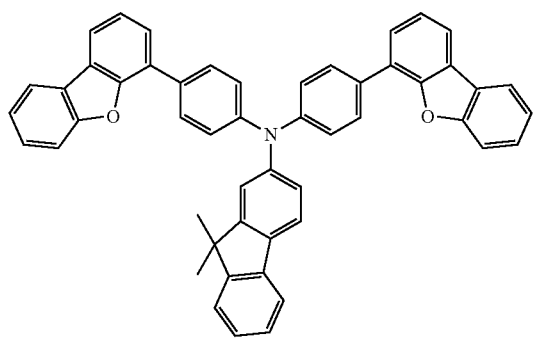
196
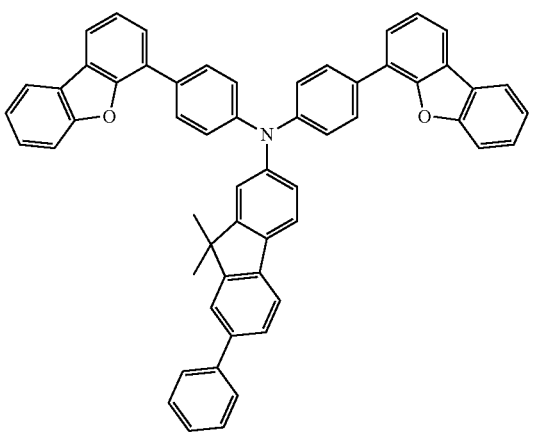
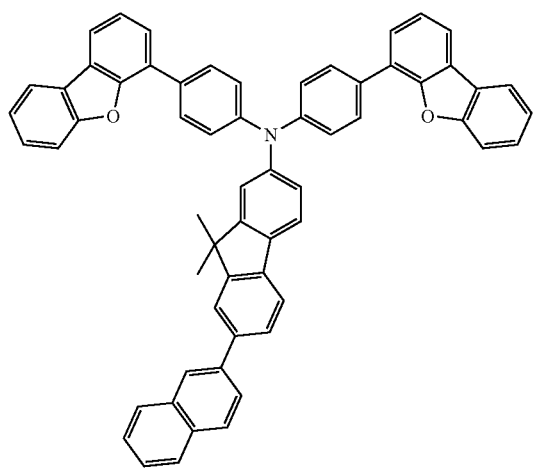
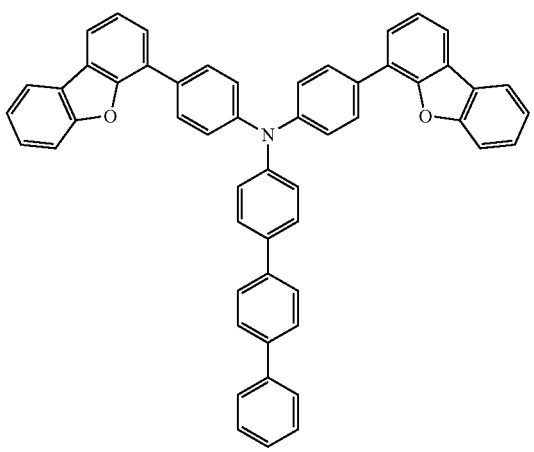
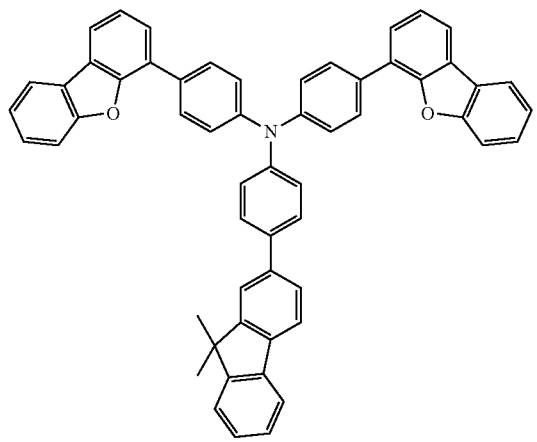
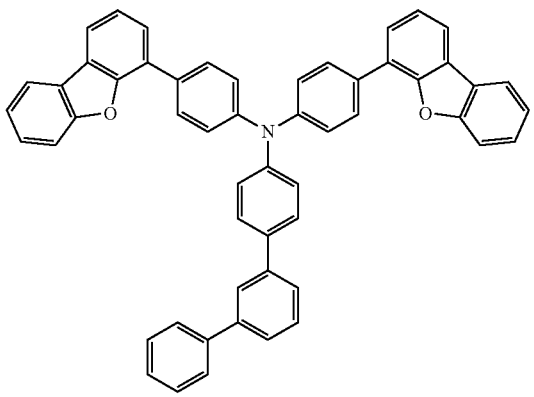

-continued
| 197 | 198 |
|---|---|
| 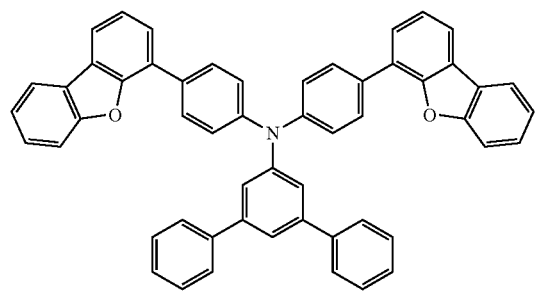 | 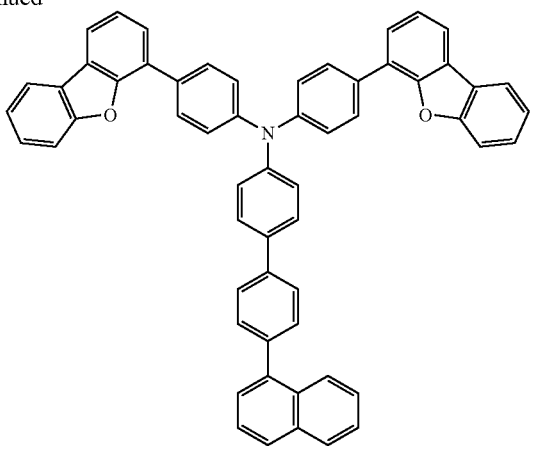 |
| 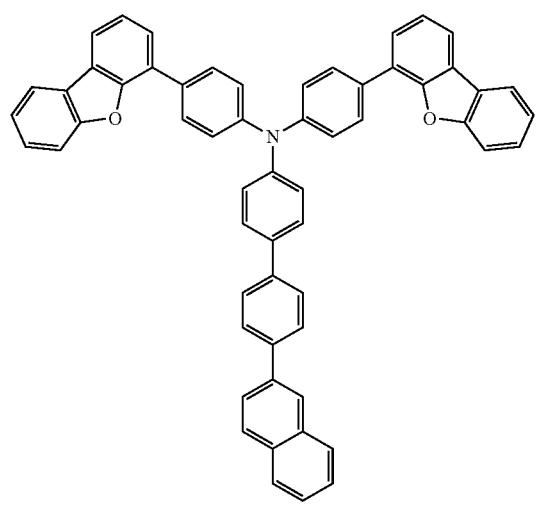 | 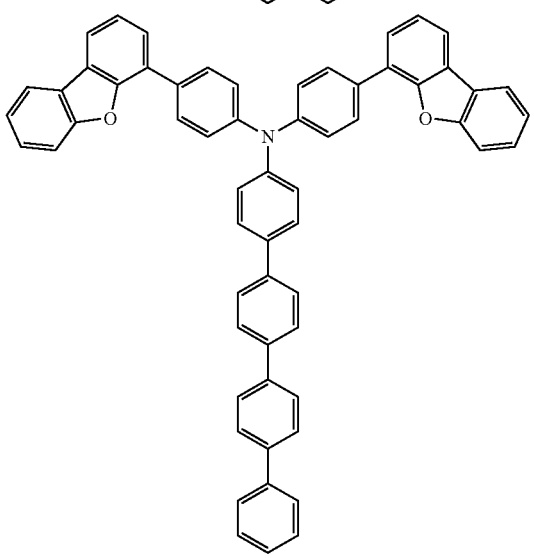 |
| 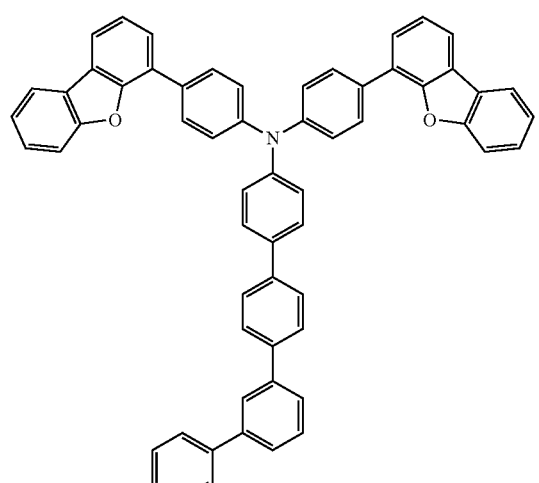 | 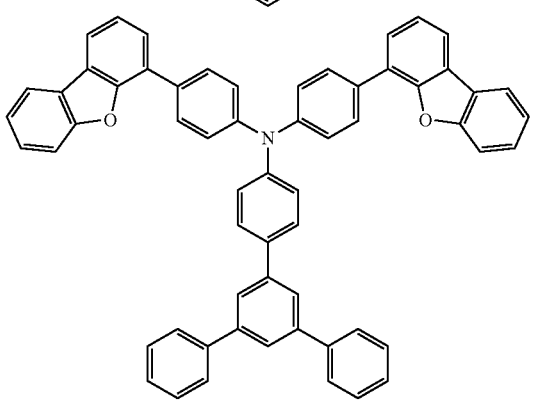 |
| 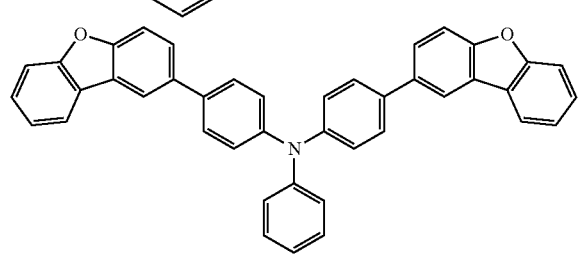 | 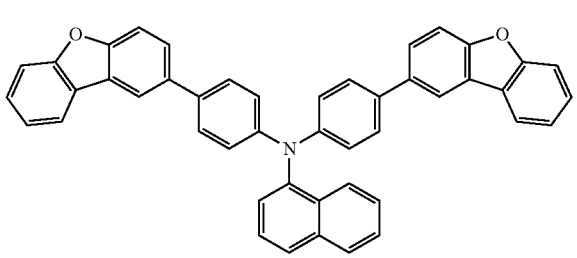 |

-continued
| 199 | 200 |
|---|---|
| 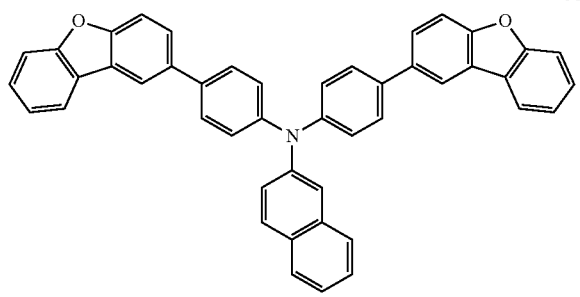 | 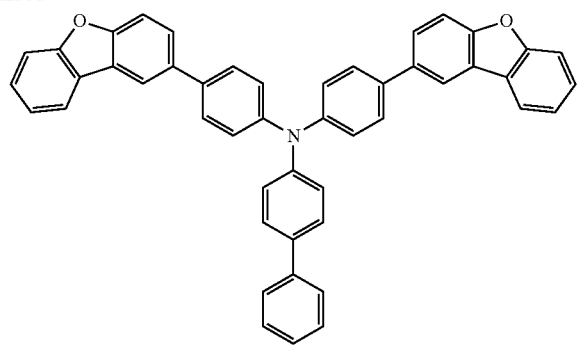 |
| 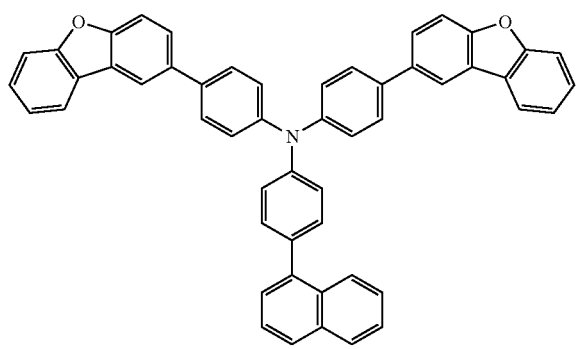 | 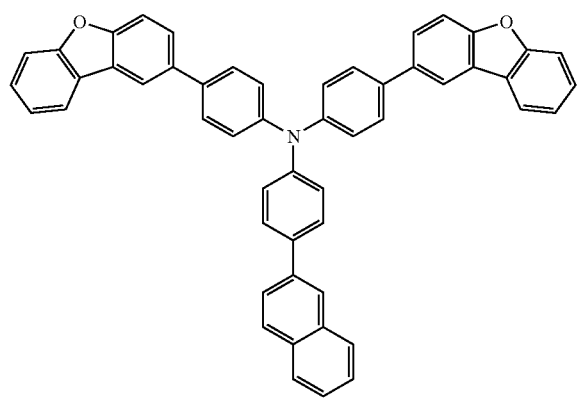 |
| 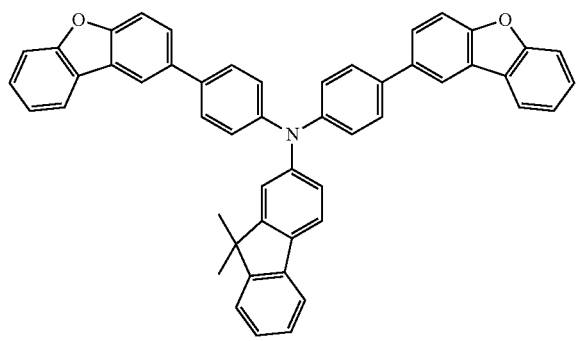 | 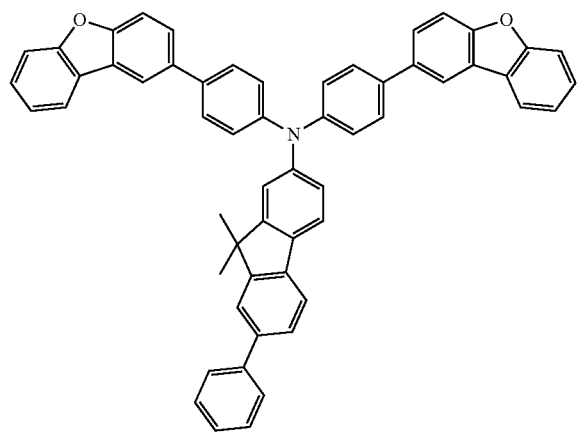 |
| 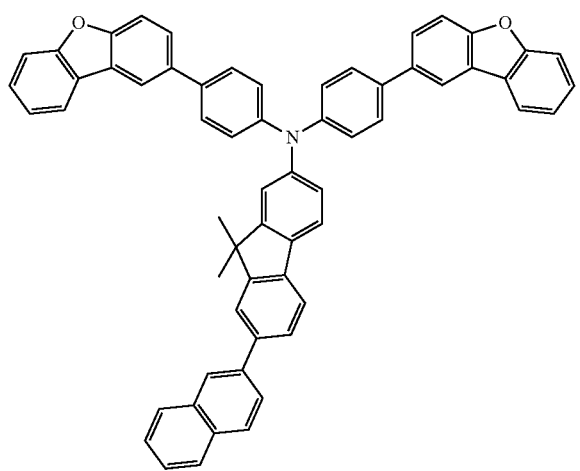 | 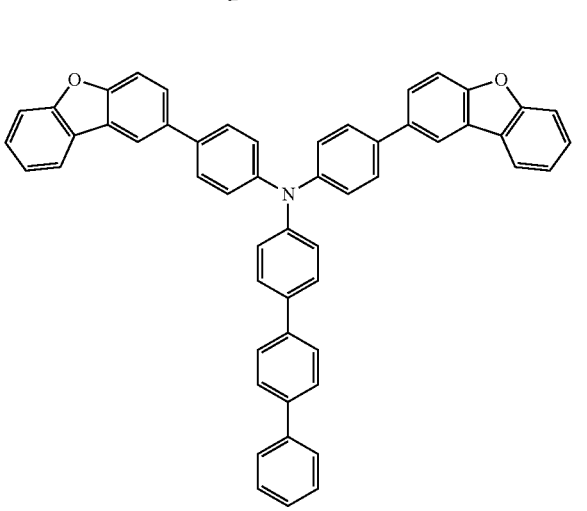 |

-continued
201 202
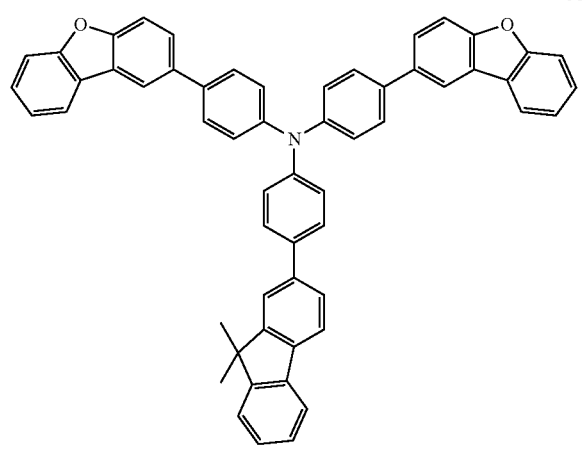 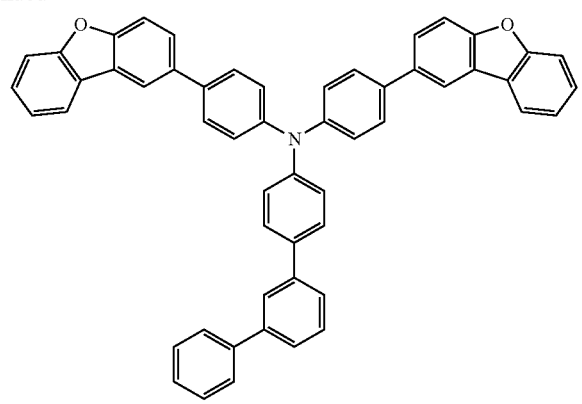
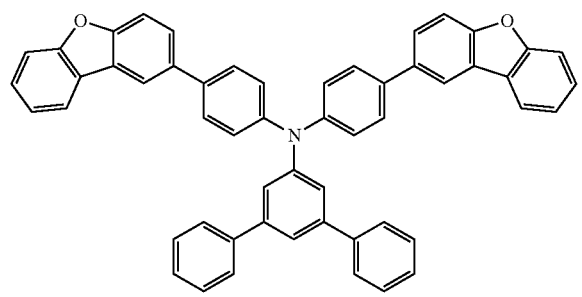 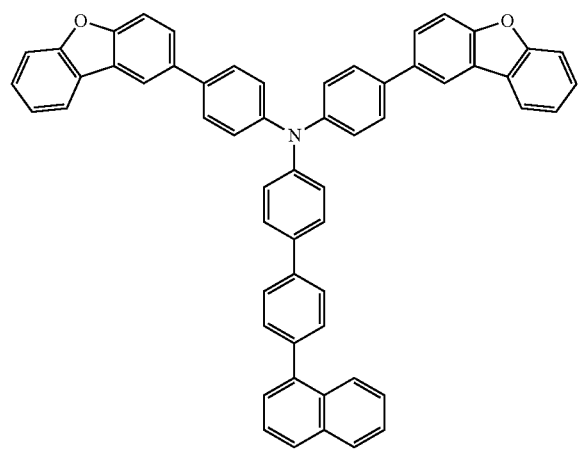
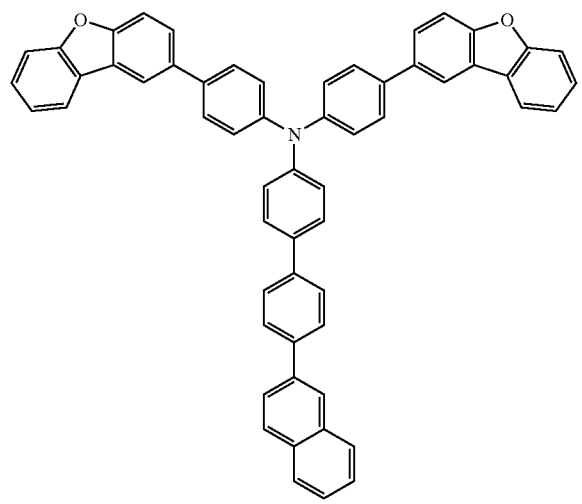 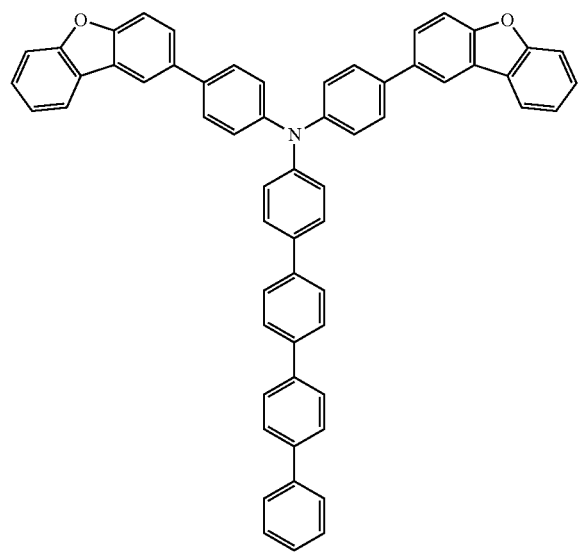

203 204
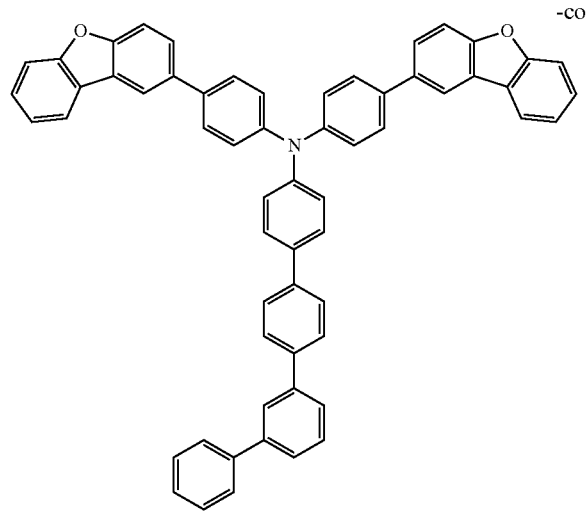
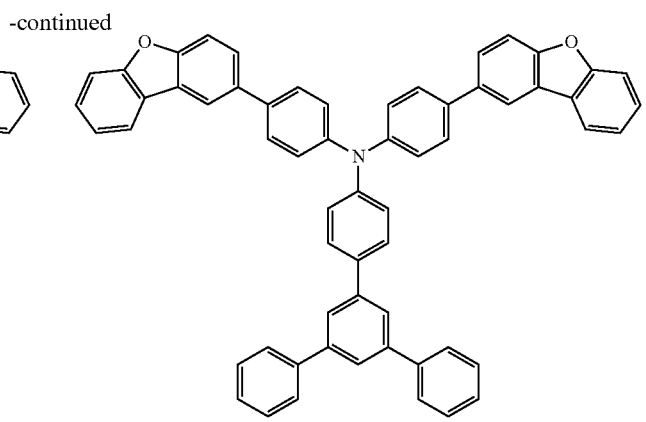
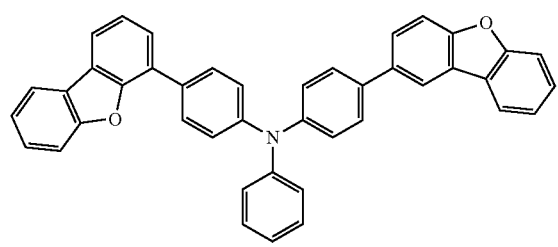
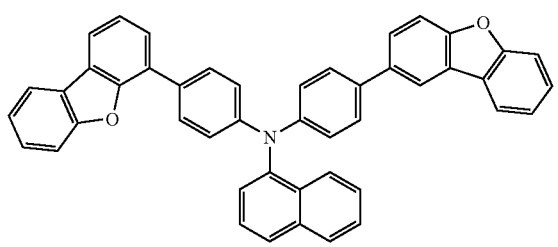
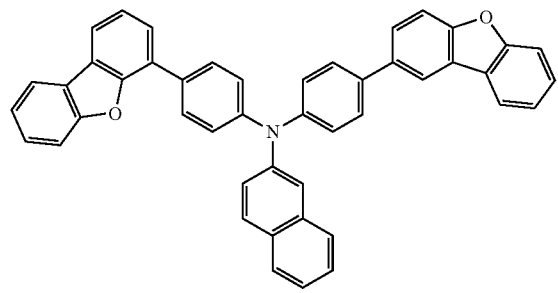
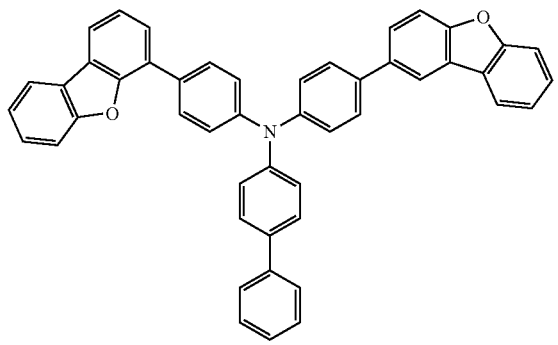
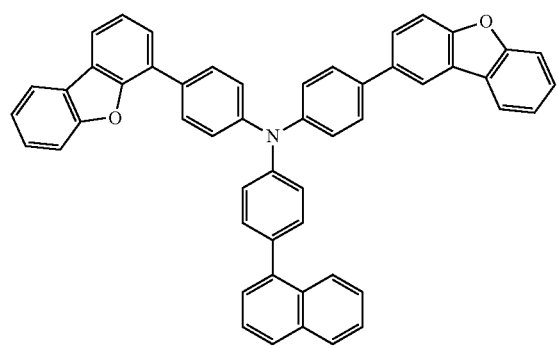
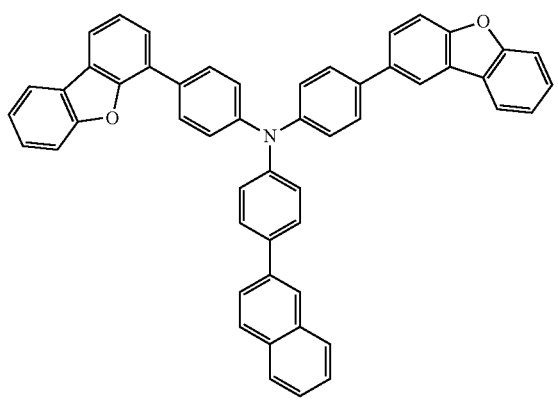

-continued
| 205 | 206 |
|---|---|
| 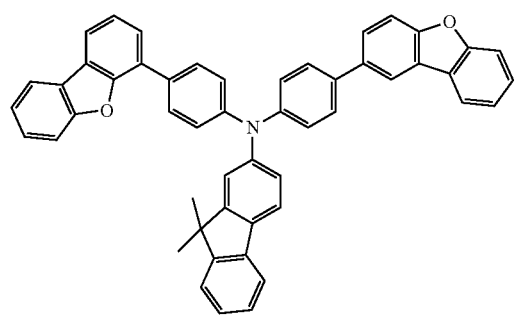 | 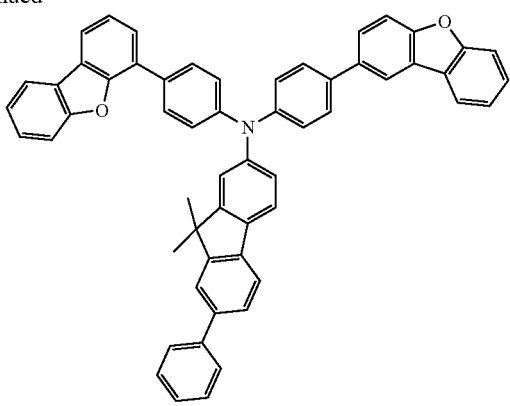 |
| 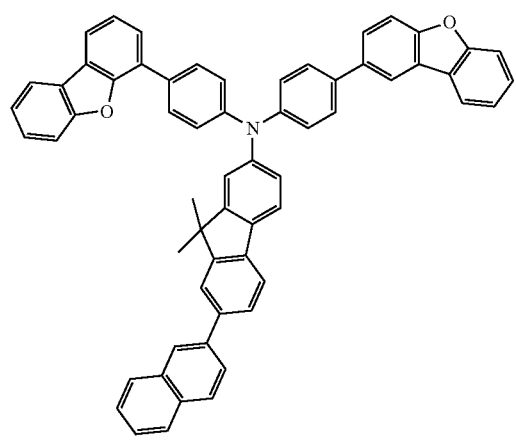 | 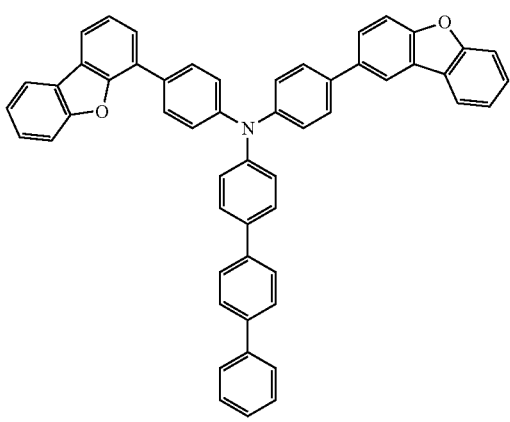 |
| 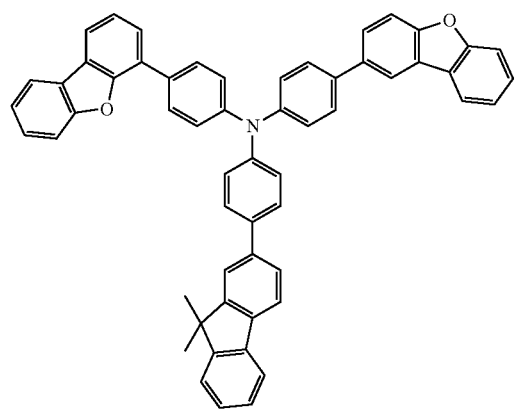 | 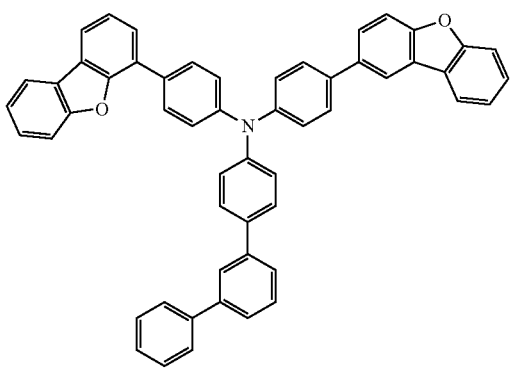 |
| 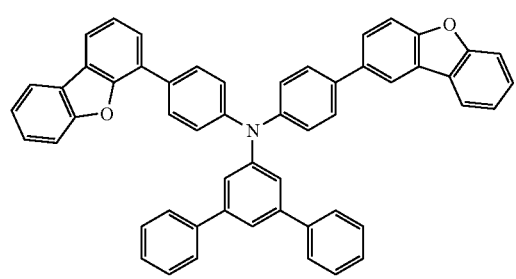 | 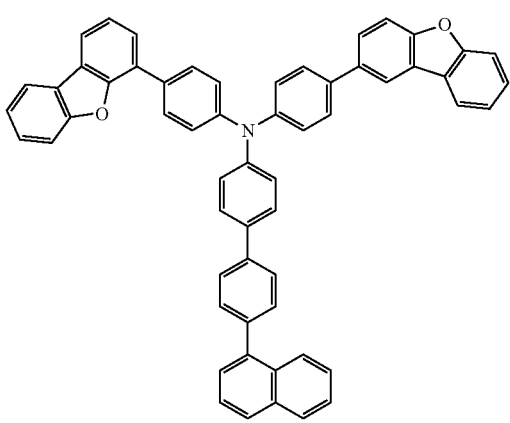 |

207
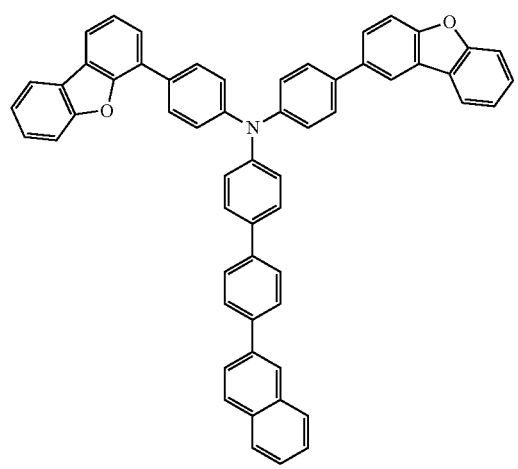
208
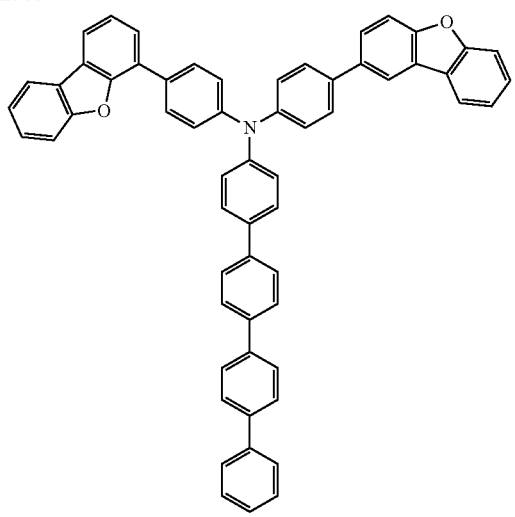
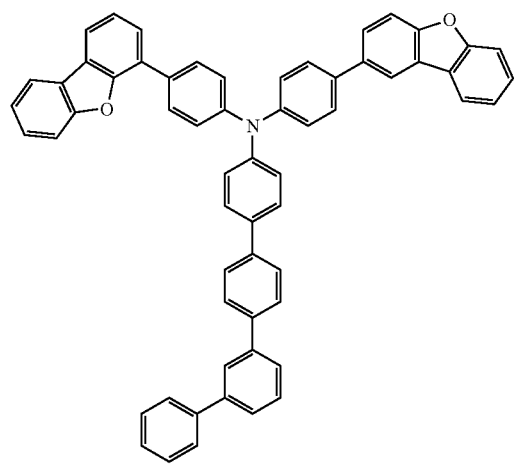
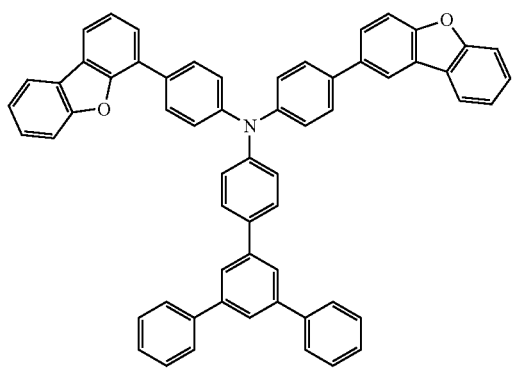
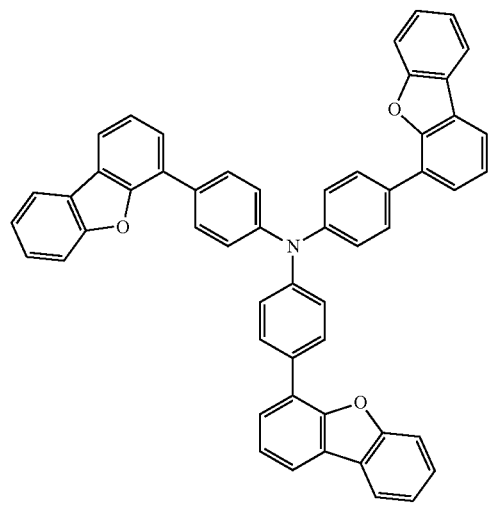
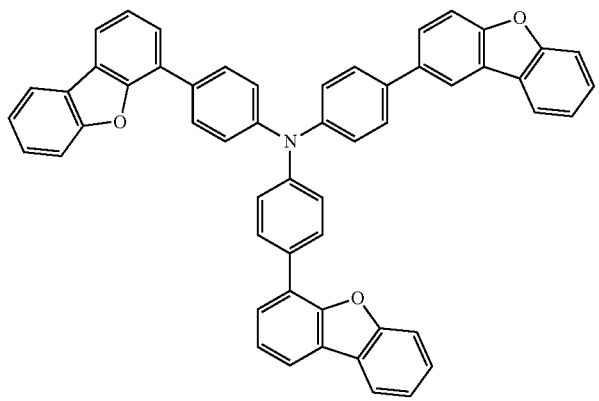

209
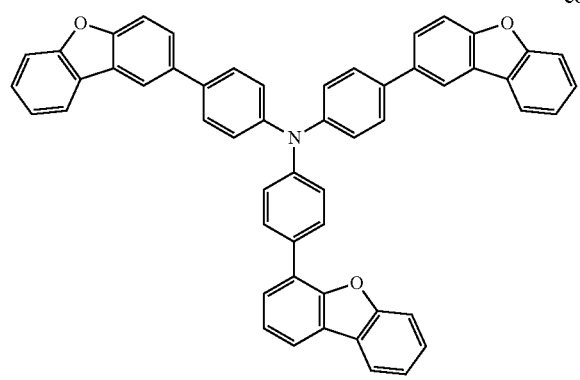
210
-continued
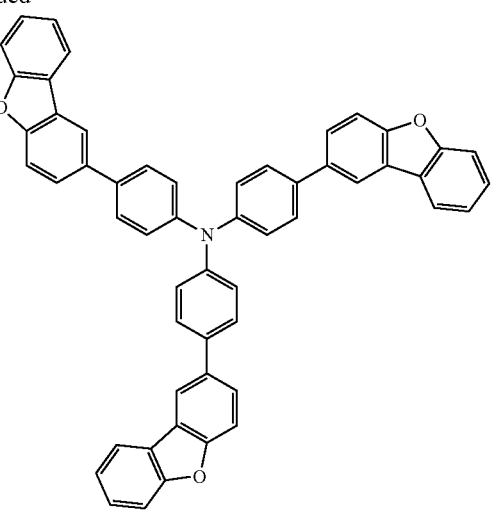
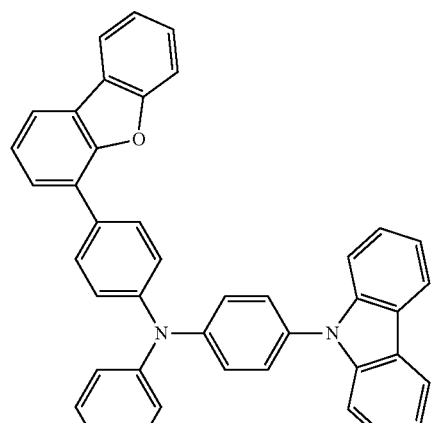
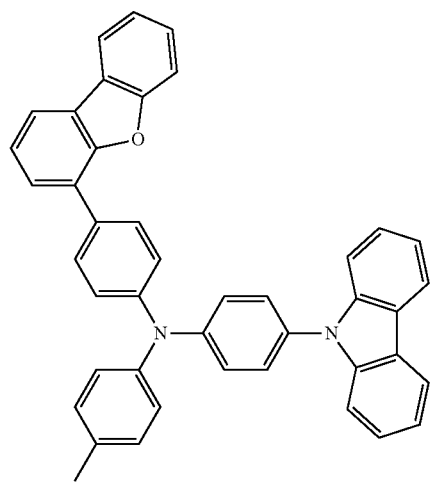
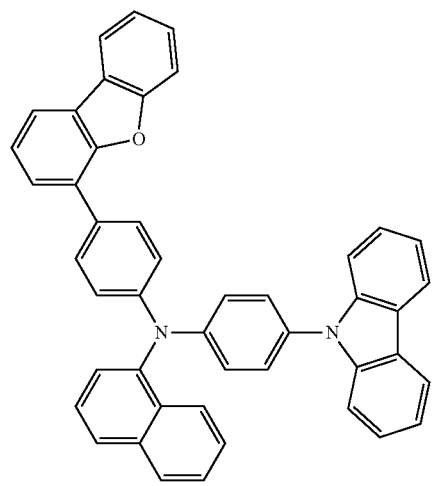
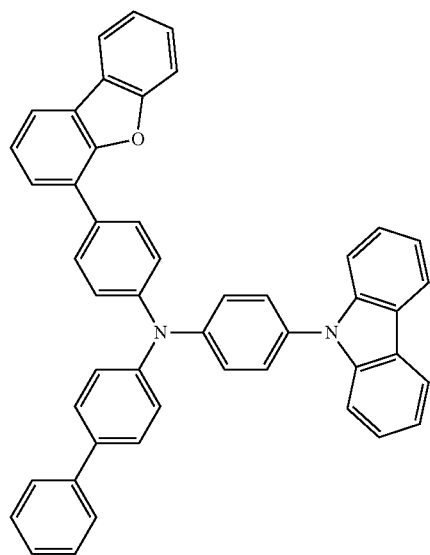

-continued
211
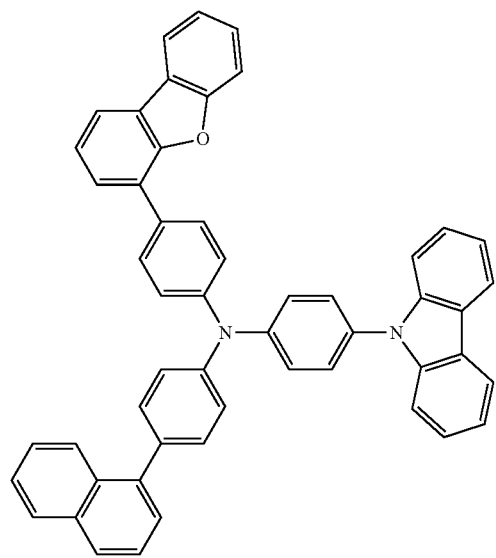
212
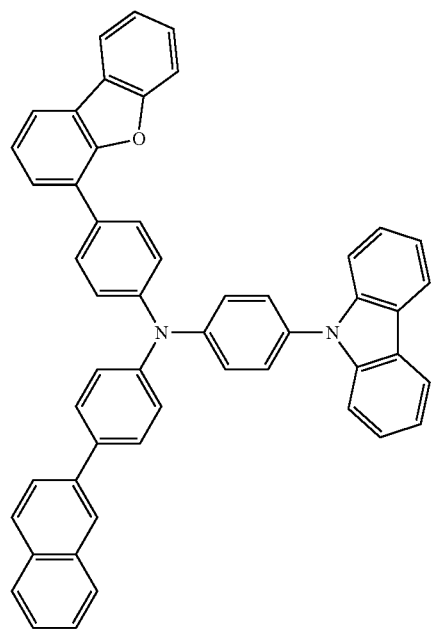
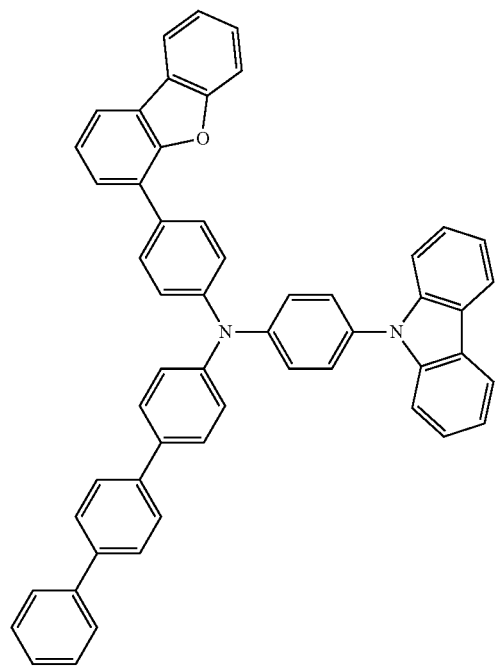
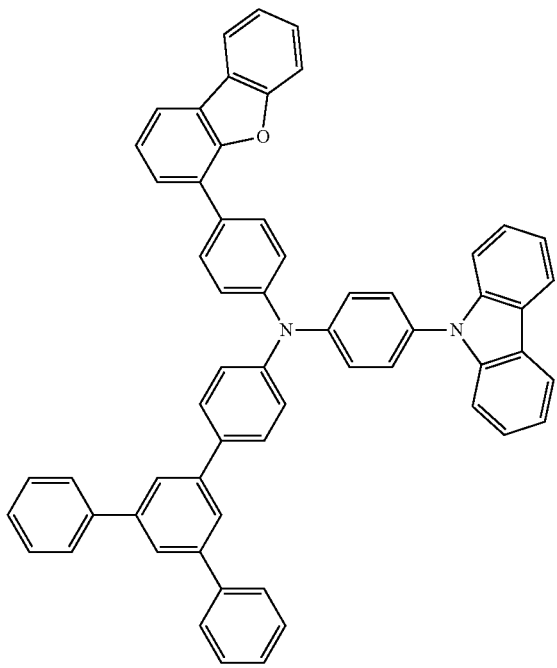

213
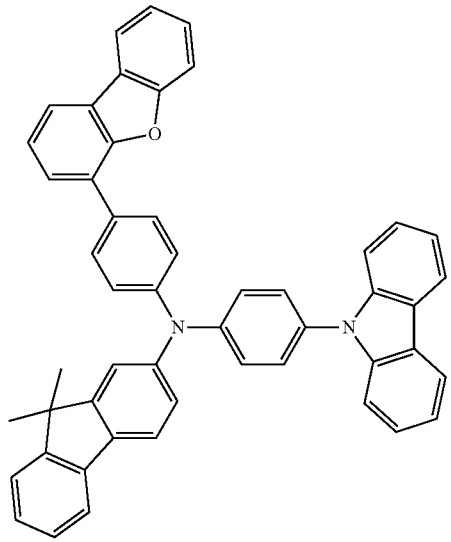
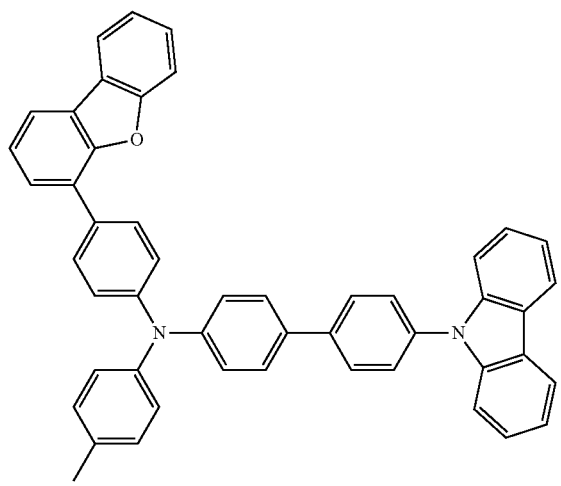
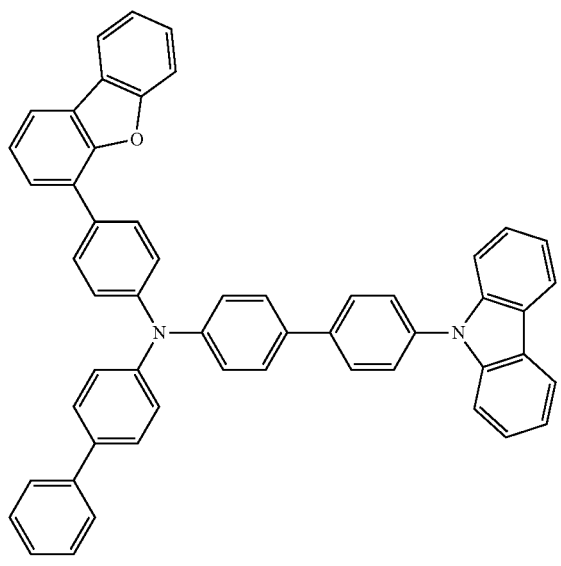
214
-continued
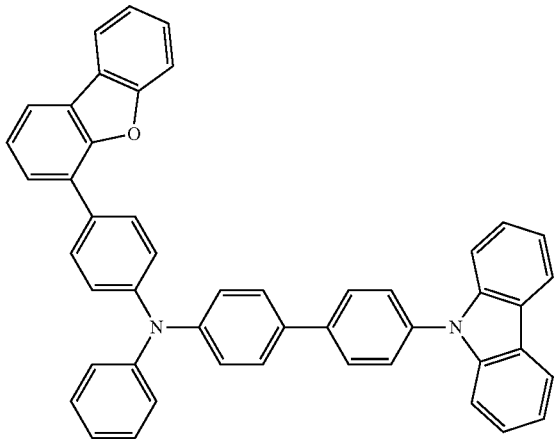
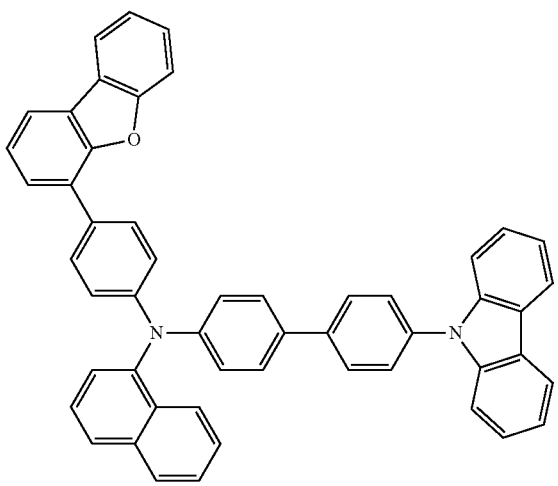
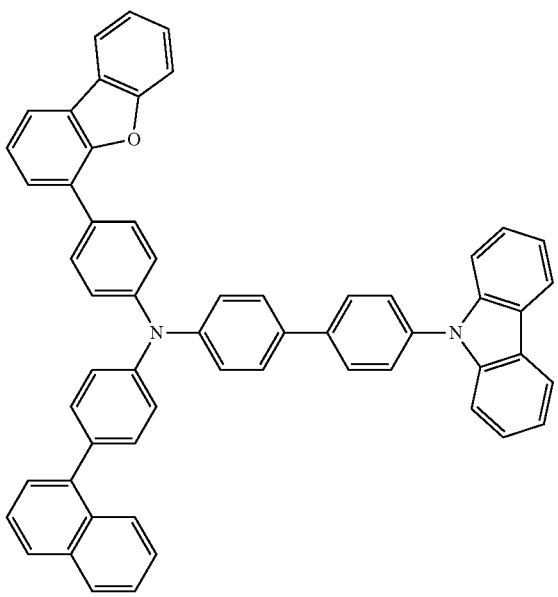

-continued
| 215 | 216 |
|---|---|
| 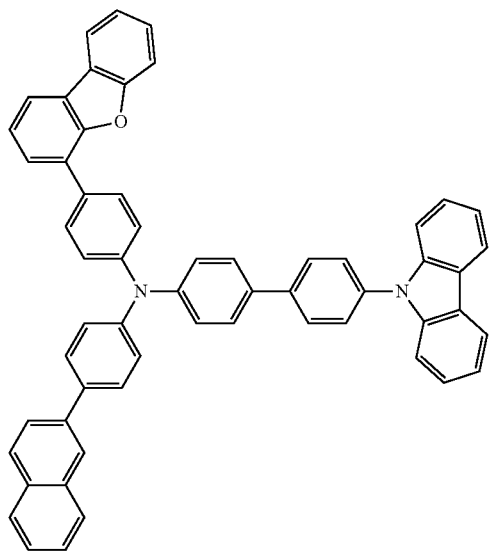 | 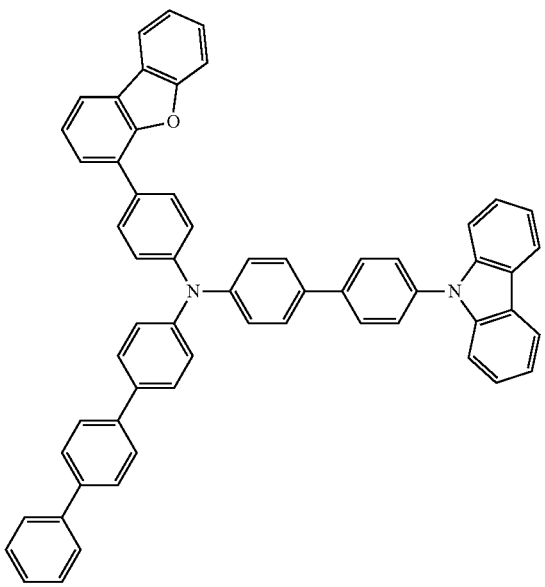 |
| 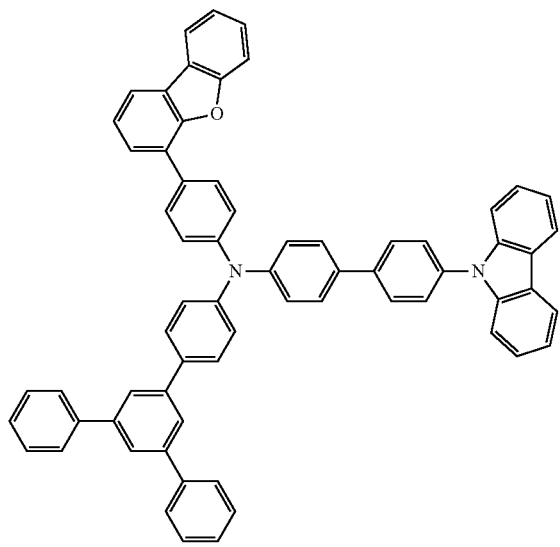 | 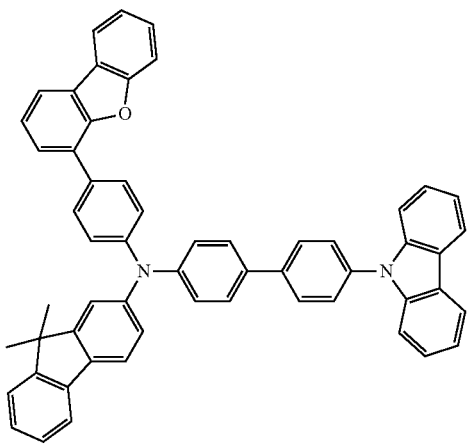 |
| 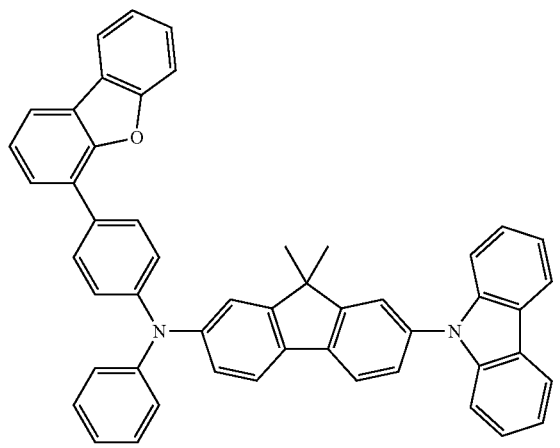 | 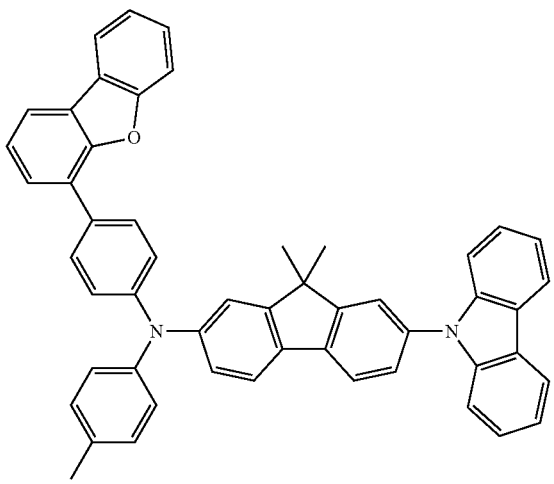 |

-continued
| 217 | 218 |
|---|---|
| 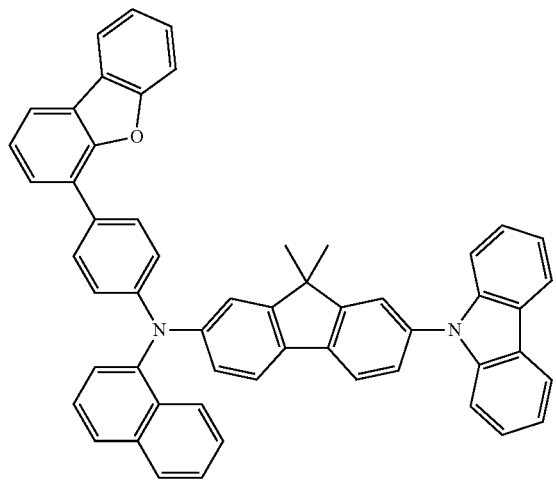 | 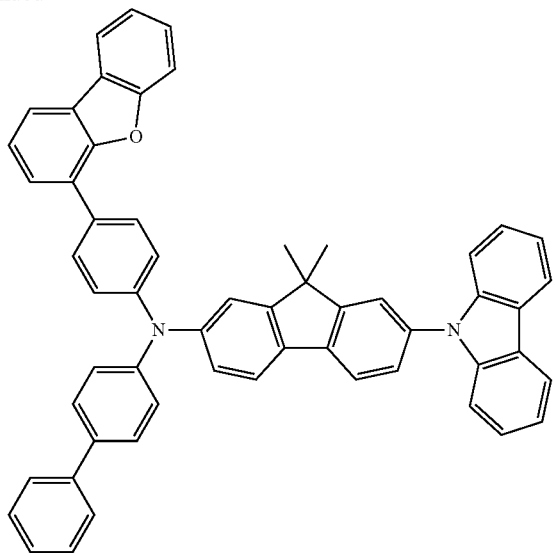 |
| 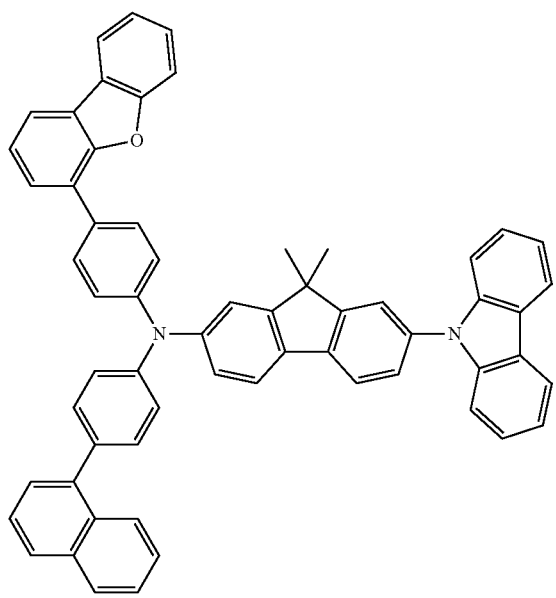 | 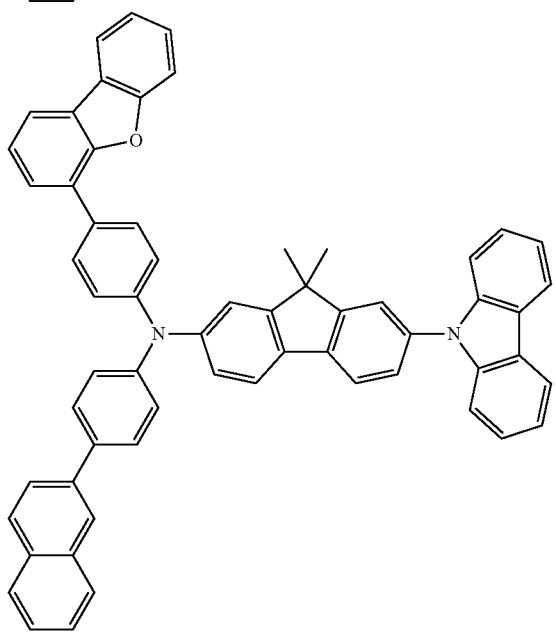 |
| 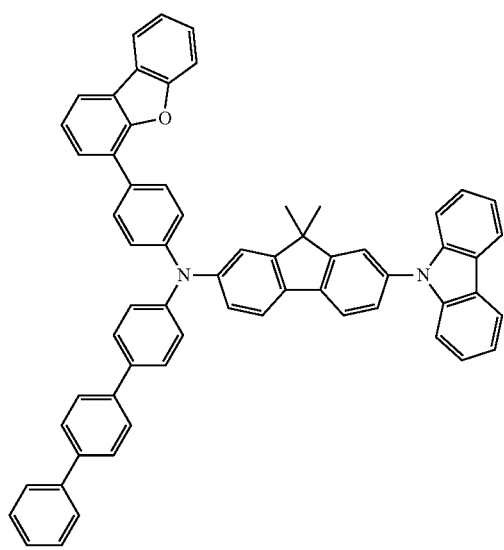 | 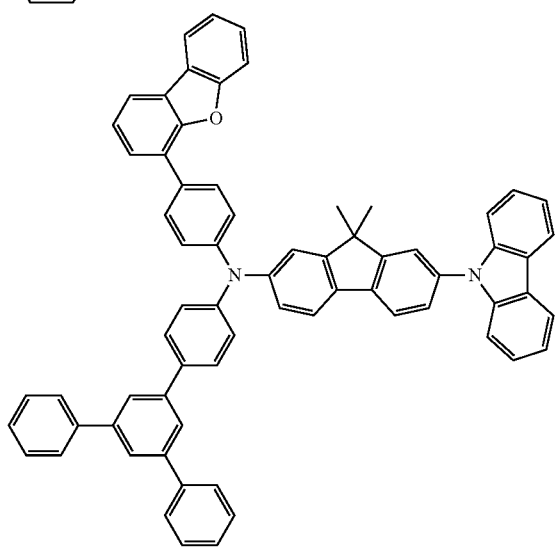 |

-continued
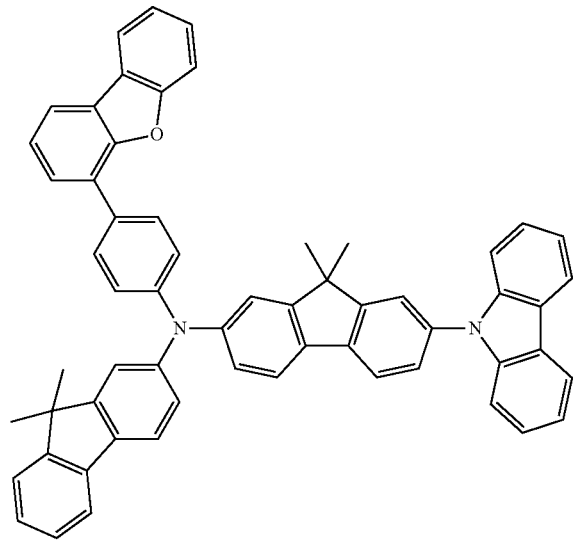
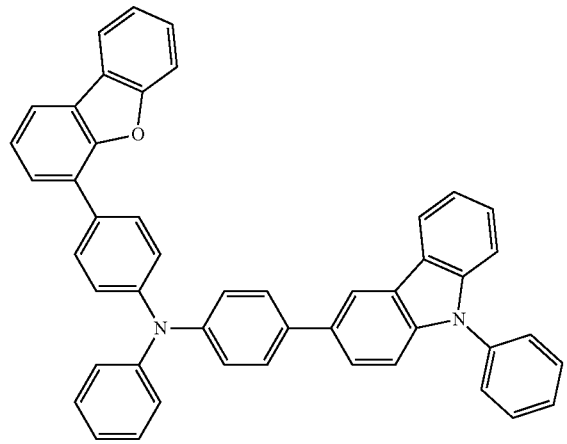
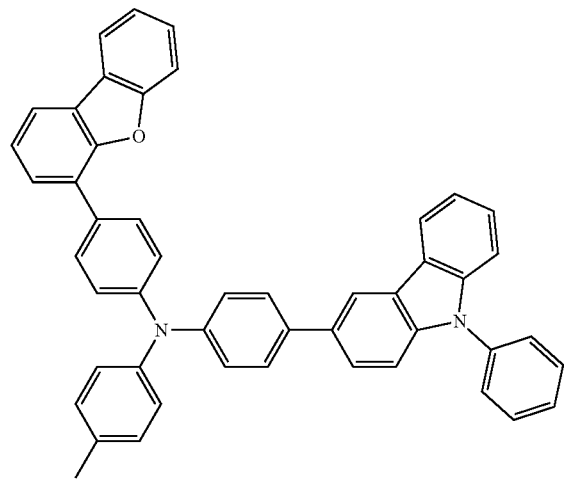
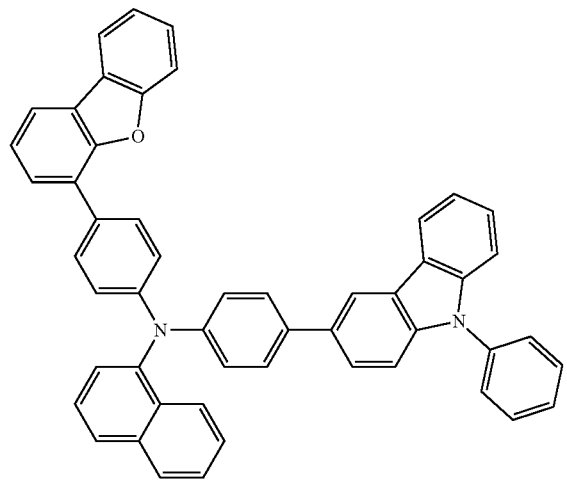
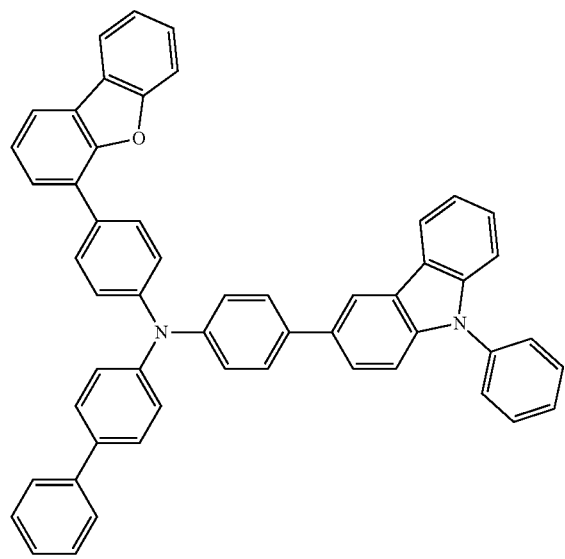
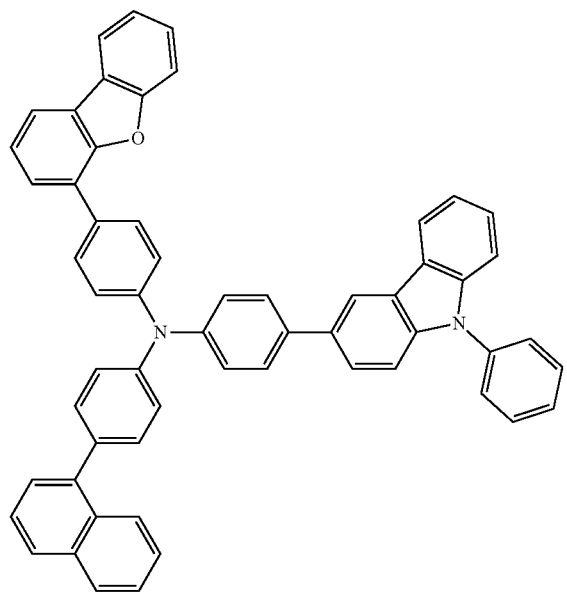

-continued
| 221 | 222 |
|---|---|
| 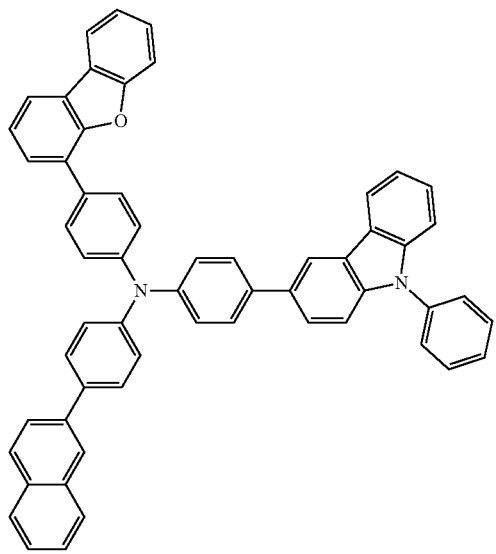 | 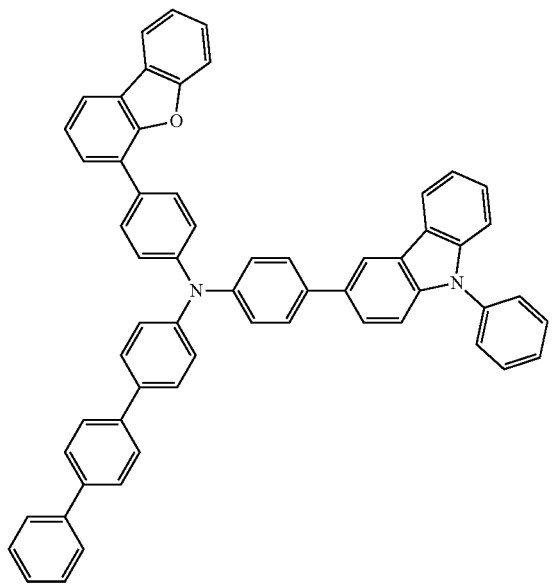 |
| 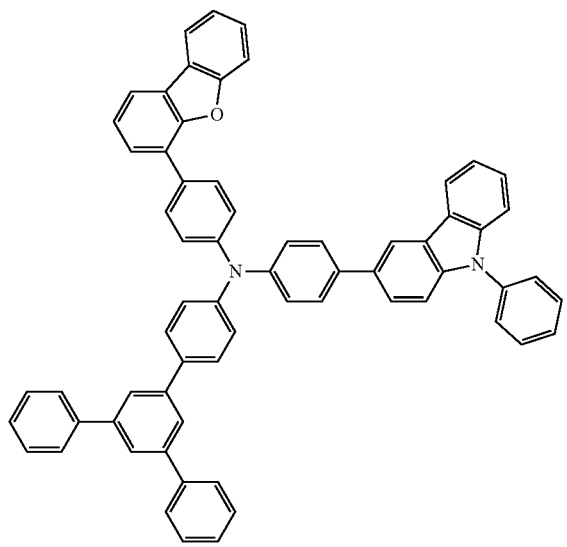 | 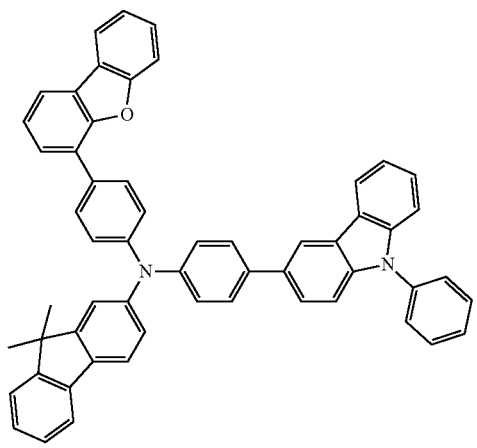 |
| 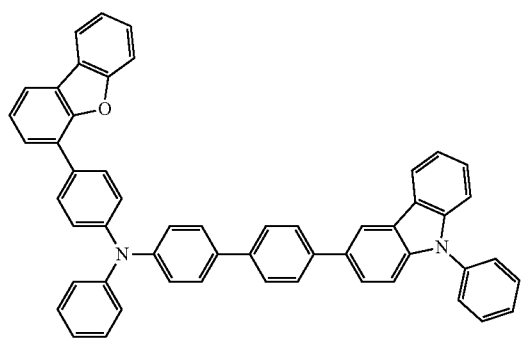 | 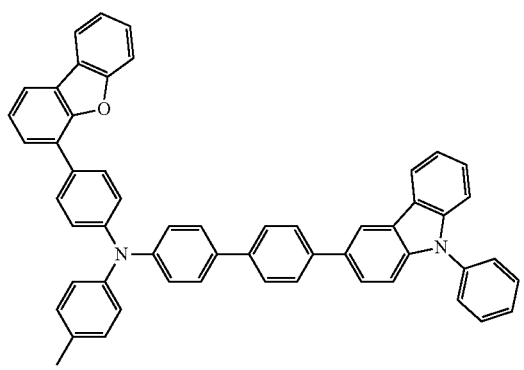 |

-continued
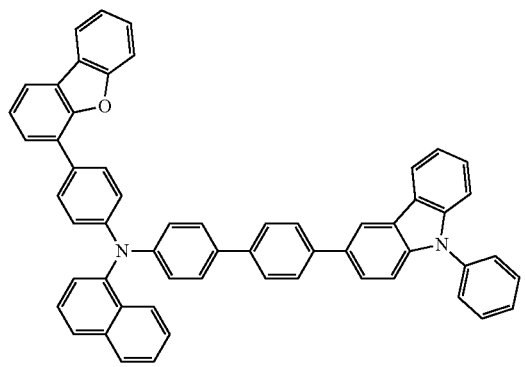
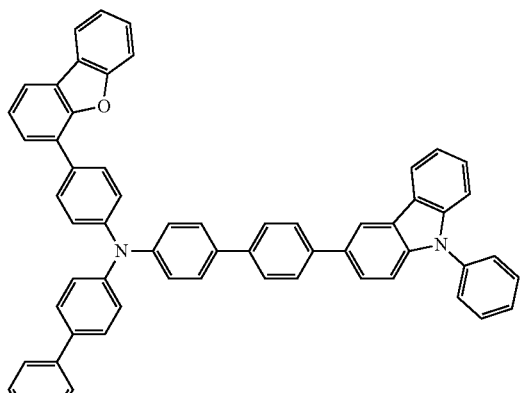
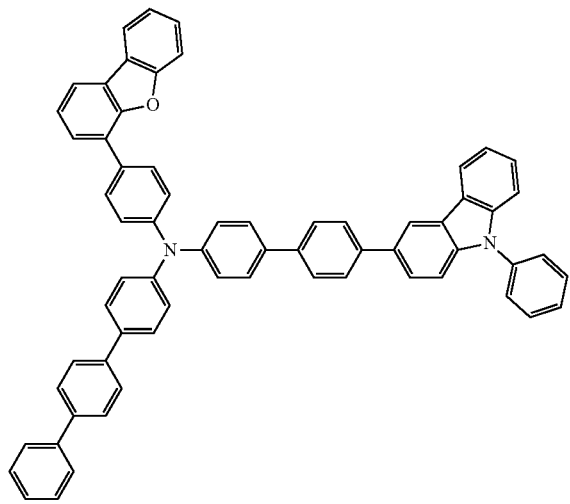
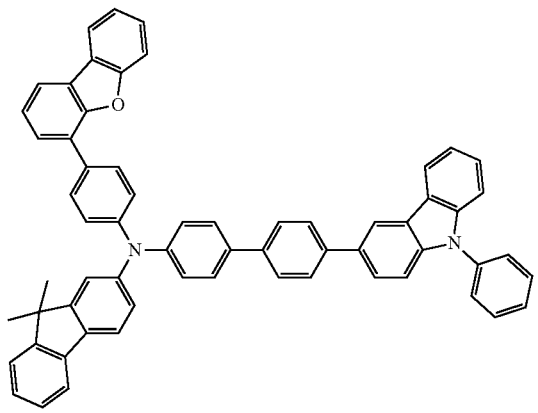
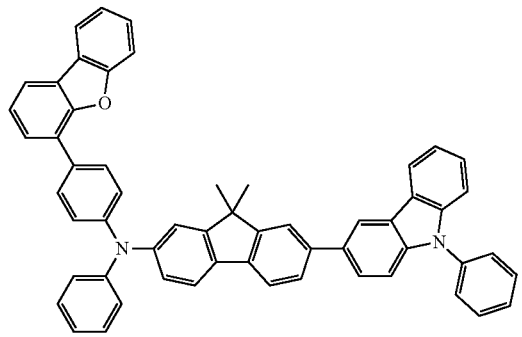
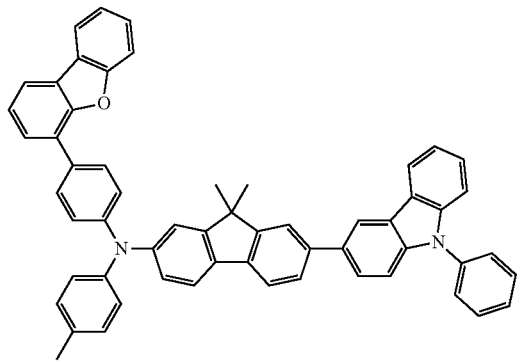
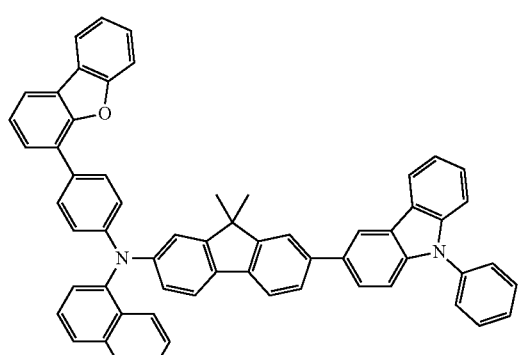
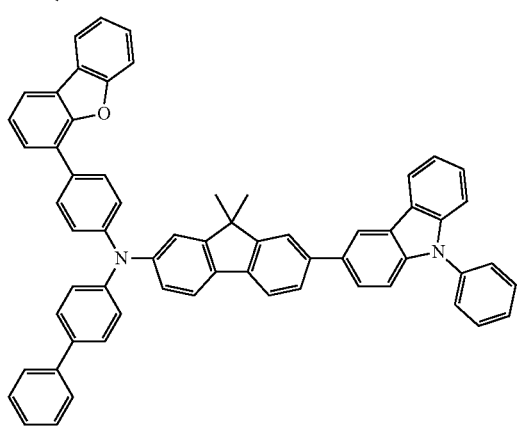

-continued
225
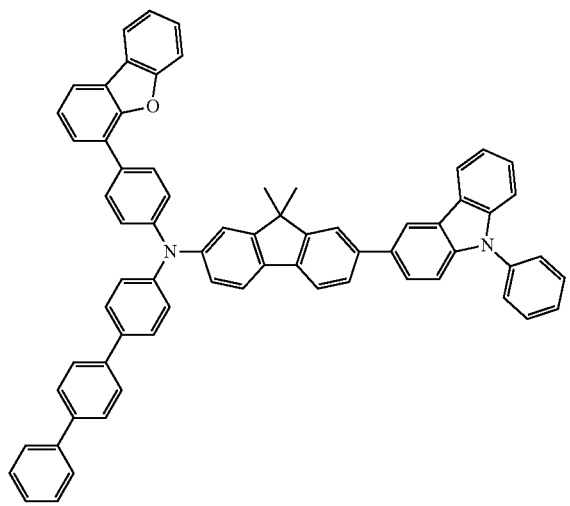
226
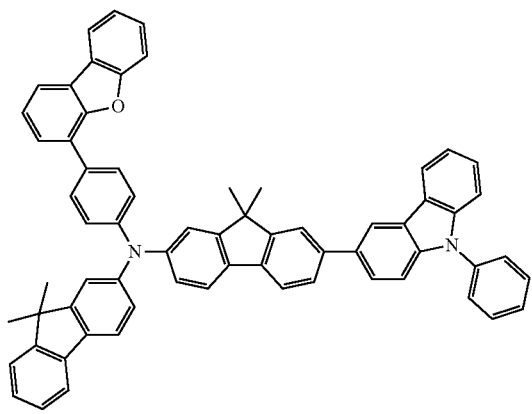
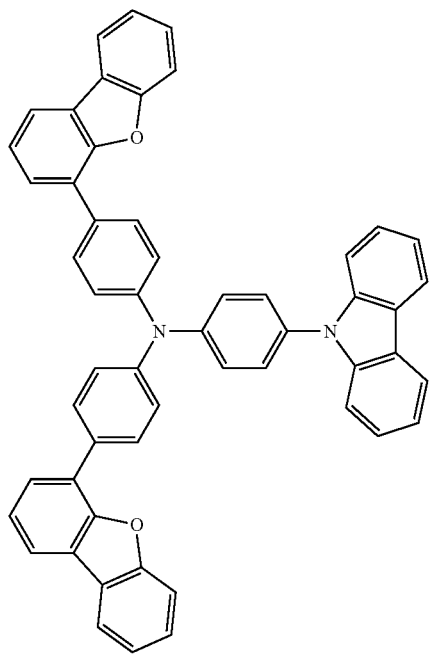
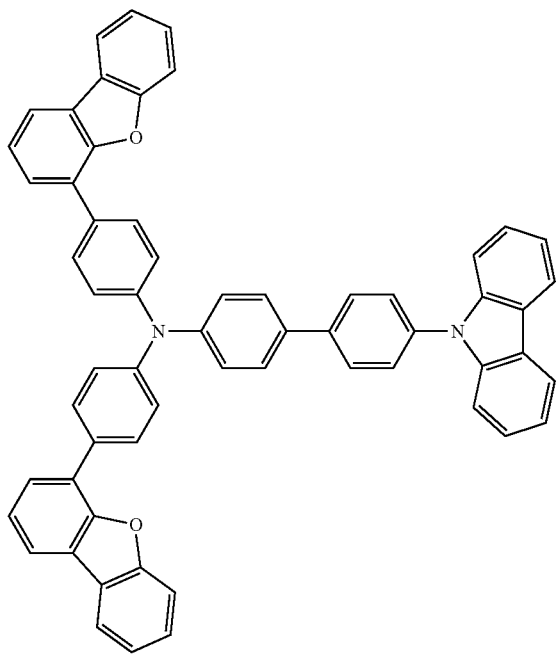

-continued
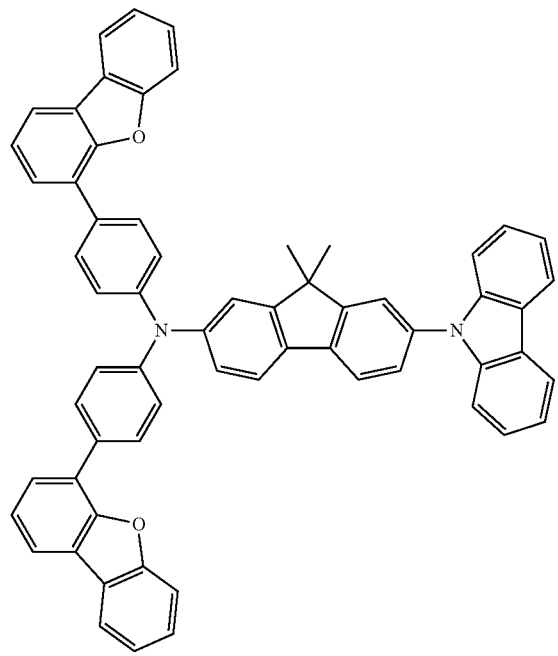
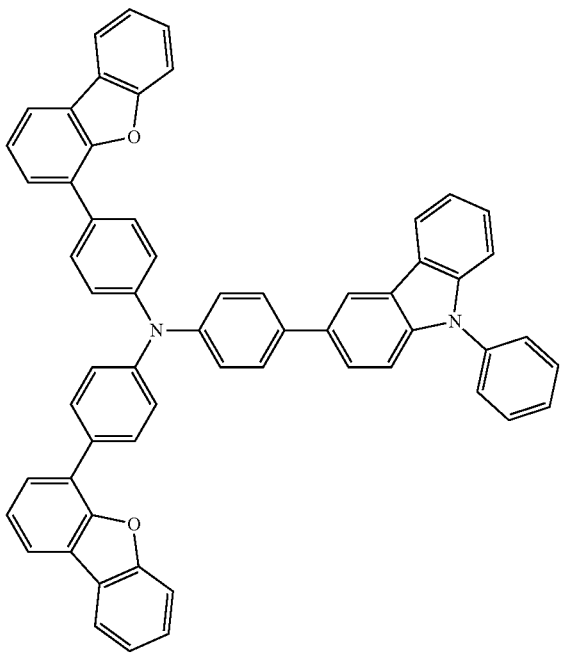
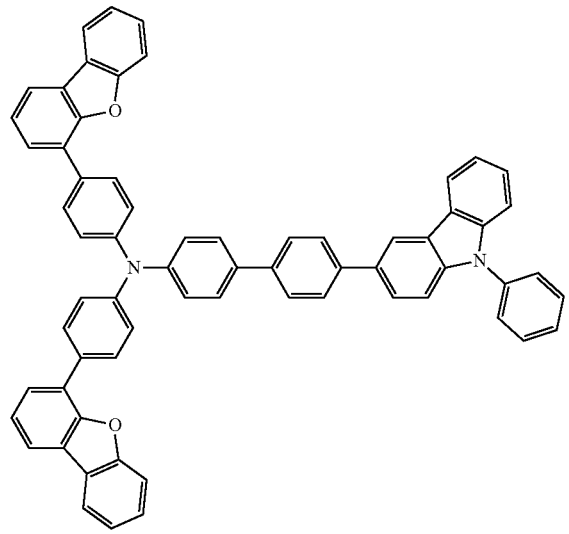
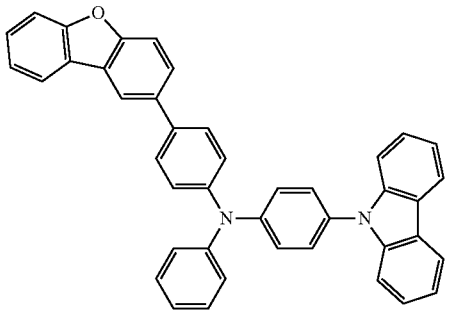
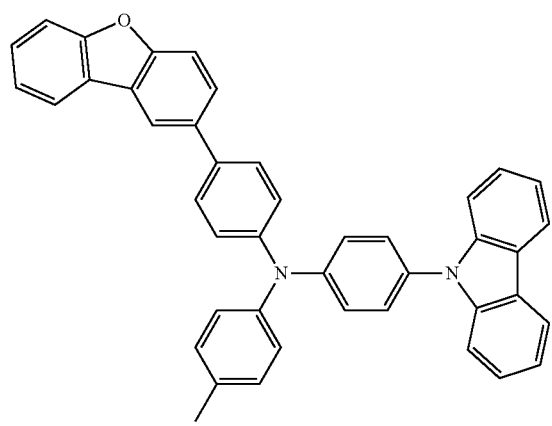
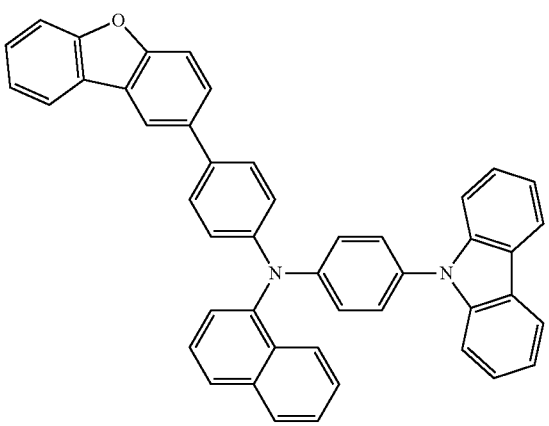

229
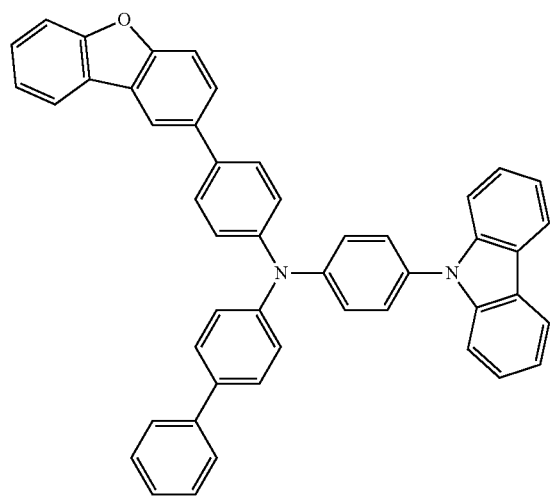
230
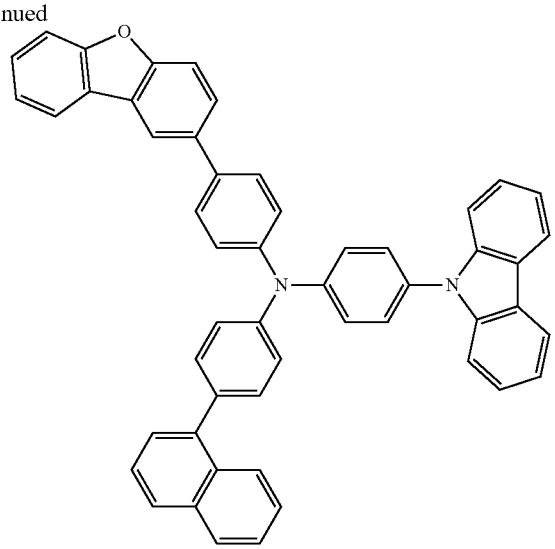
-continued
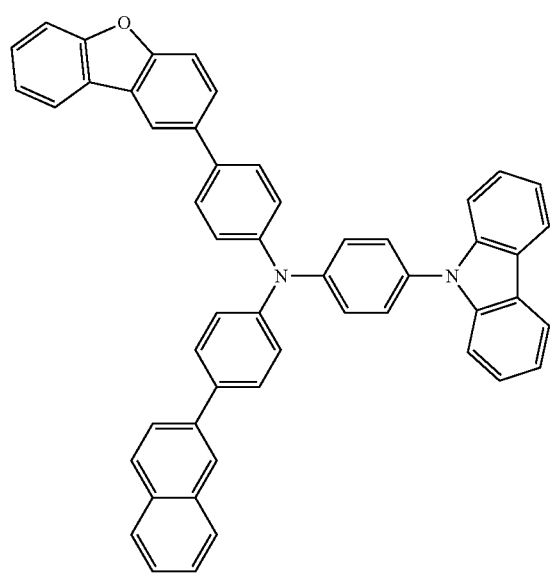
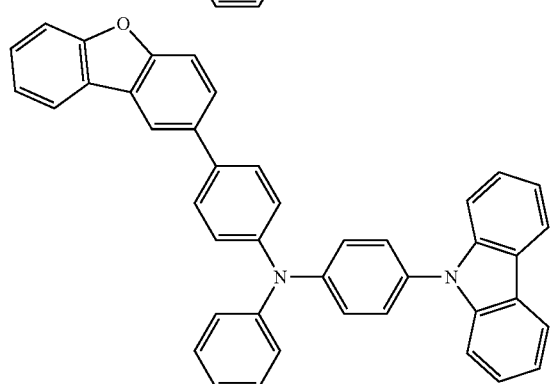
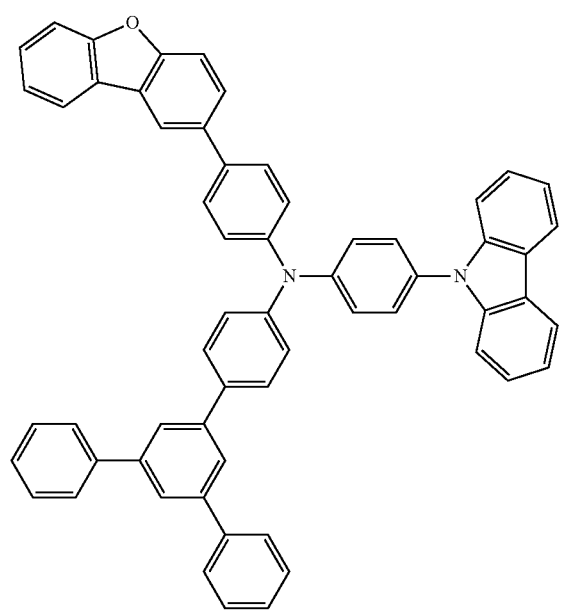
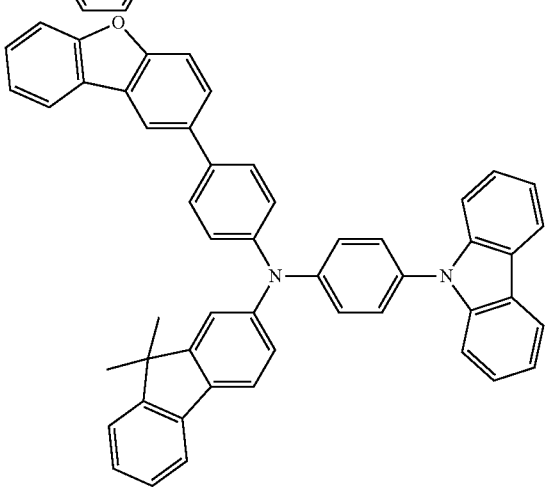

231
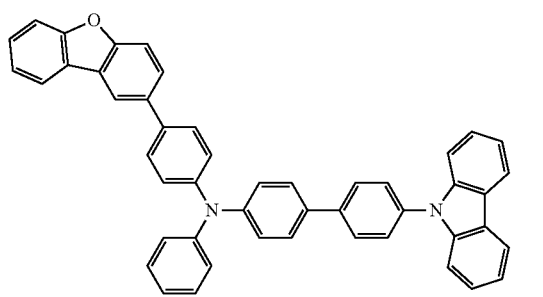
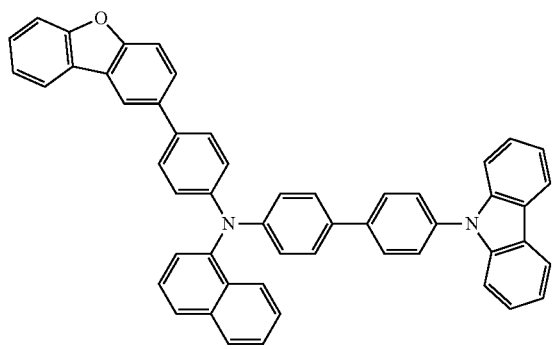
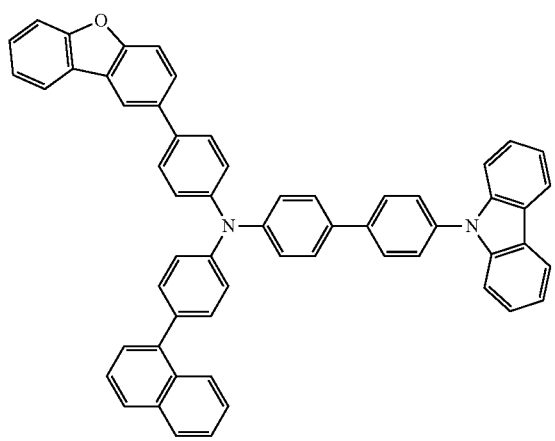
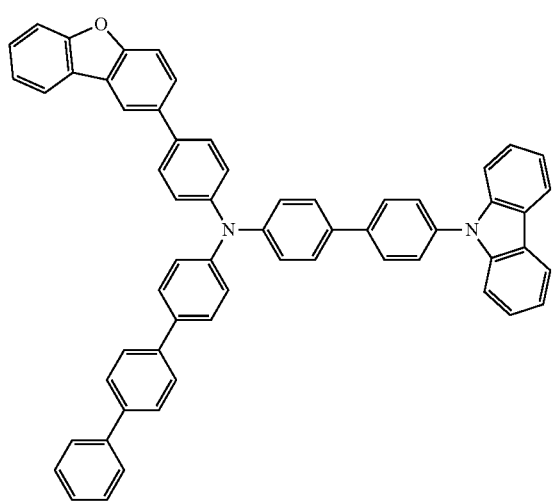
232
-continued
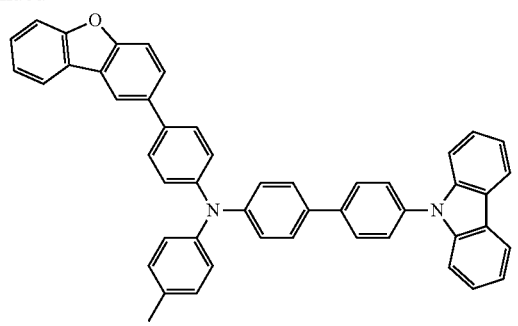
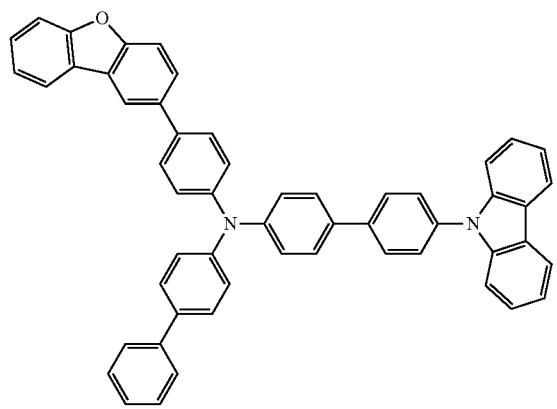
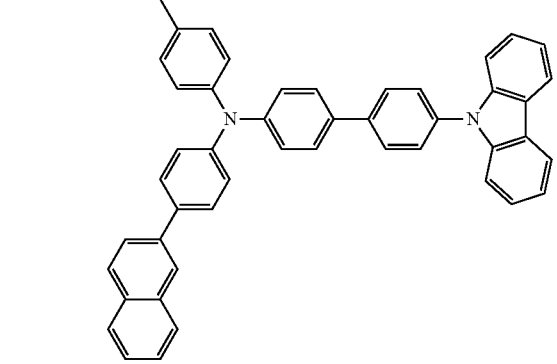
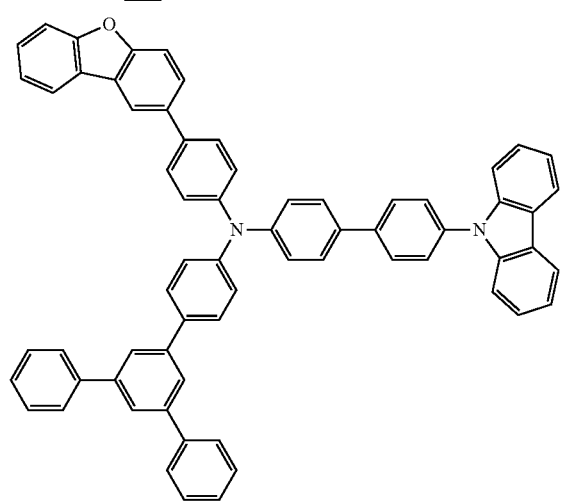

-continued
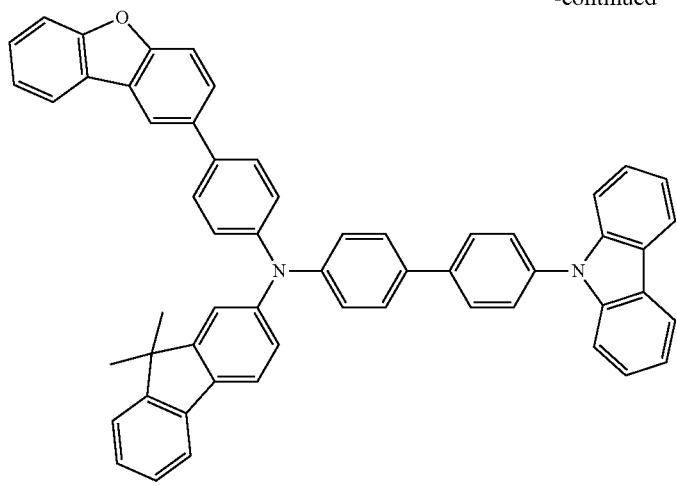
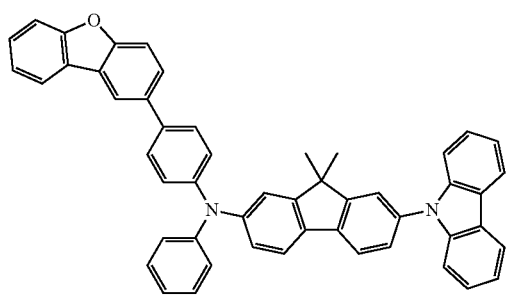
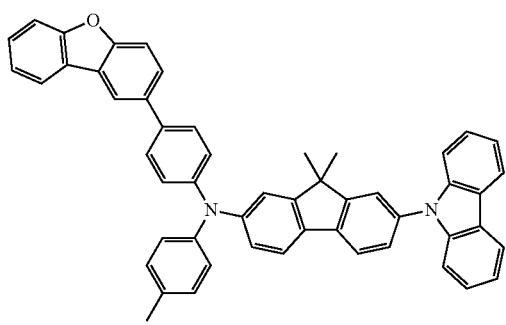
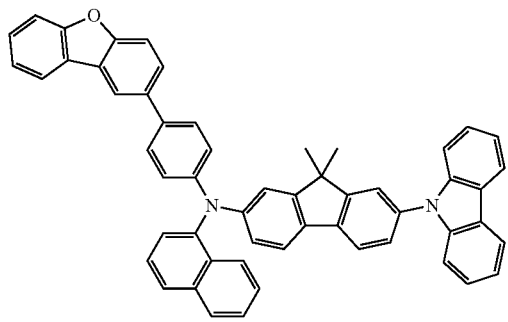
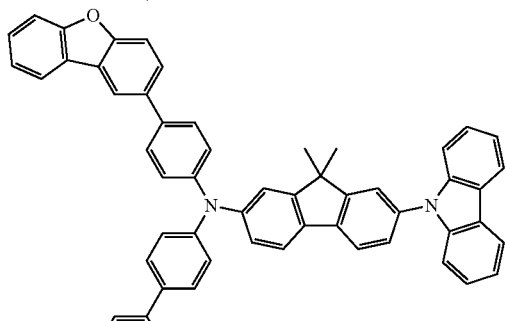
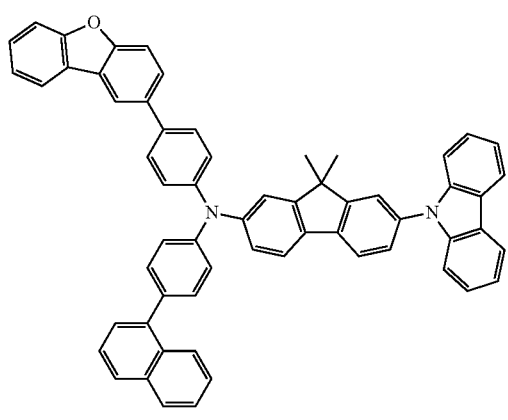
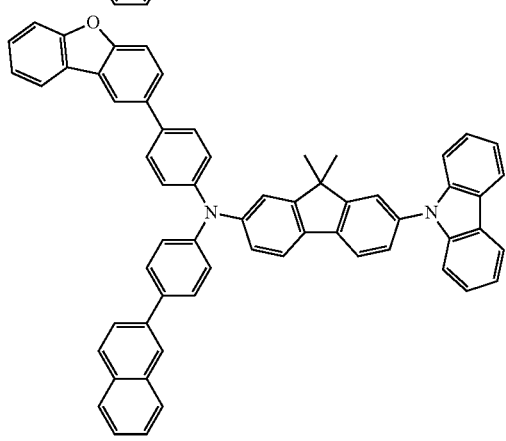

-continued
235
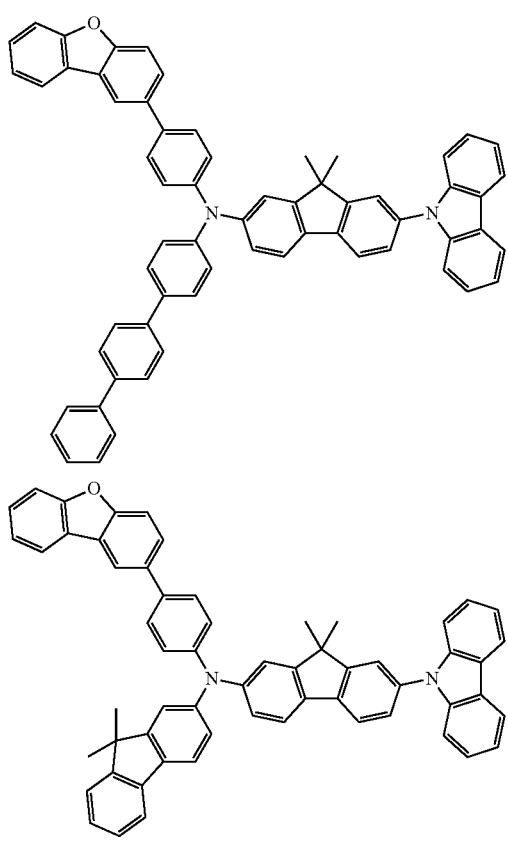
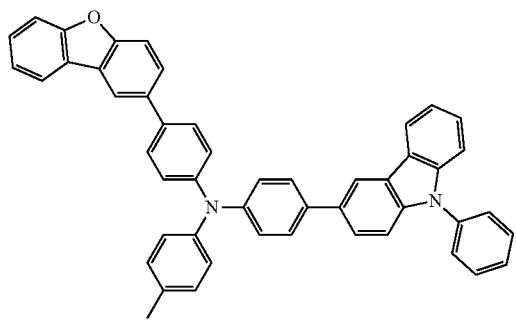
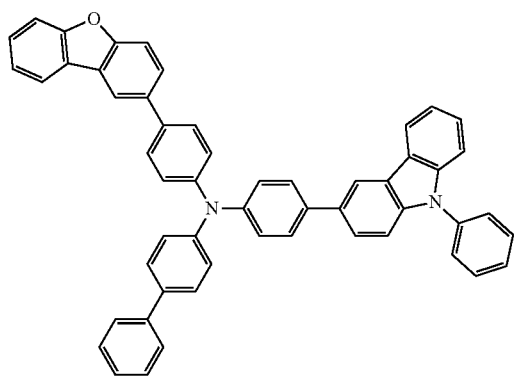
236
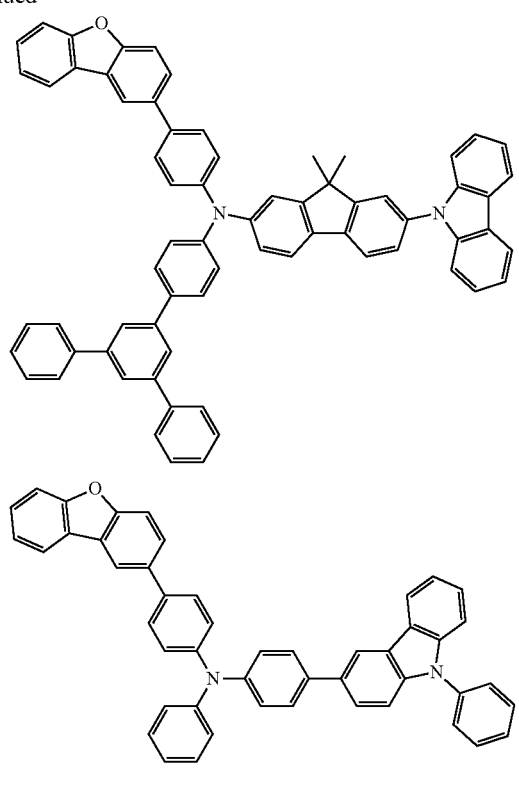
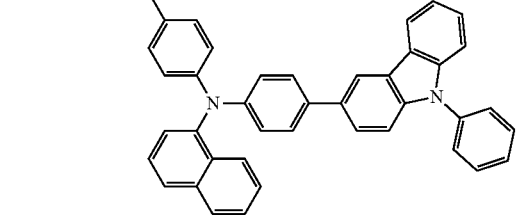
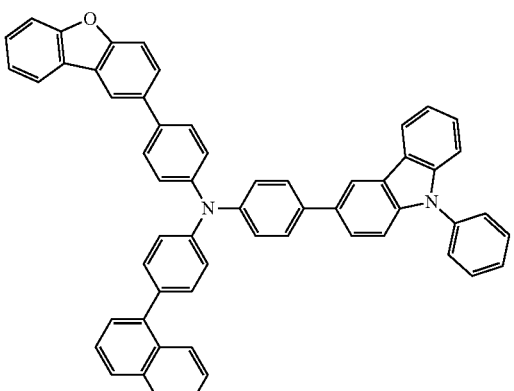

237
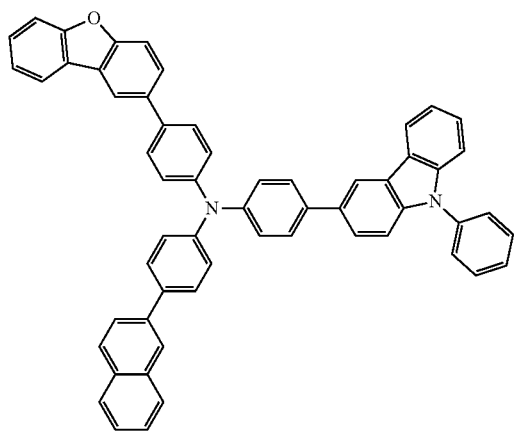
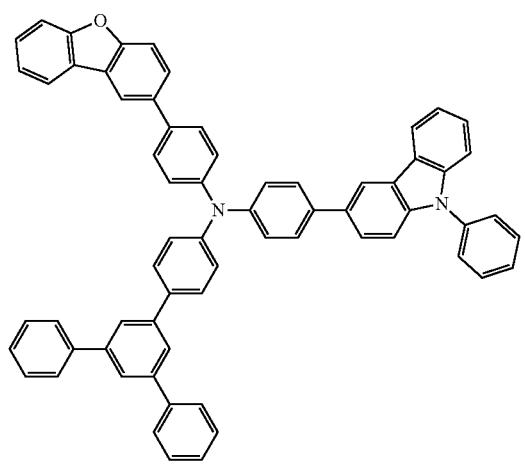
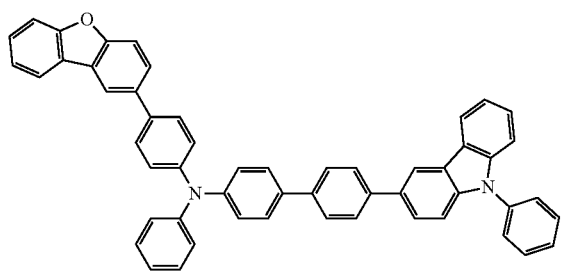
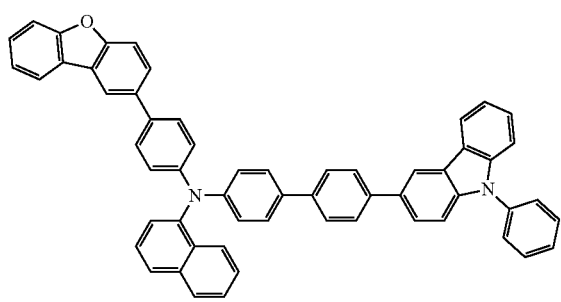
238
-continued
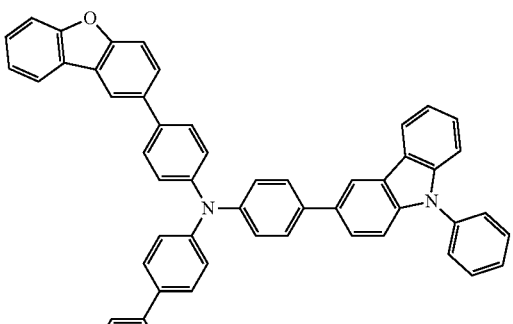
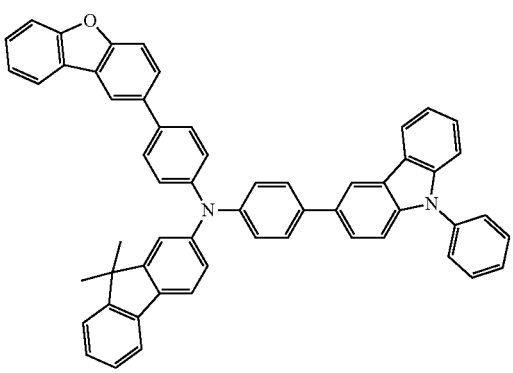
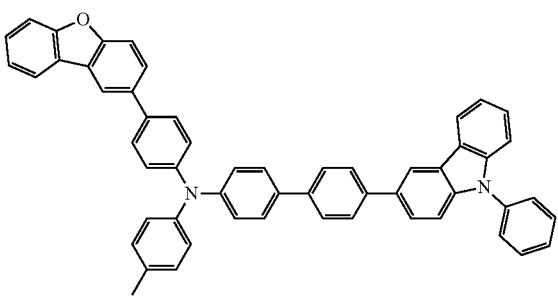
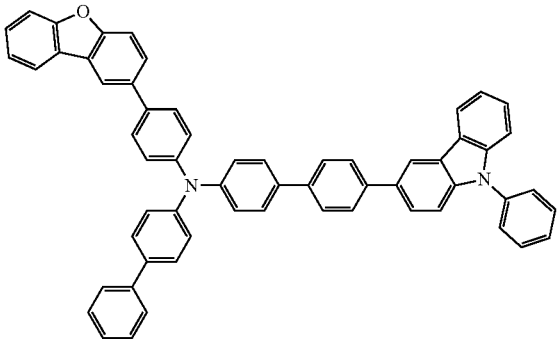

-continued
| 239 | 240 |
|---|---|
| 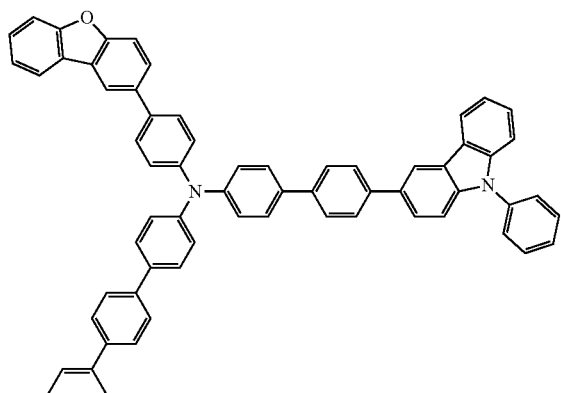 | 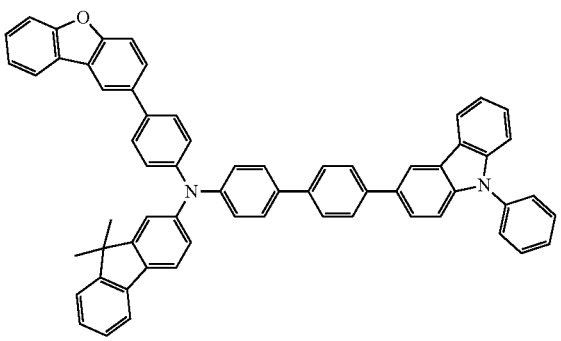 |
| 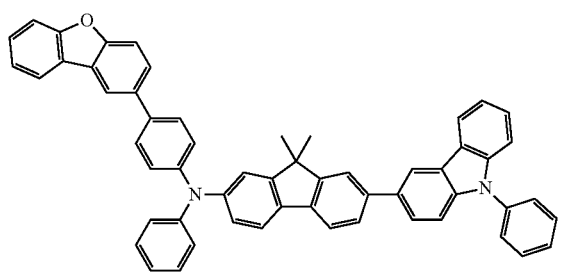 | 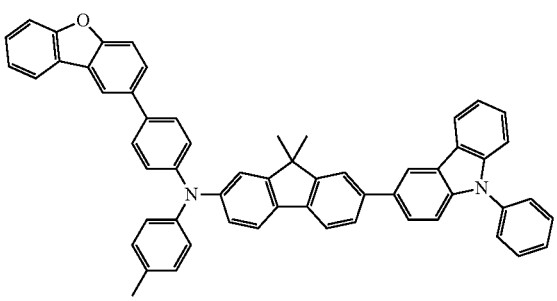 |
| 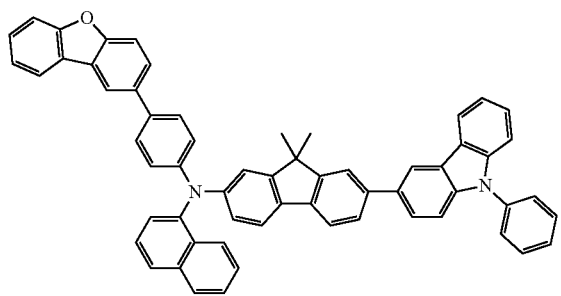 | 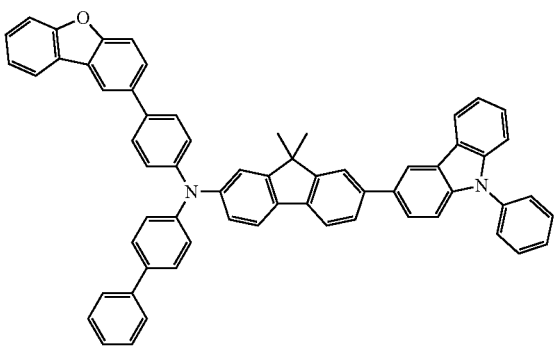 |
| 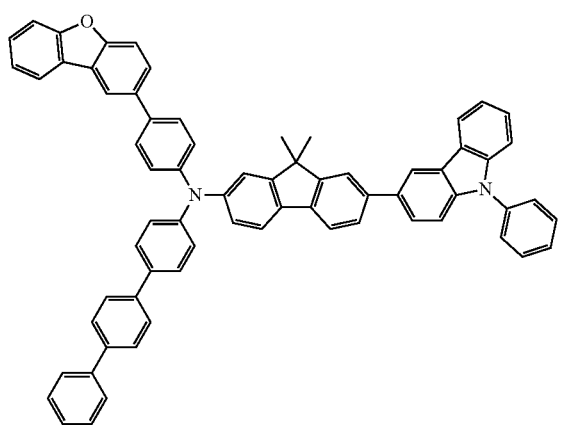 | 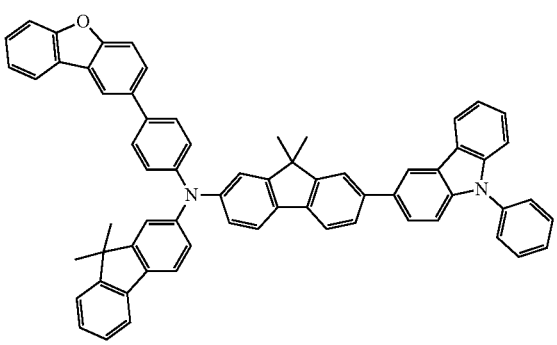 |

241 242
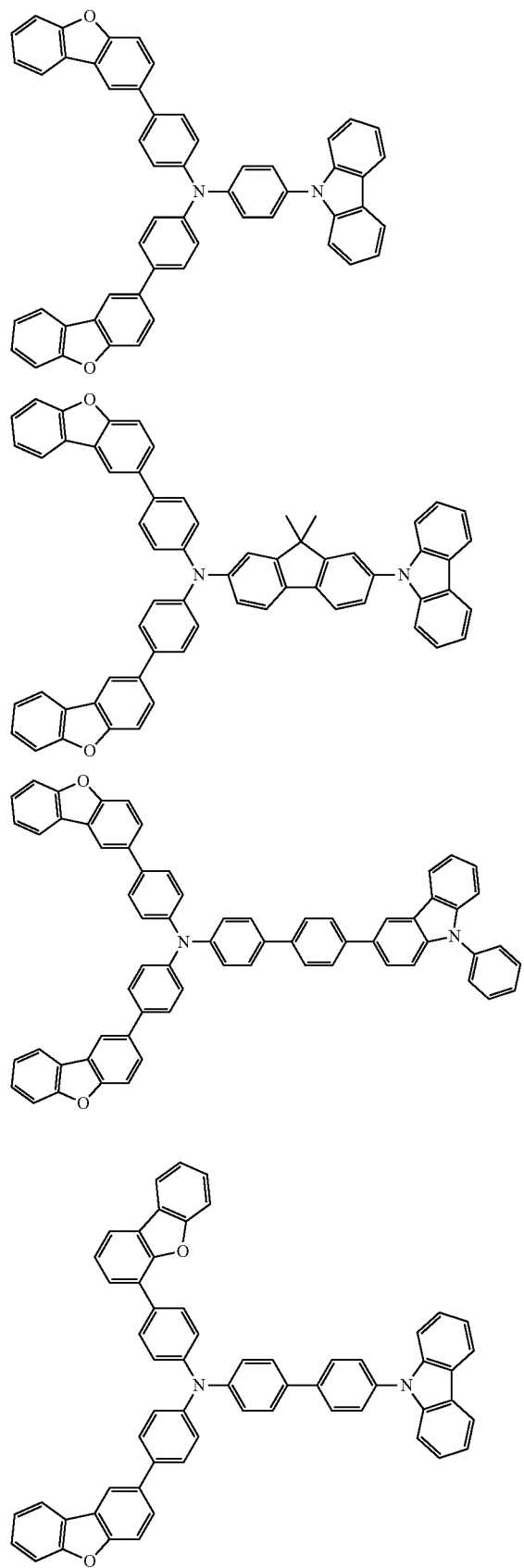
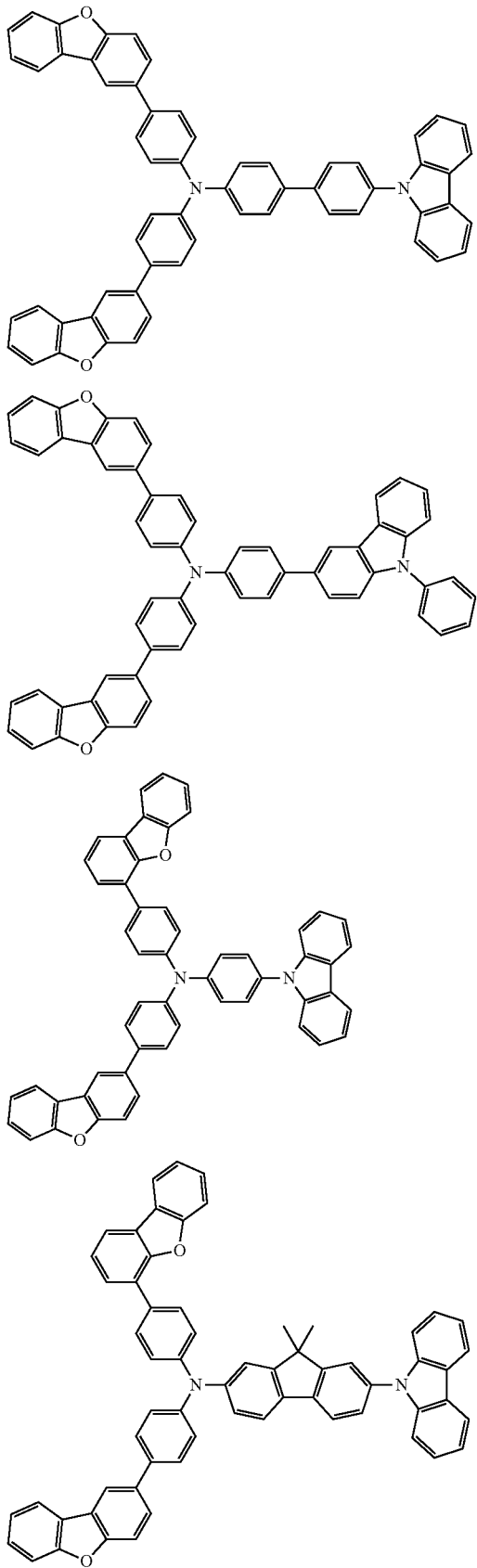

243 244
-continued
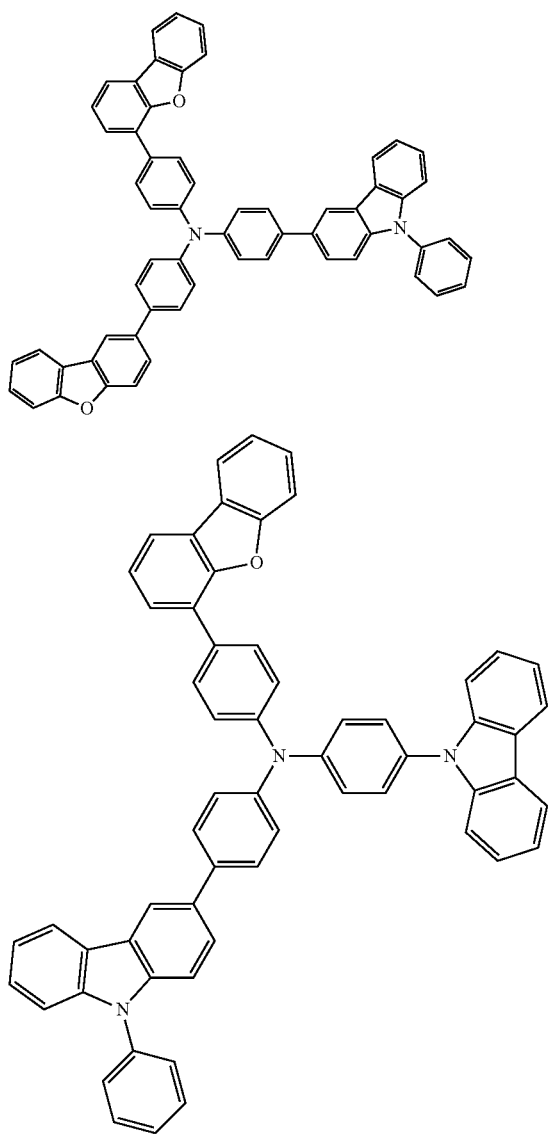
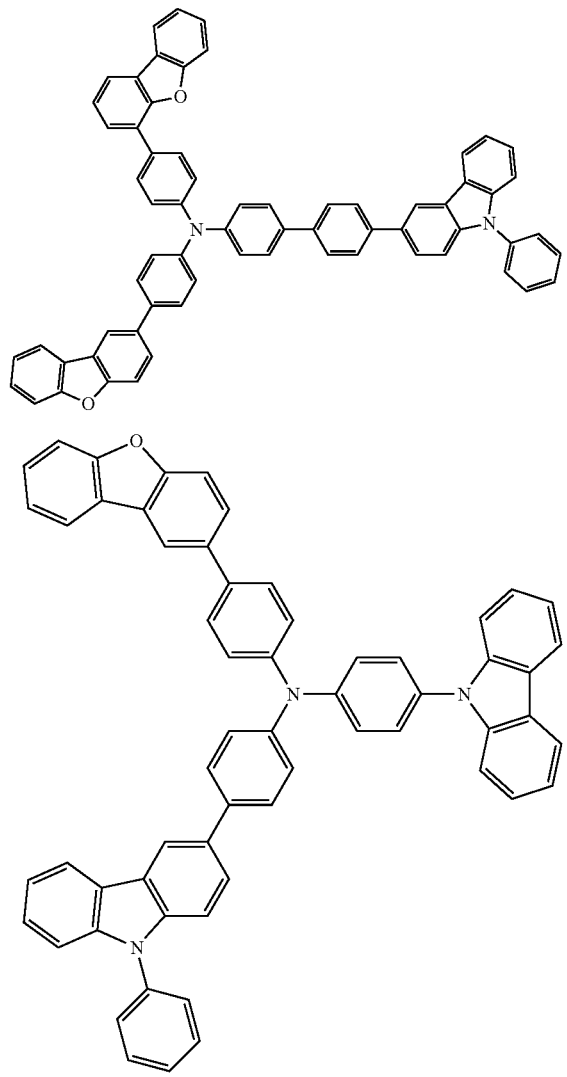
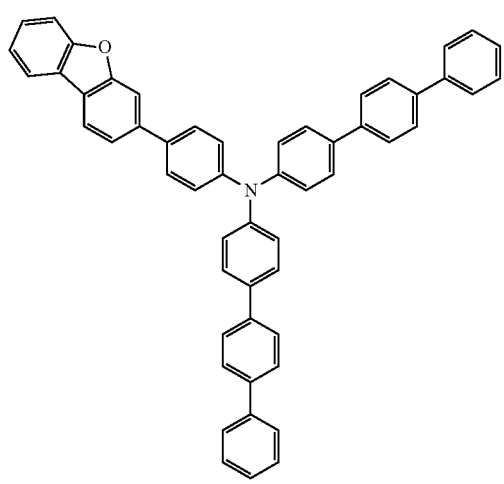
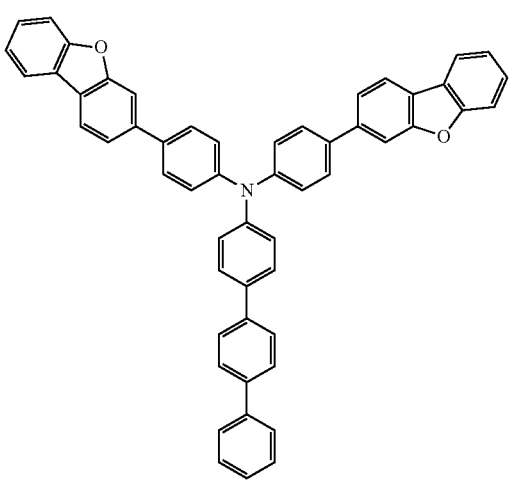

245 246
-continued
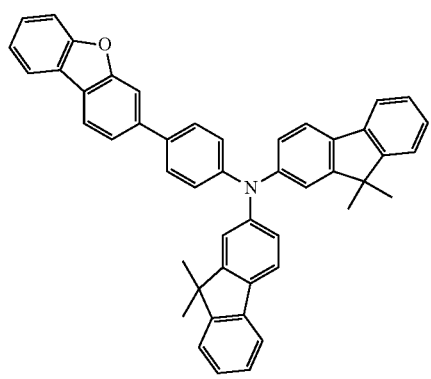
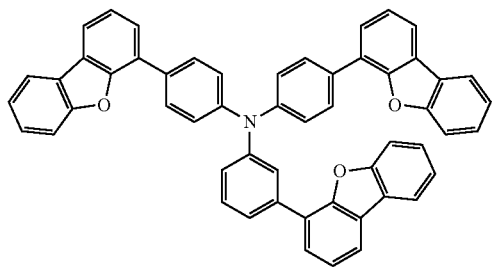
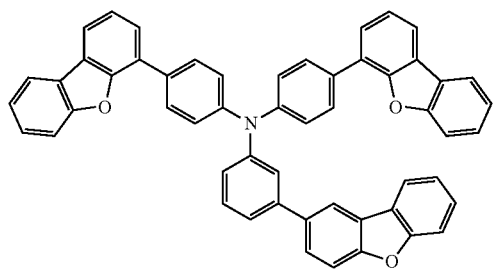
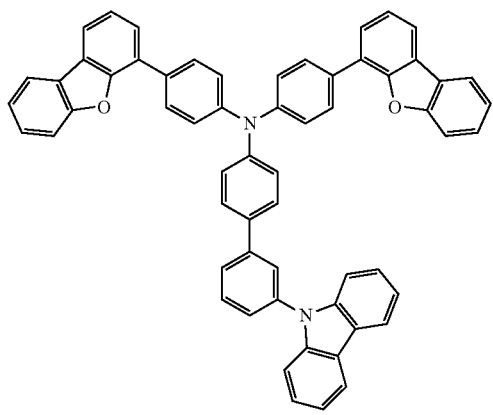
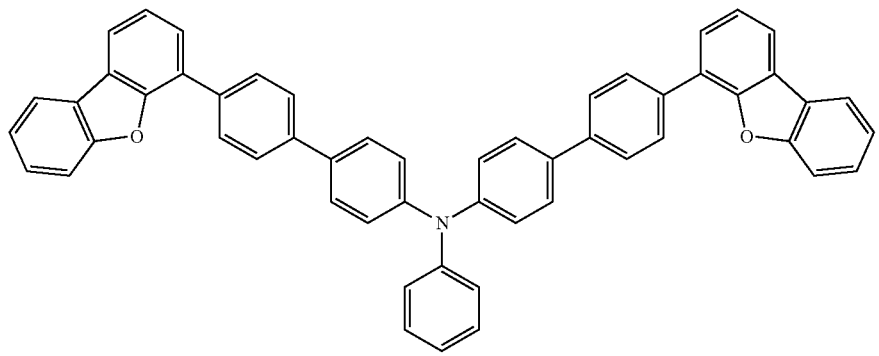
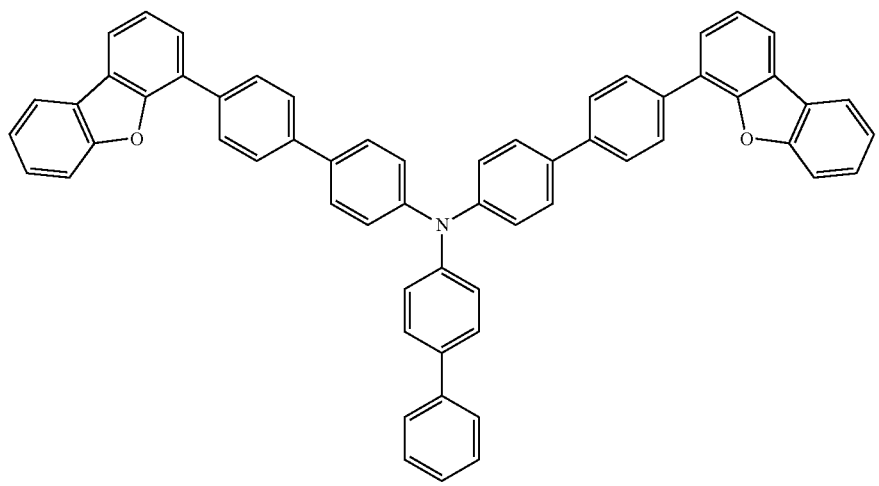

-continued
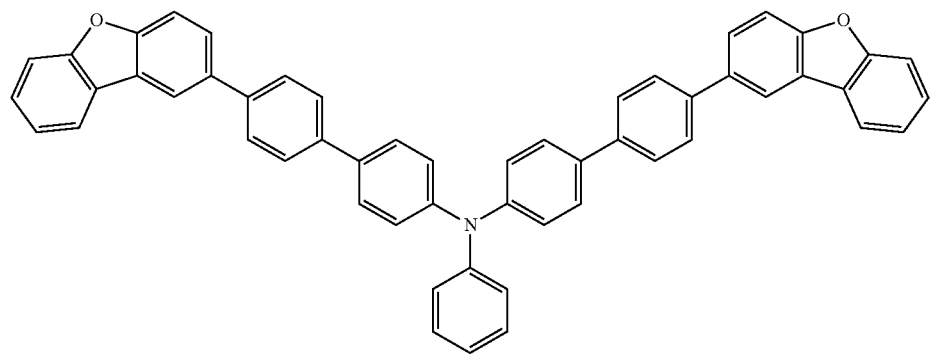
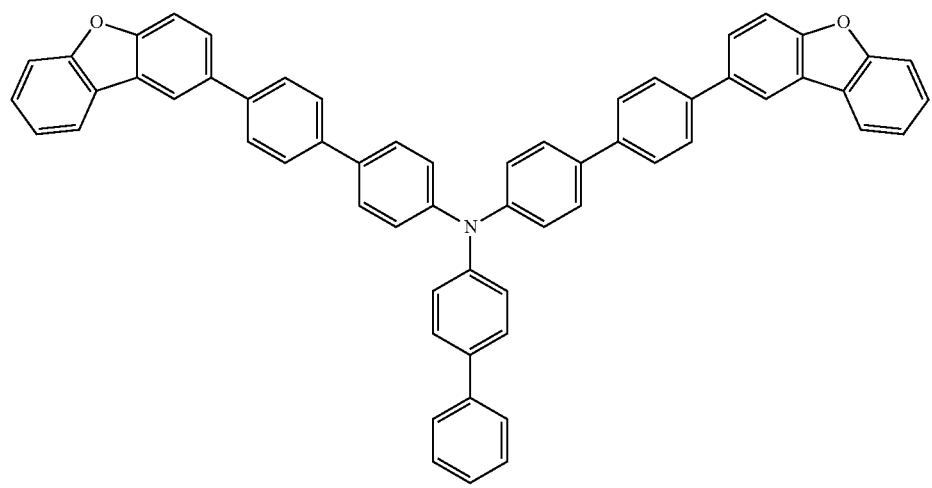
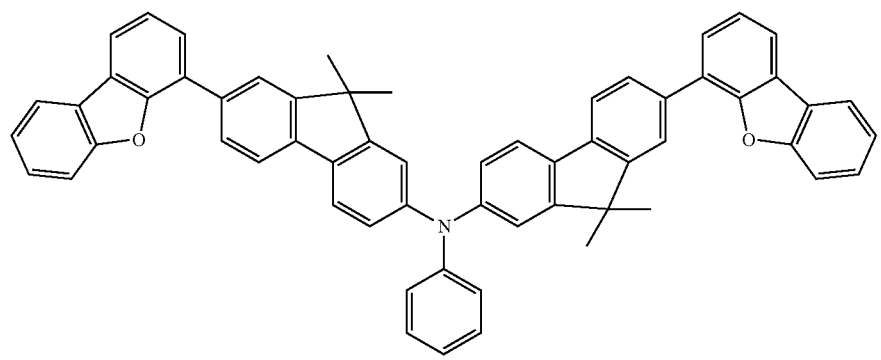
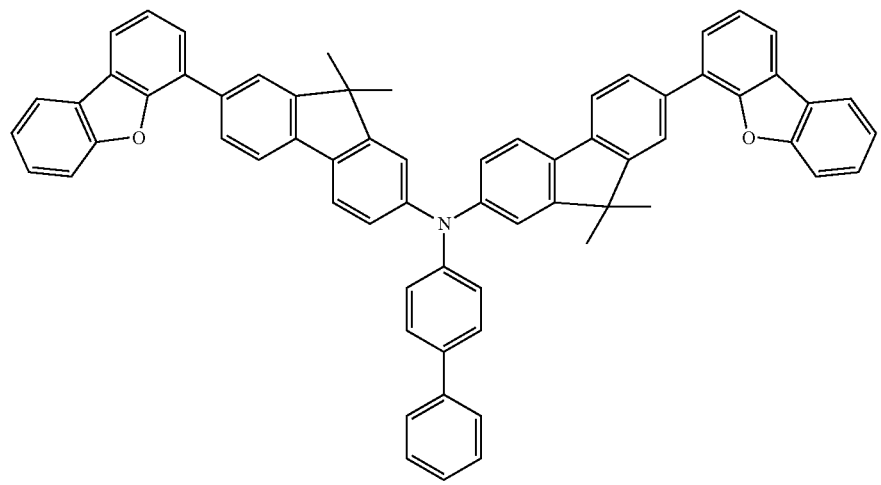

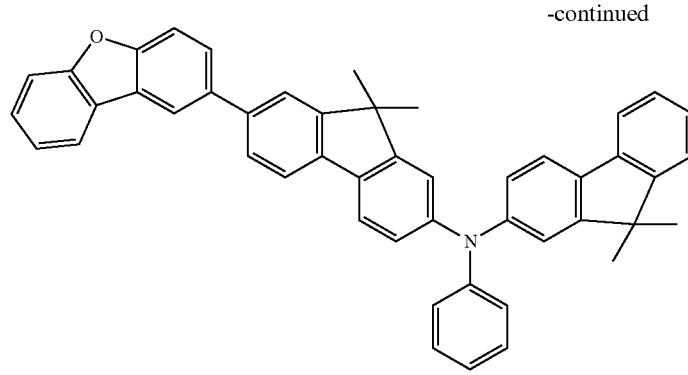

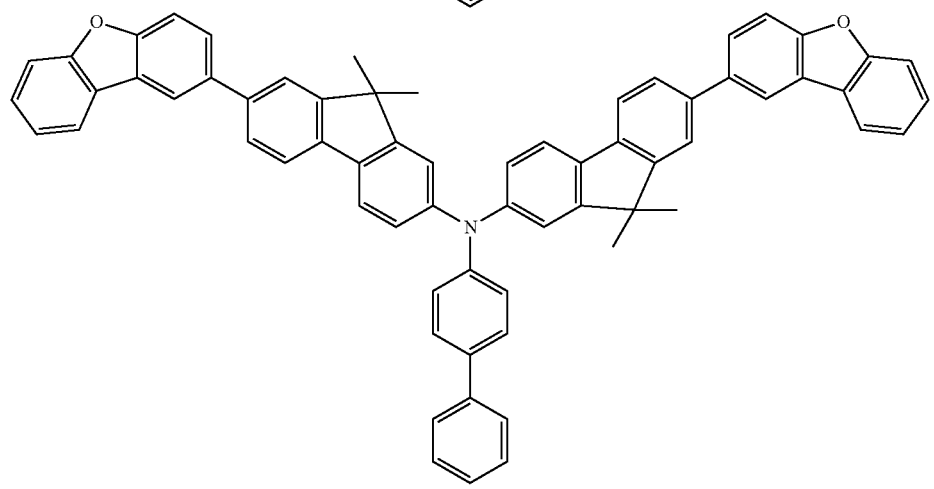

Example of Material for Hole Transporting Layer Adjacent to Light Emitting Layer (Second Hole Transporting Material), General Formulae (5) to (7)

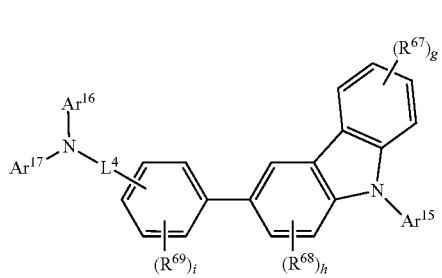

(5)

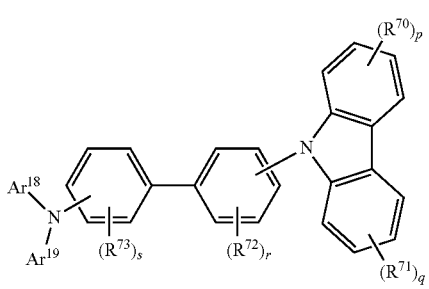

(6)

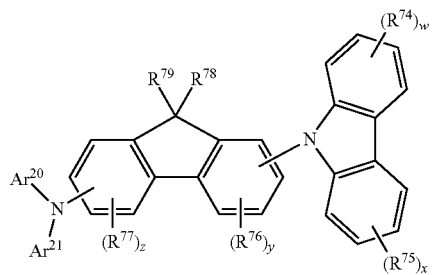

(7)

wherein in the formulae (5) to (7), $Ar^{15}$ to $Ar^{21}$ each independently represent a substituted or unsubstituted aryl group having from 6 to 50 ring carbon atoms, a substituted unsubstituted aromatic heterocyclic group having from 5 to 50 ring carbon atoms, a substituted or unsubstituted aryl group having from 8 to 50 ring carbon atoms having an aromatic amino group bonded thereto, or a substituted or unsubstituted aryl group having from 8 to 50 ring carbon atoms having an aromatic heterocyclic group bonded thereto.

$Ar^{16}$ and $Ar^{17}$, $Ar^{18}$ and $Ar^{19}$, and $Ar^{20}$ and $Ar^{21}$ each may be bonded to each other to form a ring.

$L^4$ represents a single bond or a substituted or unsubstituted arylene group having from 6 to 50 ring carbon atoms, and the substituent that may be substituted on $L^4$ is a linear or branched alkyl group having from 1 to 10 carbon atoms, a cycloalkyl group having from 3 to 10 ring carbon atoms, a trialkylsilyl group having from 3 to 10 carbon atoms, a triarylsilyl group having from 18 to 30 ring carbon atoms, an alkylarylsilyl group having from 8 to 15 carbon atoms (wherein the aryl moiety has from 6 to 14 ring carbon atoms), an aryl group having from 6 to 50 ring carbon atoms, a halogen atom or a cyano group.

$R^{67}$ to $R^{77}$ each independently represent a halogen atom, a substituted or unsubstituted alkyl group having from 1 to 40 carbon atoms, a substituted or unsubstituted heteroaryl group having from 5 to 20 ring carbon atoms, a substituted or unsubstituted non-condensed aryl group having from 6 to 40 ring carbon atoms, a substituted or unsubstituted condensed aryl group having from 6 to 12 ring carbon atoms, a substituted or unsubstituted aralkyl group having from 7 to 20 carbon atoms, a substituted or unsubstituted alkenyl group having from 2 to 40 carbon atoms, a substituted or unsubstituted alkylamino group having from 1 to 40 carbon atoms, a substituted or unsubstituted aralkylamino group having from 7 to 60 carbon atoms, a substituted or unsubstituted alkylsilyl group having from 3 to 20 carbon atoms, a substituted or unsubstituted arylsilyl group having from 6 to 40 ring carbon atoms, a substituted or unsubstituted aralkylsilyl group having from 8 to 40 carbon atoms, or a substituted or unsubstituted halogenated alkyl group having from 1 to 40 carbon atoms.

$R^{78}$ and $R^{79}$ each independently represent a substituted or unsubstituted alkyl group having from 1 to 40 carbon atoms, a substituted or unsubstituted heteroaryl group having from 5 to 20 ring carbon atoms, a substituted or unsubstituted non-condensed aryl group having from 6 to 40 ring carbon atoms, a substituted or unsubstituted condensed aryl group having from 6 to 12 ring carbon atoms, or a substituted or unsubstituted aralkyl group having from 7 to 20 carbon atoms.

g, i, p, q, r, s, w and x each independently represent an integer of from 0 to 4.

h, y and z each independently represent an integer of from 0 to 3.

Example of Material for Hole Transporting Layer Adjacent to Light Emitting Layer (Second Hole Transporting Material), General Formula (8)

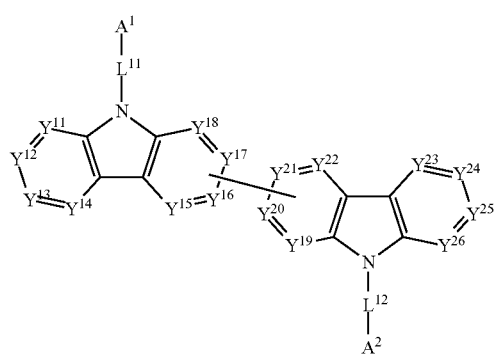

(8)

wherein in the formula (8), $A^1$ and $A^2$ each independently represent a substituted or unsubstituted aryl group having from 6 to 30 ring carbon atoms or a substituted or unsubstituted heteroaryl group having from 2 to 30 ring carbon atoms.

$Y^{11}$ to $Y^{26}$ each independently represent C(R) or a nitrogen atom, wherein R independently represents a hydrogen atom, a substituent or a bond bonded to the carbazole skeleton.

$L^{11}$ and $L^{12}$ each independently represent a single bond or a substituted or unsubstituted arylene group having from 6 to 50 ring carbon atoms, and the substituent that may be substituted on the arylene group is a linear or branched alkyl group having from 1 to 10 carbon atoms, a cycloalkyl group having from 3 to 10 ring carbon atoms, a trialkylsilyl group having from 3 to 10 carbon atoms, a triarylsilyl group having from 18 to 30 carbon atoms, an alkylarylsilyl group having from 8 to 15 carbon atoms (wherein the aryl moiety has from 6 to 14 ring carbon atoms), an aryl group having from 6 to 50 ring carbon atoms, a halogen atom or a cyano group.

(5) Light Emitting Layer

The organic EL device of the present invention may have a light emitting layer containing a fluorescent material, i.e., a fluorescent light emitting layer. In the fluorescent light emitting layer, a known fluorescent material may be used. The fluorescent material is preferably at least one selected from an anthracene derivative, a fluorantene derivative, a styrylamine derivative and an arylamine derivative, and an anthracene derivative and an arylamine derivative are more preferred. In particular, the host material is preferably an anthracene derivative, and the dopant is preferably an arylamine derivative. Specifically, the preferred materials disclosed in WO 2010/134350 and WO 2010/134352 may be selected.

The organic EL device of the present invention may have a light emitting layer containing a phosphorescent material, i.e., a phosphorescent light emitting layer. As the material for the phosphorescent layer, a known phosphorescent material may be used. Specifically, WO 2005/079118 and the like may be referred. In the phosphorescent material, preferred examples of the dopant include an ortho-metallized complex of iridium (Ir), osmium (Os) or platinum (Pt), and an ortho-metallized complex of iridium (Ir) is more preferred. In the phosphorescent material, the host material is preferably a compound having a carbazolyl group, more preferably a compound having a carbazolyl group and a triazine skeleton, and further preferably a compound having two carbazolyl groups and one triazine skeleton.

The anthracene derivative as the fluorescent material preferably has from 26 to 100, more preferably from 26 to 80, and further preferably from 26 to 60, ring carbon atoms. More specifically, the anthracene derivative is preferably an anthracene derivative represented by the following general formula (10):

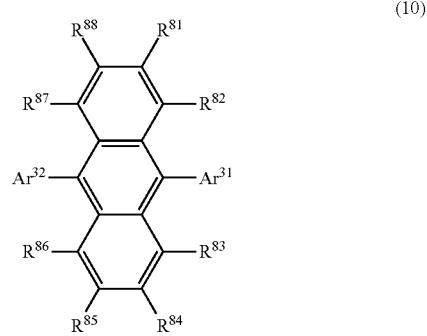

(10)

wherein in the formula (10), $Ar^{31}$ and $Ar^{32}$ each independently represent a substituted or unsubstituted aryl group having from 6 to 50 ring carbon atoms or a heterocyclic group having from 5 to 50 ring atoms.

$R^{81}$ to $R^{88}$ each independently represent a hydrogen atom, a substituted or unsubstituted aryl group having from 6 to 50 ring carbon atoms, a substituted or unsubstituted heterocyclic group having from 5 to 50 ring atoms, a substituted or unsubstituted alkyl group having from 1 to 50 carbon atoms, a substituted or unsubstituted alkoxy group having from 1 to 50 carbon atoms, a substituted or unsubstituted aralkyl group having from 7 to 50 carbon atoms, a substituted or unsubstituted aryloxy group having from 6 to 50 ring carbon atoms, a substituted or unsubstituted arylthio group having from 6 to 50 ring carbon atoms, a substituted or unsubstituted alkoxycarbonyl group having from 2 to 50 carbon atoms, a substituted or unsubstituted silyl group, a carboxyl group, a halogen atom, a cyano group, a nitro group or a hydroxyl group.

All the aryl groups having from 6 to 50 ring carbon atoms are each preferably an aryl group having from 6 to 40 ring carbon atoms, and more preferably an aryl group having from 6 to 30 ring carbon atoms.

All the heterocyclic groups having from 5 to 50 ring atoms are each preferably a heterocyclic groups having from 5 to 40 ring atoms, and more preferably a heterocyclic groups having from 5 to 30 ring atoms.

The alkyl group having from 1 to 50 carbon atoms is preferably an alkyl group having from 1 to 30 carbon atoms, more preferably an alkyl group having from 1 to 10 carbon atoms, and further preferably an alkyl group having from 1 to 5 carbon atoms.

The alkoxy group having from 1 to 50 carbon atoms is preferably an alkoxy group having from 1 to 30 carbon atoms, more preferably an alkoxy group having from 1 to 10 carbon atoms, and further preferably an alkoxy group having from 1 to 5 carbon atoms.

The aralkyl group having from 7 to 50 carbon atoms is preferably an aralkyl group having from 7 to 30 carbon atoms, and more preferably an aralkyl group having from 7 to 20 carbon atoms.

The aryloxy group having from 6 to 50 ring carbon atoms is preferably an aryloxy group having from 6 to 40 ring carbon atoms, and more preferably an aryloxy group having from 6 to 30 ring carbon atoms.

The arylthio group having from 6 to 50 ring carbon atoms is preferably an arylthio group having from 6 to 40 ring carbon atoms, and more preferably an arylthio group having from 6 to 30 ring carbon atoms.

The alkoxycarbonyl group having from 2 to 50 carbon atoms is preferably an alkoxycarbonyl group having from 2 to 30 carbon atoms, more preferably an alkoxycarbonyl group having from 2 to 10 carbon atoms, and further preferably an alkoxycarbonyl group having from 2 to 5 carbon atoms.

Examples of the halogen atom include a fluorine atom, a chlorine atom and a bromine atom.

In particular, $Ar^{31}$ and $Ar^{32}$ are each preferably a substituted or unsubstituted aryl group having from 6 to 50 ring carbon atoms.

The anthracene derivative represented by the general formula (10) is preferably an anthracene derivative represented by the following general formula (10-1):

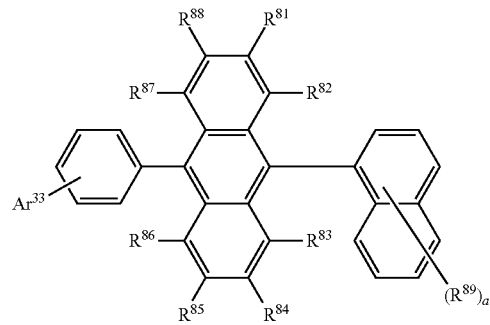

(10-1)

wherein in the formula (10-1), $Ar^{33}$ represents a substituted or unsubstituted aryl group having from 6 to 50 ring carbon atoms or a heterocyclic group having from 5 to 50 ring atoms. $R^{81}$ to $R^{88}$ have the same meanings as above. $R^{89}$ has the same meaning as $R^{81}$ to $R^{88}$. a represents an integer of from 1 to 7.

Preferred examples of $R^{81}$ to $R^{88}$ are the same as above. a preferably represents an integer of from 1 to 3, and more preferably 1 or 2. $R^{89}$ may be substituted on any one of two benzene rings of the naphthalene ring.

The aryl group having from 5 to 60 ring carbon atoms represented by $Ar^{33}$ is preferably an aryl group having from 6 to 40 ring carbon atoms, more preferably an aryl group having from 6 to 30 ring carbon atoms, further preferably an aryl group having from 6 to 20 ring carbon atoms, and particularly preferably an aryl group having from 6 to 12 ring carbon atoms.

The arylamine derivative as the fluorescent material is preferably an aryldiamine derivative, more preferably an aryldiamine derivative having a pyrene skeleton, and further preferably an aryldiamine derivative having a pyrene skeleton and a dibenzofuran skeleton.

More specifically, the aryldiamine derivative is preferably an aryldiamine derivative represented by the following general formula (11):

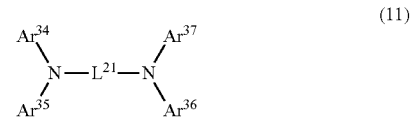

(11)

wherein in the formula (11), $Ar^{34}$ to $Ar^{37}$ each independently represent a substituted or unsubstituted aryl group having from 6 to 50 ring carbon atoms or a substituted or unsubstituted heteroaryl group having from 5 to 50 ring atoms.

$L^{21}$ represents a substituted or unsubstituted arylene group having from 6 to 50 ring carbon atoms or a substituted or unsubstituted heteroarylene group having from 5 to 50 ring atoms.

The aryl group having from 6 to 50 ring carbon atoms is preferably an aryl group having from 6 to 30 ring carbon atoms, more preferably an aryl group having from 6 to 20 ring carbon atoms, further preferably an aryl group having from 6 to 12 ring carbon atoms, and particularly preferably a phenyl group or a naphthyl group.

The heteroaryl group having from 5 to 50 ring atoms is preferably a heteroaryl group having from 5 to 40 ring atoms, more preferably a heteroaryl group having from 5 to 30 ring atoms, and further preferably a heteroaryl group having from 5 to 20 ring atoms. Examples of the heteroaryl group include a carbazolyl group, a dibenzofuranyl group and a dibenzothiophenyl group, and a dibenzofuranyl group is preferred. Preferred examples of the substituent substituted on the heteroaryl group include an aryl group having from 6 to 30 (preferably from 6 to 20, and more preferably from 6 to 12) ring carbon atoms, and a phenyl group and a naphthyl group are more preferred.

The arylene group having from 6 to 50 ring carbon atoms is preferably an arylene group having from 6 to 40 ring carbon atoms, more preferably an arylene group having from 6 to 30 ring carbon atoms, further preferably an arylene group having from 6 to 20 ring carbon atoms, and particularly preferably a pyrenyl group.

Specific examples of the compound having a carbazolyl group that is preferred as the host material in the phosphorescent material include the following compounds.

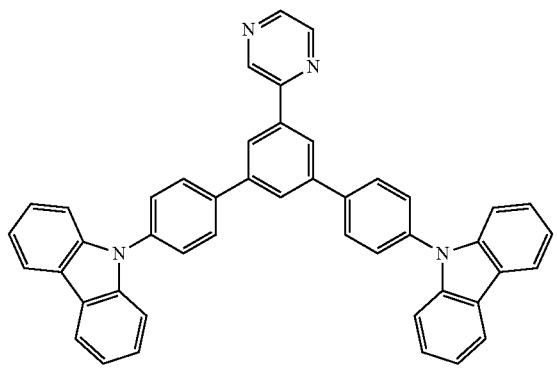

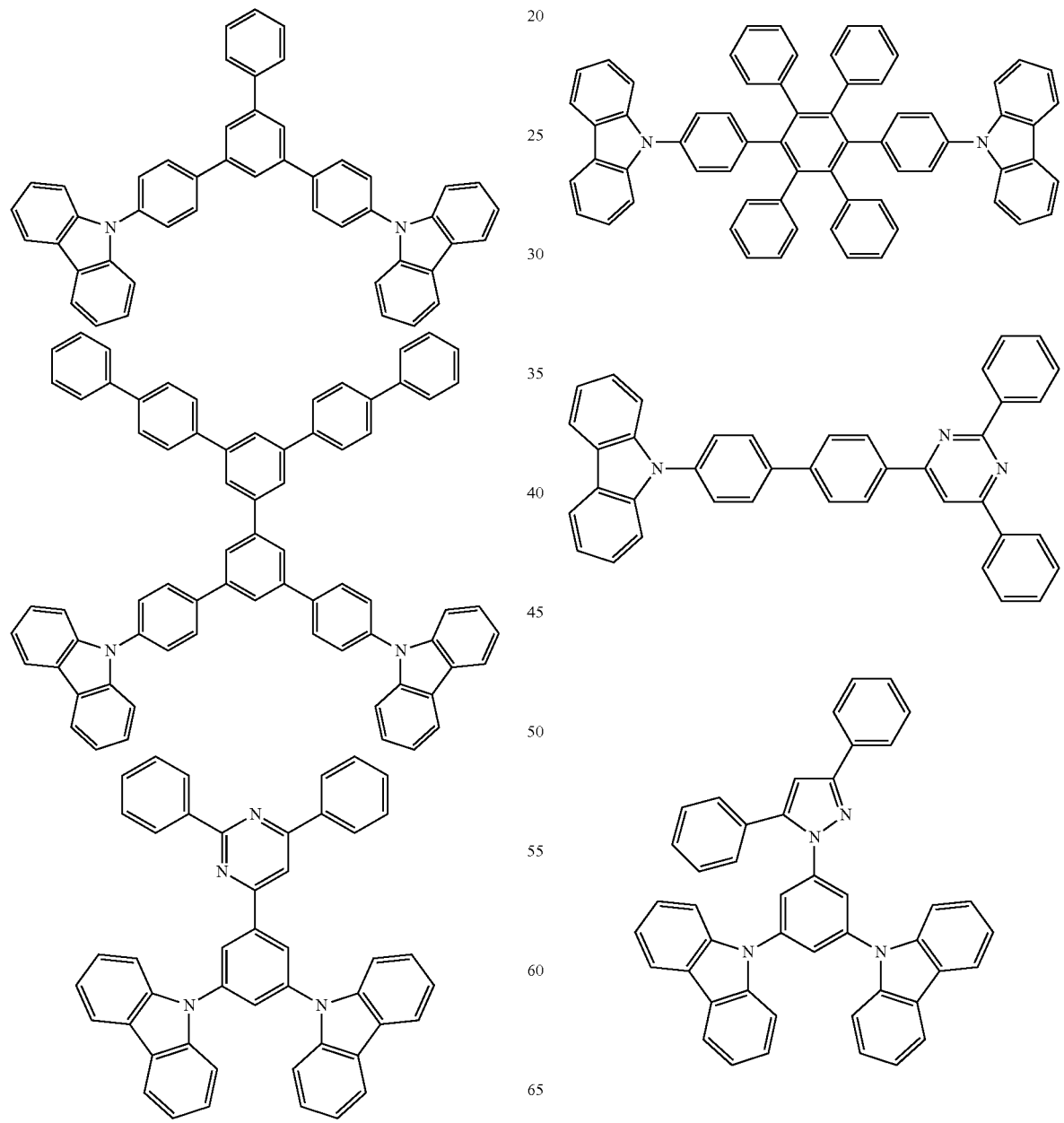

257
-continued
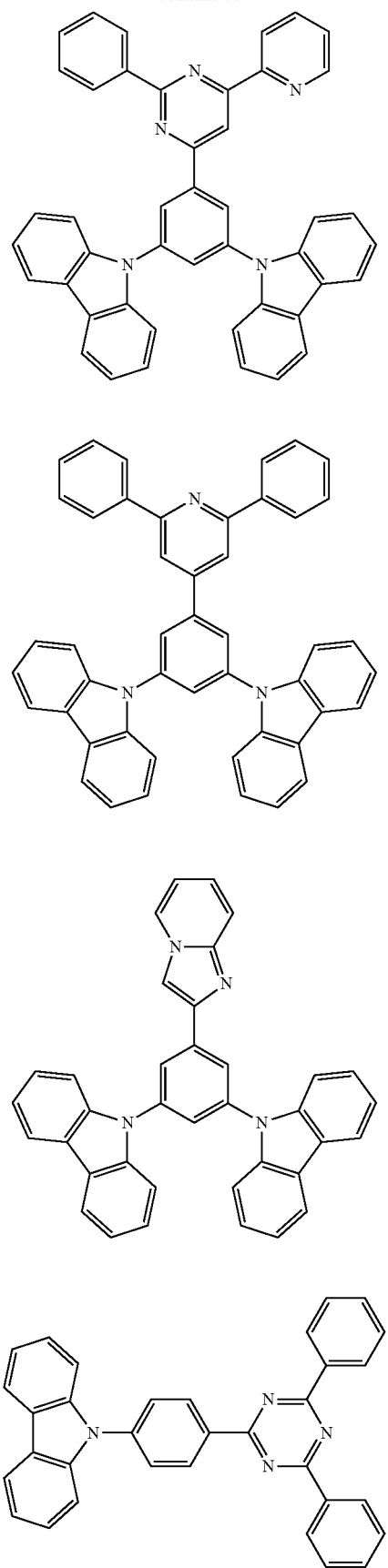 [SMILES: c1ccc(-c2nc(-c3cc(-n4c5ccccc5c5ccccc54)cc(-n4c5ccccc5c5ccccc54)c3)cc(-c3ccccn3)n2)cc1 ; c1ccc(-c2cc(-c3cc(-n4c5ccccc5c5ccccc54)cc(-n4c5ccccc5c5ccccc54)c3)cc(-c3ccccc3)n2)cc1 ; c1ccc2c(c1)c1ccccc1n2-c1cc(-c2cn3ccccc3n2)cc(-n2c3ccccc3c3ccccc32)c1 ; c1ccc(-c2nc(-c3ccccc3)nc(-c3ccc(-n4c5ccccc5c5ccccc54)cc3)n2)cc1]
258
-continued
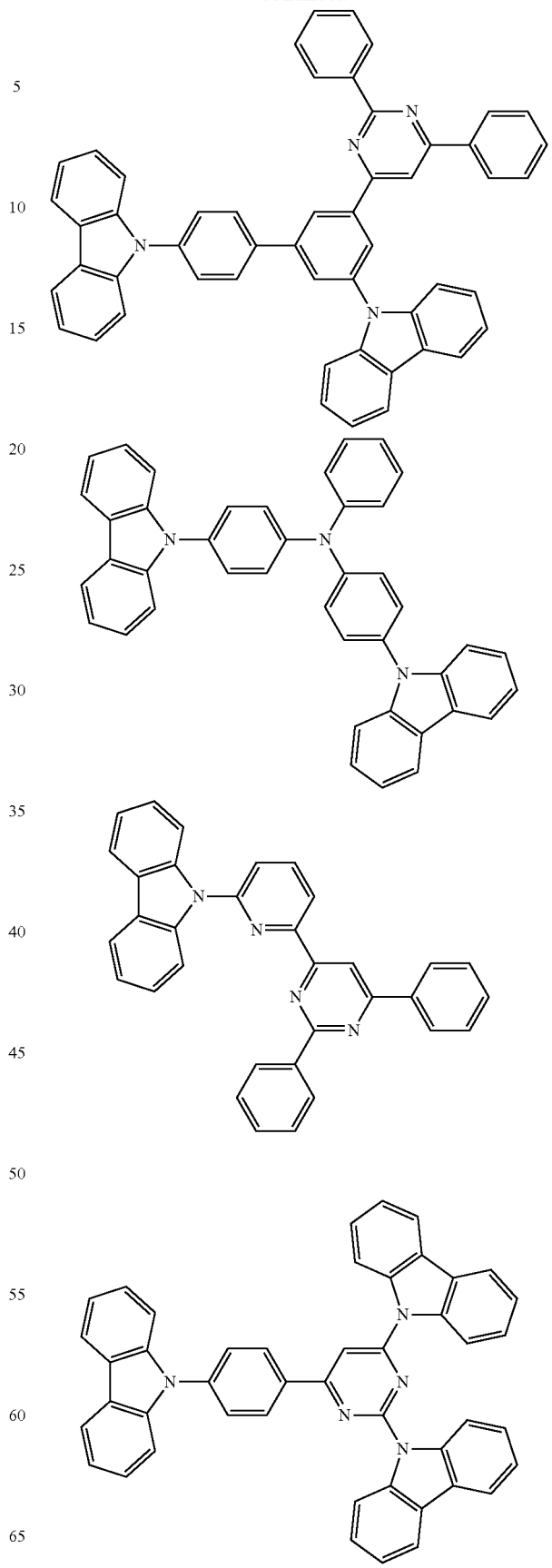

259
-continued
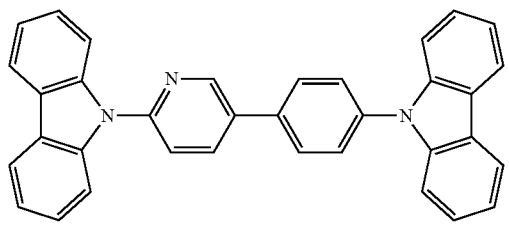
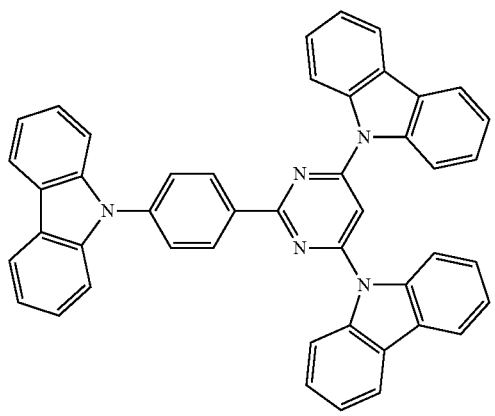
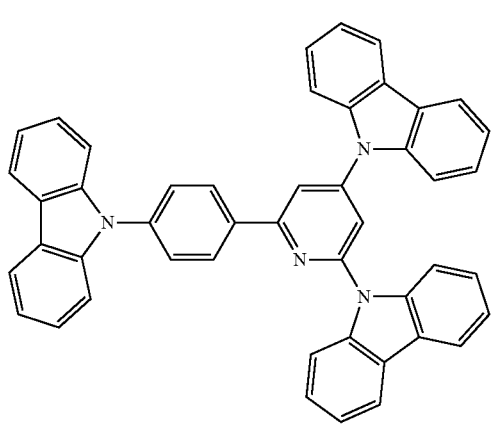
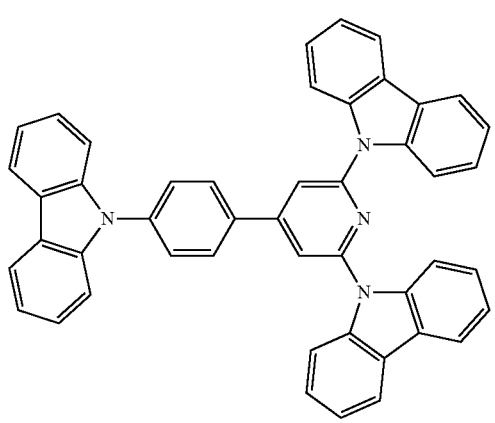
260
-continued
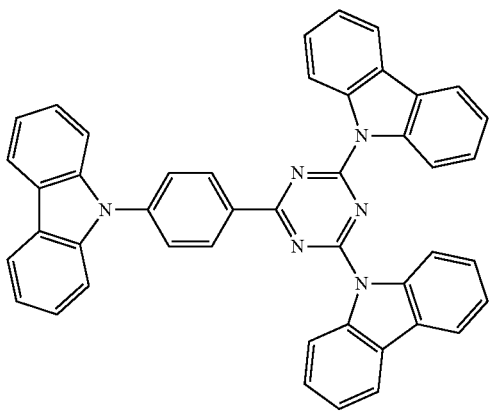
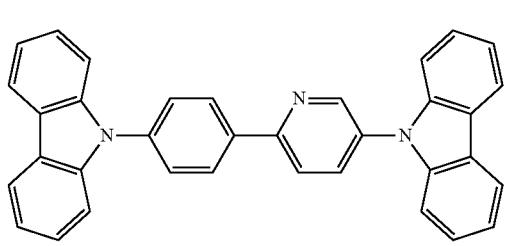
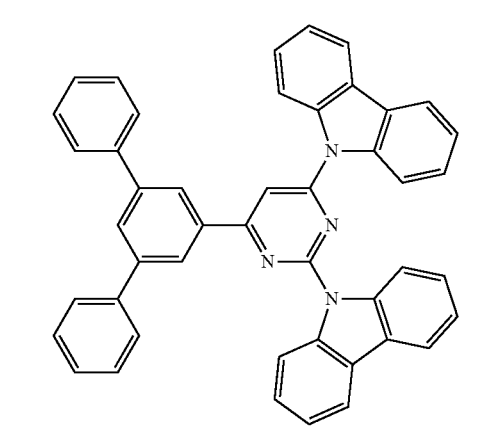
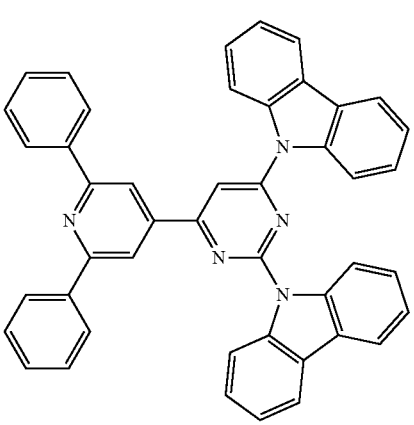

-continued

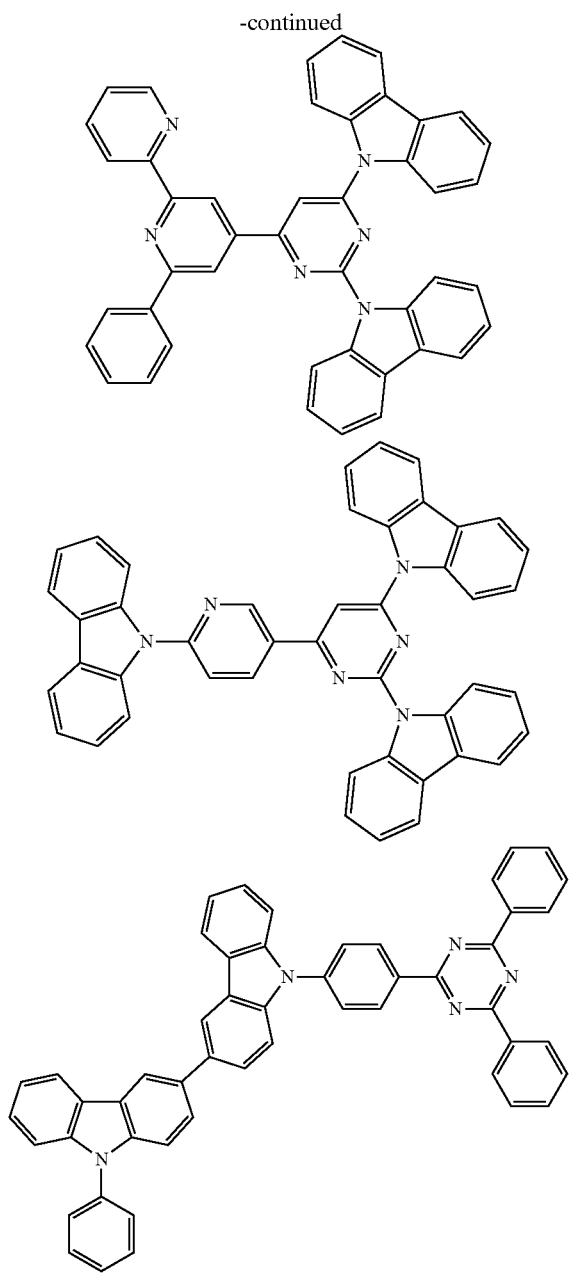

The light emitting layer may have a double host system (also referred to as a host/co-host system). Specifically, an electron transporting host material and a hole transporting host material may be combined in the light emitting layer for controlling the carrier balance in the light emitting layer.

The light emitting layer may also have a double dopant system. Specifically, two or more kinds of dopants having a high quantum yield may be added to the light emitting layer for emitting light from the dopants. For example, a red dopant and a green dopant may be vapor-deposited with a host material, thereby providing a yellow light emitting layer.

The light emitting layer may contain, depending on necessity, a hole transporting material, an electron transporting material and a polymer binder.

The thickness of the light emitting layer is preferably from 5 to 50 nm, more preferably from 7 to 50 nm, and most preferably from 10 to 50 nm. When the thickness is less than 5 nm, it may be difficult to form the light emitting layer and to control the chromaticity, and when the thickness exceeds 50 nm, the driving voltage may be increased.

(6) Electron Injection and Transporting Layer

The electron injection and transporting layer is a layer that assists injection of electrons to the light emitting layer and transportation thereof to the light emitting region and has a large electron mobility, and an adhesion improving layer in the electron injection and transporting layer is a layer formed of a material that has good adhesion to the cathode among others.

It is known that in an organic EL device, emitted light is reflected by an electrode (e.g., the cathode in this case), and therefore, emitted light that is taken out directly from the anode and the light that is taken out after reflection on the electrode interfere with each other. For utilizing the interference phenomenon effectively, the thickness of the electron injection and transporting layer is selected appropriately from a range of from several nanometer to several micrometer, and in the case where the thickness is large, the electron mobility thereof is preferably $10^{-5}$ cm$^2$/Vs or more on applying an electric field of from $10^4$ to $10^6$ V/cm for preventing the voltage from being increased.

Preferred examples of the material used in the electron injection and transporting layer include a metal complex of 8-hydroxyquinoline and a derivative thereof, and an oxadiazole derivative. Specific examples of the metal complex of 8-hydroxyquinoline and a derivative thereof include a metal chelated oxinoid compound containing a chelate of oxine (which is generally 8-quinolinol or 8-hydroxyquinoline), for example, tris(8-quinolinol)aluminum, which may be used as an electron injection material.

Examples of the electron injection material include compounds represented by one of the following general formulae (31) to (36):

(31)

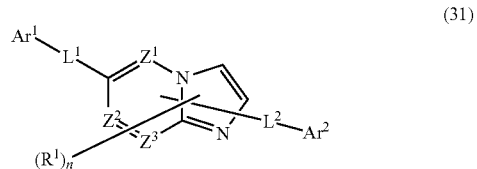

(32)

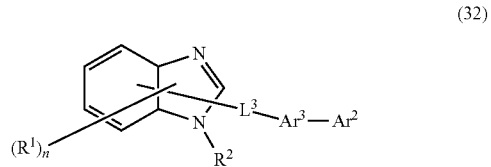

(33)

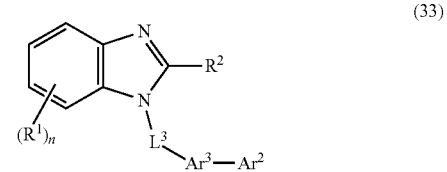

wherein in the general formulae (31) to (33), $Z^1$, $Z^2$ and $Z^3$ each independently represent a nitrogen atom or a carbon atom.

R1 and R2 each independently represent a substituted or unsubstituted aryl group having from 6 to 50 ring carbon atoms, a substituted or unsubstituted heteroaryl group having from 5 to 50 ring atoms, an alkyl group having from 1 to 20 carbon atoms, an alkyl group having from 1 to 20 carbon atoms having a halogen atom substituted thereon, or an alkoxy group having from 1 to 20 carbon atoms. $R^1$ in the general formulae (31) and (32) may be substituted on any one of the 5-membered ring or the 6-membered ring, and is preferably substituted on the 6-membered ring. $R^1$ in the general formula (33) is substituted on the 6-membered ring.

n represents an integer of from 0 to 5, and when n is an integer of 2 or more, plural groups of $R^1$ may be the same as or different from each other. The adjacent groups of $R^1$ may be bonded to form a substituted or unsubstituted aromatic hydrocarbon ring.

$Ar^1$ represents a substituted or unsubstituted aryl group having from 6 to 50 ring carbon atoms or a substituted or unsubstituted heteroaryl group having from 5 to 50 ring atoms.

$Ar^2$ represents a hydrogen atom, an alkoxy group having from 1 to 20 carbon atoms, an alkyl group having from 1 to 20 carbon atoms having a halogen atom substituted thereon, an alkoxy group having from 1 to 20 carbon atoms, a substituted or unsubstituted aryl group having from 6 to 50 ring carbon atoms or a substituted or unsubstituted heteroaryl group having from 5 to 50 ring atoms.

Herein, any one of $Ar^1$ and $Ar^2$ represents a substituted or unsubstituted condensed ring group having from 10 to 50 ring carbon atoms or a substituted or unsubstituted heterocondensed ring group having from 9 to 50 ring atoms.

$Ar^3$ represents a substituted or unsubstituted arylene group having from 6 to 50 ring carbon atoms or a substituted or unsubstituted heteroarylene group having from 5 to 50 ring atoms.

$L^1$, $L^2$ and $L^3$ each independently represent a single bond, a substituted or unsubstituted arylene group having from 6 to ring carbon atoms, a substituted or unsubstituted heterocondensed ring group having from 9 to 50 ring atoms or a substituted or unsubstituted fluorenylene group. $L^2$ in the general formula (31) and $L^3$ in the general formula (32) each may be substituted on any one of the 5-membered ring or the 6-membered ring, and is preferably substituted on the 5-membered ring.

Specific examples of the aryl group and the alkyl group represented by $R^1$, $R^2$, $Ar^1$ and $Ar^2$ include the examples described for $R^{21}$ to $R^{24}$ in the general formula (B), and specific examples of the alkoxy group represented thereby include examples obtained by bonding an oxygen atom to the alkoxy groups. Specific examples of the heteroaryl group represented by $R^1$, $R^2$, $Ar^1$ and $Ar^2$ include a pyrrolyl group, a piperidinyl group, a pyrazinyl group, a pyrimidinyl group, an indolyl group, an isoindolyl group, a furyl group, a benzofuranyl group, a isobenzofuranyl group, a quinolinyl group, an isoquinolinyl group, a quinoxalinyl group, a carbazolyl group, a phenanthridinyl group and an acridinyl group. Examples of the arylene group represented by $Ar^3$, $L^1$, $L^2$ and $L^3$ include divalent groups derived from the aryl groups, and examples of the heterocondensed ring group represented thereby include the heteroaryl groups that conform to the number of carbon atoms.

$$[X]_q\text{—}Y \tag{34}$$

wherein X represents a condensed ring containing a nitrogen atom or a sulfur atom, and Y represents one selected from a single bond, an alkyl chain, an alkylene chain, a cycloalkyl chain, an aryl chain, a heterocyclic chain, a silyl chain, an ether chain and a thioether chain, or a combination thereof. q represents a natural number of 2 or more.

The compound represented by the general formula (34) has a molecular weight of 480 or more.

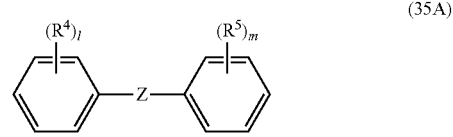

$$[A]_p\text{—}B \tag{35}$$

wherein A represents a substituent having a phenanthroline skeleton or a benzoquinoline skeleton. B represents a p-valent organic group having the structure represented by the following formula (35A). p represents a natural number of 2 or more.

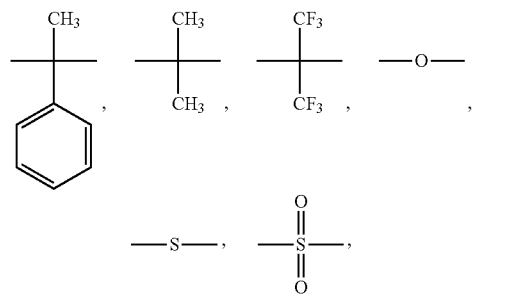

(35A)

wherein $R^4$ and $R^5$ each independently represent an alkyl group or an aryl group (which includes an aryl group condensed with a phenyl group). l and m each independently represent a natural number of from 0 to 5. Z represents at least one selected from the following formula (35B).

(35B)

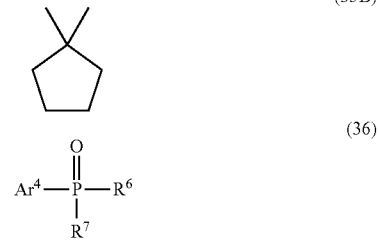

(36)

wherein $R^6$ and $R^7$ may be the same as or different from each other and each are selected from a hydrogen atom, an alkyl group, a cycloalkyl group, a heterocyclic group, an alkenyl group, a cycloalkenyl group, an alkynyl group, an alkoxy group, an alkylthio group, an arylether group, an arylthioether group, an aryl group, a heteroaryl group, a cyano group, a carbonyl group, an ester group, a carbamoyl group, an amino group, a silyl group, and a condensed ring formed with the adjacent group. $Ar^4$ represents an aryl group or a heteroaryl group.

As a preferred embodiment of the organic EL device of the present invention, the device preferably has at least one of an electron donating dopant and an organic metal complex in the interface region between the cathode and the organic thin film layer.

According to the structure, the organic EL device may be enhanced in light emission luminance and service life.

Examples of the electron donating dopant include at least one selected from an alkali metal, an alkali metal compound, an alkaline earth metal, an alkaline earth metal compound, a rare earth metal and a rare earth metal compound.

Examples of the organic metal complex include at least one selected from an organic metal complex containing an alkali metal, an organic metal complex containing an alkaline earth metal, and an organic metal complex containing a rare earth metal.

Examples of the alkali metal include lithium (Li) (work function: 2.93 eV), sodium (Na) (work function: 2.36 eV), potassium (K) (work function: 2.28 eV), rubidium (Rb) (work function: 2.16 eV) and cesium (Cs) (work function: 1.95 eV), and one having a work function of 2.9 eV or less is preferred. Among these, K, Rb and Cs are preferred, Rb and Cs are more preferred, and Cs is most preferred.

Examples of the alkaline earth metal include calcium (Ca) (work function: 2.9 eV, strontium (Sr) (work function: 2.0 to 2.5 eV) and barium (Ba) (work function: 2.52 eV), and one having a work function of 2.9 eV or less is preferred.

Examples of the rare earth metal include scandium (Sc), yttrium (Y), cerium (Ce), terbium (Tb) and ytterbium (Yb), and one having a work function of 2.9 eV or less is preferred.

The preferred metals among the above have a particularly high reducing capability, and the addition thereof in a relatively small amount to the electron injection region may enhance the light emitting luminance and the service life of the organic EL device.

Examples of the alkali metal compound include an alkali oxide, such as lithium oxide ($Li_2O$), cesium oxide ($Cs_2O$) and potassium oxide ($K_2O$), and alkali halogenide, such as lithium fluoride (LiF), sodium fluoride (NaF), cesium fluoride (CsF) and potassium fluoride (KF), and lithium fluoride (LiF), lithium oxide ($Li_2O$) and sodium fluoride (NaF) are preferred.

Examples of the alkaline earth metal compound include barium oxide (BaO), strontium oxide (SrO), calcium oxide (CaO), and mixture thereof, such as barium strontium oxide ($Ba_xSr_{1-x}O$) ($0<x<1$) and barium calcium oxide ($Ba_xCa_{1-x}O$) ($0<x<1$), and BaO, SrO and CaO are preferred.

Examples of the rare earth metal compound include ytterbium fluoride ($YbF_3$), scandium fluoride ($ScF_3$), scandium oxide ($ScO_3$), yttrium oxide ($Y_2O_3$), cerium oxide ($Ce_2O_3$), gadolinium fluoride ($GdF_3$) and terbium fluoride ($TbF_3$), and $YbF_3$, $ScF_3$ and $TbF_3$ are preferred.

The organic metal complex is not particularly limited as far as at least one of an alkali metal ion, an alkaline earth metal ion and a rare earth metal ion is contained as a metal ion, as described above. Preferred examples of the ligand include quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzoimidazole, hydroxybenzotriazole, hydroxyfluorane, bipyridyl, phenanthroline, phthalocyanine, porphyrin, cyclopentadiene, a β-diketone compound, an azomethine compound, and derivatives thereof, but the ligand is not limited thereto.

As the mode of addition of the electron donating dopant and the organic metal complex is preferably a layer form or an island form in the interface region. The formation method is preferably such a method that while vapor-depositing at least one of the electron donating dopant and the organic metal complex by a resistance heating vapor deposition method, the organic substance as the light emitting material or the electron injection material for forming the interface region is simultaneously vapor-deposited, thereby dispersing at least one of the electron donating dopant and the organic metal complex in the organic substance. The dispersion concentration, (organic substance)/(electron donating dopant and/or organic metal complex), is generally from 100/1 to 1/100, and preferably from 5/1 to 1/5, by mole.

In the case where at least one of the electron donating dopant and the organic metal complex is formed in a layer form, the light emitting material or the electron injection material as the organic layer at the interface is formed in a layer form, and then at least one of the electron donating dopant and the organic metal complex is solely vapor-deposited by a resistance heating vapor deposition method to a thickness of the layer of from 0.1 to 15 nm.

In the case where at least one of the electron donating dopant and the organic metal complex is formed in an island form, the light emitting material or the electron injection material as the organic layer at the interface is formed in an island form, and then at least one of the electron donating dopant and the organic metal complex is solely vapor-deposited by a resistance heating vapor deposition method to a thickness of the island of from 0.05 to 1 nm.

In the organic EL device of the present invention, the ratio of the major component to the electron donating dopant and/or the organic metal complex, (major component)/(electron donating dopant and/or organic metal complex), is preferably from 5/1 to 1/5, and more preferably from 2/1 to 1/2, by mole.

(7) Cathode

The cathode contains, as an electrode substance, a metal, an alloy, an electroconductive compound, or mixtures thereof, having a small work function (4 eV or less), for injecting electrons to the electron injection and transporting layer or the light emitting layer. Specific examples of the electrode substance include sodium, a sodium-potassium alloy, magnesium, lithium, a magnesium-silver alloy, an aluminum-aluminum oxide mixture, an aluminum-lithium alloy, indium, and a rare earth metal.

The cathode may be produced by forming the electrode substance into a thin film by such a method as vapor deposition and sputtering.

In the case where the light emitted from the light emitting layer is taken out on the side of the cathode, the cathode preferably has a transmittance to the emitted light of more than 10%.

The cathode preferably has a sheet resistance of several hundred Ω per square or less, and the thickness thereof is generally from 10 nm to 1 μm, and preferably from 50 to 200 nm.

(8) Dielectric Layer

The organic EL device tends to suffer pixel defects due to leakage and short circuit since an electric field is applied to an ultrathin film. For preventing the defects, it is preferred to insert a dielectric thin film layer between the pair of electrodes.

Examples of the material used in the dielectric layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide and vanadium oxide, and mixtures and laminated products of these materials may also be used.

(9) Production Method of Organic EL Device

The organic EL device may be produced by forming an anode, a light emitting layer and a hole transporting layer, and depending on necessity, an electron injection and transporting layer, and further forming a cathode, with the aforementioned materials by the aforementioned methods. The organic EL device may also be produced in the reversed order to the above, i.e., from the cathode to the anode.

A production example of the organic EL device having an anode, a hole transporting layer, a light emitting layer, an electron injection and transporting layer and a cathode formed in this order on a light transmissive substrate will be described below.

A thin film is formed with an anode material to a thickness within a range of 1 μm or less, preferably from 10 to 20 nm, on a suitable light transmissive substrate by such a method as vapor deposition or sputtering, thereby forming an anode. Two or more hole transporting layers are then formed sequentially on the anode. The hole transporting layers may be formed by a vacuum vapor deposition method, a spin coating method, a casting method and a LB method, and are preferably formed by a vacuum vapor deposition method due to such points that a uniform film may be obtained, and pinholes may not be formed. In the case where the hole transporting layer is formed by a vacuum vapor deposition method, the vapor deposition conditions may vary depending on the compound used (i.e., the material for the hole transporting layers), and the crystalline structure, the recombination structure and the like of the target hole transporting layer, and in general, may be preferably selected from the ranges of a vapor deposition source temperature of from 50 to 450° C., a vacuum degree of from $10^{-7}$ to $10^{-3}$ Torr, a vapor deposition speed of from 0.01 to 50 nm/sec, a substrate temperature of from −50 to 300° C., and a thickness of the film of from 5 nm to 5 μm.

Thereafter, a light emitting layer may also be formed on the hole transporting layer with a desired organic light emitting material into a thin film by such a method as a vapor deposition method, a sputtering method, a spin coating method and a casting method, and is preferably formed by a vacuum vapor deposition method due to such points that a uniform film may be obtained, and pinholes may not be formed. In the case where the light emitting layer is formed by a vacuum vapor deposition method, the vapor deposition conditions may vary depending on the compound used, and may be generally selected from the similar conditions as for the hole transporting layer.

Thereafter, an electron injection and transporting layer is formed on the light emitting layer. The electron injection and transporting layer is preferably formed by a vacuum vapor deposition method since a uniform film is necessarily formed, as similar to the hole transporting layer and the light emitting layer. The vapor deposition conditions may be selected from the similar conditions as for the hole transporting layer and the light emitting layer.

Finally, a cathode is accumulated to complete the organic EL device.

The cathode is formed of a metal and may be formed by a vapor deposition method or a sputtering method. For protecting the organic layers as underlayers from being damaged on formation of the film, a vacuum vapor deposition method is preferably used.

In the production of the organic EL device, all the layers including the anode to the cathode are preferably formed continuously in one time of vacuuming.

On applying a direct current voltage to the organic EL device, a voltage of from 5 to 40 V may be applied to the anode for the positive polarity and the cathode for the negative polarity, and then light emission may be observed. When the voltage is applied with the reversed polarity, no electric current flows, and no light emission occurs. On applying an alternating current voltage to the device, uniform light emission may be observed only in a period where the anode is in the positive polarity, and the cathode is in the negative polarity. The waveform of the alternating current to be applied may be selected arbitrarily.

The organic EL device of the present invention tends to provide blue light emission in the case where the device has a fluorescent light emitting layer. In the case where the device has a phosphorescent light emitting layer, there is a tendency of providing yellow light emission, green light emission or blue light emission, and in many cases, yellow light emission or green light emission.

The organic EL device obtained by using the compound of the present invention may have a thick hole transporting layer, may be controlled in optical thickness of the organic EL device, and may be enhanced in light emission efficiency and service life of the device. Accordingly, the organic EL device may be used as various kinds of electric apparatus, for example, a display member, such as an organic EL display panel module; a display member of a television set, a portable phone, a personal computer and the like; and a light emission apparatus, such as illumination and a lamp fitting for an automobile. In particular, the device is useful for a plane light emission device and a backlight for a display device.

EXAMPLE

The present invention will be described in more detail with reference to examples, but the present invention is not limited to the examples.

Intermediate Synthesis Example 1-1(Synthesis of Intermediate 1-1)

Under an argon atmosphere, 23 g (90.6 mmol) of iodine, 9.4 g (41.2 mmol) of periodic acid dihydrate, 42 mL of water, 360 mL of acetic acid and 11 mL of sulfuric acid were added to 55 g (201.3 mmol) of 2-bromo-9,9-dimethylfluorene, and the mixture was stirred at 65° C. for 30 minutes and then stirred at 90° C. for 6 hours.

After completing the reaction, the reaction product was poured into iced water, and crystals thus deposited were collected by filtering. The crystals were rinsed with water and then with methanol, thereby providing 61 g of a white solid matter, which was identified as the following intermediate 1-1 by FD-MS analysis (yield: 76%).

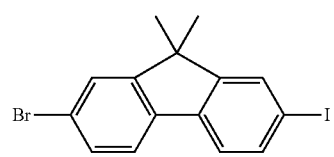

Intermediate 1-1

Intermediate Synthesis Example 1-2(Synthesis of Intermediate 1-2)

Under an argon atmosphere, 300 mL of toluene and 150 mL of a 2M sodium carbonate aqueous solution were added to 39.9 g of the intermediate 1-1, 20.8 g of 4-biphenylboronic acid and 2.31 g of tetrakis(triphenylphosphine)palladium(0), and the mixture was heated under refluxing for 10 hours.

After completing the reaction, the reaction product was immediately filtered, and then the aqueous layer was removed. The organic layer was dried over sodium sulfate and then concentrated. The residue was purified by silica gel column chromatography, thereby providing 34.3 g of white crystals, which were identified as the following intermediate 1-2 by FD-MS analysis (yield: 81%).

Intermediate 1-2

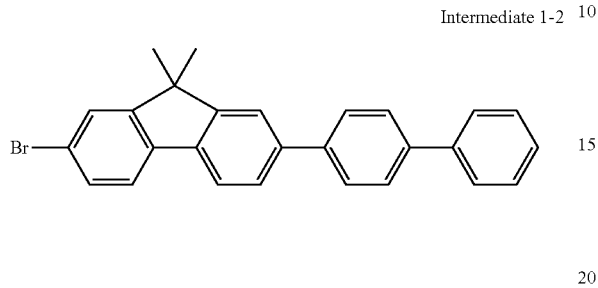

Intermediate Synthesis Example 1-3 (Synthesis of Intermediate 1-3)

The reaction was performed in the same manner as in Intermediate Synthesis Example 1-2 except that 28.8 g of 4-p-terphenylboronic acid was used instead of 4-biphenylboronic acid, thereby providing 26.6 g of a pale yellow solid matter, which was identified as the following intermediate 1-3 by FD-MS analysis (yield: 53%).

Intermediate 1-3

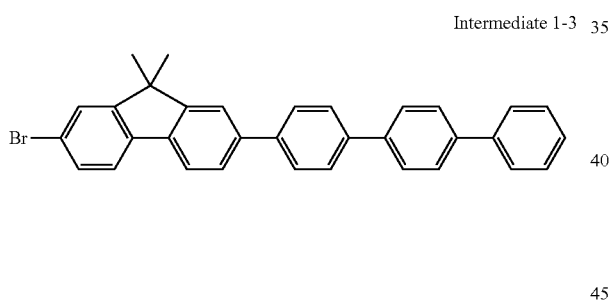

Intermediate Synthesis Example 2-1 (Synthesis of Intermediate 2-1)

Under an argon atmosphere, 500 mL of dehydrated toluene was added to 30.9 g (100.0 mmol) of 4-bromo-p-terphenyl, 9.3 g (100.0 mmol) of aniline, 13.0 g (135.3 mmol) of t-butoxysodium, 460 mg (0.5 mmol) of tris(dibenzylideneacetone)dipalladium (0) and 210 mg (1.04 mmol) of tri-t-butylphosphine, and the mixture was reacted at 80° C. for 8 hours.

After cooling, 2.5 L of water was added, the mixture was filtered with celite, and the filtrate was extracted with toluene and dried over magnesium sulfate. The filtrate was concentrated under reduced pressure, and the resulting residue was purified by silica gel chromatography, recrystallized from toluene, collected by filtering, and then dried, thereby providing 15.7 g of a pale yellow solid matter, which was identified as the following intermediate 2-1 by FD-MS analysis (yield: 49%).

Intermediate 2-1

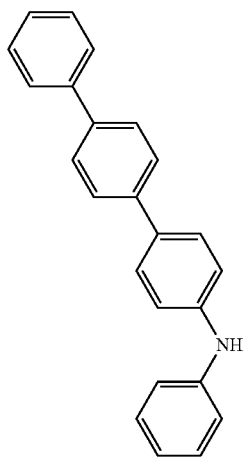

Intermediate Synthesis Example 2-2 (Synthesis of Intermediate 2-2)

The reaction was performed in the same manner as in Intermediate Synthesis Example 2-1 except that 23.3 g of 4-bromobiphenyl was used instead of 4-bromo-p-terphenyl, and 24.5 g of 4-amino-p-terphenyl was used instead of aniline, thereby providing 21.1 g of a pale yellow solid matter, which was identified as the following intermediate 2-2 by FD-MS analysis (yield: 53%).

Intermediate 2-2

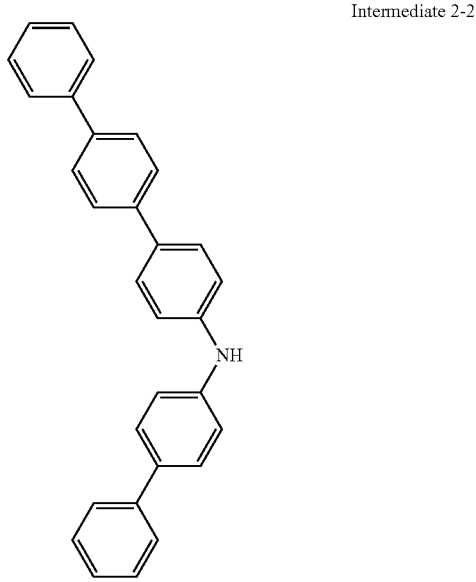 [SMILES: c1ccc(-c2ccc(Nc3ccc(-c4ccc(-c5ccccc5)cc4)cc3)cc2)cc1]

Intermediate Synthesis Example 2-3 (Synthesis of Intermediate 2-3)

The reaction was performed in the same manner as in Intermediate Synthesis Example 2-1 except that 23.3 g of 4-bromobiphenyl was used instead of 4-bromo-p-terphenyl, and 20.9 g of 9,9-dimethyl-2-aminofluorene was used instead of aniline, thereby providing 20.6 g of a pale yellow solid matter, which was identified as the following intermediate 2-3 by FD-MS analysis (yield: 57%).

Intermediate 2-3

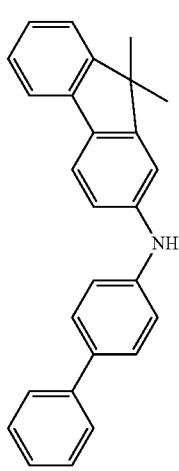

Synthesis Example 1(Synthesis of Compound (H1))

Under an argon atmosphere, 8.5 g of the intermediate 1-2, 6.4 g of N,N-bis(4-biphenyl)amine, 2.6 g of t-butoxysodium, 92 mg of tris(dibenzylideneacetone)dipalladium (0), 42 mg of tri-t-butylphosphine and 100 mL of dehydrated toluene were placed, and the mixture was reacted at 80° C. for 8 hours. After cooling, 500 mL of water was added, the mixture was filtered with celite, and the filtrate was extracted with toluene and dried over anhydrous magnesium sulfate. The filtrate was concentrated under reduced pressure, the resulting crude product was purified by column chromatography, recrystallized from toluene, collected by filtering, and then dried, thereby providing 6.7 g of pale yellow powder, which was identified as the following compound (H1) by FD-MS analysis (yield: 50%).

(H1)

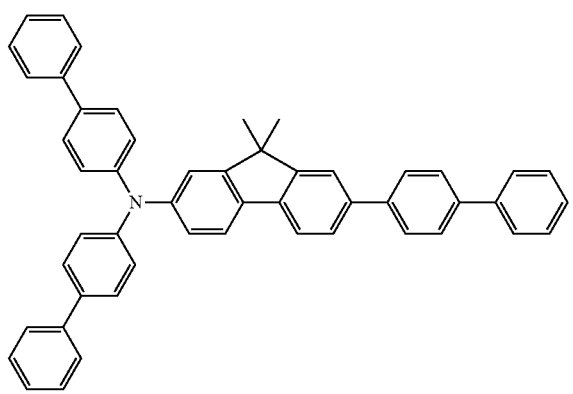

Synthesis Example 2(Production of Compound (H2))

The reaction was performed in the same manner as in Synthesis Example 1 except that 7.2 g of the intermediate 2-3 was used instead of N,N-bis(4-biphenyl)amine, thereby providing 6.2 g of white crystals, which were identified as the following compound (H2) by FD-MS analysis (yield: 44%).

(H2)

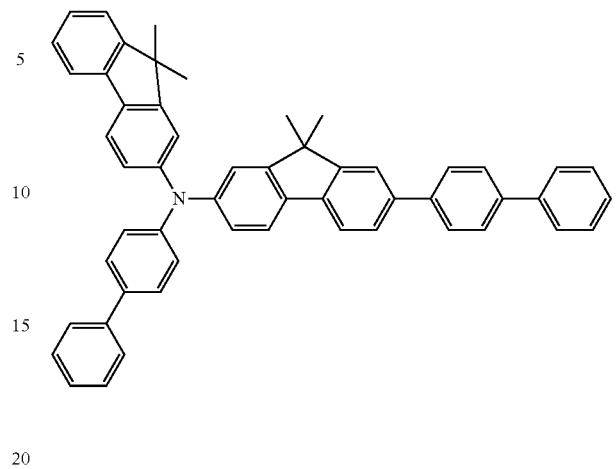

Synthesis Example 3(Production of Compound (H3))

The reaction was performed in the same manner as in Synthesis Example 1 except that 8.0 g of the intermediate 2-2 was used instead of N,N-bis(4-biphenyl)amine, thereby providing 7.1 g of white crystals, which were identified as the following compound (H3) by FD-MS analysis (yield: 48%).

(H3)

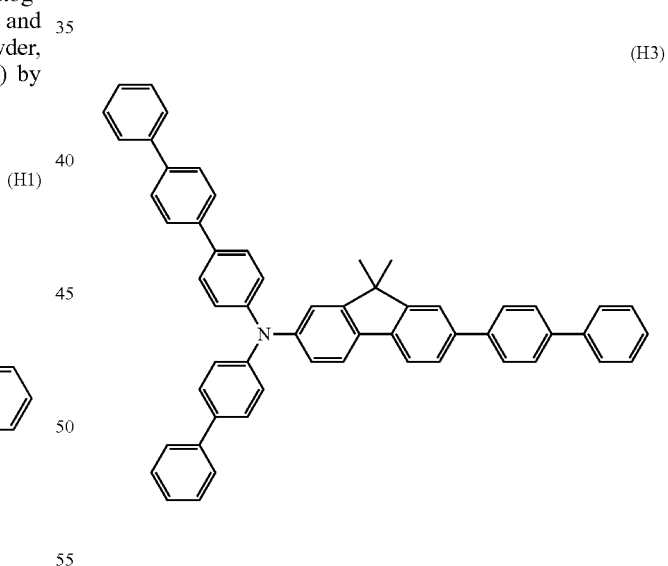

Synthesis Example 4(Production of Compound (H4))

The reaction was performed in the same manner as in Synthesis Example 1 except that 4.4 g of N-(1-naphthyl)-N-phenylamine was used instead of N,N-bis(4-biphenyl) amine, thereby providing 6.2 g of white crystals, which were identified as the following compound (H4) by FD-MS analysis (yield: 55%).

(H4)

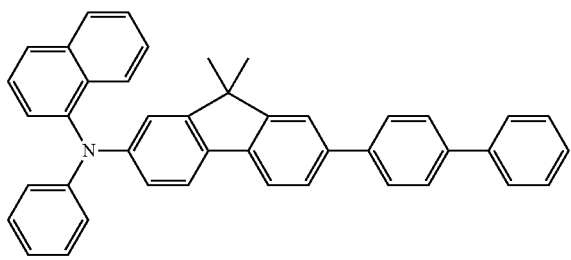

Synthesis Example 5(Production of Compound (H5))

The reaction was performed in the same manner as in Synthesis Example 1 except that 4.9 g of N-(4-biphenyl)-N-phenylamine was used instead of N,N-bis(4-biphenyl)amine, thereby providing 5.9 g of white crystals, which were identified as the following compound (H5) by FD-MS analysis (yield: 50%).

(H5)

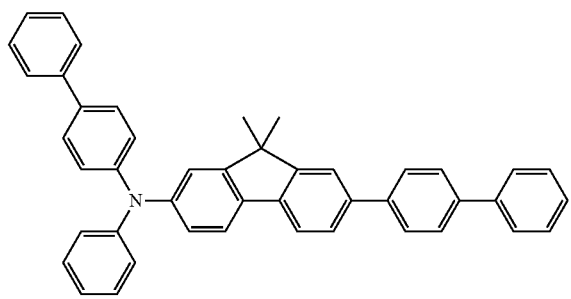

Synthesis Example 6(Production of Compound (H6))

The reaction was performed in the same manner as in Synthesis Example 1 except that 6.4 g of the intermediate 2-1 was used instead of N,N-bis(4-biphenyl)amine, thereby providing 5.9 g of white crystals, which were identified as the following compound (H6) by FD-MS analysis (yield: 44%).

(H6)

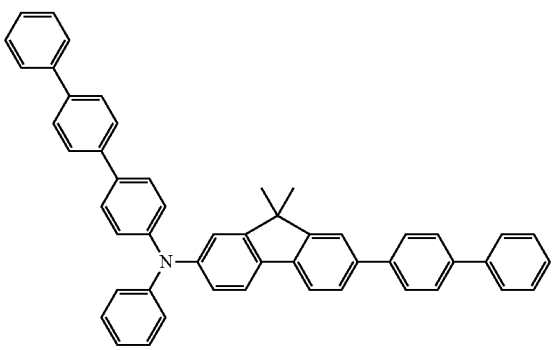

Synthesis Example 7(Production of Compound (H7))

The reaction was performed in the same manner as in Synthesis Example 1 except that 10.0 g of the intermediate 1-3 was used instead of the intermediate 1-2, thereby providing 4.7 g of white crystals, which were identified as the following compound (H7) by FD-MS analysis (yield: 32%).

(H7)

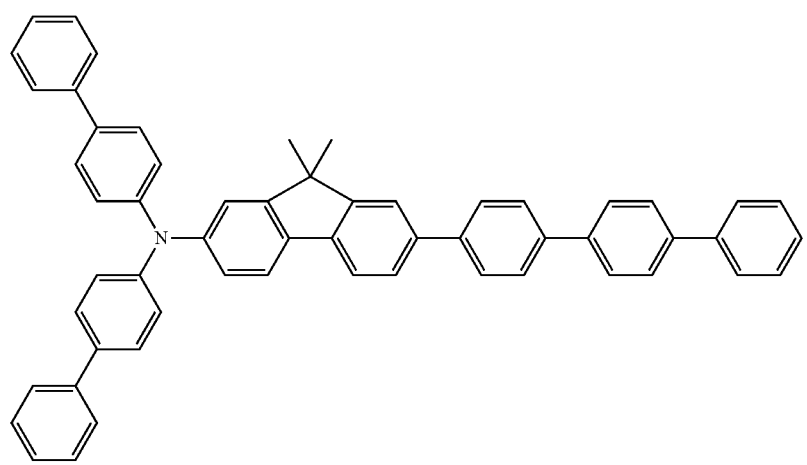

Various compounds within the scope of claim may be produced by using materials conforming to the targets with reference to the production methods of the intermediates 1-1 to 1-3, the production methods of the intermediates 2-1 to 2-3, and the production methods of the compounds (H1) to (H7).

Example 1

Production of Organic EL Device

A glass substrate, 25 mm×75 mm×1.1 mm, having ITO transparent electrode lines (produced by Geomatec Co., Ltd.) was cleaned under application of ultrasonic wave in isopropyl alcohol for 5 minutes, and further cleaned with UV (ultraviolet ray) and ozone for 30 minutes.

The glass substrate having transparent electrode lines having been cleaned was mounted on a substrate holder of a vacuum vapor deposition equipment, and the following acceptor material (A) was vapor-deposited on the surface thereof having the transparent electrode lines formed thereon to cover the transparent electrode lines, thereby forming an acceptor layer having a thickness of 5 nm. The compound (H1) obtained in Synthesis Example 1 as a first hole transporting material was vapor-deposited on the acceptor layer, thereby forming a first hole transporting layer having a thickness of 65 nm. Subsequent to the formation of the first hole transporting layer, the following compound (X) as a second hole transporting material was vapor-deposited, thereby forming a second hole transporting layer having a thickness of 10 nm.

The compound (B) as a phosphorescent host material and Ir(ppy)$_3$ as a phosphorescent dopant were co-vapor-deposited to a thickness of 25 nm on the second hole transporting layer, thereby providing a phosphorescent light emitting layer. The concentration of Ir(ppy)$_3$ was 10% by mass.

Subsequently, on the phosphorescent light emitting layer, sequentially, the compound (C) was accumulated to a thickness of 35 nm, LiF was accumulated to a thickness of 1 nm, and metallic Al was accumulated to a thickness of 80 nm, thereby forming a cathode. LiF as an electron injecting electrode was formed at a film formation speed of 1 Å/min.

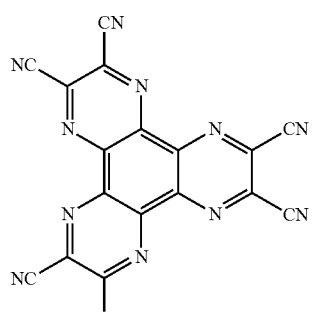

Acceptor Material (A)

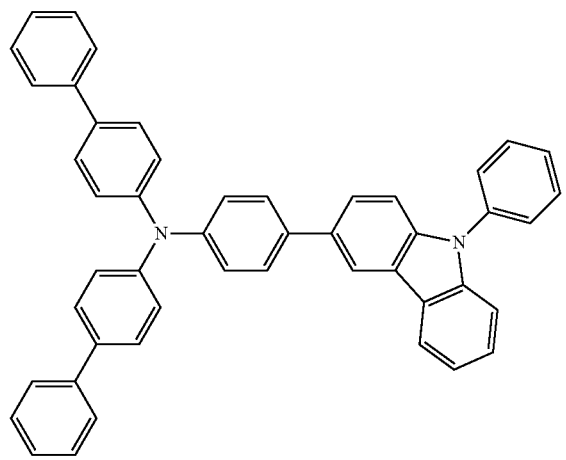

Second Hole Transporting Material (X)

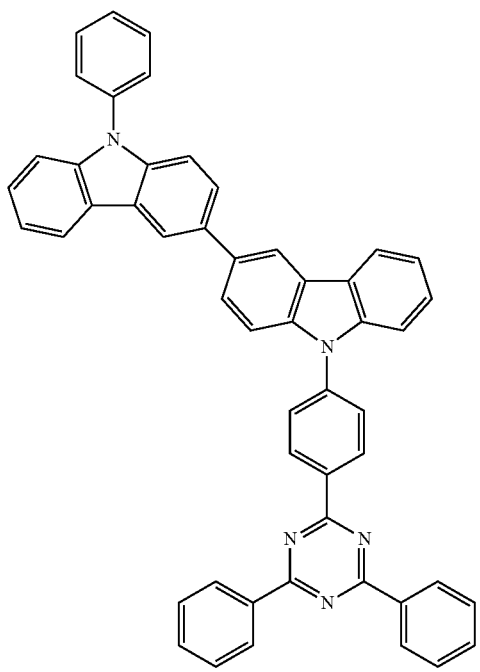

Host Material (B)

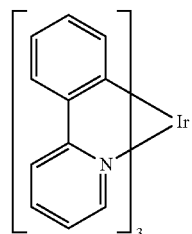

Dopant Ir(ppy)$_3$ (C)

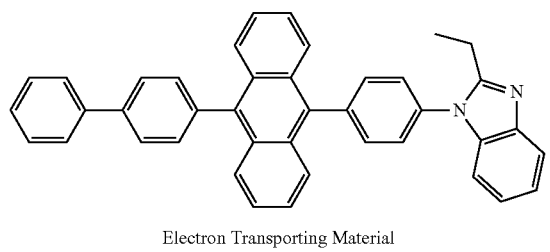

Electron Transporting Material

Evaluation of Light Emission Performance of Organic EL Device

The organic EL device thus produced above was subjected to light emission by direct current driving, the luminance (cd/m$^2$) and the electric current density were measured, and the light emission efficiency (cd/A) at an electric current density of 10 mA/cm$^2$ and the driving voltage (V) were obtained. The service life of the device (i.e., the period of time until the luminance was reduced to 80%) at an electric current density of 50 mA/cm$^2$ was obtained. The results are shown in Table 1.

Examples 2 and 3

Organic EL devices were produced in the same manner as in Example 1 except that the compounds shown in Table 1 were used as the first hole transporting material instead of the compound (H1), and were evaluated for the light emission performance. The results are shown in Table 1.

Examples 4 to 12

Organic EL devices were produced in the same manner as in Example 1 except that any one of the following compounds (Y1) to (Y9) was used as the second hole transporting material instead of the compound (X), and Ir(bzq)$_3$ was used as the phosphorescent dopant instead of Ir(ppy)$_3$, and were evaluated for the light emission performance. The results are shown in Table 1.

(Y1)

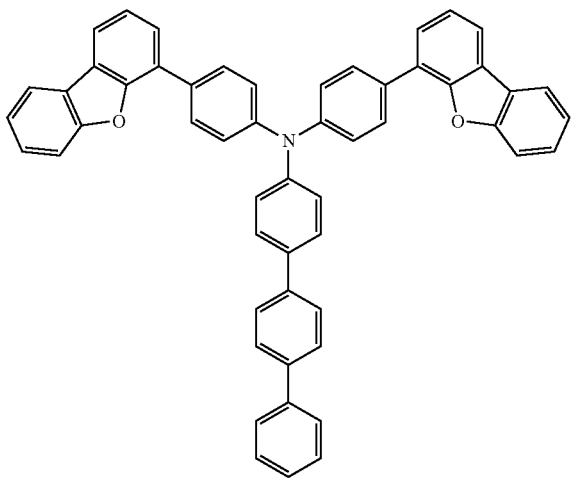

Second Hole Transporting Material (Y2)

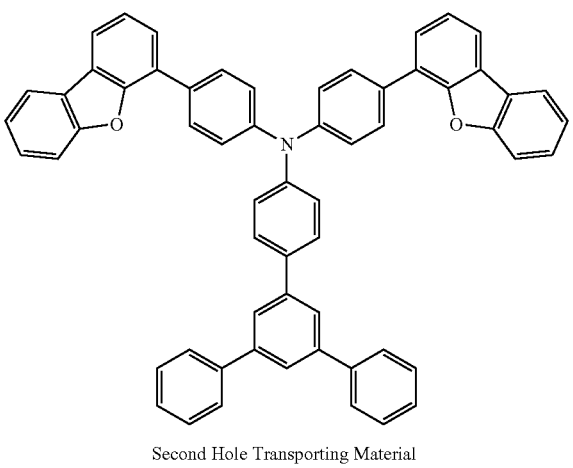

Second Hole Transporting Material (Y3)

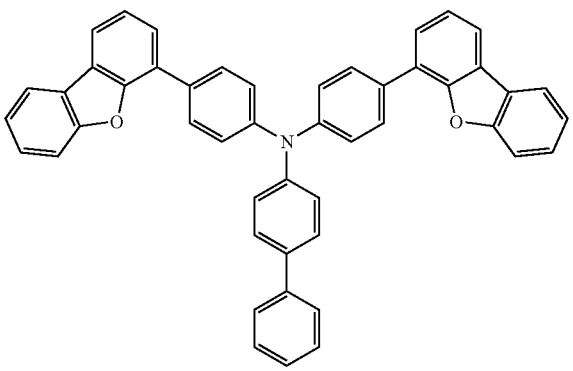

Second Hole Transporting Material (Y4)

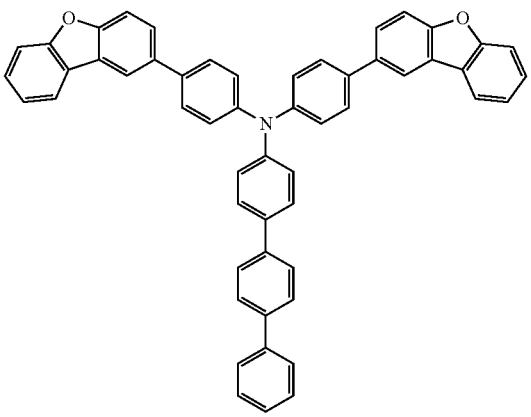

Second Hole Transporting Material (Y5)
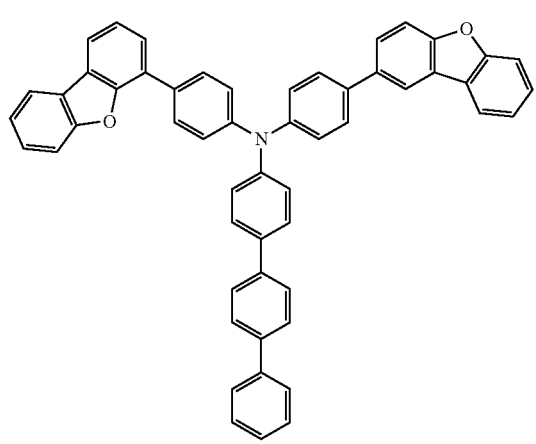
Second Hole Transporting Material
(Y6)
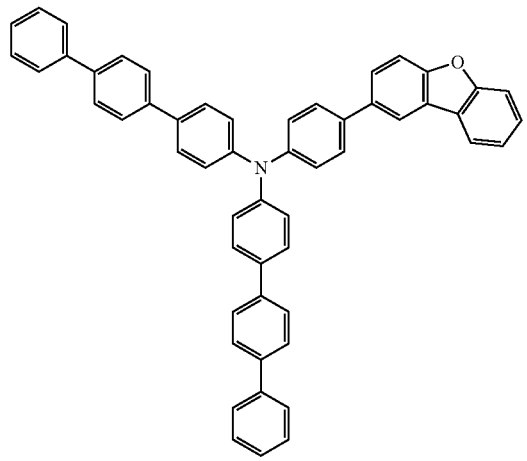
Second Hole Transporting Material
(Y7)
(Y8)
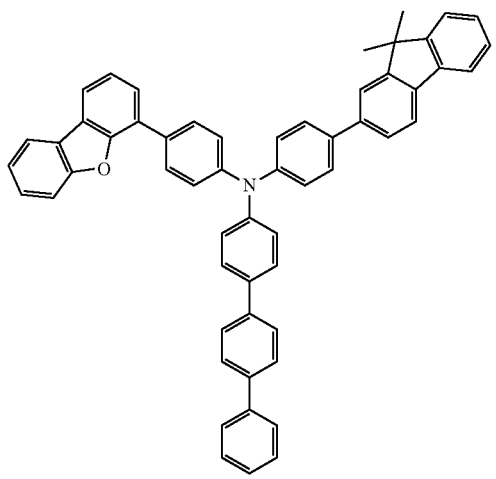
Second Hole Transporting Material
(Y9)
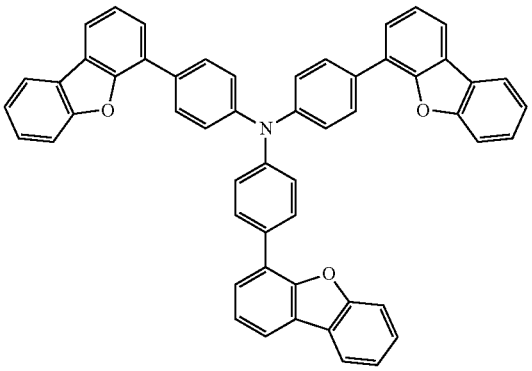
Second Hole Transporting Material
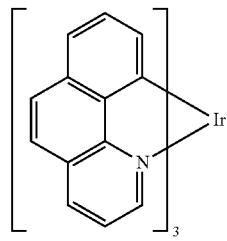
Dopant Ir(bzg)$_3$

Comparative Examples 1 and 2

Organic EL devices were produced in the same manner as in Example 1 except that the following comparative compounds 1 and 2 were used as the first hole transporting material instead of the compound (H1), and were evaluated for the light emission performance. The results are shown in Table 1.

Comparative Compound 1

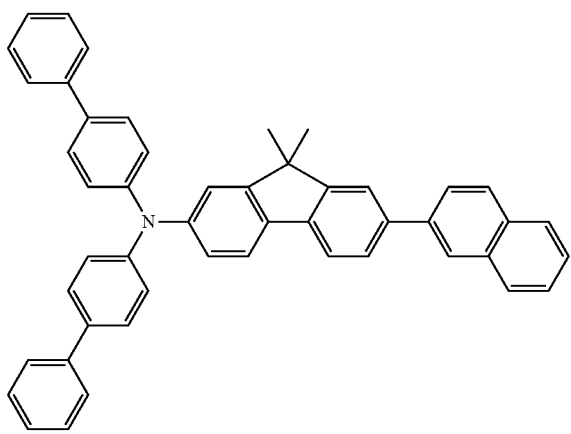

Comparative Compound 2

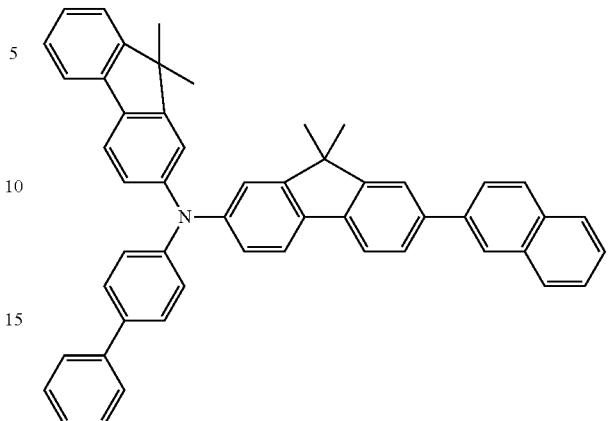

Comparative Examples 3 and 4

Organic EL devices were produced in the same manner as in Example 4 except that the comparative compounds 1 and 2 were used as the first hole transporting material instead of the compound (H1), and were evaluated for the light emission performance. The results are shown in Table 1.

TABLE 1

|  |  | Acceptor material | First hole transporting material | Second hole transporting material | Light emitting material (host material/ dopant) | Light emission efficiency (cd/A) | Driving voltage (V) | 80% service life *1 (hour) | Light emission color |
|---|---|---|---|---|---|---|---|---|---|
| Example | 1 | A | H1 | X | B/Ir(ppy)$_3$ | 57.2 | 3.0 | 150 | green |
|  | 2 | A | H2 | X | B/Ir(ppy)$_3$ | 56.5 | 3.1 | 150 | green |
|  | 3 | A | H3 | X | B/Ir(ppy)$_3$ | 56.8 | 3.1 | 160 | green |
|  | 4 | A | H1 | Y1 | B/Ir(bzq)$_3$ | 56.5 | 3.6 | 590 | yellow |
|  | 5 | A | H1 | Y2 | B/Ir(bzq)$_3$ | 56.1 | 3.6 | 590 | yellow |
|  | 6 | A | H1 | Y3 | B/Ir(bzq)$_3$ | 56.3 | 3.5 | 590 | yellow |
|  | 7 | A | H1 | Y4 | B/Ir(bzq)$_3$ | 61.4 | 3.5 | 620 | yellow |
|  | 8 | A | H1 | Y5 | B/Ir(bzq)$_3$ | 57.3 | 3.6 | 610 | yellow |
|  | 9 | A | H1 | Y6 | B/Ir(bzq)$_3$ | 57.6 | 3.7 | 610 | yellow |
|  | 10 | A | H1 | Y7 | B/Ir(bzq)$_3$ | 55.5 | 3.6 | 610 | yellow |
|  | 11 | A | H1 | Y8 | B/Ir(bzq)$_3$ | 54.4 | 3.6 | 610 | yellow |
|  | 12 | A | H1 | Y9 | B/Ir(bzq)$_3$ | 61.2 | 3.5 | 610 | yellow |
| Comparative Example | 1 | A | comparative compound 1 | X | B/Ir(ppy)$_3$ | 58.4 | 3.6 | 100 | green |
|  | 2 | A | comparative compound 2 | X | B/Ir(ppy)$_3$ | 56.1 | 3.5 | 90 | green |
|  | 3 | A | comparative compound 1 | Y1 | B/Ir(bzq)$_3$ | 49.6 | 3.8 | 370 | yellow |
|  | 4 | A | comparative compound 2 | Y1 | B/Ir(bzq)$_3$ | 50.8 | 3.8 | 300 | yellow |

*1: period of time until reducing the luminance to 80%

It is understood from the comparison between Examples 1 to 3 and Comparative Examples 1 and 2 and the comparison between Examples 4 to 12 and Comparative Examples 3 and 4 in Table 1 that the organic EL devices using the compounds of the present invention in the first hole transporting layer can be driven at a lower voltage and have a longer service life, as compared to the organic EL devices using the known aromatic amine derivatives in the hole transporting layer.

Example 13

Production of Organic EL Device

A glass substrate, 25 mm×75 mm×1.1 mm, having ITO transparent electrode lines (produced by Geomatec Co., Ltd.) was cleaned under application of ultrasonic wave in isopropyl alcohol for 5 minutes, and further cleaned with UV (ultraviolet ray) and ozone for 30 minutes.

The glass substrate having transparent electrode lines having been cleaned was mounted on a substrate holder of a vacuum vapor deposition equipment, and the following acceptor material (A) was vapor-deposited on the surface thereof having the transparent electrode lines formed thereon to cover the transparent electrode lines, thereby forming an acceptor layer having a thickness of 5 nm. The compound (H1) obtained in Synthesis Example 1 as a first hole transporting material was vapor-deposited on the acceptor layer, thereby forming a first hole transporting layer having a thickness of 138 nm. Subsequent to the formation of the first hole transporting layer, the following compound (Y1) as a second hole transporting material was vapor-deposited, thereby forming a second hole transporting layer having a thickness of 10 nm.

The compound (B2) as a phosphorescent host material and the dopant (BD) were co-vapor-deposited on the second hole transporting layer, thereby providing a fluorescent light emitting layer having a thickness of 25 nm. The concentration of the dopant (BD) in the fluorescent light emitting layer was 5% by mass.

Subsequently, on the fluorescent light emitting layer, sequentially, the following compound (C2) was accumulated to a thickness of 20 nm, the following compound (C) was accumulated to a thickness of 5 nm, LiF was accumulated to a thickness of 1 nm, and metallic Al was accumulated to a thickness of 80 nm, thereby forming a cathode. LiF as an electron injecting electrode was formed at a film formation speed of 1 Å/min.

The organic EL device thus produced above was subjected to light emission by direct current driving, the luminance (cd/m$^2$) and the electric current density were measured, and the light emission efficiency (cd/A) at an electric current density of 10 mA/cm$^2$ and the driving voltage (V) were obtained. The service life until the luminance was reduced to 80% of the device at an electric current density of 50 mA/cm$^2$ was obtained. The results are shown in Table 2.

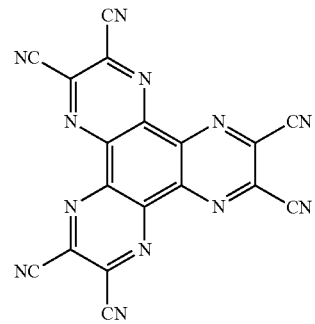

Acceptor Material (A)

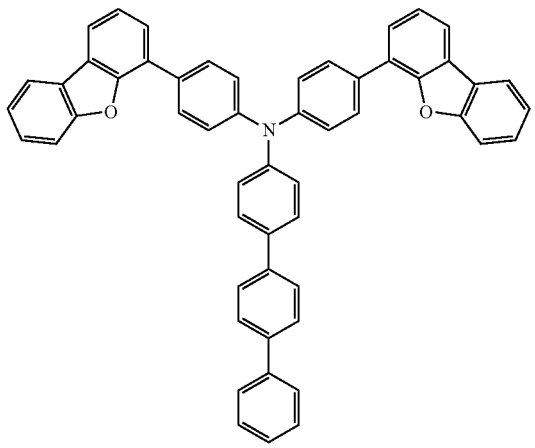

Second Hole Transporting Material (Y1)

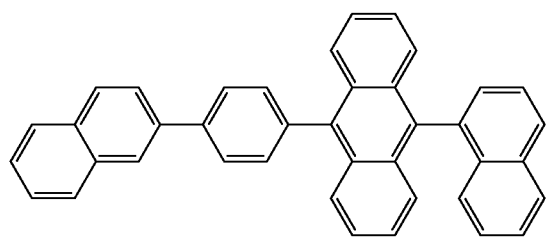

Host Material (B2)

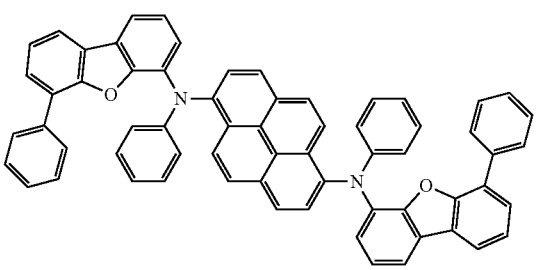

Dopant (BD)

-continued

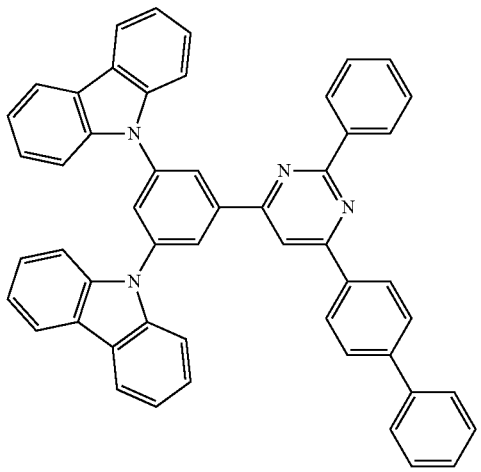

Electron Transporting Material (C)

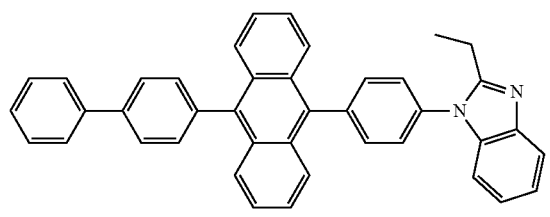

Electron Transporting Material

Examples 14 and 15

Organic EL devices were produced in the same manner as in Example 13 except that the compounds (Y2) and (Y3) were used as the second hole transporting material instead of the compound (Y1).

The resulting organic EL devices were subjected to light emission by direct current driving, and were evaluated in the same manner as in Example 1. The results are shown in Table 2.

Comparative Examples 5 and 6

Organic EL devices were produced in the same manner as in Example 13 except that the comparative compounds 1 and 2 were used as the first hole transporting material instead of the compound (H1), and were evaluated in the same manner as in Example 1. The results are shown in Table 2.

It is understood from the comparison between Examples 13 to 15 and Comparative Examples 5 and 6 in Table 2 that the organic EL devices using the compounds of the present invention in the first hole transporting layer can be driven at a lower voltage and have a longer service life, as compared to the organic EL devices using the known aromatic amine derivatives in the hole transporting layer.

The invention claimed is:
1. A compound represented by formula (1):

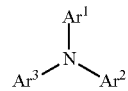

wherein in formula (1), $Ar^1$ represents an organic group A represented by the formula (A-1); $Ar^2$ represents the organic group A or an organic group B represented by formula (B-1); and $Ar^3$ represents the organic group B or an organic group C represented by formula (C-1), provided that in the case where both $Ar^1$ and $Ar^2$ are the organic groups A, the organic groups A may be the same as or different from each other,

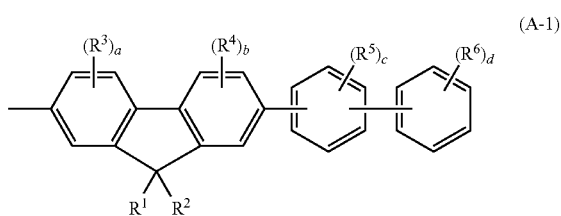

wherein in formula (A-1), $R^1$ and $R^2$ each independently represent a hydrogen atom, an alkyl group having from 1 to 10 carbon atoms or an aryl group having from 6 to 12 ring carbon atoms, provided that $R^1$ and $R^2$ may be bonded to each other to form a hydrocarbon ring;
$R^3$ each independently represent a cycloalkyl group having from 3 to 10 ring carbon atoms or an aryl group having from 6 to 12 ring carbon atoms;
$R^4$ to $R^6$ each independently represent an alkyl group having from 1 to 10 carbon atoms, a cycloalkyl group having from 3 to 10 ring carbon atoms or an aryl group having from 6 to 12 ring carbon atoms; and
a, b, c and d each independently represent an integer of from 0 to 2,

TABLE 2

|  |  | Acceptor material | First hole transporting material | Second hole transporting material | Light emitting material (host material/ dopant) | Light emission efficiency (cd/A) | Driving voltage (V) | 80% service life *1 (hour) | Light emission color |
|---|---|---|---|---|---|---|---|---|---|
| Example | 13 | A | H1 | Y1 | B2/BD | 7.5 | 4.2 | 540 | blue |
|  | 14 | A | H1 | Y2 | B2/BD | 8.1 | 4.1 | 400 | blue |
|  | 15 | A | H1 | Y3 | B2/BD | 8.0 | 4.3 | 420 | blue |
| Comparative Example | 5 | A | comparative compound 1 | Y1 | B2/BD | 7.4 | 4.3 | 250 | blue |
|  | 6 | A | comparative compound 2 | Y1 | B2/BD | 7.0 | 4.3 | 240 | blue |

*1: period of time until reducing the luminance to 80% provided that $R^3$ and $R^4$ may be bonded to each other to form a hydrocarbon ring; and in the case where a or b is 2, adjacent groups of $R^3$ or adjacent groups of $R^4$ may be bonded to each other to form a hydrocarbon ring,

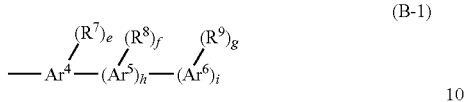
(B-1)

wherein in formula (B-1), $Ar^4$ and $Ar^5$ each independently represent a phenylene group, a naphthyiene group, an anthrylene group or a phenanthrylene group; $Ar^6$ represents a phenyl group, a naphthyl group, an anthryl group or a phenanthryl group; $R^7$ to $R^9$ each independently represent an alkyl group having from 1 to 10 carbon atoms, a cycloalkyl group having from 3 to 10 ring carbon atoms or an aryl group having from 6 to 12 ring carbon atoms; e and g each independently represent an integer of from 0 to 2; f represents an integer of from 0 to 1; and h and i each independently represent 0 or 1, provided that $R^7$ to $R^9$ may be bonded to each other to form a hydrocarbon ring; and in the case where e or g is 2, adjacent groups of $R^7$ or adjacent groups of $R^9$ may be bonded to each other to form a hydrocarbon ring,

(C-1)

wherein in formula (C-1), $Ar^7$ represents a substituted or unsubstituted aryl group having from 6 to 14 ring carbon atoms; $R^{10}$ represents an alkyl group having from 1 to 10 carbon atoms, a cycloalkyl group having from 3 to 10 ring carbon atoms or an aryl group having from 6 to 12 ring carbon atoms; and j represents an integer of from 0 to 2, provided. that in the case where j is 2, adjacent groups of $R^{10}$ may be bonded to each other to form a hydrocarbon ring.

2. The compound according to claim 1, wherein in formula (A-1). $R^1$ and $R^2$ are not bonded to each other to form a hydrocarbon ring.

3. The compound according to claim 1, wherein the organic group B is represented by formula (B-2):

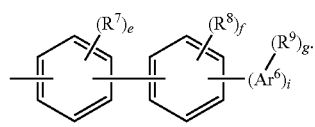
(B-2)

4. The compound according to claim 1, wherein the organic group B is represented by any one of formulae (B-3) to (B-5):

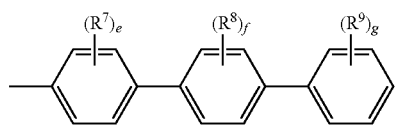
(B-3)

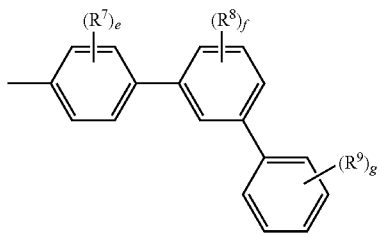
(B-4)

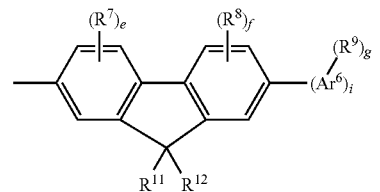
(B-5)

wherein $Ar^6$ represents a phenyl group, a naphthyl group, an anthryl group or a phenanthryl group; $R^{11}$ and $R^{12}$ each independently represent a hydrogen atom, an alkyl group having from 1 to 10 carbon atoms, a cycloalkyl group having from 3 to 10 ring carbon atoms or an aryl group having from 6 to 12 ring carbon atoms; $R^7$ to $R^9$ each independently represent an alkyl group having from 1 to 10 carbon atoms, a cycloalkyl group having from 3 to 10 ring carbon atoms or an aryl group having from 6 to 12 ring carbon atoms; e and g each independently represent an integer of from 0 to 2: f represents an integer of from 0 to 1; and i represents 0 or 1, provided that $R^7$ to $R^9$ may be bonded to each other to form a hydrocarbon ring; and in the case where e, f or g is 2, adjacent groups of $R^7$ or adjacent groups of $R^9$ may be bonded to each other to form a hydrocarbon ring.

5. The compound according to claim 1, wherein $Ar^2$ represents the organic group B.

6. The compound according to claim 1, wherein both $Ar^1$ and $Ar^2$ represent the organic groups A, and provided that $Ar^1$ and $Ar^2$ may be the same as or different from each other.

7. The compound according to claim 1, wherein the compound is selected from H1 to H7:

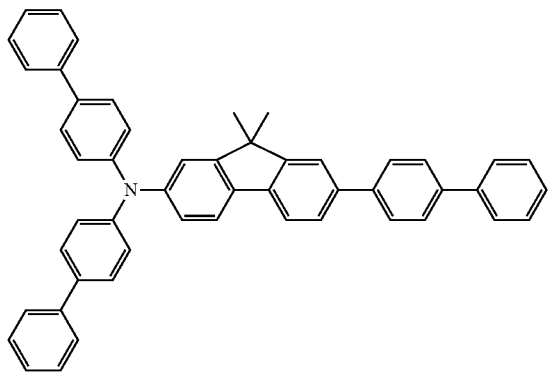
(H1)

(H2)
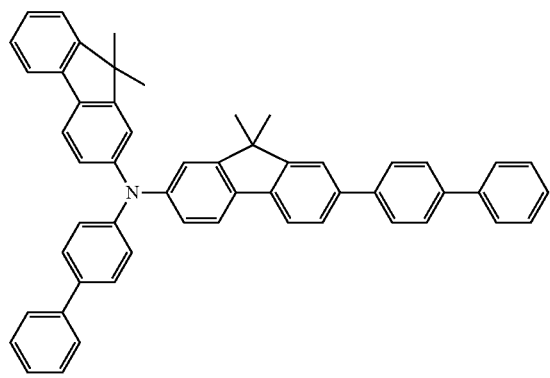

(H3)
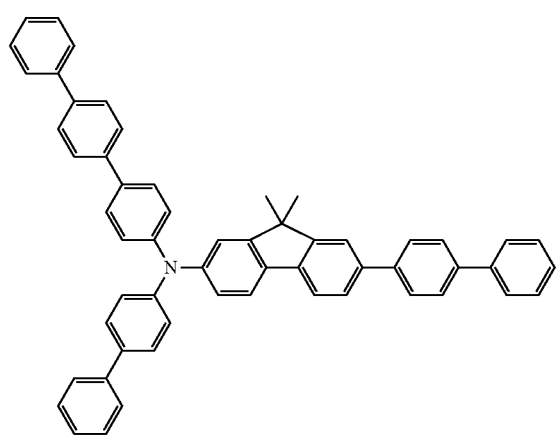

(H4)
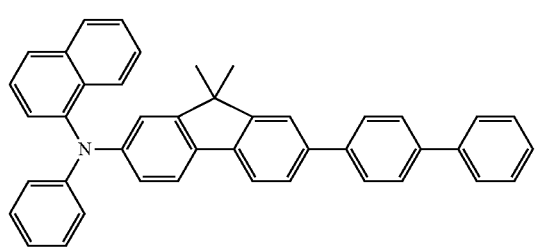

(H5)
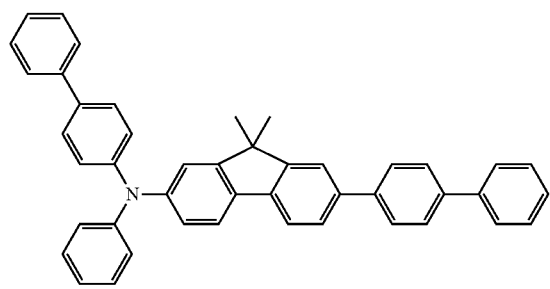

(H6)
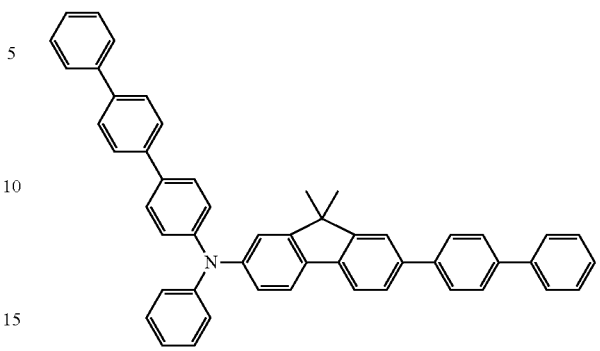

(H7)
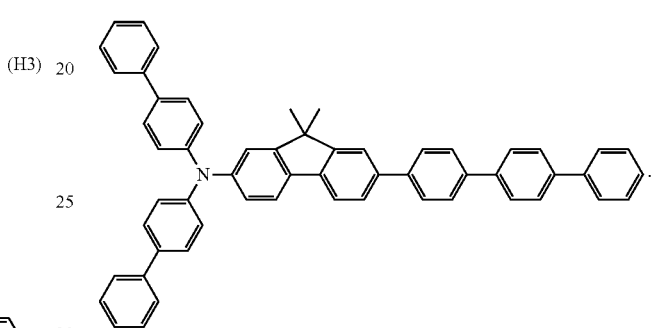

8. A material for an organic electroluminescent device, comprising the compound according to claim 1.

9. A hole transporting material for an organic electroluminescent device, comprising the compound according to claim 1.

10. A hole transporting material for an organic electrowninescent device having an acceptor layer-proximate hole transporting layer, comprising the compound according to claim 1.

11. An organic electroluminescent device comprising a cathode and an anode, and intervening therebetween an organic thin film layer, and comprising at least one organic thin film layer containing the compound according to claim 1.

12. An organic electroluminescent device comprising a cathode and an anode, and intervening therebetween at least two hole transporting layers and a light emitting layer sequentially, one of the hole transporting layer comprising the compound according to claim 1 and being not adjacent to the light emitting layer.

13. An organic electroluminescent device comprising a cathode and an anode, and intervening therebetween at least two hole transporting layers and a light emitting layer sequentially, and wherein the hole transporting layers include a first hole transporting layer on the side of the anode and a second hole transporting layer on the side of the light emitting layer, the first hole transporting layer comprising the compound according to claim 1.

14. The electroluminescent device according to claim 13, wherein the second hole transporting layer comprises a compound represented by formula (4):

(4)

wherein in the formula (4), at least one of $Ar^{11}$ to $Ar^{13}$ represents a group represented by the formula (4-2) or (4-4); the group that is not represented by the general formula (4-2) is a group represented by formula (4-3) or (4-4) or a substituted or unsubstituted aryl group having from 6 to 40 ring carbon atoms; and the group that is not represented by the general formula (4-4) is a group represented by the following general formula (4-2) or (4-3) or a substituted or unsubstituted aryl group having from 6 to 40 ring carbon atoms,

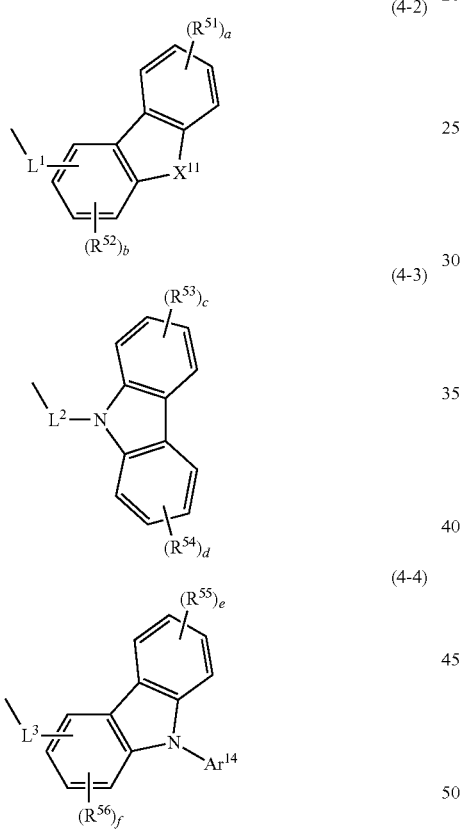

wherein $X^{11}$ represents an oxygen atom or a sulfur atom; $L^1$ to $L^3$ each independently represent a single bond or a substituted or unsubstituted arylene group having from 6 to 50 ring carbon atoms, and the substituent that may be substituted on $L^1$ to $L^3$ is a linear or branched alkyl group having from 1 to 10 carbon atoms, a cycloalkyl group having from 3 to 10 ring carbon atoms, a trialkylsilyl group having from 3 to 10 carbon atoms, a triatylsilyl group having from 18 to 30 ring carbon atoms, an alkylatylsilyl group having from 8 to 15 carbon atoms, an aryl group having from 6 to 50 ring carbon atoms, a halogen atom or a cyano group; $Ar^{14}$ represents a substituted or unsubstituted aryl group having from 6 to 50 ring carbon atoms, and the substituent that may be substituted on $Ar^{14}$ is a linear or branched alkyl group having from 1 to 10 carbon atoms, a cycloalkyl group having from 3 to 10 ring carbon atoms, a trialkylsilyl group having from 3 to 10 carbon atoms, a triarylsilyl group having from 18 to 30 ring carbon atoms, an alkylarylsilyl group having from 8 to 15 carbon atoms, an aryl group having from 6 to 50 ring carbon atoms, a halogen atom or a cyano group; $R^{51}$ to $R^{56}$ each independently represent a substituted or unsubstituted and linear or branched alkyl group having from 1 to 10 carbon atoms, a substituted or unsubstituted cycloalkyl group having from 3 to 10 ring carbon atoms, a substituted or unsubstituted trialkylsilyl group having from 3 to 10 carbon atoms, a substituted or unsubstituted triarylsilyl group having from 18 to 30 ring carbon atoms, a substituted or unsubstituted alkylarylsilyl group having from 8 to 15 carbon atoms, a substituted or unsubstituted aryl group having from 6 to 50 ring carbon atoms, a halogen atom or a cyano group, provided that the adjacent groups of $R^{51}$ to $R^{56}$ may be bonded to each other to form a ring;

b and f each independently represent an integer of from 0 to 3; and a, c, d and e each independently represent an integer of from 0 to 4.

15. The electroluminescent device according to claim 14, wherein $L^1$ represents a substituted or unsubstituted arylene group having from 6 to 50 ring carbon atoms.

16. The electroluminescent device according to claim 14, wherein $L^3$ represents a substituted or unsubstituted arylene group having from 6 to 50 ring carbon atoms.

17. The electroluminescent device according to claim 14, wherein the aryl group having from 6 to 40 ring carbon atoms of $Ar^{11}$ to $Ar^{13}$ is represented by any one of formulae (4-5) to (4-7):

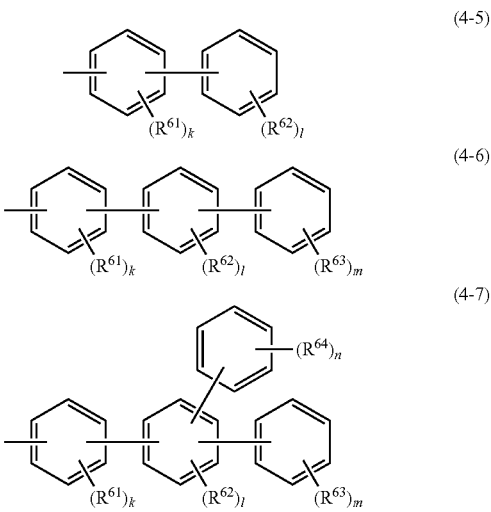

wherein $R^{61}$ $R^{64}$ each independently represent a linear or branched alkyl group having from 1 to 10 carbon atoms, a cycloalkyl group having from 3 to 10 ring carbon atoms, a trialkylsilyl group having from 3 to 10 carbon atoms, a triarylsilyl group having from 18 to 30 ring carbon atoms, an alkylaryisilyl group having from 8 to 15 carbon atoms, wherein the aryl moiety has from 6 to 14 ring carbon atoms, an aryl group having from 6 to 50 ring carbon atoms, a halogen atom or a cyano group, provided that the adjacent groups of $R^{61}$ to $R^{64}$ may be bonded to each other to form a ring; and k, l, m and n each independently represent an integer of from 0 to 4.

18. The electroluminescent device according to claim 12, further comprising an acceptor layer containing an acceptor material between the anode and the hole transporting layers.

19. The electroluminescent device according to claim 13, wherein the first hole transporting layer contains an acceptor material.

20. The electroluminescent device according claim 18, wherein the acceptor material is represented by formulae (A) to (C):

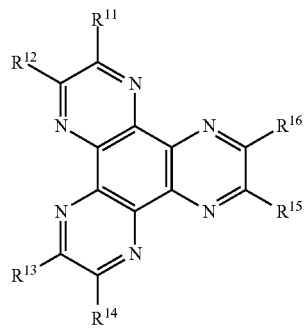

(A)

wherein in the formula (A), $R^{11}$ to $R^{16}$ each independently represent a cyano group, —$CONH_2$, a carboxyl group or —$COOR^{17}$ and $R^{17}$ represents an alkyl group having from 1 to 20 carbon atoms, or represent a group represented by —CO—O—CO—by bonding $R^{11}$ and $R^{12}$, and $R^{13}$ and $R^{14}$, or $R^{15}$ and $R^{16}$,

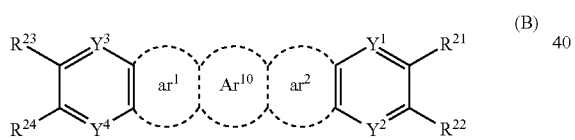

(B)

wherein in formula (B), $R^{21}$ to $R^{24}$ each independently represent a hydrogen atom, a substituted or unsubstituted alkyl group having from 1 to 20 carbon atoms, a substituted or unsubstituted aryl group having from 6 to 50 ring carbon atoms, a substituted or unsubstituted heterocyclic group having from 5 to 50 ring atoms, a halogen atom, a substituted or unsubstituted alkoxy group having from 1 to 20 carbon atoms, a substituted or unsubstituted aryloxy group having from 6 to 50 ring carbon atoms, or a cyano group, provided that $R^{21}$ and $R^{22}$, and $R^{23}$ and $R^{24}$ may be bonded to each other to form a ring;

$Y^1$ to $Y^4$ each independently represent —N=, —CH= or $C(R^{25})=$, wherein $R^{25}$ represents a substituted or unsubstituted alkyl group having from 1 to 20 carbon atoms, a substituted or unsubstituted aryl group having from 6 to 50 ring carbon atoms, a substituted or unsubstituted heterocyclic group having from 5 to 50 ring atoms, a halogen atom, a substituted or unsubstituted alkoxy group having from 1 to 20 carbon atoms, a substituted or unsubstituted aryloxy group having from 6 to 50 ring carbon s, or a cyano group;

$Ar^{10}$ represents a condensed ring having from 6 to 24 ring carbon atoms or a heterocyclic ring having from 6 to 24 ring atoms; and $ar^1$ and $ar^2$ each independently represent a ring represented by the following general formula (i) or (ii):

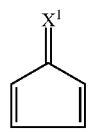

(i)

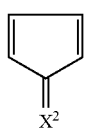

(ii)

wherein $X^1$ and $X^2$ each independently represent any one of the following divalent groups (a) to (g)

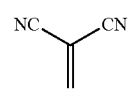

(a)

(b)

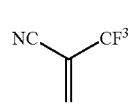

(c)

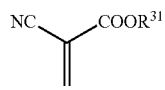

(d)

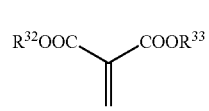

(e)

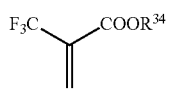

(f)

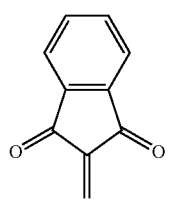

(g)

wherein $R^{31}$ to $R^{34}$ may be the same as or different from each other and each represent a hydrogen atom, a substituted or unsubstituted alkyl group having from 1 to 20 carbon atoms, a substituted or unsubstituted aryl group having from 6 to 50 ring carbon atoms or a substituted or unsubstituted heterocyclic group having from 5 to 50 ring atoms, provided that $R^{32}$ and $R^{33}$ may be bonded to each other to form a ring,

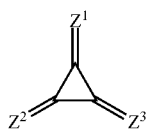

(C)

wherein $Z^1$ to $Z^3$ each independently represent a divalent group represented by formula (h):

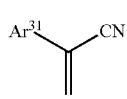

(h)

wherein $Ar^{31}$ represents a substituted or unsubstituted aryl group having from 6 to 50 ring carbon atoms or a substituted or unsubstituted heteroaryl group having from 5 to 50 ring atoms.

21. The electrolwninescent device according to claim 12, wherein the light emitting layer contains at least one fluorescent material selected from an anthracene derivative, a fluorantene derivative, a styrylamine derivative and an arylamine derivative.

22. The electroluminescent device according to claim 12, wherein the light emitting layer contains a phosphorescent material.

23. The electroluminescent device according to claim 22, wherein the phosphorescent material is an ortho-metallized complex of iridium (Ir), osmium (Os) or platinum (Pt).

24. The electroluminescent device according to claim 21, wherein said device emits blue light.

25. The electroluminescent device according to claim 22, wherein said device emits yellow light, green light or blue light.

26. An electronic apparatus comprising the organic electroluminescent device according to claim 11.

27. The compound according to claim 1, wherein in formula (B-1), e represents an integer of from 0 to 1.

28. The compound according to claim 1, wherein in formula (B-1), $R^7$ to $R^9$ are not bonded to each other to form a hydrocarbon ring.

29. The compound according to claim 1. wherein in formula (A-1), a represents an integer of 0.

30. The compound according to claim formula (C-1), $Ar^7$ represents a phenyl group, a naphthyl group, an anthryl group, or a phenanthryl group.

31. The compound according to claim 1. wherein $Ar^3$ represents the organic group C represented by the formula (C-1).

32. The compound according to claim 1, wherein:
in formula (A-1), a represents an integer of 0; and
in formula (B-1), e represents an integer of from 0 to 1, and $R^7$ to $R^9$ are not bonded to each other to form a hydrocarbon ring.

33. The compound according to claim 1, wherein:
in formula (A-1), a represents an integer of 0;
$Ar^2$ represents the organic group B.
in formula (B-1), e represents an integer of from 0 to 1, and $R^7$ to $R^9$ are not bonded to each other to form a hydrocarbon ring;
$Ar^3$ represents the organic group C represented by the formula (C-1); and in formula (C-1), $Ar^7$ represents a phenyl group, a naphthyl group, an anthryl group, or a phenanthryl group.

34. The compound according to claim 1, wherein:
$Ar^2$ represents formula (B-1), and $R^7$ to $R^9$ are not bonded to each other to form a hydrocarbon ring;
$Ar^3$ represents formula (C-1); and
in formula (C-1), $Ar^7$ represents a phenyl group, a naphthyl group, an anthryl group, or a phenanthryl group.

35. The compound according to claim 1, wherein:
$Ar^2$ is represented by any one of following formulae;

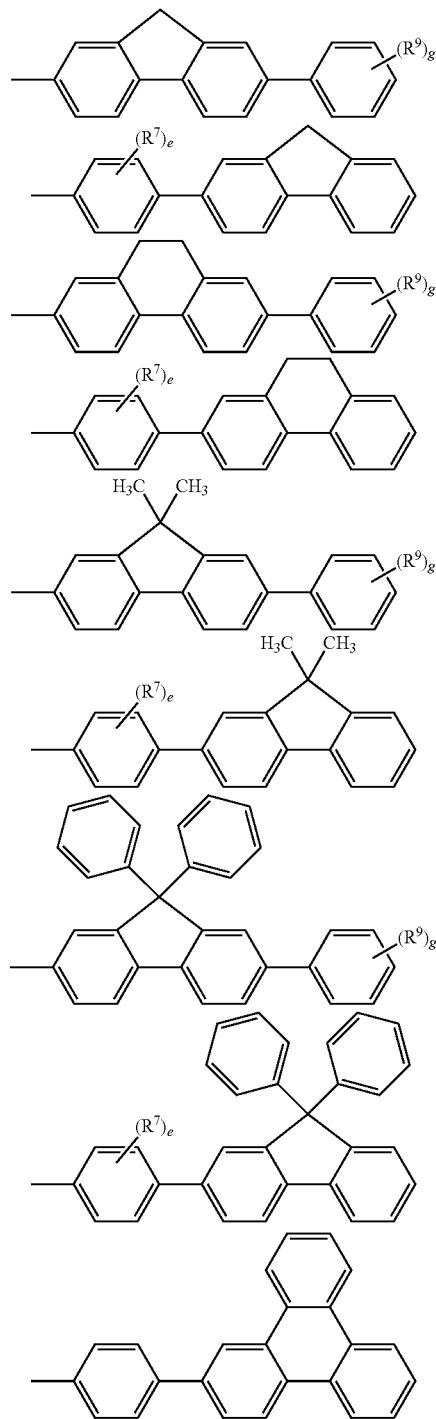

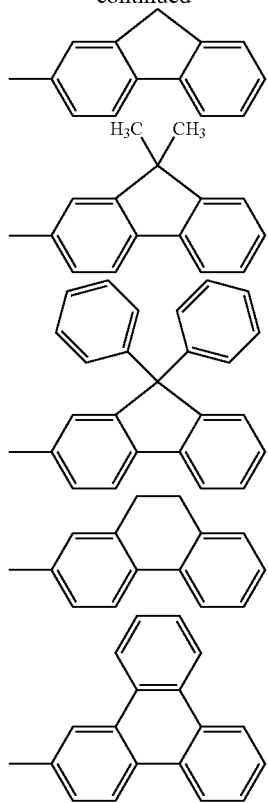

wherein R⁷, R⁹, e, and g are the same as in claim 1, Ar³ represents formula (C-1); and in formula (C-1), Ar⁷ represents a phenyl group, a naphthyl group, an anthryl group, or a phenanthryl group.

36. The compound according to claim 1, wherein:

Ar² is represented by any one of formulae (B3) to (B-5):

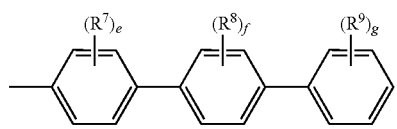
(B-3)

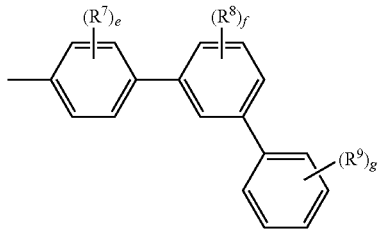
(B-4)

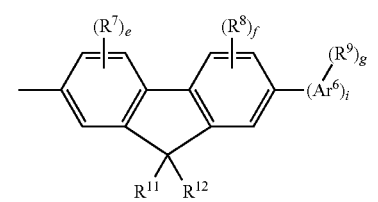
(B-5)

wherein

Ar⁶ represents a phenyl group, a naphthyl group, an anthryl group or a phenanthryl group;

$R^{11}$ and $R^{12}$ each independently represent a hydrogen atom, an alkyl group having from 1 to 10 carbon atoms, a cycloalkyl group having from 3 to 10 ring carbon atoms or an aryl group having from 6 to 12 ring carbon atoms;

$R^7$ to $R^9$ each independently represent an alkyl group having from 1 to 10 carbon atoms, a cycloalkyl group having from 3 to 10 ring carbon atoms or an aryl group having from 6 to 12 ring carbon atoms;

e and g each independently represent an integer of from 0 to 2;

f represents an integer of from 0 to 1; and i represents 0 or 1,

Ar³ represents formula (C-1); and in formula (C-1), Ar⁷ represents a phenyl group, a naphthyl group, an anthryl group, or a phenanthryl group.

* * * * *